(12) United States Patent
Dong et al.

(10) Patent No.: US 10,117,840 B2
(45) Date of Patent: Nov. 6, 2018

(54) SULFUR(VI) FLUORIDE COMPOUNDS AND METHODS FOR THE PREPARATION THEREOF

(71) Applicant: The Scripps Research Institute, La Jolla, CA (US)

(72) Inventors: Jiajia Dong, Shanghai (CN); K. Barry Sharpless, La Jolla, CA (US); Jeffery W. Kelly, La Jolla, CA (US); Wentao Chen, Walnut Creek, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/316,742

(22) PCT Filed: Jun. 5, 2015

(86) PCT No.: PCT/US2015/034516
§ 371 (c)(1),
(2) Date: Dec. 6, 2016

(87) PCT Pub. No.: WO2015/188120
PCT Pub. Date: Dec. 10, 2015

(65) Prior Publication Data
US 2017/0196985 A1   Jul. 13, 2017

Related U.S. Application Data

(60) Provisional application No. 62/008,925, filed on Jun. 6, 2014.

(51) Int. Cl.
| C07C 305/26 | (2006.01) |
| C07K 2/00 | (2006.01) |
| C07K 1/02 | (2006.01) |
| A61K 31/05 | (2006.01) |
| C07D 277/82 | (2006.01) |
| C07D 295/088 | (2006.01) |
| C07D 295/185 | (2006.01) |
| C07D 295/26 | (2006.01) |
| A61K 31/136 | (2006.01) |
| A61K 31/14 | (2006.01) |
| A61K 31/197 | (2006.01) |
| A61K 31/198 | (2006.01) |
| A61K 31/397 | (2006.01) |
| A61K 31/40 | (2006.01) |
| A61K 31/4045 | (2006.01) |
| A61K 31/407 | (2006.01) |
| A61K 31/4168 | (2006.01) |
| A61K 31/4245 | (2006.01) |
| A61K 31/4353 | (2006.01) |
| A61K 31/439 | (2006.01) |
| A61K 31/47 | (2006.01) |
| A61K 31/4709 | (2006.01) |
| A61K 31/473 | (2006.01) |
| A61K 31/4745 | (2006.01) |
| A61K 31/485 | (2006.01) |
| A61K 31/505 | (2006.01) |

(Continued)

(52) U.S. Cl.
CPC ............ *A61K 31/05* (2013.01); *A61K 31/136* (2013.01); *A61K 31/14* (2013.01); *A61K 31/197* (2013.01); *A61K 31/198* (2013.01); *A61K 31/397* (2013.01); *A61K 31/40* (2013.01); *A61K 31/407* (2013.01); *A61K 31/4045* (2013.01); *A61K 31/4168* (2013.01); *A61K 31/4245* (2013.01); *A61K 31/439* (2013.01); *A61K 31/4353* (2013.01); *A61K 31/47* (2013.01); *A61K 31/473* (2013.01); *A61K 31/4709* (2013.01); *A61K 31/4745* (2013.01); *A61K 31/485* (2013.01); *A61K 31/505* (2013.01); *A61K 31/515* (2013.01); *A61K 31/53* (2013.01); *A61K 31/5513* (2013.01); *A61K 31/56* (2013.01); *A61K 31/65* (2013.01); *A61K 31/655* (2013.01); *A61K 31/70* (2013.01); *A61K 31/7048* (2013.01); *A61K 38/31* (2013.01); *A61K 47/48023* (2013.01); *A61K 47/54* (2017.08); *A61K 51/0497* (2013.01); *C07C 305/26* (2013.01); *C07D 277/82* (2013.01); *C07D 295/088* (2013.01); *C07D 295/185* (2013.01); *C07D 295/26* (2013.01); *C07K 1/02* (2013.01); *C07K 1/1136* (2013.01); *C07K 2/00* (2013.01); *C07C 2601/14* (2017.05); *C07C 2603/18* (2017.05)

(58) Field of Classification Search
None
See application file for complete search history.

(56) References Cited

U.S. PATENT DOCUMENTS

2012/0283296 A1* 11/2012 Campbell .......... A61K 31/4162
514/338

* cited by examiner

*Primary Examiner* — Samantha L Shterengarts
(74) *Attorney, Agent, or Firm* — Olson & Cepuritis, Ltd.

(57) ABSTRACT

This application describes a compound represented by Formula (I): (I) wherein: Y is a biologically active organic core group comprising one or more of an aryl group, a heteroaryl aryl group, a nonaromatic hydrocarbyl group, and a nonaromatic heterocyclic group, to which Z is covalently bonded; n is 1, 2, 3, 4 or 5; m is 1 or 2; Z is O, NR, or N; $X^1$ is a covalent bond or $-CH_2CH_2-$, $X^2$ is O or NR; and R comprises H or a substituted or unsubstituted group selected from an aryl group, a heteroaryl aryl group, a nonaromatic hydrocarbyl group, and a nonaromatic heterocyclic group. Methods of preparing the compounds, methods of using the compounds, and pharmaceutical compositions comprising the compounds are described as well.

4 Claims, 30 Drawing Sheets
Specification includes a Sequence Listing.

(51) Int. Cl.
*A61K 31/515* (2006.01)
*A61K 31/53* (2006.01)
*A61K 31/5513* (2006.01)
*A61K 31/56* (2006.01)
*A61K 31/65* (2006.01)
*A61K 31/655* (2006.01)
*A61K 31/70* (2006.01)
*A61K 31/7048* (2006.01)
*A61K 38/31* (2006.01)
*A61K 47/48* (2006.01)
*A61K 51/04* (2006.01)
*C07K 1/113* (2006.01)
*A61K 47/54* (2017.01)

Prazosin
an alpha-blocker, antihypertensive

Pregabalin (LYRICA)
anticonvulsive; neuropathic pain treatment

Palbociclib
breast cancer drug

Procainamide
antiarrhythmic agent

Procarbazine
an antineoplastic agent

Pseudoephedrine
a nasal decongestant; stimulant

Ramipril
an antihypertensive

Rasagiline
a monoamine oxidase inhibitor

Reboxetine
an antidepressant; norepinephrine reuptake inhibitor

Rimantadine
an antiviral agent

Bupropion
antidepressant; hydrochloride salt sold as WELLBUTRIN

Gabapentin
an anticonvulsive; analgesic

Lisinopril
angiotensin-converting enzyme (ACE) inhibitor; antihypertensive

Amphetamine
a stimulant

Fluoxetine (PROZAC)
selective serotonin reuptake inhibitor; antidepressant

Cefadroxil
a cephem antibiotic

Salbutamol (albuterol)
beta-2 adrenergic receptor agonist, bronchodilator

Warfarin (coumadin)
an anticoagulant

Butorphanol
morphine analog; analgesic

Hydromorphone
opioid; analgesic

Rotigotine
dopamine agonist; Parkinson's treatment

Estradiol
estrogenic hormone; menstrual regulator

Ritodrine
beta-2 adrenergic receptor agonist; anti-contraction agent

Salicyclic acid
analgesic

Terbutaline
beta-2 adrenergic receptor agonist; anti-contraction agent;
asthma treatment

US 10,117,840 B2

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Synthetically modified human epidermal growth
      factor receptor (EGFR) peptide
<221> NAME/KEY: SULFATATION
<222> LOCATION: 5
<221> NAME/KEY: AMIDATION
<222> LOCATION: 6

<400> SEQUENCE: 1

Asp Ala Asp Glu Tyr Leu
1               5
```

```
<210> SEQ ID NO 2
<211> LENGTH: 8
<212> TYPE: PRT
<213> ORGANISM: Artificial Sequence
<220> FEATURE:
<223> OTHER INFORMATION: Synthetically modified human P selectin
      glycoprotein ligand 1 (PGSL-1) peptide
<221> NAME/KEY: SULFATATION
<222> LOCATION: 3
<221> NAME/KEY: AMIDATION
<222> LOCATION: 8

<400> SEQUENCE: 2

Tyr Glu Tyr Leu Asp Tyr Asp Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetically modified human P selectin
      glycoprotein ligand 1 (PGSL-1) peptide
<221> NAME/KEY: SULFATATION
<222> LOCATION: 1, 3, 6
<221> NAME/KEY: AMIDATION
<222> LOCATION: 8

<400> SEQUENCE: 3

Tyr Glu Tyr Leu Asp Tyr Asp Phe
1               5

<210> SEQ ID NO 4
<211> LENGTH: 22
<212> TYPE: PRT
<213> ORGANISM: Artificial Sequence
<220> FEATURE:
<223> OTHER INFORMATION: Synthetically modified human G protein coupled
      receptor C5aR peptide
<221> NAME/KEY: SULFATATION
<222> LOCATION: 5, 8
<221> NAME/KEY: AMIDATION
<222> LOCATION: 22

<400> SEQUENCE: 4

Thr Thr Pro Asp Tyr Gly His Tyr Asp Asp Lys Asp Thr Leu Asp Leu
1               5                   10                  15

Asn Thr Pro Val Asp Lys
            20

<210> SEQ ID NO 5
<211> LENGTH: 20
<212> TYPE: PRT
<213> ORGANISM: Artificial Sequence
<220> FEATURE:
<223> OTHER INFORMATION: Synthetically modified human chemokine receptor
      D6 peptide
<221> NAME/KEY: SULFATATION
<222> LOCATION: 10, 11, 12, 14
<221> NAME/KEY: AMIDATION
<222> LOCATION: 20

<400> SEQUENCE: 5

Asp Ala Asp Ser Glu Asn Ser Ser Phe Tyr Tyr Tyr Asp Tyr Leu Asp
1               5                   10                  15

Glu Val Ala Phe
            20

<210> SEQ ID NO 6
```

```
<211> LENGTH: 6
<212> TYPE: PRT
<213> ORGANISM: Artificial Sequence
<220> FEATURE:
<223> OTHER INFORMATION: Synthetically modified human epidermal growth
      factor receptor (EGFR) peptide
<221> NAME/KEY: MOD_RES
<222> LOCATION: 5
<223> OTHER INFORMATION: tyrosine-O-fluorosulfate
<221> NAME/KEY: AMIDATION
<222> LOCATION: 6

<400> SEQUENCE: 6

Asp Ala Asp Glu Tyr Leu
1               5

<210> SEQ ID NO 7
<211> LENGTH: 12
<212> TYPE: PRT
<213> ORGANISM: Artificial Sequence
<220> FEATURE:
<223> OTHER INFORMATION: Synthetically modified human CXC chemokine
      receptor type 4 (CXCR4) peptide
<221> NAME/KEY: SULFATATION
<222> LOCATION: 3
<221> NAME/KEY: AMIDATION
<222> LOCATION: 12

<400> SEQUENCE: 7

Gly Asp Tyr Asp Ser Met Lys Glu Pro Cys Phe Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetically modified human CXC chemokine
      receptor type 4 (CXCR4) peptide
<221> NAME/KEY: MOD_RES
<222> LOCATION: 3
<223> OTHER INFORMATION: tyrosine-O-fluorosulfate
<221> NAME/KEY: AMIDATION
<222> LOCATION: 12

<400> SEQUENCE: 8

Gly Asp Tyr Asp Ser Met Lys Glu Pro Cys Phe Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetically modified thymopentin, a peptide
      immunostimulant
<221> NAME/KEY: MOD_RES
<222> LOCATION: 5
<223> OTHER INFORMATION: tyrosine-O-fluorosulfate
<221> NAME/KEY: MOD_RES
<222> LOCATION: 7
<223> OTHER INFORMATION: Xaa = alpha-propargylglycine

<400> SEQUENCE: 9

Arg Lys Asp Val Tyr Gly Xaa Gly
1               5

<210> SEQ ID NO 10
<211> LENGTH: 11
<212> TYPE: PRT
<213> ORGANISM: Artificial Sequence
```

```
<220> FEATURE:
<223> OTHER INFORMATION: Synthetically modified human hormone oxytocin
<221> NAME/KEY: MOD_RES
<222> LOCATION: 2
<223> OTHER INFORMATION: tyrosine-O-fluorosulfate
<221> NAME/KEY: MOD_RES
<222> LOCATION: 10
<223> OTHER INFORMATION: Xaa = alpha-propargylglycine
<221> NAME/KEY: DISULFID
<222> LOCATION: (1)...(6)

<400> SEQUENCE: 10

Cys Tyr Ile Gln Asn Cys Pro Leu Gly Xaa Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetically modified human hormone arginine
      vasopressin
<221> NAME/KEY: DISULFID
<222> LOCATION: (1)...(6)
<221> NAME/KEY: MOD_RES
<222> LOCATION: 2
<223> OTHER INFORMATION: tyrosine-O-fluorosulfate
<221> NAME/KEY: MOD_RES
<222> LOCATION: 10
<223> OTHER INFORMATION: Xaa = alpha-propargylglycine

<400> SEQUENCE: 11

Cys Tyr Phe Gln Asn Cys Pro Arg Gly Xaa Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetically modified bovine peptide known as
      indolicidin
<221> NAME/KEY: MOD_RES
<222> LOCATION: 2
<223> OTHER INFORMATION: Xaa = alpha-propargylglycine
<221> NAME/KEY: MOD_RES
<222> LOCATION: 8
<223> OTHER INFORMATION: tyrosine-O-fluorosulfate
<221> NAME/KEY: AMIDATION
<222> LOCATION: 13

<400> SEQUENCE: 12

Ile Xaa Pro Trp Lys Trp Pro Tyr Trp Pro Trp Arg Arg
1               5                   10
```

SULFUR(VI) FLUORIDE COMPOUNDS AND METHODS FOR THE PREPARATION THEREOF

CROSS-REFERENCE TO RELATED APPLICATIONS

This application is a U.S. National Stage of PCT/US2015/034516, file Jun. 5, 2015, which claims priority benefit to U.S. Provisional Application No. 62/008,925, filed on Jun. 6, 2014, both of which are incorporated herein by reference in their entirety.

GOVERNMENT SUPPORT

This invention was made with government support from National Institutes of Health, Grants No. U01NS058046 and EB015663, and National Science Foundation, Grant No. CHE 1011796. The United States government has certain rights in this invention.

INCORPORATION OF SEQUENCE LISTING

Biological sequence information for this application is included in an ASCII text file having the file name "TSRI-1613-1-SEQ-V2.TXT", created on Feb. 28, 2018, and having a file size of 4,924 bytes, which is incorporated herein by reference.

FIELD OF THE INVENTION

The present invention relates to sulfur(VI) fluoride compounds, including therapeutic compounds and compositions, as well as and methods of using and producing the compounds and compositions.

BACKGROUND

"Click" chemistry was introduced as a conceptual framework for functional molecular assembly a decade ago, emphasizing the importance of carbon-heteroatom linkages in joining modular building blocks (see H. C. Kolb, M. G. Finn, K. B. Sharpless, *Angew. Chem.* 2001, 123, 2056-2075; *Angew. Chem. Int. Ed.* 2001, 2040, 2004-2021). Taking inspiration from nature, click reactions were identified as processes that work under operationally simple, oxygen- and water-friendly conditions, and generate products in high yields with minimal requirements for product purification. Such reactions invariably have an unusual combination of strong thermodynamic driving forces and consistent, well-controlled reaction pathways. In tandem, these two features allow the use of widely varying substrates with great reliability.

The azide-alkyne cycloaddition reaction (see R. Huisgen, *Angew. Chem.* 1963, 75, 604-637; *Angew. Chem. Int. Ed. Engl.* 1963, 1962, 1565-1598) is especially useful because of the unobtrusive nature of its participating functional groups and the ability to turn on their ligating ability (to different extents, and for different purposes) by Cu(I) catalysts (see (a) C. W. Tornøe, C. Christensen, M. Meldal, *J. Org. Chem.* 2002, 67, 3057-3062. (b) V. V. Rostovtsev, L. G. Green, V. V. Fokin, K. B. Sharpless, *Angew. Chem.* 2002, 114, 2708-2711; *Angew. Chem. Int. Ed.* 2002, 2741, 2596-2599.), installing strain in the alkyne component (see (a) G. Wittig, A. Krebs, *Chem. Ber. Recl.* 1961, 94, 3260-3275. (b) N. J. Agard, J. A. Prescher, C. R. Bertozzi, *J. Am. Chem. Soc.* 2004, 126, 15046-15047), or holding them in close spatial proximity (see (a) W. G. Lewis, L. G. Green, F. Grynszpan, Z. Radic, R. P. Carlier, P. Taylor, M. G. Finn, K. B. Sharpless, *Angew. Chem.* 2002, 114, 1095-1099; *Angew. Chem. Int. Ed.* 2002, 1041, 1053-1057. (b) H. D. Agnew, R. D. Rhode, S. W. Millward, A. Nag, W. S. Yeo, J. E. Hein, S. M. Pitram, A. A. Tariq, V. M. Burns, R. J. Krom, V. V. Fokin, K. B. Sharpless, J. R. Heith, *Angew. Chem.* 2009, 121, 5044-5048; *Angew. Chem. Int. Ed.* 2009, 5048, 4944-4948). Thus, this click reaction emerged by finding ways to induce two functional groups to react with each other that otherwise have very little propensity to react with anything, in spite of their highly energetic nature. In contrast, most other click reactions find a useful window of activity by moderating the properties of at least one highly reactive partner.

There is an ongoing need for new click chemistry methods, particularly for the preparation of biologically active materials with useful and uncommon functional groups and pharmacophores. The compounds and methods described herein address these needs.

SUMMARY

A new aspect of "click" chemistry—dubbed Sulfonyl Fluoride Exchange (SuFEx)—is described herein. SuFEx is made possible by the interplay between the unique hydrogen-bonding requirements of the fluoride ion and the thermodynamic and kinetic properties of fluoride bonds to sulfur(VI) and silicon centers. Click reactions rarely involve acid-base chemistry, because acid-base reactions generally exhibit low selectivity; however, SuFEx transformations are an exception. The special nature of the fluoride ion makes this possible, requiring guidance by "$H^+$" or "$R_3Si^+$" under strict spatial and kinetic constraints. SuFEx chemistry uses interfacial (aqueous/organic) and homogeneous conditions to advantage. The muted polarity of the $SO_2$ group allows the properties of the molecules built with $SO_2$ linkages to be influenced to a great degree by the motifs being connected. The resulting sulfonyl/sulfate connector toolbox is also powerfully enhanced by another click reaction, the conjugate (Michael) addition of nucleophiles to the special electrophile ethenesulfonyl fluoride (also known as ethylenesulfonyl fluoride).

The compounds described herein are analogs of biologically active materials such as drugs, other therapeutic agents, herbicides, pesticides, antimicrobial agents, veterinary medical agents, and the like, which include at least one —Z—$X^1$—(S)(O)($X^2$)F group, as described below, generally in place of an —OH, —$NH_2$ or —NHR substituent of the drug or therapeutic agent. In some cases, the —Z—$X^1$—(S)(O)($X^2$)F substituent of the analog replaces another group on the drug, therapeutic or other biologically active agent, such as a —$CF_3$, —$OCF_3$, —OMe, —OEt, or halogen (e.g., Cl or Br) substituent, or a hydrogen on a carbon of the drug or therapeutic agent.

In some embodiments, a biologically active compound described herein is represented by Formula (I):

(I)

wherein:
Y is a biologically active organic core group comprising one or more unsubstituted or substituted moiety selected from an aryl group, a heteroaryl aryl group, a nonaromatic hydrocarbyl group, and a nonaromatic heterocyclic group, to which each Z independently is covalently bonded;
n is 1, 2, 3, 4 or 5;
each Z independently is O, NR, or N;

when Z is O, m is 1, $X^1$ is a covalent bond, and the Z is covalently bonded to an aryl or a heteroaryl moiety of Y;

when Z is NR, m is 1, $X^1$ is a covalent bond or $CH_2CH_2$, and the Z is covalently bonded to a nonaromatic hydrocarbyl, a nonaromatic heterocyclic, an aryl, or a heteroaryl moiety of Y;

when Z is N, either (a) m is 2, $X^1$ is $CH_2CH_2$ and the Z is covalently bonded to a nonaromatic hydrocarbyl, a nonaromatic heterocyclic, an aryl, or a heteroaryl moiety of Y; or (b) m is 1, $X^1$ is a covalent bond or $CH_2CH_2$, and the Z is a nitrogen in an aromatic or non-aromatic heterocyclic ring portion of core group Y;

each $X^2$ independently is O or NR; and each R independently comprises H or a substituted or unsubstituted group selected from an aryl group, a heteroaryl aryl group, a nonaromatic hydrocarbyl group, and a nonaromatic heterocyclic group.

Substituents that may be present on the various hydrocarbyl, aryl, heteroaryl, and heterocyclic components of the compounds of Formula (I), include, e.g., one or more substituent selected from the group consisting of a hydrocarbyl moiety (e.g., an alkyl, alkenyl, alkynyl, aryl, alkylaryl, arylalkyl, or any combination of two or more thereof), $—OR^4$, $—N(R^4)_2$, $—N^+(R^4)_3$, $—SR^4$, $—OC(=O)R^4$, $—N(R^4)C(=O)R^4$, $—SC(=O)R^4$, $—OC(=O)OR^5$, $—N(R^4)C(=O)OR^5$, $—SC(=O)OR^5$, $—OC(=O)N(R^4)_2$, $—N(R^4)C(=O)N(R^4)_2$, $—SC(=O)N(R^4)_2$, $—OC(=O)SR^5$, $—N(R^4)C(=O)SR^5$, $—SC(=O)SR^5$, $—C(=O)R^4$, $—C(=O)OR^4$, $—C(=O)N(R^4)_2$, $—C(=O)SR^4$, $—OC(=NR^4)R^4$, $—N(R^4)C(=NR^4)R^4$, $—SO_2R^4$, $—SO_2OR^4$, $—SO_2(NR^4)_2$, $—N(R^4)SO_2OR^5$, $—N(R^4)SO_2N(R^4)_2$, $—OSO_2OR^5$, $—OSO_2N(R^4)_2$, $—P(=O)(OR^4)_2$, $—OP(=O)(OR^4)_2$, $—OP(=O)R^5(OR^4)$, fluoro, chloro, bromo, iodo, $—NO_2$, $—N_3$, $—N=N—Ar^1$, $—CN$, a heteroaryl moiety (including heteroaryl materials comprising a single aromatic ring, or multiple fused aromatic rings in which at least one of the fused rings includes a heteroatom), a nonaromatic heterocyclic moiety, a fused 5-member nonaromatic carbocyclic ring, a fused 5-member heterocyclic ring, a fused 6-member nonaromatic carbocyclic ring, a fused 6-member nonaromatic nitrogen-containing heterocyclic ring, and any combination of two or more thereof. In the foregoing substituents, each $R^4$ independently is H, hydrocarbyl, heteroaryl, or a nonaromatic heterocyclic moiety; each $R^5$ independently is hydrocarbyl, heteroaryl, or a nonaromatic heterocyclic moiety; and each $Ar^1$ independently is aryl or heteroaryl.

Certain compounds of Formula (I) can be prepared by reacting a compound $Y—(ZH)_n$ with a reagent comprising a $—S(O)(X^2)F$ group, such as $SO_2F_2$, $CH_2=CHSO_2F$, and other reactions described in detail herein, including, e.g., conversion of the corresponding chloride containing molecules to the fluoro compounds by nucleophilic displacement of Cl by F (e.g., using a fluoride salt or a bifluoride salt). In some embodiments, $Y—(ZH)_n$ is a known, commercial drug that includes one or more primary or secondary amino substituent and/or aromatic OH substituent, which is reactive toward the reagent. In other embodiments, $Y—(ZH)_n$ is an analog of a known, commercial drug that includes one or more primary or secondary amino substituent and/or aromatic OH substituent, which is reactive toward the reagent, in place of a hydrogen or another substituent, e.g., in place of OMe, $OCF_3$, $CF_3$, halogen, etc.) of a known, commercial drug.

In some embodiments, the compound of Formula (I) can be represented by Formula (II) or Formula (III):

wherein each $X^2$ independently is O or $NR^5$. In preferred embodiments, $X^2$ is O, and the compounds can be represented by Formula (III):

In Formula (II) and Formula (III), A is a biologically active organic core group. In some embodiments, A comprises at least one moiety, $R^1$, and "n" is 1, 2, 3, 4 or 5. In other words, the compounds of Formula (II) include an A group which has therapeutic/medicinal activity, in which one or more —ZH group (i.e., —OH, $—NH_2$, or —NHR) of an $R^1$ moiety of A is substituted by a $[—Z—(X^1—S(O)(X^2)F)_m]_n$ group, generally by reaction with a reagent that will condense with the ZH or otherwise react with the ZH group with elimination of the H therefrom. The compounds of Formula (II) retain the therapeutic activity of the core group A. Each Z independently is O, NR, or N; each Z is covalently bonded to an $R^1$ moiety of A; and each R independently comprises a hydrocarbyl group. When Z is O, m is 1, and each $X^1$ is a covalent bond. When Z is NR, m is 1, and each $X^1$ independently is a covalent bond or $CH_2CH_2$. When Z is N, m is 2, and $X^1$ is $CH_2CH_2$. Each $R^1$ independently is an aryl group, a heteroaryl group, or a substituted aryl group having the formula:

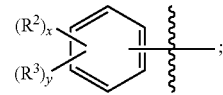

wherein x and y are 0, 1 or 2; and the sum of x and y is at least 1 when $R^1$ is the substituted aryl; and each $R^2$ and $R^3$ independently is a substituent selected from the group consisting of a hydrocarbyl moiety, $—OR^4$, $—N(R^4)_2$, $—N^+(R^4)_3$, $—SR^4$, $—OC(=O)R^4$, $—N(R^4)C(=O)R^4$, $—SC(=O)R^4$, $—OC(=O)OR^5$, $—N(R^4)C(=O)OR^5$, $—SC(=O)OR^5$, $—OC(=O)N(R^4)_2$, $—N(R^4)C(=O)N(R^4)_2$, $—SC(=O)N(R^4)_2$, $—OC(=O)SR^5$, $—N(R^4)C(=O)SR^5$, $—SC(=O)SR^5$, $—C(=O)R^4$, $—C(=O)OR^4$, $—C(=O)N(R^4)_2$, $—C(=O)SR^4$, $—OC(=NR^4)R^4$, $—N(R^4)C(=NR^4)R^4$, $—SO_2R^4$, $—SO_2OR^4$, $—SO_2(NR^4)_2$, $—N(R^4)SO_2OR^5$, $—N(R^4)SO_2N(R^4)_2$, $—OSO_2OR^5$, $—OSO_2N(R^4)_2$, $—P(=O)(OR^4)_2$, $—OP(=O)(OR^4)_2$, $—OP(=O)R^5(OR^4)$, fluoro, chloro, bromo, iodo, $—NO_2$, $—N_3$, $—N=N—Ar^1$, $—CN$, a heteroaryl moiety, a nonaromatic heterocyclic moiety, and any combination of two or more thereof. Alternatively, an $R^2$ and an $R^3$ together form a ring selected from a fused 5-member nonaromatic carbocyclic ring, a fused 5-member heterocyclic ring, a fused 6-member nonaromatic carbocyclic ring, and a fused 6-member nonaromatic nitrogen-containing heterocyclic ring. In the foregoing substituents, each $R^4$ independently is H, hydrocarbyl, heteroaryl, or a nonaromatic heterocyclic moiety; each $R^5$ independently is hydrocarbyl, heteroaryl, or a nonaromatic heterocyclic moiety; and each $Ar^1$ independently is aryl or heteroaryl. In some embodiments, when Z is N, the Z alternatively can be a nitrogen in an aromatic or non-aromatic heterocyclic ring portion of the core group A, in which case, m is 1, and $X^1$ can be a covalent bond or a $—CH_2CH_2—$ group.

In the compounds of Formulas (II) and (III), each $Ar^1$, hydrocarbyl, heteroaryl, nonaromatic heterocyclic moiety, fused 5-member nonaromatic carbocyclic ring, fused 5-member heterocyclic ring, fused 6-member nonaromatic carbocyclic ring, and fused 6-member nonaromatic nitrogen-containing heterocyclic ring independently can be unsubstituted or can be substituted with a group comprising at least one atom other than carbon.

In some embodiments of the compounds of Formula (I) and Formula (II), each $X^2$ is O, each Z independently is O, NR, or N; and at least one Z is O. In some other embodiments of the compounds of Formula (I) and Formula (II), each $X^2$ is O, each Z independently is O, NR, or N; and at least one Z is NR. In yet other embodiments of the compounds of Formula (I) and Formula (II), each $X^2$ is O, each Z independently is O, NR, or N; and at least one Z is N.

In some embodiments of the compounds of Formula (I) and Formula (II), each $X^2$ is O, each $X^1$ is a covalent bond, and each Z is O. In some other embodiments of the compounds of Formula (I) and Formula (II), each $X^2$ is O, each $X^1$ is a covalent bond, and each Z is NR. In yet other embodiments of the compounds of Formula (I) and Formula (II), each $X^2$ is O, each $X^1$ is —$CH_2CH_2$—, and each Z independently is NR or N.

In one embodiment of the compound represented by Formula (III), each m is 1; each Z independently is O or NR; and each $X^1$ is a covalent bond.

In one embodiment of the compound represented by Formula (III), each Z independently is O, NR, or N; at least one Z is O; when Z is O, m is 1, and each $X^1$ is a covalent bond; when Z is NR, m is 1, and each $X^1$ independently is a covalent bond or $CH_2CH_2$; and when Z is N, m is 2, and $X^1$ is $CH_2CH_2$.

In one embodiment of the compound represented by Formula (III), each Z independently is O, NR, or N; at least one Z is NR; when Z is O, m is 1, and $X^1$ is a covalent bond; when Z is NR, m is 1, and each $X^1$ independently is a covalent bond or $CH_2CH_2$; when Z is N, m is 2, and each $X^1$ is $CH_2CH_2$.

In one embodiment of the compound represented by Formula (III), each Z independently is O, NR, or N; at least one Z is N; when Z is O, m is 1, and $X^1$ is a covalent bond; when Z is NR, m is 1, and each $X^1$ independently is a covalent bond or $CH_2CH_2$; and when Z is N, m is 2, and each $X^1$ is $CH_2CH_2$.

In one embodiment of the compound represented by Formula (III), each m is 1; each Z is O; and each $X^1$ is a covalent bond.

In one embodiment of the compound represented by Formula (III), each Z is NR; and each $X^1$ independently is a covalent bond or $CH_2CH_2$.

In one embodiment of the compound represented by Formula (III), each m is 2; each Z is N; and each $X^1$ is $CH_2CH_2$.

In some embodiments of the compounds of Formulas (I), (II) and (III), Y or A comprises, e.g., an antimicrobial agent in which one or more hydrogen on an oxygen, nitrogen or a combination thereof is substituted by [—$X^1$—$SO_2F)_m]_n$; an enzyme inhibitor in which one or more hydrogen on an oxygen, nitrogen or a combination thereof is substituted by [—$X^1$—$SO_2F)_m]_n$; a medicament for treating a non-microbial disease in which one or more hydrogen on an oxygen, nitrogen or a combination thereof is substituted by [—$X^1$—$SO_2F)_m]_n$; or a therapeutic agent that targets a pathogen (e.g., an antibiotic such as vancomycin, rifamycin, rifampicin, teicoplanin, sulfacetamide, amoxicillin, novobiocin, a tetracycline compound, tetracycline, oxytetracycline, methacycline, minocycline, chlorotetracycline, doxycycline, rolitetracycline, demeclocycline, sulfanilamide, sulfamethoxazole, norfloxacin, gatifloxacin, gemifloxacin, an antitubercular compound, isoniazid, rifampicin, streptomycin, ciprofloxacin, moxifloxacin, aminosalicylic acid, and the like; or an protozoal agent such as an anti-malarial agent, quinine, quinocrine, atovaquone, mefloquine, sulfadoxine, hydrochloroquine iodoquinol, paramomycin, and the like).

In some embodiments of the compounds of Formulas (I), (II) and (III), Y or A comprises, a therapeutic agent that targets an active site in a host subject, e.g., a non-steroidal anti-inflammatory agents (NSAIDs) such as naproxen, ibuprofen, aspirin, tolmetin, flurbiprofen, sulindac, piroxicam, nabumeton, flufenamic acid, tolfenamic acid, diclofenac, and the like; antineoplastic agents such as bleomycin, cytarabine, dacarbazine, anthracyclines (e.g., daunorubicin, doxorubicin, and the like), epirubicin, etoposide, flutamide, gemcitabine, idarubicin, leuprolide, leuprorelin, mercaptopurine, methotrexate, mitomycin, mitoxantrone, pemetrexed, pentostatin, procarbazine, suramin, teniposide, thioguanine, thiotepa, uracil mustard (uramastine), and the like; opiates such as morphine, buprenorphine, hydromorphone, oxymorphone, dihydromorphone, methyldihydromorphinone, butorphanol, and the like; analgesics such as pregabalin, tetrahydrocannabinol, fentanyl, flupirtine, oxycodone, acetaminophen, salicylamide, and the like; antidepressants such as fluoxetine (PROZAC), sertraline (ZOLOFT), duloxetine (CYMBALTA), amoxapine, maprotiline, mianserin, nomifensin, trazodine, viloxazine, aripirazole, bupropion (WELLBUTRIN), desvenlafaxine, duloxetine, paroxetine, and the like; COX 2 inhibitors such as celecoxib, rofecoxib, lumiracoxib, etoricoxib, firocoxib, nimesulide, and the like; COX-LOX inhibitors such as licofelone, clonidine, and the like; opioid receptor antagonists such as naltrexone, naloxone, naltrindole, and the like; Alzheimer's disease medications such as epigallocatechin gallate (EGCG), memantine, galantamine, and the like; statins such as atorvstatin (LIPITOR), rosuvastatin, and the like; erectile dysfunction medications such as sildenafil (VIAGRA), tadalafil (CIALIS), vardenafil (LEVITRA), apomorphine, and the like; anti-asthma medications such as salbutamol (albuterol), salmeterol, terbutaline, formoterol, metaproterenol, and the like; cholinesterase inhibitors such as edrophonium, tacrine, and the like; sympathomimetic drugs such as phenylephrine, amphetamine, methoxamine, prenalterol, terbutaline, ritodrine, and the like; anti-seizure agents such as lamotrigine, vigabatrine, gabapentin, pregabalin, and the like; neuromuscular blockers such as tubocurarine, cisatracurium, and the like; intestinal steroid absorption inhibitors such as ezetimibe, (3R,4S)-1,4-bis(4-methoxyphenyl)-3-(3-phenylpropyl)-2-azetidinone, and the like; endocrine drugs such as thyroxine, somatostatin, and the like; estrogenic agents, antagonists and agonists, such as raloxifene, estradiol, ethynylestradiol, diethylstilbesrol, and the like; antiviral agents such as acyclovir, valacyclovir, penciclovir, cidofovir, zalcitibine, adefovir, entacavir, and the like; anorectic agents such as phentermine, and the like; anticoagulants such as warfarin, acenocoumarol, and the like; antihypertives and beta blockers such as lisinopril, nadolol, atenolol, acebutolol, betaxolol, carvediol, esmolol, and the like; seratonin receptor agonists and seratonin uptake inhibitors such as seratonin, sertraline, dolasetron, fluoxetine, and the like; diuretics such as hydrochlorothiazide, bumetanide, furosemide, pinoresinol, and the like; calcium channel blockers such as amlodipine besylate, mibefradin hydrochloride, and the like; as well as female libido enhancing compounds such as flibanserin (1-(2-{4-[3-(Trifluoromethyl)phenyl]piperazin-1-yl}ethyl)-1,3-dihydro-2H-benzimidazol-2-one; Sprout Pharmaceuticals). Other suitable materials include peptide-based and amino acid-based agents, particularly tyrosine, 2,6-dimethyltyrosine, lysine, and peptides comprising one or more residues selected from tyrosine, 2,6-dimethyltyrosine, and lysine such as leuprolide (ENANTONE, a tyrosine-containing peptide pituitary GnRH receptor antagonist), glatiramer (a random copolymer of lysine alanine aspartic acid and tyrosine, tradename CAPDXONE, an immunomodulator). As is well known in the medical art, drugs within in a particular classification (e.g., antibiotic, estrogenic agent, antineoplastic agent, and the like) may have therapeutic uses and indications for more than one type of disease or condition.

In some embodiments, the compounds of Formulas (I), (II) and (III), Y or A are therapeutic agents that exhibit activity toward substantially the same therapeutic target as the pharmaceutically active organic core group, A.

The compounds of Formulas (I), (II) and (III), Y or A that have therapeutic activity can be formulated as a pharmaceutical composition in combination with a pharmaceutically acceptable carrier, vehicle, or diluent.

The present invention also provides methods for preparing the compounds of Formula (II) and Formula (I). In one embodiment, a method of preparing a compound of Formula (II) or Formula (I) comprises reacting a compound of Formula (IV) or (V), respectively, with $SO_2F_2$ in the presence of a base:

   (IV)

   (V)

in which A, Y, m and n are as defined for compounds of Formulas (I) and (II), and Z is O or NR. Examples of suitable bases include (e.g., an alkali metal hydroxide, such as NaOH, KOH and the like), an alkali metal alkoxide (e.g., potassium tert-butoxide, sodium methoxide, and the like), a nitrogen base (preferably a tertiary amine, such as triethylamine or diisopropylethylamine; an amidine such as DBU (1,8-diazabicyclo[5.5.0]undec-7-ene, and the like); a guanidine such as tetramethylguanidine, and the like), and the like.

In another embodiment, a method of preparing a compound of Formula (II) or Formula (I) in which each m is 2, each Z is N, and each $X^1$ is $CH_2CH_2$, comprises reacting a compound of Formula (IV) or (V), respectively, with $CH_2=CH-SO_2F$ ("ESF"), which readily condenses with amino compounds comprising at least one N—H bond.

The compounds of Formula (I) and Formula (II), including the compounds of Formula (III), have a number of useful and surprising characteristics. In many embodiments, the compounds have therapeutic activity toward substantially the same therapeutic target as the corresponding compound comprising the core group Y or A, but with one or more useful additional properties of characteristics, such as enhanced solubility, enhanced bioavailability, ability to covalently link with a target group in a subject or pathogen, a lower water/octanol partition coefficient (LogP) than the parent compound (particularly when —$OSO_2F$ replaces a —$OCF_3$ group in the parent therapeutic compound), and providing a handle for selectively attaching the compound of Formula (II) to a useful group such as a dye (e.g., a fluorescent dye), biotin, a polymer (e.g., a polystyrene resin or other conventional polymer, as well as polymers described in commonly owned copending PCT Application Serial No. PCT/US2013/072871, which is incorporated herein by reference in its entirety) by displacement of F. The —$OSO_2F$ group, can be considered as a bioisostere for —$OCF_3$, making the —$OSO_2F$ group an attractive replacement for —$OCF_3$, particularly if a lower LogP is desired.

In addition to biological activity, per se, Ar—$OSO_2F$ groups provide an effective protecting group or precursor for ArOH and $ArOSO_3^-$ compounds. The $SO_2F$ moiety, in the various forms described herein also provides a handle for covalent attachment of organic compounds to substrates that bear a phenolic OH group, an amino group, and the like, e.g., attachment to a surface, such as a modified polystyrene bead or a glass surface, or attachment to another molecule, such as a protein (e.g., via a nucleophilic side chain of an amino acid residue in the active site of a protein). The —$OSO_2F$ group also can be useful as a leaving group in nucleophilic aromatic substitution reactions, or other displacement or coupling reactions in place of, e.g., a halogen group, a triflate, a mesylate, or other leaving group. In addition, the biologically active $SO_2F$ compounds described herein can be utilized as screening agents to identify drug targets, e.g., by covalent binding to the active site for the drugs.

The following non-limiting listing illustrates various embodiments of the compounds, compositions, methods and uses described herein:

Embodiment 1 is a compound represented by Formula (I):

   (I)

wherein:

Y is a biologically active organic core group comprising one or more unsubstituted or substituted moiety selected from an aryl group, a heteroaryl aryl group, a nonaromatic hydrocarbyl group, and a nonaromatic heterocyclic group, to which each Z independently is covalently bonded;

n is 1, 2, 3, 4 or 5;

each Z independently is O, NR, or N;

when Z is O, m is 1, $X^1$ is a covalent bond, and the Z is covalently bonded to an aryl or heteroaryl moiety of Y;

when Z is NR, m is 1, $X^1$ is a covalent bond or $CH_2CH_2$, and the Z is covalently bonded to a nonaromatic hydrocarbyl, a nonaromatic heterocyclic, an aryl, or heteroaryl moiety of Y;

when Z is N, either (a) m is 2, $X^1$ is $CH_2CH_2$ and the Z is covalently bonded to a nonaromatic hydrocarbyl, a nonaromatic heterocyclic, an aryl, or a heteroaryl moiety of Y; or (b) m is 1, $X^1$ is a covalent bond or $CH_2CH_2$, and the Z is a nitrogen in an aromatic or non-aromatic heterocyclic ring portion of core group Y;

each $X^2$ independently is O or NR; and each R independently comprises H or a substituted or unsubstituted group selected from an aryl group, a heteroaryl aryl group, a nonaromatic hydrocarbyl group, and a nonaromatic heterocyclic group.

Embodiment 2 is a compound of Embodiment 1, wherein each $X^2$ is O, each Z independently is O, NR, or N; and at least one Z is O.

Embodiment 3 is a compound of Embodiment 1, wherein, each $X^2$ is O, each Z independently is O, NR, or N; and at least one Z is NR.

Embodiment 4 is a compound of Embodiment 1, wherein, each $X^2$ is O, each Z independently is O, NR, or N; and at least one Z is N.

Embodiment 6 is a compound of Embodiment 1, wherein, each $X^2$ is O, each $X^1$ is a covalent bond, and each Z is NR.

Embodiment 7 is a compound of Embodiment 1, wherein, each $X^2$ is O, each $X^1$ is —$CH_2CH_2$—, and each Z independently is NR or N.

Embodiment 8 is a compound of any one of Embodiments 1 to 7, wherein at least one Z is covalently bonded to a heteroaryl moiety of Y.

Embodiment 9 is a compound of any one of Embodiments 1 to 8, wherein at least one Z is covalently bonded to an aryl moiety of Y.

Embodiment 10 is a compound of any one of Embodiments 1 to 9, wherein at least one Z is covalently bonded to a non-aromatic carbon of Y.

Embodiment 11 is a compound of any one of Embodiments 1 to 10, wherein one or more of the aryl, heteroaryl aryl, nonaromatic hydrocarbyl, or nonaromatic heterocyclic portions of the compounds of Formula (I), include one or more substituent selected from a hydrocarbyl moiety, —OR⁴, —N(R⁴)₂, —N⁺(R⁴)₃, —SR⁴, —OC(=O)R⁴, —N(R⁴)C(=O)R⁴, —SC(=O)R⁴, —OC(=O)OR⁵, —N(R⁴)C(=O)OR⁵, —SC(=O)OR⁵, —OC(=O)N(R⁴)₂, —N(R⁴)C(=O)N(R⁴)₂, —SC(=O)N(R⁴)₂, —OC(=O)SR⁵, —N(R⁴)C(=O)SR⁵, —SC(=O)SR⁵, —C(=O)R⁴, —C(=O)OR⁴, —C(=O)N(R⁴)₂, —C(=O)SR⁴, —OC(=NR⁴)R⁴, —N(R⁴)C(=NR⁴)R⁴, —SO₂R⁴, —SO₂OR⁴, —SO₂(NR⁴)₂, —N(R⁴)SO₂OR⁵, —N(R⁴)SO₂N(R⁴)₂, —OSO₂OR⁵, —OSO₂N(R⁴)₂, —P(=O)(OR⁴)₂, —OP(=O)(OR⁴)₂, —OP(=O)R⁵(OR⁴), fluoro, chloro, bromo, iodo, —NO₂, —N₃, —N=N—Ar¹, —CN, a heteroaryl moiety (including heteroaryl materials comprising a single aromatic ring, or multiple fused aromatic rings in which at least one of the fused rings include a heteroatom), a non-aromatic heterocyclic moiety, a fused 5-member nonaromatic carbocyclic ring, a fused 5-member heterocyclic ring, a fused 6-member nonaromatic carbocyclic ring, a fused 6-member nonaromatic nitrogen-containing heterocyclic ring, and any combination of two or more thereof; each R⁴ independently is H, hydrocarbyl, heteroaryl, or a nonaromatic heterocyclic moiety; each R⁵ independently is hydrocarbyl, heteroaryl, or a nonaromatic heterocyclic moiety; and each Ar¹ independently is aryl or heteroaryl.

Embodiment 12 is a compound of any one of Embodiments 1 to 11, wherein the compound is an estrogenic steroid that includes at least one —Z—X¹—(S)(O)(X²)F group. As used herein, "estrogenic steroid" refers to steroids in which the "A-ring" of the archetypical tetracyclic steroid structure is aromatic, e.g., as illustrated below:

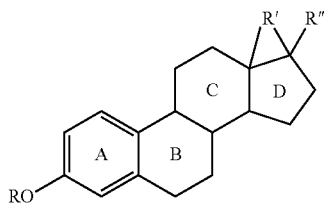

in which R generally is H or alkyl, R' typically is OH, and R" typically is H or ethynyl, and which can be substituted on any of the A, B, C, or D rings thereof or on R by one or more substituent such as described herein with respect to embodiment 11, above, and the —Z—X¹—(S)(O)(X²)F group can be present on any of the A, B, C, or D rings, on R, R' R" or another substituent thereof, in place of OR, R' or R". Non-limiting examples of such estrogenic steroids include, e.g., estradiol, estrone, estriol, ethynylestradiol, and the like.

Embodiment 13 is a compound of any one of Embodiments 1 to 11, wherein the compound is a corticosteroid that includes at least one —Z—X¹—(S)(O)(X²)F group. As used herein, "corticosteroid" refers to steroids having the archetypical corticosteroid structure illustrated below:

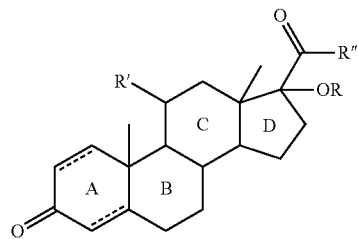

in which R typically is H, R' generally is OH or oxo (=O), and R" typically is —CH₂OH, and which can be substituted on any of the A, B, C, or D rings thereof or on R, R' or R", by one or more substituent such as described herein with respect to embodiment 11, above, and the —Z—X¹—(S)(O)(X²)F group can be present on any of the A, B, C, or D rings, on another substituent attached to one of the rings, on an R, R' or R" group, or in place of an R, R' or R" group, (e.g., attached to an aryl or heteroaryl substituent when Z is O). Non-limiting examples of such corticosteroids include, e.g., cortisone, hydrocortisone, prednisone, prednisolone, triamcinolone, methyl prednisolone, prednylidene, fluocortilone, parametasone, dexamethasone, betamethasone, and the like.

Embodiment 14 is a compound of any one of Embodiments 1 to 11, wherein the compound is an amphetamine compound that includes at least one —Z—X¹—(S)(O)(X²)F group. As used herein, "amphetamine compound" refers to compounds which include the archetypal amphetamine core substructure:

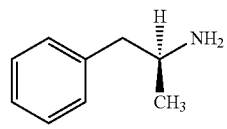

and which can be substituted on any portion thereof by one or more substituent such described herein with respect to Embodiment 11, above, and the —Z—X¹—(S)(O)(X²)F group can be present on any portion of the amphetamine core or can be covalently attached to another substituent on the amphetamine core. Non-limiting examples of such amphetamine compounds include, e.g., psychostimulants such as amphetamine, metamphetamine, amfetaminil, fenetylline, methylphenidate, prolintane; and anorectics such as cathine (norpseudoephedrine), amfepramone, mefanorex, fenfluramine, and the like.

Embodiment 15 is a compound of any one of Embodiments 1 to 11, wherein the compound is benzodiazepine compound that includes at least one —Z—X¹—(S)(O)(X²)F group. As used herein, "benzodiazepine compound" refers to compounds which include the archetypal benzodiazepine core substructure:

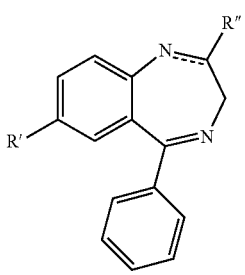

in which R' typically is a halogen or nitro group, R" typically is an oxo (=O) or NR group, and which can be substituted on any portion thereof by one or more substituent such as described herein with respect to Embodiment 11, above, and the —Z—$X^1$—(S)(O)($X^2$)F group can be present on any portion of the benzodiazepine core or can be covalently attached to another substituent on the benzodiazepine core, or in place of R' or R". Non-limiting examples of such benzodiazepine compounds include, e.g., chlorodiazepine, demoxepam, chlordiazepoxide, diazapam, prazepam, oxazepam, dipotassoim chlorazepate, lorazepam, clonazepam, bromazepam, clobazam, temazepam, flurazepam, lormetazepam, nitrazepam, and the like.

Embodiment 16 is a compound of any one of Embodiments 1 to 11, wherein the compound is a barbiturate compound that includes at least one —Z—$X^1$—(S)(O)($X^2$)F group. As used herein, "barbiturate compound" refers to compounds which include the archetypal barbiturate core substructure:

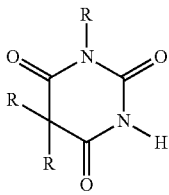

in which the R groups can be substituent such as described in Embodiment 11, above, and the —Z—$X^1$—(S)(O)($X^2$)F group can be present on any portion of the benzodiazepine core or can be covalently attached to another substituent on the amphetamine core, or in place of an R group. Non-limiting examples of such barbiturate compounds include, e.g., such as vinylbital, aprobarbital, secbutabarbital, pentobarbital, cyclobarbital, phenobarbital, and the like.

Embodiment 17 is a compound of any one of Embodiments 1 to 11, wherein the compound is a morphine derivative that includes at least one —Z—$X^1$—(S)(O)($X^2$)F group. As used herein, "morphine derivative" refers to compounds which include the archetypal morphine core substructure:

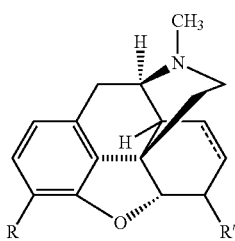

in which R typically is hydroxyl or alkoxy, R' typically is OH or oxo, and the compound can be substituted by a substituent such described in Embodiment 11 on any portion of the core structure or on included on or in place of R or R', and, and the —Z—$X^1$—(S)(O)($X^2$)F group can be present on any portion of the morphine core or can be covalently attached to another substituent on the morphine core or in place of R or R'. Non-limiting examples of such morphine derivatives include, e.g., morphine, codeine, diamorphine, dihydrocodeine, hydromorphone, hydrocodone, oxycodone, oxymorphone, levorphanol, and the like.

Embodiment 18 is a compound of any one of Embodiments 1 to 11, wherein the compound is penam antibiotic that includes at least one —Z—$X^1$—(S)(O)($X^2$)F group. As used herein, "penam antibiotic" refers to an antibiotic comprising the archetypical penam core structure:

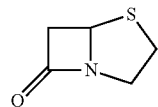

and which can be substituted on any portion thereof by one or more substituent such described herein with respect to Embodiment 11, above, and the —Z—$X^1$—(S)(O)($X^2$)F group can be present on any portion of the penam core or can be covalently attached to another substituent on the penam core. Non-limiting examples of such penam antibiotics include, e.g., penicillin, benzylpenicillin (penicillin G), phenoxymethylpenicillin (penicillin V), oxacillin, dicloxacilin, flucloxacillin, ampicillin, amoxicillin, epicillin, azlocillin, mezlocillin, piperacillin, apalcillin, carbenicillin, ticarcillin, temocillin, and the like.

Embodiment 19 is a compound of any one of Embodiments 1 to 11, wherein the compound is a cephem antibiotic that includes at least one —Z—$X^1$—(S)(O)($X^2$)F group. As used herein, "cephem antibiotic" refers to an antibiotic comprising the archetypical cephem core structure:

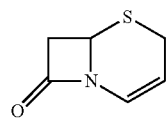

and which can be substituted on any portion thereof by one or more substituent such described herein with respect to Embodiment 11, above, and the —Z—$X^1$—(S)(O)($X^2$)F group can be present on any portion of the cephem core or can be covalently attached to another substituent on the cephem core. Non-limiting examples of such cephem antibiotics include, e.g., cephalosporin, cefalotin, cefazolin, cefazedone, cefamandole, cefuroxime, cefotiam, cefotaxime, ceftizoxime, ceftriaxone, ceftazidime, cefoperazone, cefixime, cefmetazole, cefonicid, cefapirin, ceforanide, cefalexin, cefaclor, cefradine, cefadroxil, and the like.

Embodiment 20 is a compound of any one of Embodiments 1 to 11, wherein the compound is a carbapenem antibiotic that includes at least one —Z—$X^1$—(S)(O)($X^2$)F group. As used herein, "carbapenem antibiotic" refers to an antibiotic comprising the archetypical carbapenem core structure:

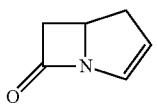

and which can be substituted on any portion thereof by one or more substituent such described herein with respect to embodiment 11, above, and the —Z—X$^1$—(S)(O)(X$^2$)F group can be present on any portion of the carbopenem core or can be covalently attached to another substituent on the carbapenem core. Non-limiting examples of such carbapenem antibiotics include, e.g., thienamycin, imipenem, meropenem, ertapenem, doripenem, biapenem, razupenem, tebipenem, lenapenem, and tomopenem.

Embodiment 21 is a compound of any one of Embodiments 1 to 11, wherein the compound is a tetracycline antibiotic that includes at least one —Z—X$^1$—(S)(O)(X$^2$)F group. As used herein, "tetracycline antibiotic" refers to an antibiotic comprising the archetypical tetracycline core structure:

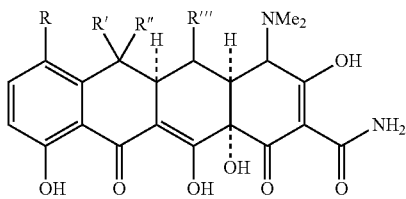

in which R typically is a hydrogen, halogen (e.g., Cl), dialkylamino (e.g., dimethylamino), R' and R'' typically are hydrogen, hydroxyl or methyl, R''' typically is hydrogen or hydroxyl, and which can be substituted on any portion thereof by one or more substituent such as described herein with respect to Embodiment 11, above, and the —Z—X$^1$—(S)(O)(X$^2$)F group can be present on any portion of the tetracycline core or can be covalently attached to another substituent on the tetracycline core, or in place of R, R', R'' or R'''. Non-limiting examples of such tetracycline antibiotic compounds include, e.g., tetracycline, oxytetracycline, demiclocycline, doxycycline, minocycline, and rolitetracycline.

Embodiment 22 is a compound of any one of Embodiments 1 to 11, wherein the compound is a quinolone antibiotic that includes at least one —Z—X$^1$—(S)(O)(X$^2$)F group. As used herein, "quinolone antibiotic" refers to an antibiotic comprising the archetypical quinolone core structure:

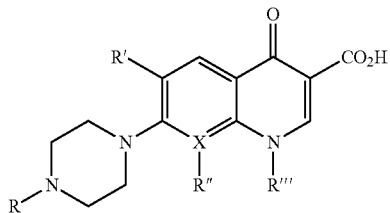

in which X typically is C or N, R typically is a hydrogen or methyl, R' typically is hydrogen or F, and R'' typically is hydrogen when X is C and absent when X is N, R''' typically is alkyl (e.g., ethyl) or cycloalkyl (e.g., cyclopropyl), and which can be substituted on any portion thereof by one or more substituent such as described herein with respect to Embodiment 11, above, and the —Z—X$^1$—(S)(O)(X$^2$)F group can be present on any portion of the quinolone core or can be covalently attached to another substituent on the quinolone core, or in place of R, R', R'' or R'''. Non-limiting examples of such quinolone antibiotic compounds include, e.g., norfloxacine, ciprofloxacin, and enoxacine.

Embodiment 23 is a compound of any one of Embodiments 1 to 11, wherein the compound is macrolide antibiotic that includes at least one —Z—X$^1$—(S)(O)(X$^2$)F group. As used herein, "macrolide antibiotic" refers to an antibiotic having a macrocyclic lactone core structure. In some embodiments the macrolide antibiotic has an archetypal erythromycin-type core structure:

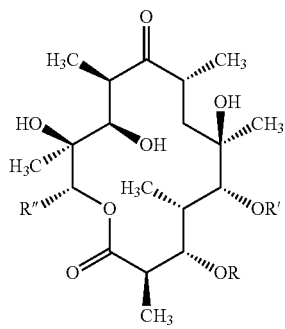

in which R typically is a glycoside (sugar) group, R' is an aminoglycoside (amino sugar) group, and R''' typically is ethyl. The macrolide antibiotics can be substituted on any portion thereof by one or more substituent such as described herein with respect to Embodiment 11, above, and the —Z—X$^1$—(S)(O)(X$^2$)F group can be present on any portion of the macrolide core or can be covalently attached to another substituent on the macrolide core. Non-limiting examples of such macrolide antibiotic compounds include, e.g., azithromycin, clarithromycin, erythromycin, fidaxomicin, telithromycin, carbomycin a, josamycin, kitasamycin, oleandomycin, solithromycin, spiramycin, roleandomycin, and the like.

Embodiment 24 is a compound of any one of Embodiments 1 to 11, wherein the compound is an aminoglycoside antibiotic that includes at least one —Z—X$^1$—(S)(O)(X$^2$)F group. As used herein, "aminoglycoside antibiotic" refers to an oligosaccharide (typically a trisaccharide or tetrasaccharide) antibiotic comprising at least one amino sugar component (e.g., streptamine or 2-desoxystreptamine) in the oligosaccharide chain thereof. The aminoglycoside antibiotics can be substituted on any portion thereof by one or more substituent such as described herein with respect to Embodiment 11, above, and the —Z—X$^1$—(S)(O)(X$^2$)F group can be present on any portion of the aminoglycoside core or can be covalently attached to another substituent on the aminoglycoside core. Non-limiting examples of such aminoglycoside antibiotics, include, e.g., streptomycin, neomycin B, gentamicin, kanamycin, and the like.

Embodiment 25 is a compound of any one of Embodiments 1 to 11, wherein the compound is a transthyretin (TTR) binding compound represented by Formula (VI) or Formula (VIa):

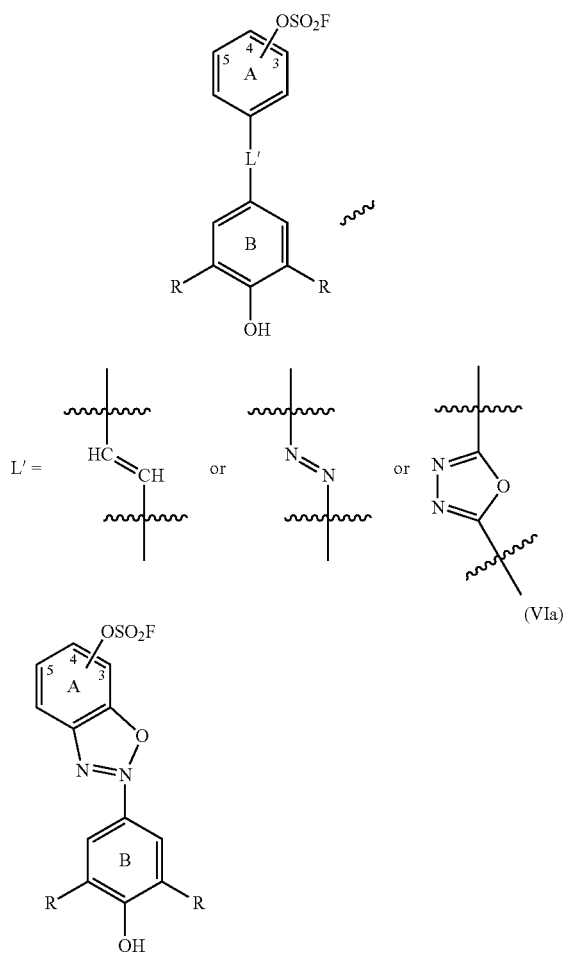

in which each R is alkyl (e.g., methyl, ethyl, propyl) or halogen (e.g., Cl, Br), L' is as shown (i.e., trans vinyl, diazo, or 1O,3N,4N-oxadiazol-2,5-diyl, and the —OSO2F group in each formula can be bonded to the 3, 4, or 5 position on the "A" ring of the compound. Some of the compounds of Formula (VI) and (VIa) can irreversibly bind to the TTR binding site, stabilizing the TTR protein tertiary structure.

Embodiment 26 is a compound of any one of Embodiments 1 to 11, wherein the compound is an analog of a biologically active material selected from an antimicrobial agent, an enzyme inhibitor, a medicinal agent having activity for treating a non-microbial disease, a medicinal agent targets a pathogen, an antibiotic, an anti-protozoal agent, and a therapeutic agent that targets an active site in a host subject; which analog includes at least one —Z—X$^1$—(S)(O)(X$^2$)F group.

Embodiment 27 is a compound of Embodiment 26, wherein the antibiotic is selected from vancomycin, rifamycin, rifampicin, teicoplanin, sulfacetamide, amoxicillin, novobiocin, a tetracycline compound, tetracycline, oxytetracycline, methacycline, minocycline, chlorotetracycline, doxycycline, rolitetracycline, demeclocycline, sulfanilamide, sulfamethoxazole, norfloxacin, gatifloxacin, gemifloxacin, trimethoprim, pyrimethamine, cefadroxil, an antitubercular compound, isoniazid, rifampicin; streptomycin, ciprofloxacin, moxifloxacin, and aminosalicylic acid.

Embodiment 28 is a compound of Embodiment 26, wherein the anti-protozoal agent is an anti-malarial agent selected from quinine, quinocrine, atovaquone, mefloquine, sulfadoxine, hydrochloroquine iodoquinol, and paramomycin.

Embodiment 29 is a compound of Embodiment 26, wherein the therapeutic agent that targets an active site in a host subject comprises a non-steroidal anti-inflammatory agent (NSAID) selected from naproxen, ibuprofen, aspirin, tolmetin, flurbiprofen, sulindac, piroxicam, nabumeton, flufenamic acid, tolfenamic acid, and diclofenac.

Embodiment 30 is a compound of Embodiment 26, wherein the therapeutic agent that targets an active site in a host subject comprises an antineoplastic agent selected from bleomycin, cytarabine, dacarbazine, an anthracycline, daunorubicin, doxorubicin, epirubicin, etoposide, flutamide, gemcitabine, idarubicin, leuprolide, mercaptopurine, methotrexate, mitomycin, mitoxantrone, pemetrexed, pentostatin, procarbazine, suramin, teniposide, thioguanine, thiotepa, and uracil mustard (uramastine).

Embodiment 31 is a compound of Embodiment 26, wherein the therapeutic agent that targets an active site in a host subject comprises an opiate selected from buprenorphine, hydromorphone, oxymorphone, dihydromorphone, and methyldihydromorphinone.

Embodiment 32 is a compound of Embodiment 26, wherein the therapeutic agent that targets an active site in a host subject comprises an analgesic selected from pregabalin, tetrahydrocannabinol, fentanyl, flupirtine, oxycodone, acetaminophen, and salicylamide.

Embodiment 33 is a compound of Embodiment 26, wherein the therapeutic agent that targets an active site in a host subject comprises an anti-depressant selected from fluoxetine, sertraline, duloxetine, amoxapine, maprotiline, mianserin, nomifensin, trazodine, viloxazine, aripirazole, bupropion, desvenlafaxine, duloxetine, and paroxetine.

Embodiment 34 is a compound of Embodiment 26, wherein the therapeutic agent that targets an active site in a host subject comprises a COX 2 inhibitor selected from celecoxib, rofecoxib, lumiracoxib, etoricoxib, firocoxib, and nimesulide.

Embodiment 35 is a compound of Embodiment 26, wherein the therapeutic agent that targets an active site in a host subject comprises a COX-LOX inhibitor selected from licofelone, and clonidine.

Embodiment 36 is a compound of Embodiment 26, wherein the therapeutic agent that targets an active site in a host subject comprises a opioid receptor antagonist selected from naltrexone, naloxone, and naltrindole.

Embodiment 37 is a compound of Embodiment 26, wherein the therapeutic agent that targets an active site in a host subject comprises an Alzheimer's disease medication selected from epigallocatechin gallate (EGCG), memantine, and galantamine.

Embodiment 38 is a compound of Embodiment 26, wherein the therapeutic agent that targets an active site in a host subject comprises a statin selected from atorvastatin and rosuvastatin.

Embodiment 39 is a compound of Embodiment 26, wherein the therapeutic agent that targets an active site in a host subject comprises an erectile dysfunction medication selected from sildenafil, tadalafil, vardenafil, and apomorphine.

Embodiment 40 is a compound of Embodiment 26, wherein the therapeutic agent that targets an active site in a host subject comprises an anti-asthma medication selected from salbutamol, salmeterol, terbutaline, formoterol, and metaproterenol.

Embodiment 41 is a compound of Embodiment 26, wherein the therapeutic agent that targets an active site in a host subject comprises a cholinesterase inhibitor selected from edrophonium and tacrine.

Embodiment 42 is a compound of Embodiment 26, wherein the therapeutic agent that targets an active site in a host subject comprises a sympathomimetic drug selected from phenylephrine, amphetamine, methoxamine, prenalterol, terbutaline, and ritodrine.

Embodiment 43 is a compound of Embodiment 26, wherein the therapeutic agent that targets an active site in a host subject comprises an anti-seizure agent selected from lamotrigine and vigabatrine.

Embodiment 44 is a compound of Embodiment 26, wherein the therapeutic agent that targets an active site in a host subject comprises a neuromuscular blocker selected from tubocurarine and cisatracurium.

Embodiment 45 is a compound of Embodiment 26, wherein the therapeutic agent that targets an active site in a host subject comprises an intestinal steroid absorption inhibitor selected from ezetimibe and (3R,4S)-1,4-bis(4-methoxyphenyl)-3-(3-phenylpropyl)-2-azetidinone.

Embodiment 46 is a compound of Embodiment 26, wherein the therapeutic agent that targets an active site in a host subject comprises an endocrine drug selected from thyroxine and somatostatin.

Embodiment 47 is a compound of Embodiment 26, wherein the therapeutic agent that targets an active site in a host subject comprises an estrogenic agent, agonist or antagonist selected from raloxifene, estradiol, ethynylestradiol, and diethylstilbestrol.

Embodiment 48 is a compound of Embodiment 26, wherein the therapeutic agent that targets an active site in a host subject comprises an anti-viral agent selected from acyclovir, valacyclovir, penciclovir, cidofovir, zalcitibine, adefovir, and entacavir.

Embodiment 49 is a compound of Embodiment 26, wherein the therapeutic agent that targets an active site in a host subject comprises a seratonin receptor agonist selected from dolasetron and seratonin.

Embodiment 50 is a compound of any one of Embodiments 1 to 11, wherein the compound is an analog of tyrosine, 2,6-dimethyltyrosine, or a peptide comprising one or more residues selected from tyrosine and 2,6-dimethyltyrosine, in which the phenolic OH of the tyrosine or 2,6-dimethyltyrosine is substituted by —OSO$_2$F.

Embodiment 51 is a compound of Embodiment 50, wherein the compound is O-fluorosulfonyltyrosine or O-fluorosulfonyl-2,6-dimethyltyrosine.

Embodiment 52 is a compound of Embodiment 50, wherein the peptide is selected from leuprolide and glatiramer, and is modified to include a —OSO$_2$F group in place of the phenolic OH of a tyrosine residue thereof.

Embodiment 53 is a compound of any one of Embodiments 1 to 11, wherein the compound comprises an analog of amino acid comprising a nucleophilic side chain or a peptide comprising one or more amino acid residue comprising a nucleophilic side chain, which includes an SO$_2$F or —CH$_2$CH$_2$SO$_2$F group in place of a hydrogen on a hydroxyl or amino substituent of the nucleophilic side chain.

Embodiment 54 is a compound of Embodiment 53, wherein the amino acid is selected from lysine, serine, tyrosine, histidine, and arginine.

Embodiment 55 is a compound of Embodiment 53, wherein the compound is a peptide comprising the amino acid residue selected from the group consisting of lysine, serine, tyrosine, histidine, and arginine, which includes an SO$_2$F or —CH$_2$CH$_2$SO$_2$F group in place of a hydrogen on a hydroxyl or amino substituent of the nucleophilic side chain.

Embodiment 56 is a compound of any one of Embodiments 1 to 55, wherein the compound of Formula (I) has biological activity toward substantially the same target as the biologically active core group Y.

Embodiment 57 is a compound of any one of Embodiments 1 to 56, wherein the fluorine (F) of one or more of the —Z—X$^1$—(S)(O)(X$^2$)F groups thereof is enriched in $^{18}$F.

Embodiment 58 is a pharmaceutical composition comprising a compound of any one of Embodiments 1 to 57, and a pharmaceutically acceptable carrier, vehicle, or diluent.

Embodiment 59 is a method of preparing a compound of Embodiment 1, in which at least one Z thereof is O; the method comprising reacting a precursor bearing an aromatic and/or heteroaromatic OH substituent with SO$_2$F$_2$ in the presence of a base to replace the hydrogen of the aromatic and/or heteroaromatic OH with SO$_2$F.

Embodiment 60 is a method of preparing a compound of Embodiments 1, in which at least one Z thereof is NR; the method comprising reacting a precursor bearing an NHR substituent with SO$_2$F$_2$ in the presence of a base to replace the hydrogen of the NHR with SO$_2$F.

Embodiment 61 is a method of preparing a compound of Embodiments 1, in which at least one Z thereof is N or NR; the method comprising reacting a precursor bearing an NH$_2$ or NHR substituent with CH$_2$=CH—SO$_2$F by a Michael addition to replace the hydrogens of the NH$_2$ or the hydrogen of the NHR with —CH$_2$CH$_2$—SO$_2$F.

Embodiment 62 is a compound of any one of Embodiments 1 to 57 for treating a disease or condition.

Embodiment 63 is the use of a compound of any one of Embodiments 1 to 57, for treating a disease or condition.

Embodiment 64 is the use of a compound of any one of Embodiments 1 to 57, for the preparation of a medicament for treating a disease or condition.

Embodiment 65 is the use of a library comprising a plurality of the compounds of any one of Embodiments 1 to 57 in a screening assay against a biologically active receptor protein.

Embodiment 66 is a method for preparing a compound of Embodiment 57, comprising treating a compound of any one of Embodiments 1 to 56 with bifluoride ion enriched in $^{18}$F to replace at least a portion of $^{19}$F in the compound with $^{18}$F.

Embodiment 67 is an-amino protected O-fluorosulfonyl-L-tyrosine of formula:

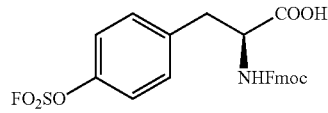

wherein "Fmoc" represents a 9-fluorenylmethyloxycarbonyl protecting group.

Embodiment 68 is the use of a compound of Embodiment 67 for the preparation of a peptide or protein comprising an O-fluorosulfonyl-L-tyrosine residue.

Embodiment 69 is a peptide or protein comprising an O-fluorosulfonyl-L-tyrosine residue.

Embodiment 70 is a polypeptide of Embodiment 69, wherein the polypeptide is selected from an anolog of oxytocin, indolicin, thymopentin, and arginine vassopressin, in which the tyrosine residue thereof is replaced by an O-fluorosulfonyl-L-tyrosine residue.

Embodiment 71 is the use of a compound of Embodiment 57 as an imaging agent for positron emission tomography.

Embodiment 72 is the use of a compound of any one of Embodiments 1 to 57 or a peptide or protein of Embodiment 69 for covalently binding of the compound to an active site in a receptor molecule.

Embodiment 73 is a method of preparing a sulfated polypeptide comprising contacting the peptide of Embodiment 69 with cesium carbonate and a solution of ammonia in methanol to selectively hydrolyze the fluoro group of a fluorosulfonyl-L-tyrosine residue thereof and form a sulfated tyrosine residue therefrom.

DETAILED DESCRIPTION

Figure 1:
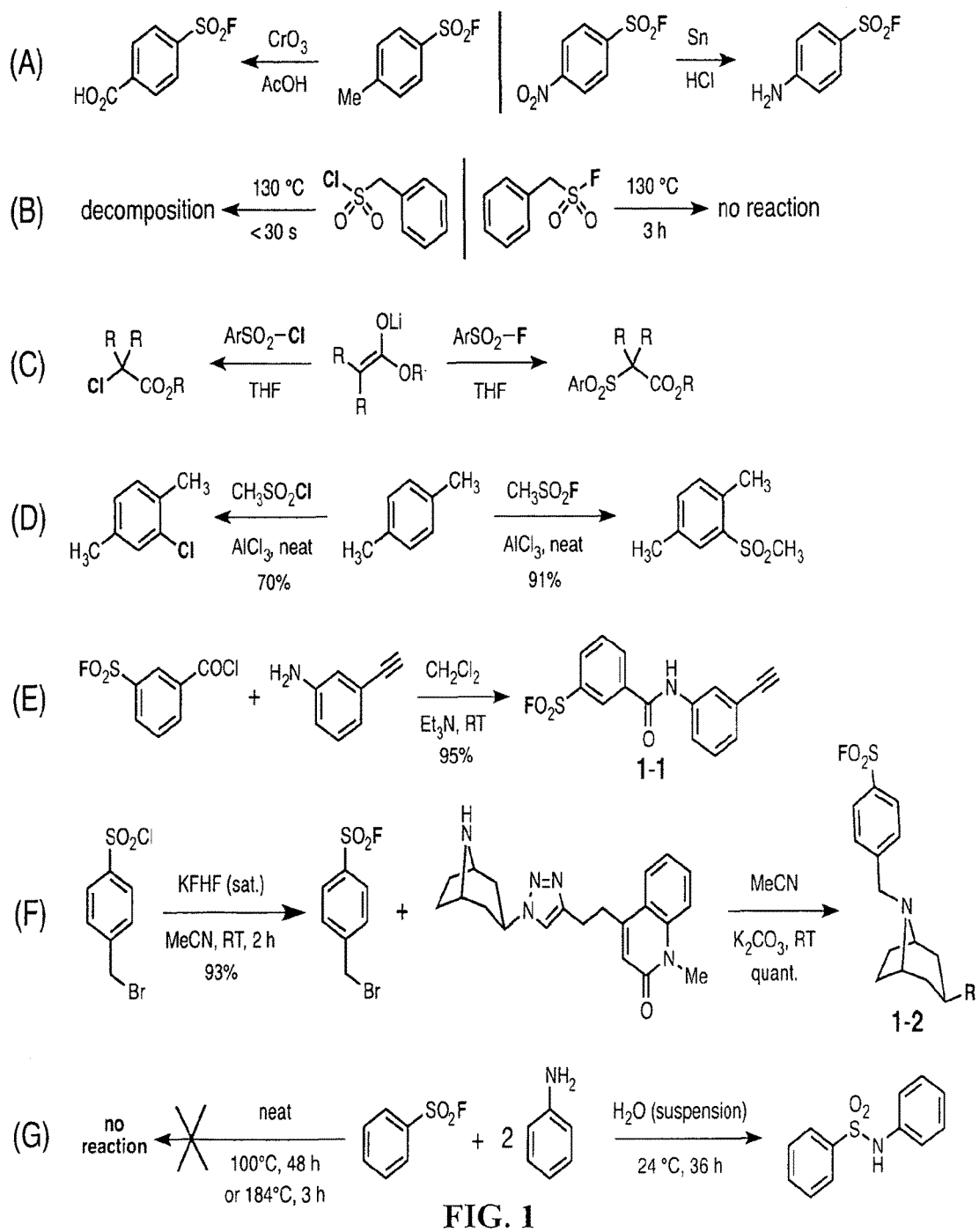
FIG. 1 shows reactions illustrating the properties of sulfonyl fluorides vs. other sulfonyl halides. (A) resistance of $ArSO_2F$ toward both oxidation and reduction; (B) greater stability of sulfonyl fluoride toward thermolysis; (C, D) chlorination vs. desired sulfonylation in reactions with ester enolates and under Friedel-Crafts conditions; (E, F) greater reactivity of acyl chloride and benzylic bromide compared to sulfonyl fluoride under non-activating conditions; (G) the power of water in activating sulfonyl fluoride reactivity.

The term "alkyl" as used herein denotes saturated hydrocarbon moieties. Preferably, an alkyl group comprises 1 to 20 carbon atoms in the principal chain (e.g., 1 to 12 carbon atoms) and e.g., up to 30 total carbon atoms. These moieties may be straight or branched chain and include methyl, ethyl, propyl, isopropyl, butyl, hexyl, octyl, and the like groups.

The term "alkenyl" as used herein denotes a univalent hydrocarbon group containing a double bond. Preferably, alkenyl groups comprise 2 to 20 carbon atoms (e.g., 2 to 12 carbon atoms) in the principal chain, and up to 30 total carbon atoms. The alkenyl groups may be straight or branched chain, or cyclic, and include ethenyl, propenyl, isopropenyl, butenyl, isobutenyl, hexenyl, octenyl, oleyl, and the like.

The term "alkynyl" as used herein denotes a univalent hydrocarbon group containing a triple bond. Preferably, alkynyl groups comprise 2 to 20 carbon atoms (e.g., 2 to 12 carbon atoms) in the principal chain, and up to 30 total carbon atoms. The alkynyl groups may be straight or branched chain, and include ethynyl, propynyl, butynyl, isobutynyl, hexynyl, octynyl, and the like.

The term "aromatic" as used herein denotes chemical compounds or groups that contain conjugated planar ring systems with delocalized pi electron clouds instead of discrete alternating single and double bonds. The term "aromatic" encompasses the "aryl" and "heteroaryl" groups defined below.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, anthracenyl, substituted phenyl, substituted biphenyl or substituted naphthyl.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or groups consisting exclusively of the elements carbon and hydrogen. These moieties include alkyl, alkenyl, alkynyl, aryl, carbocyclic moieties, and any combination of two or more thereof. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 total carbon atoms.

As used herein, the term "organic" and grammatical variations thereof, in reference to a group or moiety, refers to a material comprising carbon, typically in combination with at least some hydrogen, and optionally including one or more other elements, such as oxygen, sulfur, nitrogen, phosphorous, a halogen, or another non-metal or metalloid element from groups II-A (e.g., B), IV-A (e.g., Si), V-A (e.g., As), VI-A (e.g., Se) of the Periodic Table. The term "organic" also refers to materials traditionally described as organometallic materials (e.g., comprising one or more main group of or transition metal atoms covalently bound to a carbon atom), as well as materials that include metallic elements in a complex or as a salt with an organic moiety. Non-limiting examples of organic moieties or groups include, hydrocarbons, heterocycles (including materials comprising at least one saturated, unsaturated and/or aromatic ring comprising at least one carbon atom, and one or more other elements), carbohydrates (including sugars and polysaccharides), amino acids, polypeptides (including proteins and other materials comprising at least two amino acid groups bound together via a peptide bond), peptide analogs (including materials comprising two or more amino acids linked by a bond other than a peptide bond, e.g., ester bonds), and a combination of two or more thereof.

The "substituted" moieties described herein (e.g., substituted hydrocarbyl, heteroaryl, aryl and heterocyclic moieties) are groups that are substituted with a group comprising at least one atom other than carbon, including moieties in which a carbon chain atom is substituted with a hetero atom such as nitrogen, oxygen, silicon, phosphorous, boron, sulfur, or a halogen atom. In some embodiments, these substituents include, e.g., one or more of halogen (F, Cl, Br, I), heterocyclo, alkoxy, alkenoxy, alkynoxy, aryloxy, hydroxy, protected hydroxy, acyl, acyloxy, nitro, amino, amido, nitro, cyano, ketals, acetals, esters and ethers. In some embodiments such substituent groups can be, e.g., —$OR^4$, —$N(R^4)_2$, —$N^+(R^4)_3$, —$SR^4$, —$OC(=O)R^4$, —$N(R^4)C(=O)R^4$, —$SC(=O)R^4$, —$OC(=O)OR^5$, —$N(R^4)C(=O)OR^5$, —$SC(=O)OR^5$, —$OC(=O)N(R^4)_2$, —$N(R^4)C(=O)N(R^4)_2$, —$SC(=O)N(R^4)_2$, —$OC(=O)SR^5$, —$N(R^4)C(=O)SR^5$, —$SC(=O)SR^5$, —$C(=O)R^4$, —$C(=O)OR^4$, —$C(=O)N(R^4)_2$, —$C(=O)SR^4$, —$OC(=NR^4)R^4$, —$N(R^4)C(=NR^4)R^4$, —$SO_2R^4$, —$SO_2OR^4$, —$SO_2(NR^4)_2$, —$N(R^4)SO_2OR^5$, —$N(R^4)SO_2N(R^4)_2$, —$OSO_2OR^5$, —$OSO_2N(R^4)_2$, —$P(=O)(OR^4)_2$, —$OP(=O)(OR^4)_2$, —$OP(=O)R^5(OR^4)$, fluoro, chloro, bromo, iodo, —$NO_2$, —$N_3$, —N=N—$Ar^1$, —CN, a heteroaryl moiety, or a nonaromatic heterocyclic moiety; wherein each $R^4$ independently is H, hydrocarbyl, heteroaryl, or a nonaromatic heterocyclic moiety; each $R^5$ independently is hydrocarbyl, heteroaryl, or a nonaromatic heterocyclic moiety; and each $Ar^1$ independently is aryl or heteroaryl, which can be substituted as described above, or can be unsubstituted.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All numerical values obtained by measurement (e.g., weight, concentration, physical dimensions, removal rates, flow rates, and the like) are not to be construed as absolutely precise numbers, and should be considered to encompass values within the known limits of the measurement techniques commonly used in the art, regardless of whether or not the term "about" is explicitly stated. All methods described herein can be performed in any suitable order unless otherwise indicated herein or otherwise clearly contradicted by context. The use of any and all examples, or exemplary language (e.g., "such as") provided herein, is intended merely to better illuminate certain aspects of the invention and does not pose a limitation on the scope of the invention unless otherwise claimed. No language in the specification should be construed as indicating any non-claimed element as essential to the practice of the invention.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers, vehicles, or diluents.

"Individual," "patient," or "subject" are used interchangeably and include any animal, including mammals, preferably mice, rats, other rodents, rabbits, dogs, cats, swine, cattle, sheep, horses, or primates, and most preferably humans. Disclosed compounds may be administered to a mammal, such as a human, but may also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds disclosed herein contain one or more chiral centers and, therefore, exist as stereoisomers. The term "stereoisomers" when used herein consists of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds disclosed herein may contain one or more double bonds and, therefore, exist as geometric isomers resulting from the arrangement of substituents around a carbon-carbon double bond. The symbol ⁓ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds disclosed herein may contain a carbocyclic or heterocyclic ring and therefore, exist as geometric isomers resulting from the arrangement of substituents around the ring. Substituents around a carbocyclic or heterocyclic ring may be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like. It is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds as disclosed herein which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atoms replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

Compounds and pharmaceutical compositions (e.g., therapeutic agents or medicaments, and compositions comprising the compounds or therapeutic agents or medicaments) are described herein, which comprise a compound represented by Formula (I):

$$Y + Z + X^1 - S(O)(X^2)F]_m]_n \qquad (I)$$

wherein: Y is a biologically active organic core group comprising one or more unsubstituted or substituted moiety selected from an aryl group, a heteroaryl aryl group, a nonaromatic hydrocarbyl group, and a nonaromatic heterocyclic group, to which each Z independently is covalently bonded; n is 1, 2, 3, 4 or 5; each Z independently is O, NR, or N; when Z is O, m is 1, $X^1$ is a covalent bond, and the Z is covalently bonded to an aryl or heteroaryl moiety of Y; when Z is NR, m is 1, $X^1$ is a covalent bond or $CH_2CH_2$, and the Z is covalently bonded to a nonaromatic hydrocarbyl, a nonaromatic heterocyclic, an aryl, or heteroaryl moiety of Y; when Z is N, either (a) m is 2, $X^1$ is $CH_2CH_2$, and the Z is covalently bonded to a nonaromatic hydrocarbyl, a nonaromatic heterocyclic, an aryl, or a heteroaryl moiety of Y; or (b) m is 1, $X^1$ is a covalent bond or $CH_2CH_2$, and the Z is a nitrogen in an aromatic or non-aromatic heterocyclic ring portion of core group Y; each $X^2$ independently is O or NR; and each R independently comprises H or a substituted or unsubstituted group selected from an aryl group, a heteroaryl aryl group, a nonaromatic hydrocarbyl group, and a nonaromatic heterocyclic group.

In some embodiments, a therapeutic compound or medicament represented by Formula (II) is described:

$$A + Z + X^1 - S(O)(X^2)F]_m]n \qquad (II)$$

wherein A is an organic moiety comprising at least one substituent, $R^1$; n is 1, 2, 3, 4 or 5; each Z independently is O, NR, or N; each Z is covalently bonded to an $R^1$ moiety of A; each R independently comprises a hydrocarbyl group; when Z is O, m is 1, and $X^1$ is a covalent bond. Each $X^2$ independently can be O or $NR^5$ (preferably, $X^2$ is O). When Z is NR, m is 1, and each $X^1$ independently is a covalent bond or $CH_2CH_2$. When Z is N, m is 2, and $X^1$ is $CH_2CH_2$. Each $R^1$ independently is an aryl group, a heteroaryl group, and a substituted aryl group having the formula:

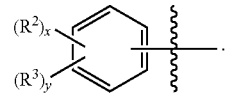

Each $R^2$ and $R^3$ independently is a substituent selected from the group consisting of a hydrocarbyl moiety, $-OR^4$, $-N(R^4)_2$, $-N^+(R^4)_3$, $-SR^4$, $-OC(=O)R^4$, $-N(R^4)C(=O)R^4$, $-SC(=O)R^4$, $-OC(=O)OR^5$, $-N(R^4)C(=O)OR^5$, $-SC(=O)OR^5$, $-OC(=O)N(R^4)_2$, $-N(R^4)C(=O)N(R^4)_2$, $-SC(=O)N(R^4)_2$, $-OC(=O)SR^5$, $-N(R^4)C(=O)SR^5$, $-SC(=O)SR^5$, $-C(=O)R^4$, $-C(=O)OR^4$, $-C(=O)N(R^4)_2$, $-C(=O)SR^4$, $-OC(=NR^4)R^4$, $-N(R^4)C(=NR^4)R^4$, $-SO_2R^4$, $-SO_2OR^4$, $-SO_2(NR^4)_2$, $-N(R^4)SO_2OR^5$, $-N(R^4)SO_2N(R^4)_2$, $-OSO_2OR^5$, $-OSO_2N(R^4)_2$, $-P(=O)(OR^4)_2$, $-OP(=O)(OR^4)_2$, $-OP(=O)R^5(OR^4)$, fluoro, chloro, bromo, iodo, $-NO_2$, $-N_3$, $-N=N-Ar^1$, $-CN$, a heteroaryl moiety, and a nonaromatic heterocyclic moiety. Alternatively, an $R^2$ and an $R^3$ together form a ring selected from a fused 5-member nonaromatic carbocyclic ring, a fused 5-member heterocyclic ring, a fused 6-member nonaromatic carbocyclic ring, and a fused 6-member nonaromatic nitrogen-containing heterocyclic ring. Each R[4] independently is H, hydrocarbyl, heteroaryl, or a nonaromatic heterocyclic moiety. Each R[5] independently is hydrocarbyl, heteroaryl, or a nonaromatic heterocyclic moiety. Each Ar[1] independently is aryl or heteroaryl. Each Ar[1], hydrocarbyl, heteroaryl, nonaromatic heterocyclic moiety, fused 5-member nonaromatic carbocyclic ring, fused 5-member heterocyclic ring, fused 6-member nonaromatic carbocyclic ring, and fused 6-member nonaromatic nitrogen-containing heterocyclic ring independently is unsubstituted or is substituted with a group comprising at least one atom other than carbon. The parameters x and y are 0, 1 or 2; and the sum of x and y is at least 1 when R[1] is the substituted aryl.

Certain compounds of Formula (II) or Formula (I) can be made by reacting a compound of Formula (IV) or (V), respectively, with $SO_2F_2$ in the presence of a base:

  (IV)

  (V)

in which A, Y, m and n are as defined for compounds of Formulas (II) and (I), and Z is O or NR. Examples of suitable bases include (e.g., an alkali metal hydroxide, such as NaOH, KOH and the like), an alkali metal alkoxide (e.g., potassium tert-butoxide, sodium methoxide, and the like), a nitrogen base (preferably a tertiary amine, such as triethylamine or diisopropylethylamine; an amidine such as DBU; a guanidine such as tetramethylguanidine), and the like.

In another embodiment, a method of preparing a compound of Formula (II) or Formula (I) in which each m is 2, each Z is N, and each X[1] is $CH_2CH_2$, comprises reacting a compound of Formula (IV) or (V), respectively, with $CH_2$=$CH$—$SO_2F$ ("ESF"), which readily condenses with amino compounds comprising at least one N—H bond.

The incorporation of a fluorosulfonyl (e.g., as $CH_2CH_2SO_2F$) or fluorosulfonyloxy (i.e., —$OSO_2F$) group into a therapeutically active compound (a medicament) in many cases surprisingly increases the metabolic stability of such compounds and contributes to bioavailability. In some cases, a non-covalent drug can be converted to a covalent drug by the incorporation of —$SO_2F$ or —$OSO_2F$. In other cases, the solubility of the compounds of Formula (II) are enhanced relative to the parent therapeutic agents comprising the core, for example when an —$OSO_2F$ replaces a $CF_3$ or $OCF_3$ group.

The therapeutically active compounds can be those which target a pathogen, as well as compounds that target a site of action in a host subject (e.g., a patient).

Illustrative therapeutically active compounds that target a pathogen and are suitable for incorporation of a —$SO_2F$ or —$OSO_2F$ group include, e.g., antibiotics such as vancomycin, rifamycin, rifampicin, teicoplanin, sulfacetamide, amoxicillin, novobiocin, tetracyclines (e.g., tetracycline, oxytetracycline, methacycline, minocycline, chlorotetracycline, doxycycline, rolitetracycline, demeclocycline, and the like), sulfanilamide, sulfamethoxazole, norfloxacin, gatifloxacin, gemifloxacin, trimethoprim, pyrimethamine, cefadroxil, anti-tubercular antibiotics (e.g., isoniazid, rifampicin; streptomycin, ciprofloxacin, moxifloxacin, aminosalicylic acid, and the like); and anti-protozoal agents such as iodoquinol, paramomycin, anti-malarial agents (e.g., quinine (by replacement of OMe with $OSO_2F$), quinocrine, atovaquone (e.g., by replacement of Cl or by reaction with an OH), mefloquine, sulfadoxine, hydrochloroquine, proguanil (e.g., by replacement of Cl with $OSO_2F$), and the like.

Illustrative therapeutically active compounds that target a site of activity in host subject and are suitable for incorporation of a —$SO_2F$ or —$OSO_2F$ group include, e.g., non-steroidal anti-inflammatory agents (NSAIDs) such as naproxen, ibuprofen, aspirin, tolmetin, flurbiprofen, sulindac, piroxicam, nabumeton, flufenamic acid, tolfenamic acid, diclofenac, and the like; antineoplastic agents such as bleomycin, cytarabine, dacarbazine, anthracyclines (e.g., daunorubicin, doxorubicin, and the like), epirubicin, etoposide, flutamide, gemcitabine, idarubicin, leuprolide, leuprorelin, mercaptopurine, methotrexate, mitomycin, mitoxantrone, pemetrexed, pentostatin, procarbazine, suramin, teniposide, thioguanine, thiotepa, uracil mustard (uramastine), and the like; opiates such as morphine, buprenorphine, hydromorphone, oxymorphone, dihydromorphone, methyldihydromorphinone, butorphanol, and the like; analgesics such as pregabalin, tetrahydrocannabinol, fentanyl, flupirtine, oxycodone, acetaminophen, salicylamide, and the like; anti-depressants such as fluoxetine (PROZAC), sertraline (ZOLOFT), duloxetine (CYMBALTA), amoxapine, maprotiline, mianserin, nomifensin, trazodine, viloxazine, aripirazole, bupropion (WELLBUTRIN), desvenlafaxine, duloxetine, paroxetine, and the like; COX 2 inhibitors such as celecoxib, rofecoxib, lumiracoxib, etoricoxib, firocoxib, nimesulide, and the like; COX-LOX inhibitors such as licofelone, clonidine, and the like; opioid receptor antagonists such as naltrexone, naloxone, naltrindole, and the like; Alzheimer's disease medications such as epigallocatechin gallate (EGCG), memantine, galantamine, and the like; statins such as atorvstatin (LIPITOR), rosuvastatin, and the like; erectile dysfunction medications such as sildenafil (VIAGRA), tadalafil (CIALIS), vardenafil (LEVITRA), apomorphine, and the like; anti-asthma medications such as salbutamol (albuterol), salmeterol, terbutaline, formoterol, metaproterenol, and the like; cholinesterase inhibitors such as edrophonium, tacrine, and the like; sympathomimetic drugs such as phenylephrine, amphetamine, methoxamine, prenalterol, terbutaline, ritodrine, and the like; anti-seizure agents such as lamotrigine, vigabatrine, gabapentin, pregabalin, and the like; neuromuscular blockers such as tubocurarine, cisatracurium, and the like; intestinal steroid absorption inhibitors such as ezetimibe, (3R,4S)-1,4-bis(4-methoxyphenyl)-3-(3-phenylpropyl)-2-azetidinone, and the like; endocrine drugs such as thyroxine, somatostatin, and the like; estrogenic agents, antagonists and agonists, such as raloxifene, estradiol, ethynylestradiol, diethylstilbesrol, and the like; antiviral agents such as acyclovir, valacyclovir, penciclovir, cidofovir, zalcitibine, adefovir, entacavir, and the like; anorectic agents such as phentermine, and the like; anticoagulants such as warfarin, acenocoumarol, and the like; antihypertives and beta blockers such as lisinopril, nadolol, atenolol, acebutolol, betaxolol, carvediol, esmolol, and the like; seratonin receptor agonists and seratonin uptake inhibitors such as seratonin, sertraline, dolasetron, fluoxetine, and the like; diuretics such as hydrochlorothiazide, bumetanide, furosemide, pinoresinol, and the like; calcium channel blockers such as amlodipine besylate, mibefradin hydrochloride, and the like; as well as female libido enhancing compounds such as flibanserin (1-(2-{4-[3-(Trifluoromethyl)phenyl]piperazin-1-yl}ethyl)-1,3-dihydro-2H-benzimidazol-2-one; Sprout Pharmaceuticals). Other suitable materials include peptide-based and amino acid-based agents, particularly tyrosine, 2,6-dimethyltyrosine, lysine, and peptides comprising one or more residues selected from tyrosine, 2,6-dimethyltyrosine, and lysine such as leuprolide (ENANTONE, a tyrosine-containing peptide pituitary GnRH receptor antagonist), glatiramer (a random copolymer of lysine alanine aspartic acid and tyrosine, tradename CAPOXONE, an immunomodulator), and the like. As is well known in the medical art, drugs within in a particular classification (e.g., antibiotic, estrogenic agent, antineoplastic agent, and the like) may have therapeutic uses and indications for more than one type of disease or condition.

In many cases, the $SO_2F$ group can attach to the biologically active core by replacement of a hydrogen of an aromatic or heteroaromatic OH or a hydrogen of an amino group of the core to form the an —$OSO_2F$, or —$NRSO_2F$ group. Particularly in the case of amino groups bearing a hydrogen atom present in the medicament structure, a $NRCH_2CH_2SO_2F$ or $N(CH_2CH_2SO_2F)_2$ group can be introduced by replacement of the hydrogen atom. These replacements are readily accomplished by reaction of virtually any OH or NHR group with $SO_2F_2$ in the former case and reaction of an $NH_2$ or NHR with ESF in the latter cases. In other embodiments, an $OSO_2F$ group can be attached to the medicament as a replacement for a methoxy or trifluoromethoxy group, or can be added to the medicament in place of a hydrogen of a CH or in place of some other substituent group by methods of organic synthesis that are well known in the chemical arts. Preferably, the $SO_2F$ group is attached to the medicament by replacement of a hydrogen of an aromatic or heteroaromatic OH or a hydrogen of an amino group as described herein. Compounds comprising a —$S(O)(NR^5)F$ group can be obtained by replacement of Cl from a corresponding —$S(O)(NR^5)Cl$ prepared by well-known conventional means as described herein.

Therapeutically active compounds comprising —S(O)($X^2$)F groups (e.g., $NCH_2CH_2SO_2F$, $NSO_2F$, $OSO_2F$ and/or $S(O)(NR^5)F$ groups) described herein are suitable, e.g., as medicaments for humans and animals, since these functional groups generally do not significantly interfere with the biological/therapeutic activity of the parent therapeutic agents. In addition, the —$S(O)(X^2)F$ groups provide useful handles for selectively derivatizing the therapeutic agent, e.g., to add a useful functional or diagnostic group such as a dye, biotin, and the like.

Such therapeutic compounds can be formulated as a pharmaceutical composition in combination with a pharmaceutically acceptable carrier, vehicle, or diluent, such as an aqueous buffer at a physiologically acceptable pH (e.g., pH 7 to 8.5), a polymer-based nanoparticle vehicle, a liposome, and the like. The pharmaceutical compositions can be delivered in any suitable dosage form, such as a liquid, gel, solid, cream, or paste dosage form. In one embodiment, the compositions can be adapted to give sustained release of the compound of Formula (I).

Pharmaceutical compositions comprising therapeutic compounds of Formula (I) can be administered to a subject or patient in a therapeutically effective amount to treat a disease or condition, e.g., a disease or condition for which the biologically active core group, A, is active.

In some embodiments, the pharmaceutical compositions include, but are not limited to, those forms suitable for oral, rectal, nasal, topical, (including buccal and sublingual), transdermal, vaginal, or parenteral (including intramuscular, subcutaneous, and intravenous) administration, in a form suitable for administration by inhalation or insufflation, or injection into amniotic fluid. The compositions can, where appropriate, be conveniently provided in discrete dosage units. The pharmaceutical compositions of the invention can be prepared by any of the methods well known in the pharmaceutical arts. Some preferred modes of administration include intravenous (iv), topical, subcutaneous, and injection into amniotic fluid.

Pharmaceutical formulations suitable for oral administration include capsules, cachets, or tablets, each containing a predetermined amount of one or more of the compounds of Formula (I), as a powder or granules. In another embodiment, the oral composition is a solution, a suspension, or an emulsion. Alternatively, the compounds of Formula (I) can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art. The compounds of Formula (I) will be included in the compositions within a therapeutically useful and effective concentration range, as determined by routine methods that are well known in the medical and pharmaceutical arts. For example, a typical composition can include one or more of the compounds of Formula (I) at a concentration in the range of at least about 0.01 nanomolar to about 1 molar, preferably at least about 1 nanomolar to about 100 millimolar.

Pharmaceutical compositions for parenteral administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agent, and dispersing agents. Alternatively, the compounds of Formula (I) can be provided in powder form, obtained by aseptic isolation of sterile solid or by lyophilization from solution, for constitution with a suitable vehicle, e.g. sterile, pyrogen-free water, before use. The additives, excipients, and the like typically will be included in the compositions for parenteral administration within a range of concentrations suitable for their intended use or function in the composition, and which are well known in the pharmaceutical formulation art. The compounds of Formula (I) will be included in the compositions within a therapeutically useful and effective concentration range, as determined by routine methods that are well known in the medical and pharmaceutical arts. For example, a typical composition can include one or more of the compounds of Formula (I) at a concentration in the range of at least about 0.01 nanomolar to about 100 millimolar, preferably at least about 1 nanomolar to about 10 millimolar.

Pharmaceutical compositions for topical administration of the compounds to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. The additives, excipients, and the like typically will be included in the compositions for topical administration to the epidermis within a range of concentrations suitable for their intended use or function in the composition, and which are well known in the pharmaceutical formulation art. The compounds of Formula (I) will be included in the compositions within a therapeutically useful and effective concentration range, as determined by routine methods that are well known in the medical and pharmaceutical arts. For example, a typical composition can include one or more of the compounds of Formula (I) at a concentration in the range of at least about 0.01 nanomolar to about 1 molar, preferably at least about 1 nanomolar to about 100 millimolar.

Pharmaceutical compositions suitable for topical administration in the mouth (e.g., buccal or sublingual administration) include lozenges comprising the compound in a flavored base, such as sucrose, acacia, or tragacanth; pastilles comprising the peptide in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired. The additives, excipients, and the like typically will be included in the compositions of topical oral administration within a range of concentrations suitable for their intended use or function in the composition, and which are well known in the pharmaceutical formulation art. The compounds of Formula (I) will be included in the compositions within a therapeutically useful and effective concentration range, as determined by routine methods that are well known in the medical and pharmaceutical arts. For example, a typical composition can include one or more of the compounds of Formula (I) at a concentration in the range of at least about 0.01 nanomolar to about 1 molar, preferably at least about 1 nanomolar to about 100 millimolar.

A pharmaceutical composition suitable for rectal administration comprises a compound of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art. The additives, excipients, and the like typically will be included in the compositions of rectal administration within a range of concentrations suitable for their intended use or function in the composition, and which are well known in the pharmaceutical formulation art. The compounds of Formula (I) will be included in the compositions within a therapeutically useful and effective concentration range, as determined by routine methods that are well known in the medical and pharmaceutical arts. For example, a typical composition can include one or more of the compounds of Formula (I) at a concentration in the range of at least about 0.01 nanomolar to about 1 molar, preferably at least about 1 nanomolar to about 100 millimolar.

According to one embodiment, pharmaceutical compositions of the present invention suitable for vaginal administration are provided as pessaries, tampons, creams, gels, pastes, foams, or sprays containing a compound of Formula (I) of the invention in combination with a carriers as are known in the art. Alternatively, compositions suitable for vaginal administration can be delivered in a liquid or solid dosage form. The additives, excipients, and the like typically will be included in the compositions of vaginal administration within a range of concentrations suitable for their intended use or function in the composition, and which are well known in the pharmaceutical formulation art. The compounds of Formula (I) will be included in the compositions within a therapeutically useful and effective concentration range, as determined by routine methods that are well known in the medical and pharmaceutical arts. For example, a typical composition can include one or more of the compounds of Formula (I) at a concentration in the range of at least about 0.01 nanomolar to about 1 molar, preferably at least about 1 nanomolar to about 100 millimolar.

Pharmaceutical compositions suitable for intra-nasal administration are also encompassed by the present invention. Such intra-nasal compositions comprise a compound of Formula (I) in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the peptide. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the peptide. Alternatively, pharmaceutical compositions for administration by inhalation or insufflation can be provided in the form of a dry powder composition, for example, a powder mix of the compounds of Formula (I) and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art. The compounds of Formula (I) will be included in the compositions within a therapeutically useful and effective concentration range, as determined by routine methods that are well known in the medical and pharmaceutical arts. For example, a typical composition can include one or more of the compounds of Formula (I) at a concentration in the range of at least about 0.01 nanomolar to about 1 molar, preferably at least about 1 nanomolar to about 100 millimolar.

Optionally, the pharmaceutical compositions of the present invention can include one or more other therapeutic agent, e.g., as a combination therapy.

Sulfonyl chlorides are the most commonly used S(VI) electrophiles. $RSO_2Cl$ and $ClSO_2Cl$ often cannot serve as reliable connective units because of the facile reductive failure of the bond between sulfur(VI) and chlorine (eq. 1). This emerges most vexingly in the attempted formation of inorganic sulfate, sulfamide, and sulfamate linkages such as $RO-SO_2-OR'$, $RNH-SO_2-NHR'$ and $ArO-SO_2-NRR'$. Attempts to develop quick and robust inorganic connectors for the fast assembly of sophisticated molecules has been delayed by these side reactions. As described herein, sulfonyl fluoride and related groups demonstrated to constitute components of a versatile new click chemistry, encompassing both carbon-(C—SO$_2$F) and heteroatom-bound (N—SO$_2$F and O—SO$_2$F) species; see e.g., Equation (1).

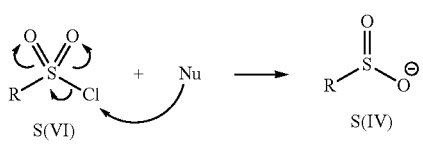

(1)

An understanding of the unique stability-reactivity pattern of sulfonyl fluorides rests on five contributing factors, illustrated by the results in FIG. 1.

(1) Resistance to reduction. Since fluorine is the most electronegative element in the periodic table, sulfonyl-fluorine bond cleavage is exclusively heterolytic with the formation of fluoride ion (although rarely, if ever, as uncomplexed F$^-$). In contrast, homolytic scission of S—Cl bonds is quite common. For aromatic cases, irreversible reduction to the sulfinic acid level (ArS(O)OR) occurs easily for ArSO$_2$Cl with many nucleophiles, except alcohols and amines under limited conditions. Sulfonyl bromides and iodides are even more prone to reduction and radical reactions than sulfonyl chlorides, allowing sulfonyl chlorides, sulfonates, and sulfonic acids to be reduced cleanly if the iodide is generated in situ. A remarkable example of the differences between chlorine and fluorine in sulfuryl chemistry is provided by the parent compounds: SO$_2$Cl$_2$ is a powerful oxidant, whereas sodium metal can be melted in hot SO$_2$F$_2$ without chemical change in either species.

(2) Thermodynamic stability. Whereas substitution at all sulfur centers in oxidation states below VI is kinetically accessible, including the sulfur(IV) oxyhalides SOF$_2$ and SOCl$_2$, the very sluggishness of S(VI) substitution chemistry makes it superior as a connector. Furthermore, sulfonyl fluorides are much more stable than other sulfonyl halides toward nucleophilic substitution (including hydrolysis) and thermolysis, making them the sulfonyl reagents of choice under demanding reaction conditions. These observations are consistent with the measured bond strengths of SO$_2$—F relative to SO$_2$—Cl: the homolytic bond dissociation energy of the S—F bond in SO$_2$F$_2$ (90.5±4.3 kcal/mol, 81±2 kcal/mol) is far larger than the S—Cl bond in SO$_2$Cl$_2$ (46±4 kcal/mol). The difference is of similarly large magnitude (41 kcal/mol) in comparing the bond strengths of S—F vs. S—Cl bonds in SO$_2$FCl.

These factors produce a surprising and highly useful passivity in the —SO$_2$F group. An aliphatic example is provided by methanedisulfonyl fluoride [(FSO$_2$)$_2$CH$_2$, MDSF]. The SO$_2$F groups in this compound survive severe electrochemical oxidation conditions in the fluorination of the methylene group, and base-mediated and catalyzed alkylation and condensation reactions proceed perfectly (Eq. 3). The chloride analogue (ClSO$_2$)$_2$CH$_2$ decomposes under these circumstances. As a building block, MDSF is especially useful for its dual potential to link with electrophiles at carbon via its conjugate base and with nucleophiles at each O$_2$S—F bond. Importantly, sulfonyl fluorides are surprisingly stable to aqueous conditions.

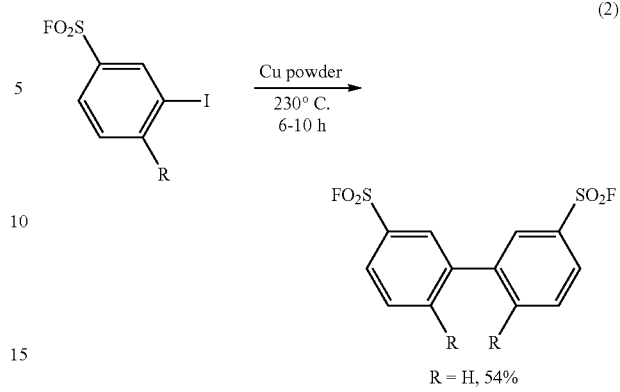

(2)

R = H, 54%
R = Me, 41%

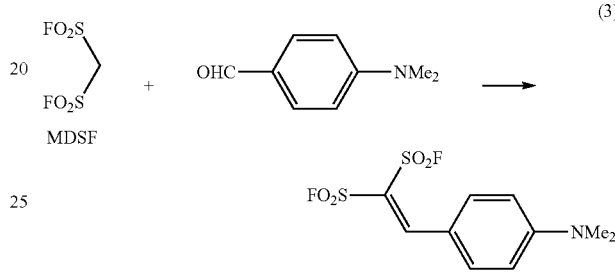

(3)

(3) Exclusive reaction at sulfur. Because of its polarizability, the chlorine center in —SO$_2$Cl and related groups is vulnerable to nucleophilic or reductive attack, so that reactions with carbon nucleophiles usually give mixtures of products resulting from both sulfonylation and chlorination pathways.

(4) Special nature of the fluoride proton interaction. Both addition-elimination and direct substitution pathways are reasonable for nucleophilic substitution reactions of sulfonyl fluorides. While the details of the SO$_2$ center's participation in this reaction are both relevant and incompletely understood, the key feature that makes SuFEx chemistry unique is that it depends very much on stabilization of the developing fluoride ion in the substitution process. Other halides can be subject to similar effects, but fluoride stands alone in the magnitude and environmental sensitivity of the phenomenon. Furthermore, the agents that accomplish such fluoride stabilization under practical conditions are H$^+$ and silyl groups (FIG. 2), making the SuFEx process controllable and useful in both biological and synthetic settings.

Figure 2:
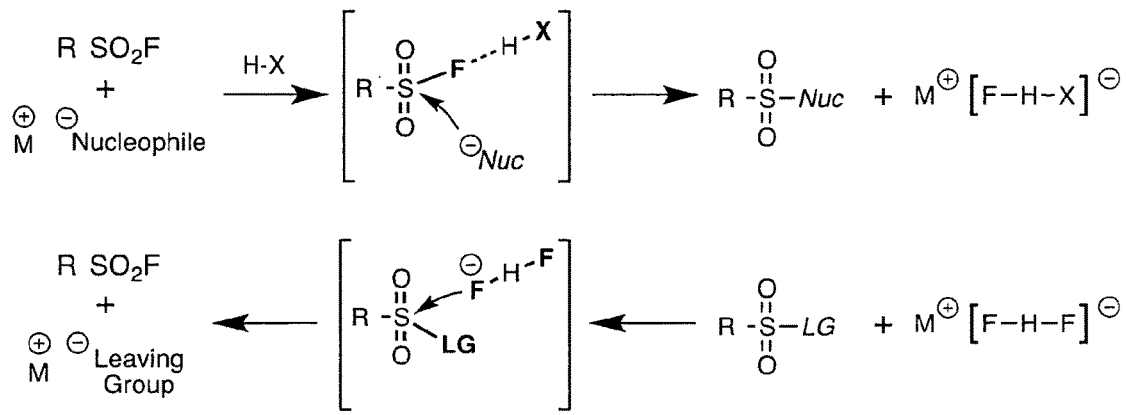
FIG. 2 illustrates the essential role of fluoride stabilization and bifluoride attack in SuFEx chemistry.

The special nature of the fluoride ion in water has long been recognized, but is not often taken advantage of in a synthetic context. In FIG. 2, the role of "HX" in stabilizing fluoride represents the potential virtues of specific protic centers in accelerating reactions of —SO$_2$F electrophiles (as in reactions with proteins, discussed below), and the power of aqueous environments to transmit acidic stabilization to the fluoride center. To understand the unique properties of fluoride as a base and leaving group, an appreciation of the bifluoride ion (HF$_2$)$^-$ is essential. The bifluoride bond is a strong, centrosymmetric, three atom-four electron bond, worth a remarkable 40 kcal/mol. The bifluoride bond is short and strong, and is not to be confused with the time-honored, albeit weak, hydrogen bond/hydrogen bonding phenomenon. Hence, when fluoride encounters any acid in water, the bifluoride ion, [F—H—F]$^-$, is formed, which also is in equilibrium with substantial quantities of higher adducts such as [F—H—F—H—F]$^-$. In other words, F$^-$ is a unique base: it gains strong stabilization in water by trapping a proton between two of itself. The proton is therefore uniquely effective at stabilizing fluoride as a leaving group. The reactivity of the bifluoride nucleophile, discussed below, is the complement to the helpful role of hydrogen bonding in the chemistry of sulfonyl fluorides in protic solvents.

(5) Closely related functional groups.

Aliphatic sulfonyl fluorides. Aryl sulfonyl fluorides are significantly more resistant to hydrolysis than alkyl derivatives with (-hydrogens, and electron-withdrawing substituents on the aromatic ring increase the electrophilic nature of S(VI) and make it more reactive. Sulfonyl halides, including fluorides, bearing acidic protons in the (-position undergo reactions that often proceed via elimination to form sulfene-type intermediates (RR'C=SO$_2$). A good example is phenylmethanesulfonyl fluoride (PMSF), a serine protease inhibitor widely used in the preparation of cell lysates. However, this reaction pathway is fast only in the presence of base, allowing PMSF and other aliphatic sulfonyl fluorides to be stable and to selectively modify proteins in aqueous solution at moderate pH. Also noteworthy is the far better AlCl$_3$-assisted Friedel-Crafts reactivity of alkyl-SO$_2$F compounds compared to alkyl-SO$_2$Cl. Thus, while the current focus is on arylsulfonyl connectors, aliphatic derivatives also benefit from the unique chemistry of the SO$_2$F group. The PMSF homologue with an additional CH$_2$ group, i.e., PhCH$_2$CH$_2$SO$_2$F, is less reactive towards hydrolysis, whether enzymatic or otherwise.

Sulfonimidoyl fluorides. Sulfonimidoyl fluorides generally have the same advantageous properties as sulfonyl fluorides, and reactivity comparisons with sulfonimidoyl chlorides are similarly striking. However, the nitrogen substituent gives sulfonimidoyl fluorides an additional point of modification, and their reactivities toward nucleophiles can be dramatically altered by the nature of that substituent. Electron-withdrawing groups, such as acyl, carbonate and sulfonyl enhance the electrophilicity of S, making these classes of compounds similar in reactivity to sulfonyl fluorides, ranging from more to less reactive. In contrast, sulfonimidoyl fluorides with alkyl and aryl groups on N are much more stable than sulfonyl chlorides, even under basic conditions (vide infra).

Figure 3:
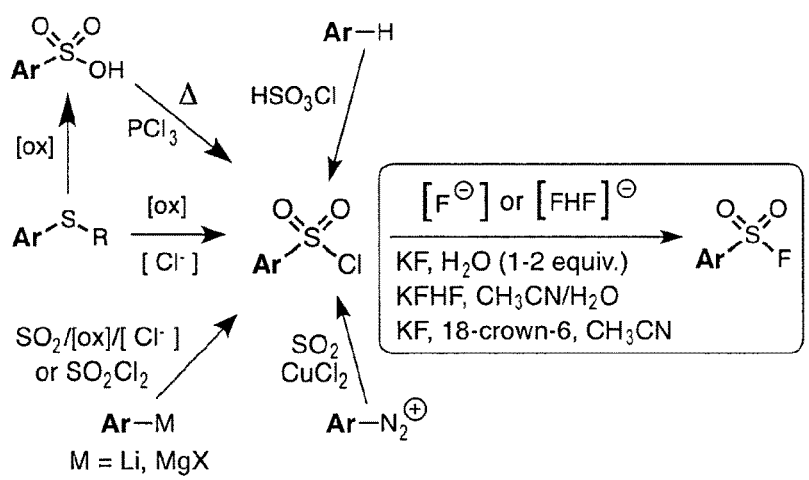
FIG. 3 illustrates common methods for the synthesis of aryl (top) and alkyl (bottom) sulfonyl chlorides and fluorides. The C—S bonds of these derivatives can be formed by nucleophilic attack of S(IV) on organic electrophiles or attack of organic nucleophiles on electrophilic S(VI) centers.
Figure 3:
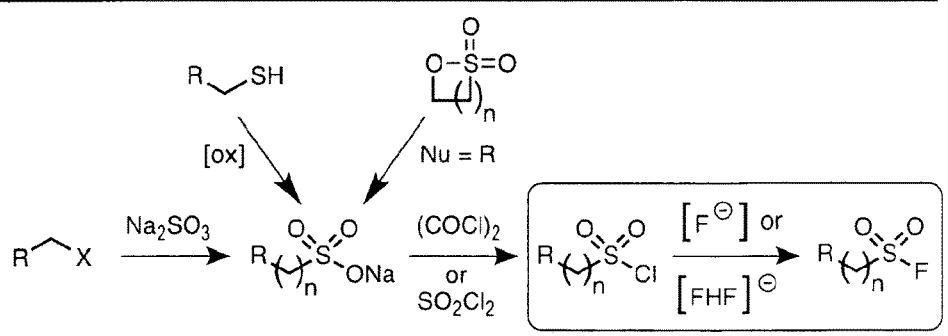

The most common processes of sulfonylation of aromatic and aliphatic molecules are summarized in FIG. 3. The majority of these produce sulfonyl chlorides, making them the least expensive and most available substrates. The exchange of fluoride for chloride in these systems would seem to be a simple matter, but the transformation's history is unusual in several instructive ways.

Figure 4:
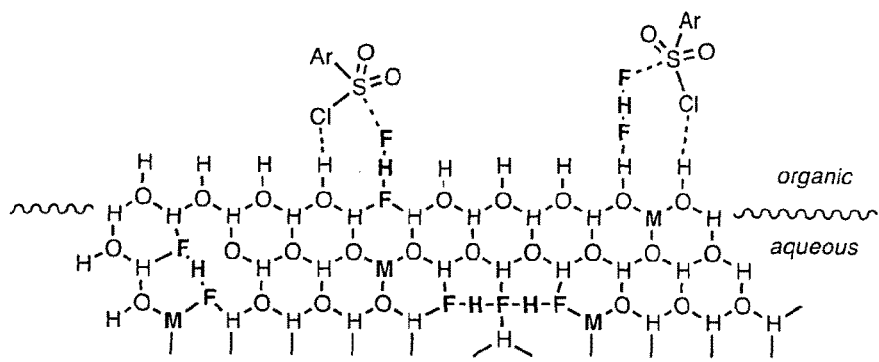
FIG. 4 illustrates the special reactivity of bifluoride ion at a water-organic interface. $[FHF]^-$ molecules at the surface lose the key H-bonding interactions with water that stabilize this species in the bulk. As a result, bifluoride at the surface or interface is far more nucleophilic. Interactions with $ArSO_2Cl$ leading to substitution are shown. M=the counterion for bifluoride, usually $K^+$. Also shown is the $[H_2F_3]$ ion, which is present in significant quantities along with bifluoride.

The presence of water was found to be beneficial, and typical reaction conditions involve refluxing the water-organic biphasic mixtures. However, yields rarely exceed 80%. While "naked" fluoride (KF, dry acetonitrile, 18-crown-6) can be used, the bifluoride anion (F—H—F)$^-$ (e.g., from potassium bifluoride) is consistently and substantially superior to other reagents for sulfonyl chloride-to-fluoride conversion, allowing the use of mild reaction conditions, broad substrate scope, simple reaction setup, effortless product isolation, and easy scale up. Bifluoride seems to be especially effective when it can be used "on water"—that is, in reactions performed with a vigorously stirred or agitated water-organic interface. Since solvation and H-bonding is important to the state and reactivity of fluoride, [FHF]$^-$ at aqueous-organic interfaces presents a more nucleophilic, albeit less basic and less solvated, fluoride source to electrophiles in the organic phase, shown in schematic fashion in FIG. 4. Strong acid (HX) has the effect of enhancing the utility of fluoride as a nucleophile, but not as a base, by generating a form of the anion (bifluoride) that can be presented more effectively at water interfaces.

Figure 5:
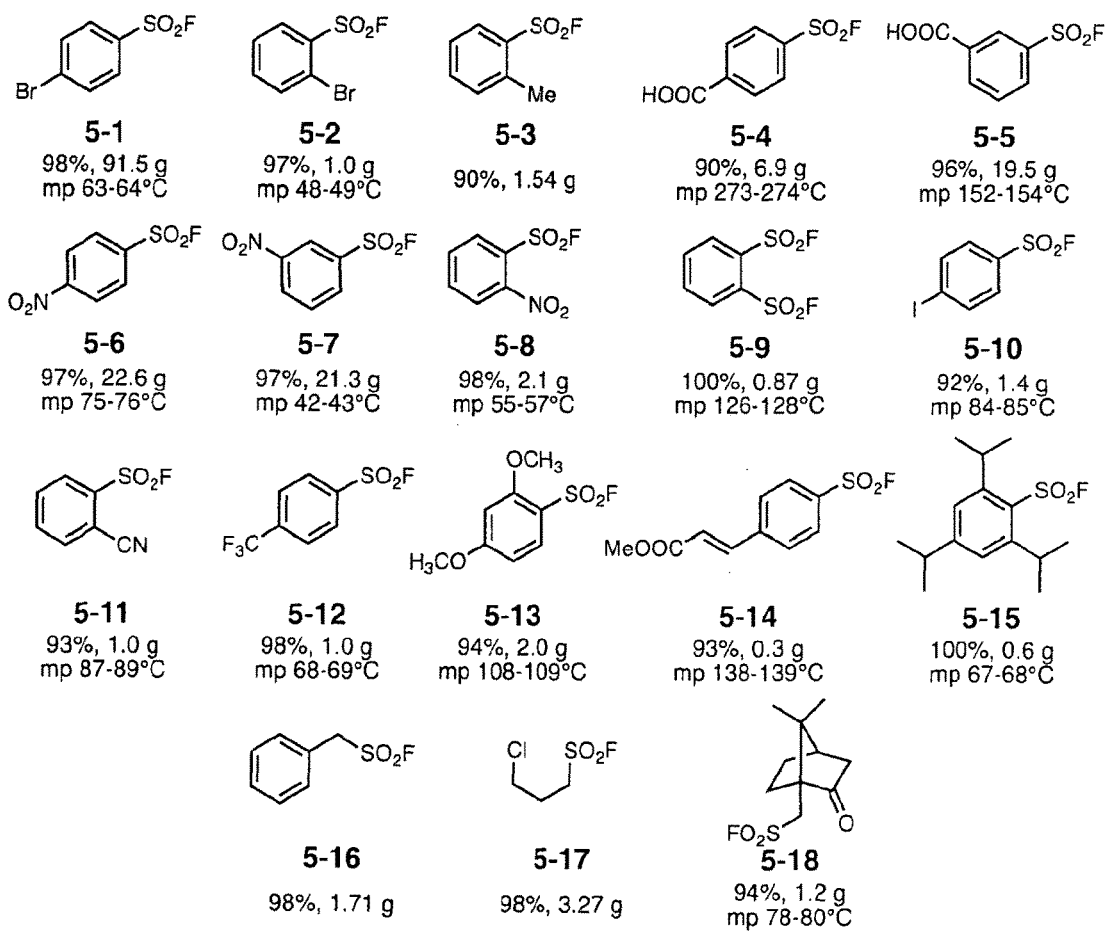
FIG. 5 provides examples of sulfonyl fluorides made with potassium bifluoride.

Examples of sulfonyl fluorides made from the corresponding chlorides in this way are shown in FIG. 5. If technical grade starting material is used, the sulfonyl fluoride product occasionally requires purification by a wash with aqueous base and/or by chromatography on a short silica gel column. The crude product, however, is virtually free of impurities. Liquid sulfonyl chlorides are simply stirred vigorously with saturated aqueous KFHF solution. Otherwise, acetonitrile (MeCN) generally is the co-solvent of choice. THF or CH$_2$Cl$_2$ optionally can be used as diluents to dissolve a hydrophobic substrate and present it to the aqueous interface where the reaction with bifluoride likely occurs. Full conversion generally is achieved within several hours. When, as often happens, starting chloride and product fluoride overlap on TLC, reaction progress can be monitored by GC, LCMS, or $^{19}$F NMR.

Figure 6:
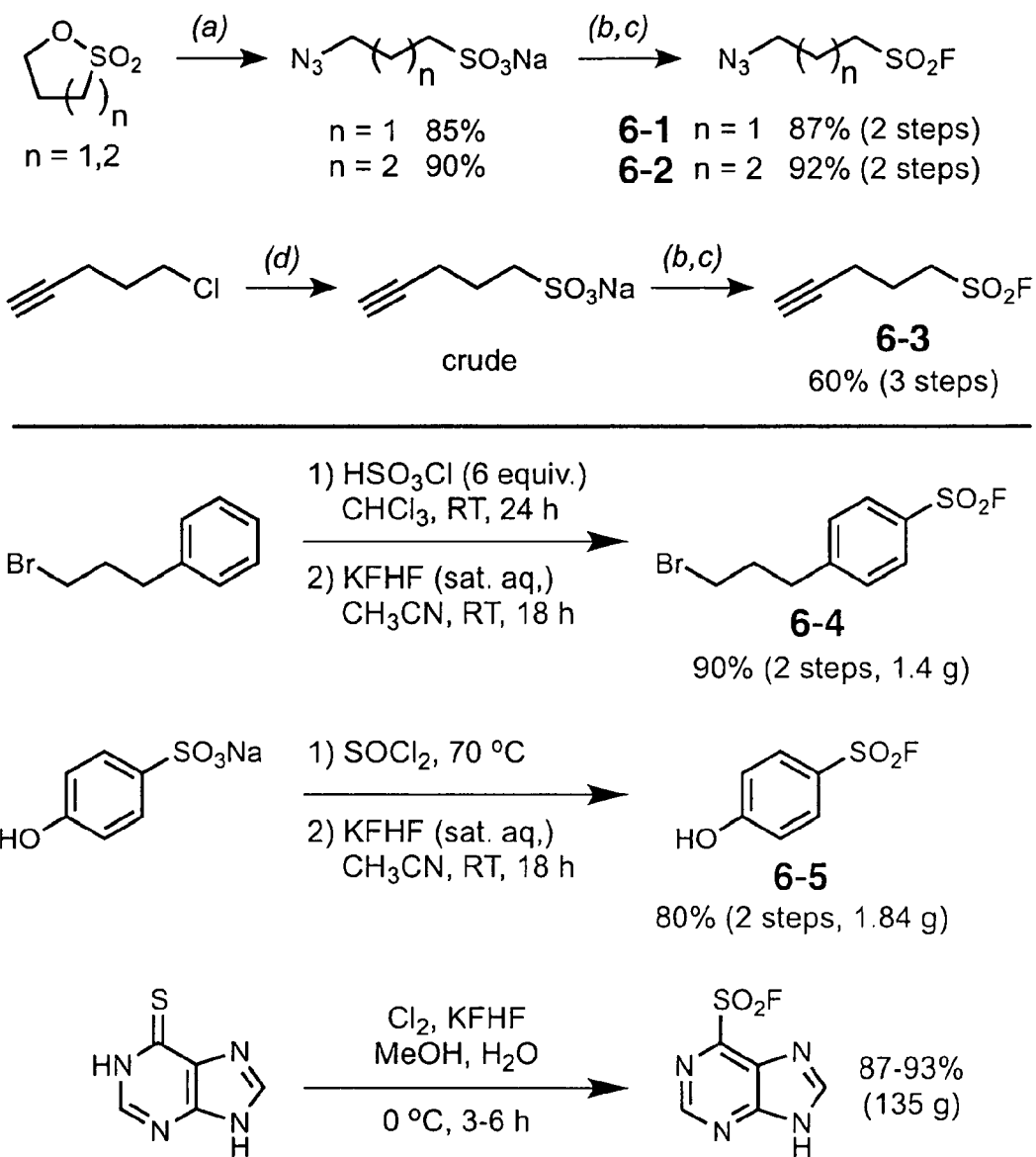
FIG. 6 illustrates alkyl (top) and aryl (bottom) sulfonyl fluorides made from sulfonic acids. (a) $NaN_3$, acetone, $H_2O$, reflux, 8 hours; (b) $(COCl)_2$, $CH_2Cl_2$, DMF (cat.), room temperature (RT), 18 hours; (c) KFHF (sat.), $CH_3CN$, RT, 6 hours. (d) $Na_2SO_3$ (1 equiv.), $H_2O$, 95° C., 16 h.

Examples of the easy installation of alkyl (W. Qiu, D. J. Burton, *J. Fluor. Chem.* 1992, 60, 93-100) and aryl sulfonyl groups using the general methods of FIG. 3 are shown in FIG. 6. In all cases, the intermediate sulfonyl chloride was subjected without purification to an aqueous phase of saturated KFHF. The desired fluoride product can be easily purified if necessary by simple washing, recrystallization, or column chromatography. Such in situ conversion to the fluoride is particularly advantageous for certain heterocyclic sulfonyl chlorides, often generated by oxidation of thiols such as the 6-mercaptopurine shown in FIG. 6, that are unstable. KFHF, optimally already present during the Cl$_2$ oxidation stage, acts as both nucleophile and buffer, in this case carrying the Het-SO$_2$—Cl on to the Het-SO$_2$—F before it collapses to Het-Cl and SO$_2$.

Figure 7:
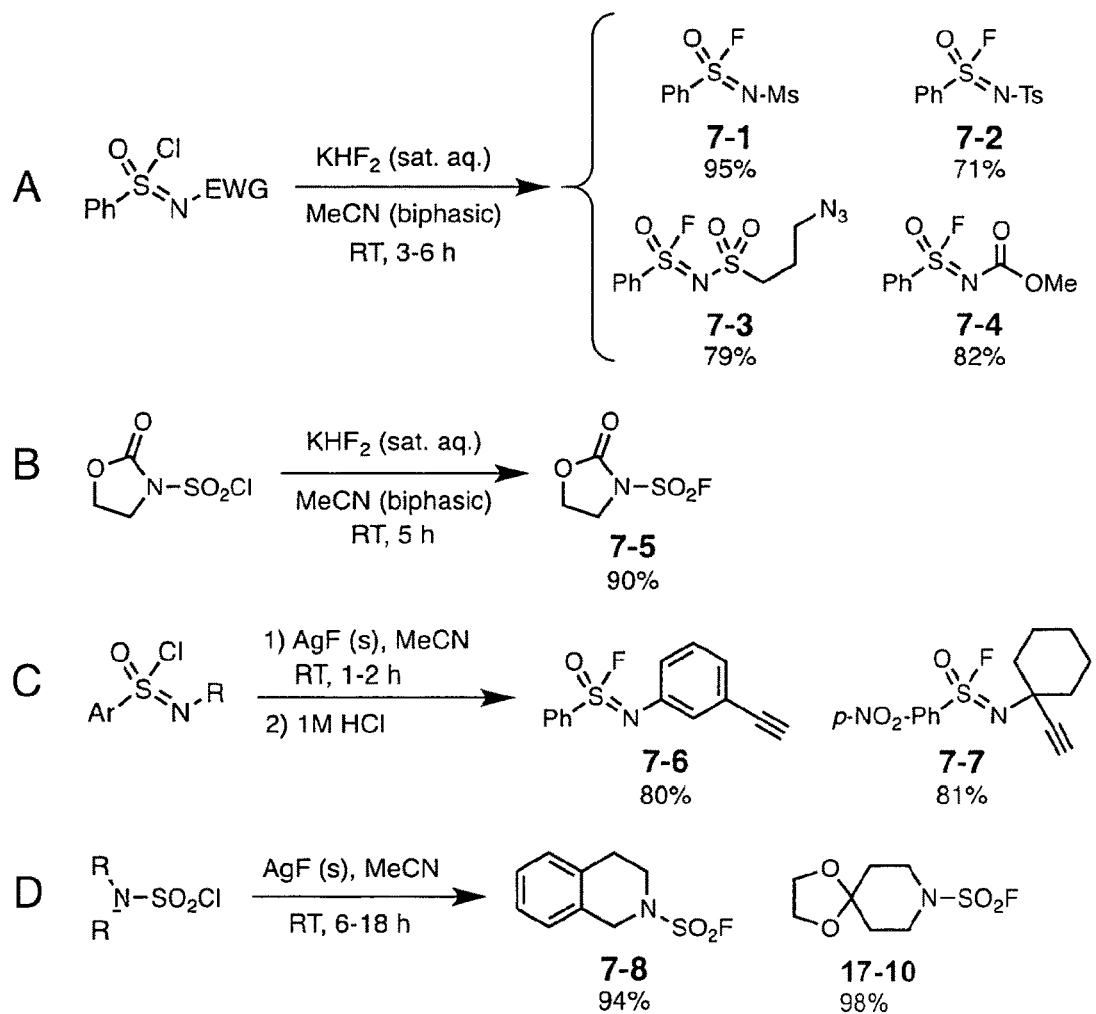
FIG. 7 shows sulfonimidoyl and sulfamoyl fluorides prepared from the corresponding chlorides. The acidic workup in reaction C is required to hydrolyze the silver acetylide formed under these conditions.

Sulfonimidoyl chlorides and sulfamoyl chlorides with electron withdrawing substituents on nitrogen are very similar in their reactivity to sulfonyl chlorides (vide supra) and can be converted to the corresponding fluorides by treatment with saturated aqueous KFHF (FIG. 7, Panels A,B). When electron donating groups are present on nitrogen, bifluoride is not reactive enough, giving low yields under standard conditions. In these cases, Bolm's silver fluoride in acetonitrile conditions are used to produce the sulfonyl fluoride on a preparative scale (FIG. 7, Panels C,D).

Figure 9:
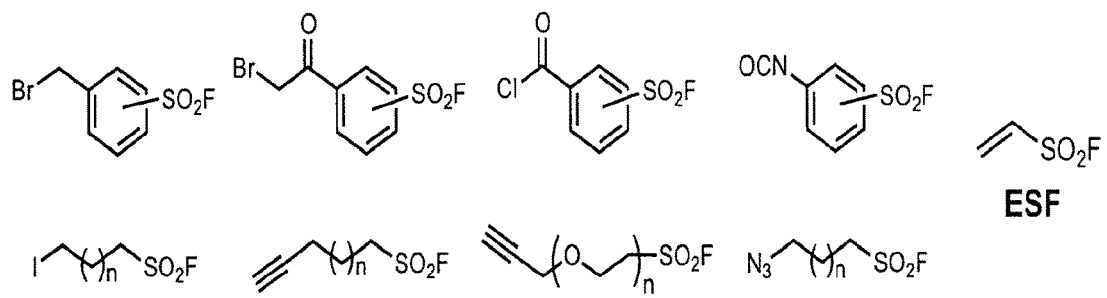
FIG. 9 illustrates synthesis (top) and use (bottom) of ESF in the decoration of nitrogen, oxygen, and carbon nucleophiles. Reaction conditions: (A) ESF, 95:5 EtOH:$H_2O$, 5 minutes to hours; (B) ESF, solvent (usually $CH_2Cl_2$ or THF), 5 min to hours; (C) ESF, $PR_3$ (10 mol %), $CH_2Cl_2$, 24 hours; (D) ESF, AcOH, reflux, 2 hours; (E) ESF, $Bu_4NF$ (10 mol %), THF; (F) ESF, quinine (10 mol %), $CH_2Cl_2$.

Several useful reagents are shown in FIG. 9, involving reactive electrophilic groups such as benzyl bromide, phenacyl bromide, acyl halide, isocyanate, and iodide. The lower reactivity of —SO$_2$F allows these reagents to be selectively attached via the other electrophilic site. Azide- and alkyne-modified sulfonyl fluorides will also be useful since the SO$_2$F group does not interfere with any form of the catalyzed or strain-promoted azide-alkyne ligation methods.

Figure 8:
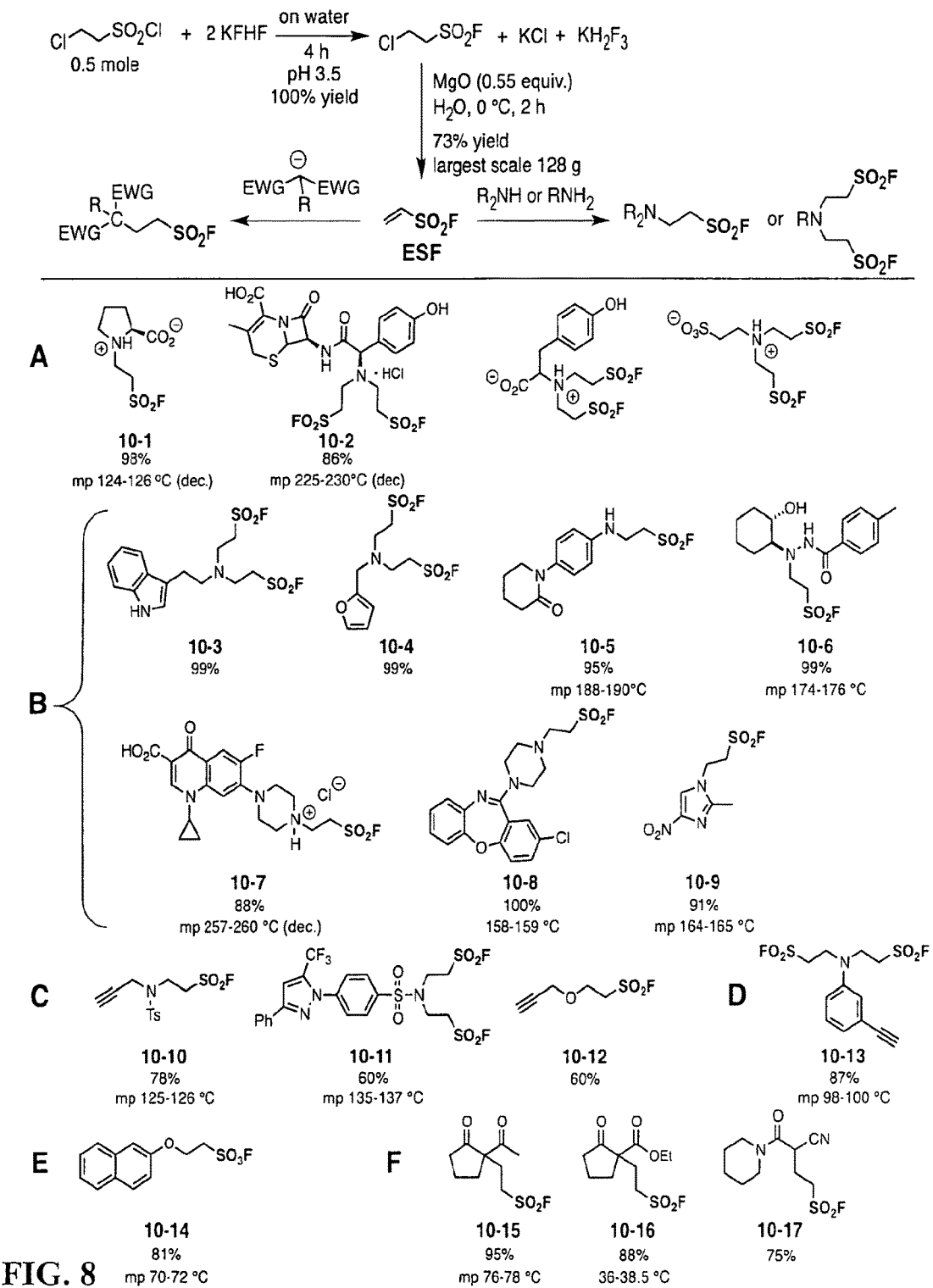
FIG. 8 illustrates small connector molecules allowing the installation of sulfonyl fluorides onto other functional structures.

One of the most powerful reagents for introduction of an SO$_2$F group is ethenesulfonyl fluoride (ESF), a strong Michael acceptor as well as Diels-Alder dienophile. ESF is derived by elimination from 2-chloroethylsulfonyl fluoride, first described from the sulfonyl chloride in 1932 and reported in large scale with elimination as a side reaction in 1979. Using the new KFHF-modification (vida supra) in the first stage from ClCH$_2$CH$_2$SO$_2$Cl, ESF can be readily prepared in large quantities (FIG. 8). The related large-scale preparation of ESF from ethenylsulfonyl chloride (ESCl) was patented in 1950 by Hedrick (Dow Chemical), but with KF as the nucleophile rather than KFHF, resulting in a relatively low yield (75%).

Several examples of reactions of ESF are shown in FIG. 8. Reactions with active amines are usually complete within a few minutes at room temperature. The participation of amine-containing zwitterions such as amino acids achieves the full level of generality and convenience required of click reactions (FIG. 8, Panel A). One simply stirs a slurry of starting zwitterion in aqueous ethanol, adds the requisite amount of ESF (one molar equivalent for secondary amines like proline, two equivalents for primary amines), and monitors the stirred suspension for conversion to the new zwitterion. Upon completion, the product is harvested by concentration and filtration. Indeed, for most ESF-amine conjugate additions, purification is rarely required. Details of the improved preparative procedure for ESF (FIG. 8, top) can be found below. The literature also describes examples of fluorinated derivatives of ESF, which should be similarly useful. ESF is a toxic molecule, so strict attention to proper procedures for handling this volatile compound is recommended.

The smallest member of the S(VI) oxyfluorides family, $SO_2F_2$ was first described in 1901 by Moissan and subsequently developed by Dow Chemical in the 1950s as VIKANE pest control agent. At normal temperature and pressure, $SO_2F_2$ is a colorless, odorless gas, 3.5 times heavier than air (see Table 1). These properties, coupled with its high vapor pressure and ability to saturate air at concentrations lethal to pests, make $SO_2F_2$ an effective fumigant, presently used against insects and rodents. The global production of $SO_2F_2$ since 2000 averages approximately 3 million kilograms per year.

TABLE 1

| Physical properties of $SO_2F_2$. | |
| --- | --- |
| CAS number | 2699-79-8 |
| molecular weight | 102.1 |
| specific gravity | 4.18 |
| boiling point | −55° C. |
| vapor pressure | 1611.47 kPa at 20° C. |
| odor | odorless |
| appearance | colorless gas |
| flammability | non-flammable |
| solubility (25° C., g/L) | water = 0.75, 1-octanol = 14, heptane = 22, 1,2-dichloroethane = 25, MeOH = 33, EtOAc = 59, acetone = 71 |

$SO_2F_2$ is relatively inert in gaseous form and is stable up to 400° C. when dry, but decomposes when heated in air, generating toxic fumes of HF and $SO_2$. It is slowly hydrolyzed in water under neutral conditions and more rapidly under basic conditions to produce fluorosulfate and fluoride ions. $SO_2F_2$ has relatively small magnetic and quadrupole moments, does not undergo photolysis in the actinic region of solar radiation, and is inert toward ozone and the active radicals of the atmosphere (Cl., OH.). Again, comparison to sulfuryl chloride is instructive: $SO_2Cl_2$ is less thermally stable (decomposes at 100° C. in an open system to chlorine and sulfur dioxide) and easily generates chlorine radicals.

Early published syntheses of fluorosulfates (also called sulfoxyl fluorides or sulfurofluoridates; fluorosulfonate is also used although this term should be reserved for compounds containing at least one carbon-sulfur bond) from phenols used $ClSO_2F+SOF_4$ or $SO_2F_2$ at high temperatures, giving poor results. Chlorosulfates ($ROSO_2Cl$), unlike the organic sulfonyl chlorides described above, respond poorly to attempted substitution with KF. Furthermore, chlorosulfates are unattractive starting materials, as they are prone to self-chlorination and other radical decomposition processes at low temperatures. The reaction of $SO_2F_2$ with preformed sodium and lithium phenolates had previously been shown to provide better yields of fluorosulfates, but these procedures did not catch on. $SO_2F_2$ therefore represents a curious combination of ton-scale application in the field and poor appreciation in the laboratory.

Figure 10:
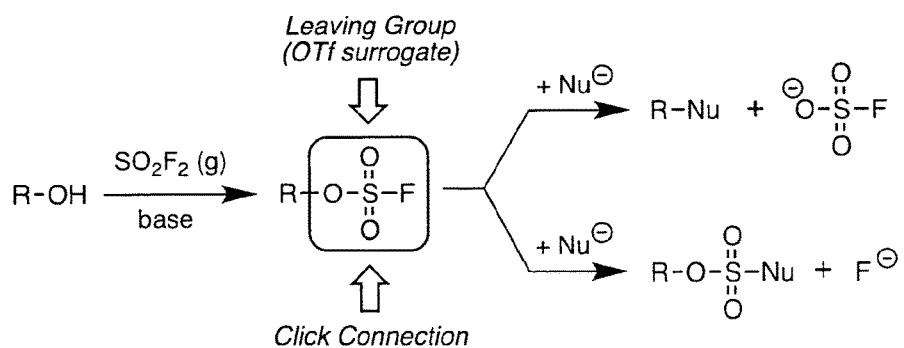
FIG. 10 illustrates dual modes of reactivity of fluorosulfates.

Reaction of $SO_2F_2$ with oxygen nucleophiles in the presence of base gives fluorosulfates (FIG. 10), which have long been known to be quite stable toward hydrolysis under neutral or acidic conditions. Depending on the nature of the substituent R, the $OSO_2F$ unit can be a good leaving group or a robust connector. The former reactivity pattern includes the conversion of carboxylic acids and primary alcohols to acyl and aliphatic fluorides, respectively, using $SO_2F_2$ in the presence of base. Secondary fluorosulfates can be made and isolated when the carbinol center is embedded in the molecule between electron-withdrawing substituents that make both $S_N1$ and $S_N2$ substitution difficult, as is the case with a C6-fluorosulfate penicillin analogue tested as a covalent inhibitor of porcine pancreatic elastase. In addition, certain perfluorinated aliphatic fluorosulfates can be isolated and were shown to form stable sulfate and sulfamate connections (T. Huang, J. M. Shreeve, Inorg. Chem. 1986, 25, 496-498).

Figure 11:
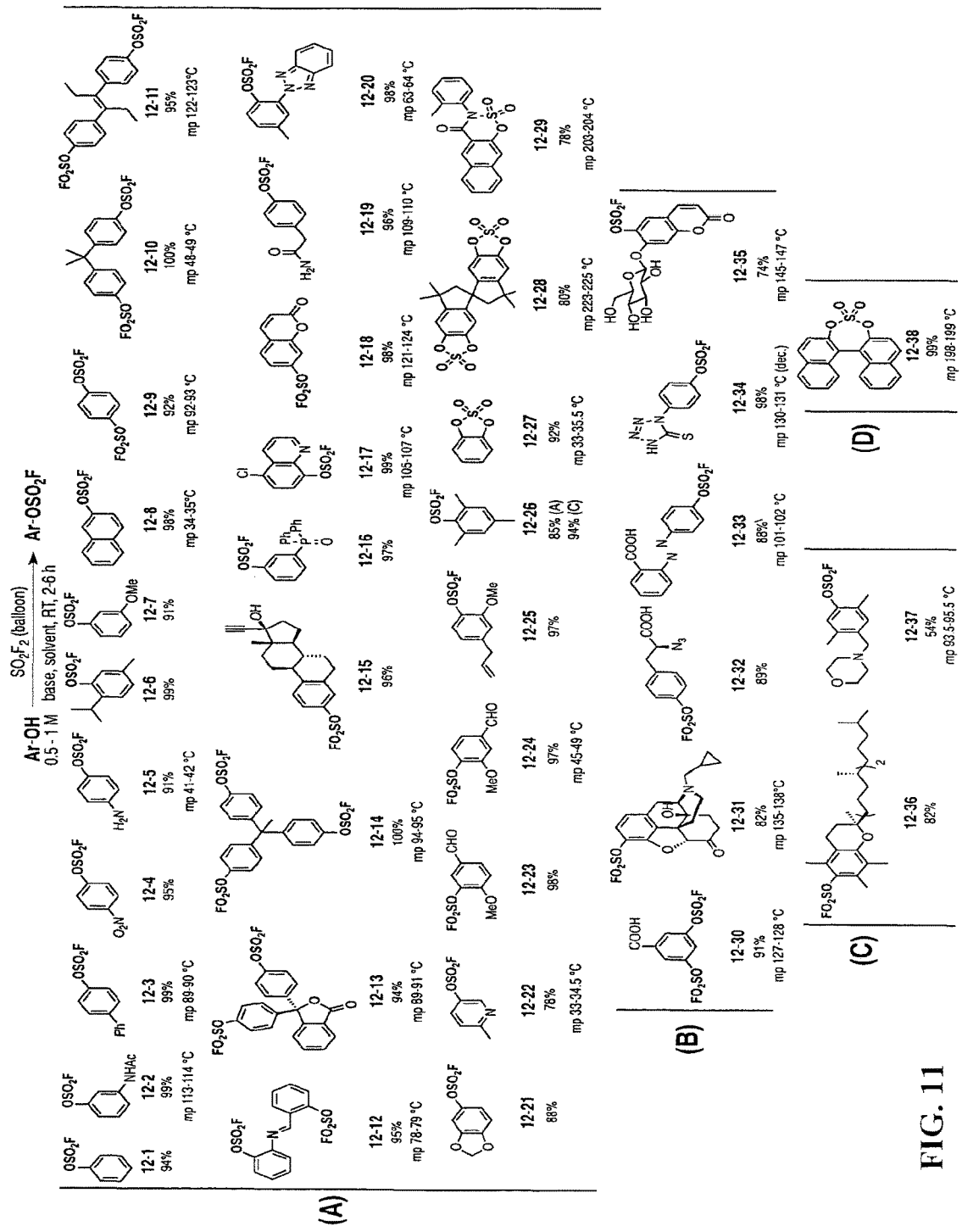
FIG. 11 shows aryl fluorosulfates prepared by a convenient procedure with gaseous $SO_2F_2$, in the presence of the following bases: (A) $Et_3N$ in $CH_2Cl_2$, (B) $Et_3N$ or $iPr_2NEt$ in biphasic mixture ($CH_2Cl_2$/water), (C) NaH in THF, (D) DBU in MeCN.

The reaction of $SO_2F_2$ with alcohols reaches its zenith for aromatic substrates, since the derived aryloxyfluorosulfates are very stable. Even more importantly for biological applications, aromatic alcohols undergo selective modification by $SO_2F_2$ gas, leaving aliphatic alcohols, aliphatic and aromatic amines, and carboxylates untouched. A wide variety of phenols can be converted to fluorosulfates in quantitative yields by exposure to gaseous $SO_2F_2$ and triethylamine (FIG. 11). For reactions described herein, $SO_2F_2$ was introduced from a balloon after the reaction flask was septum sealed, and the reactions were conducted with vigorous stirring of the liquid to facilitate gas dissolution in the condensed phases. The products were isolated by evaporative removal of solvent followed by acidic aqueous extraction to eliminate traces of base. Aqueous-organic biphasic conditions were found to suppress, almost completely, competitive fluorosulfonation of groups other than phenols in diversely functionalized molecules such as vancomycin. This selectivity for phenolic hydroxyls is remarkable; see FIG. 11, Panel B. Sterically hindered substrates performed best when phenolate anions were pre-formed. Cyclic sulfates are the exclusive products from 1,2-catechols under standard reaction conditions, obtained in much greater yields than is usually the case with sulfuryl chloride.

Since no reliable methods were previously available for the synthesis of fluorosulfates, their chemistry has remained mostly unexplored. The aryl-sulfate connection (Ar—O—$SO_2$—) is a vastly underappreciated linkage, now formed with sufficient reliability to be applied to a wide variety of targets in biology and materials science. For example, sulfates are phosphate isosteres, and several members of the alkaline phosphatase superfamily can cross-catalyze both phosphoryl and sulfuryl transfer. The reactivity of aryl fluorosulfates towards nucleophiles, including hydroxide, is much diminished compared to the analogous sulfonyl fluorides. Thus, the unassisted reaction of fluorosulfates with secondary amines requires elevated temperatures in organic solvents. A very good way to activate these reagents for synthetic chemistry is with tertiary amine catalysts such as DBU as described below. The process can also be facilitated by vigorous stirring with an immiscible buffered aqueous phase. The blending of water with miscible cosolvents such as THF or acetonitrile will also aid the process, but with longer time for completion. A benefit of the two-phase process previously noted but not widely appreciated is that the interfacially-controlled biphasic reactions are usually cleaner than their homogeneous counterparts, even if rates are similar. Water-tolerant or water-assisted reactions, such as the addition of nucleophiles to arylfluorosulfates, preferably are tried first in a two-phase format with organic solvent. The productive interplay between $O_2S$—F and $F^-/H^+$ interactions makes this especially true for SuFEx chemistry, as highlighted in FIG. 2.

The synthesis and use of aryl fluorosulfates finds another powerful set of applications when silicon is brought into play. Aryl silyl ethers are excellent substrates for conversion to fluorosulfates with sulfuryl fluoride gas in the presence of catalytic amounts of 1,8-diazabicyclo[5.4.0]undec-7-ene (DBU, FIG. 12, reaction A). Trimethylsilyl ethers to give fluorosulfates rapidly (substantially complete within minutes or seconds), whereas the bulkier tert-butyldimethylsilyl group requires several hours for the reaction to reach completion.

Figure 12:
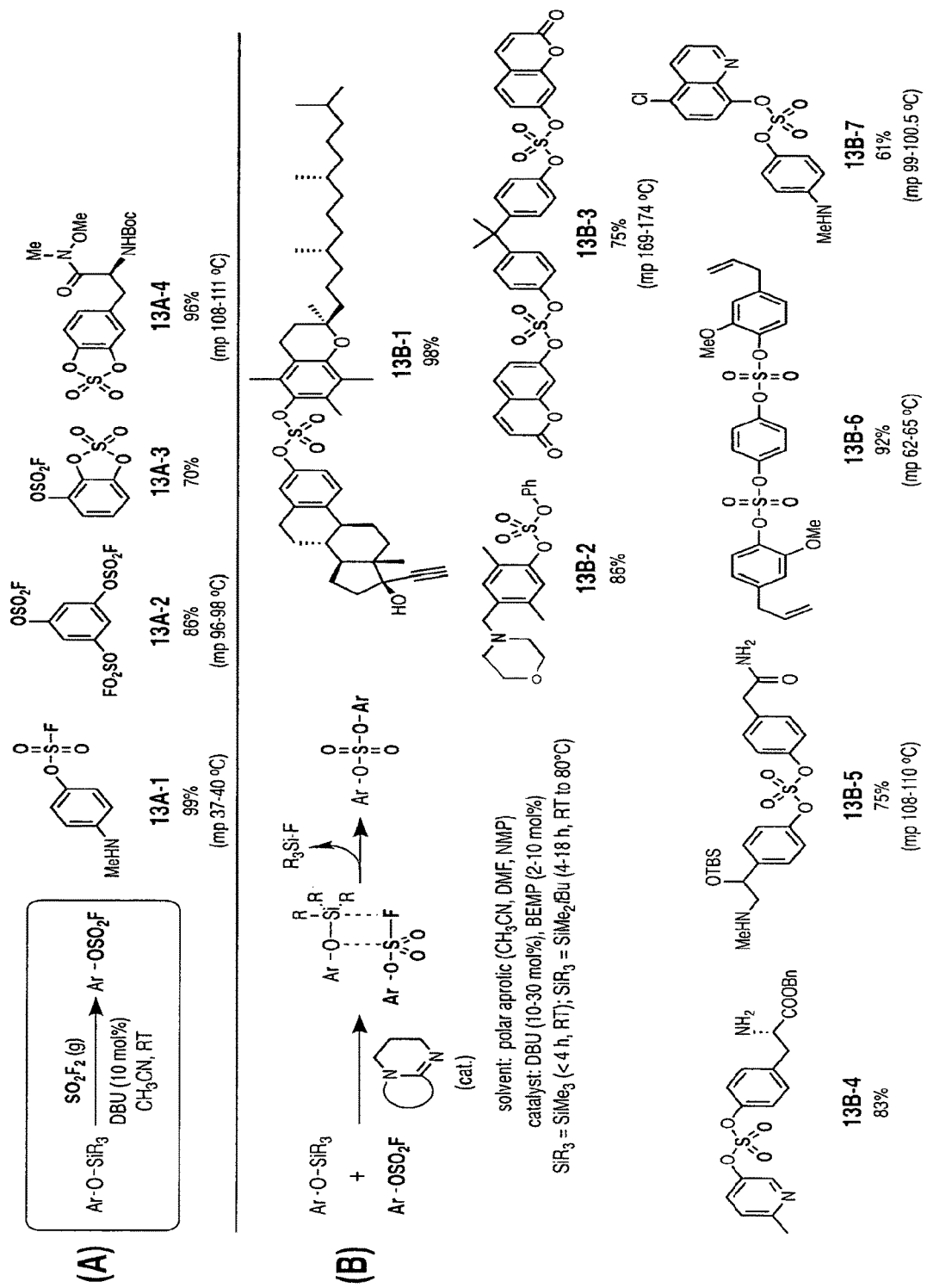
FIG. 12 illustrates DBU-mediated conversions of aryl silyl ethers to fluorosulfates and diarylsulfates. The dotted lines in reaction B are meant to show connectivity, not mechanism.

In a similar fashion, Lewis bases such as DBU mediate coupling between silyl ethers and fluorosulfates, representing the best synthesis of stable sulfate connections (FIG. 12, reaction B). Arylsulfates are generated in high yields with only inert (and sometimes volatile) silyl fluorides as byproducts. A wide variety of functional groups can be tolerated (FIG. 12), limited only by steric bulk at silicon and the presence of acidic protons that can quench the basic catalyst.

The conversion of aromatic silyl ethers into fluorosulfates and diarylsulfates is quite different from the popular use of silyl sulfonates (usually triflates) as catalysts in processes such as acetalization, aldol, and allylation reactions. In these and many other cases, the reaction is fundamentally one of electron deficiency, being accelerated by the Lewis acidity of silyl sulfonate; the electron-rich silicon component (silyl enol ether or allyl) is nucleophilic enough to capture an activated intermediate. Silicon-oxygen bonds are swapped, or Si—C is exchanged for Si—O. In the present case, the reaction is electron-rich, pushed by base catalyst and the ability of sulfuryl and/or silicon centers to achieve higher coordination number and become nucleophilic. The sulfuryl-F bond is strong enough to avoid unwanted side reactions while allowing fluorine to be delivered to silicon as the thermodynamically favored destination.

Figure 13:
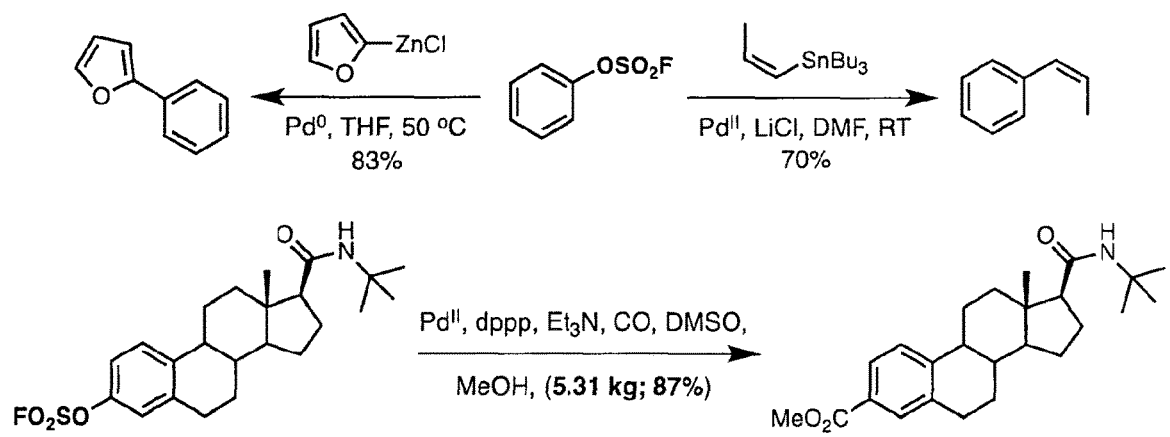
FIG. 13 illustrates aryl fluorosulfates in Pd-catalyzed coupling reactions.

Another important property of aromatic fluorosulfates is their ability to participate in transition metal catalyzed coupling reactions (FIG. 13). The participation of fluorosulfates as electrophilic components in Negishi and Stille cross-couplings (G. P. Roth, C. E. Fuller, *J. Org. Chem.* 1991, 56, 3493-3496), as well as palladium catalyzed alkoxycarbonylation reactions ((a) G. P. Roth, J. A. Thomas, *Tetrahedron Lett.* 1992, 33, 1959-1962. (b) G. P. Roth, C. Sapino, *Tetrahedron Lett.* 1991, 32, 4073-4076). Competition studies between phenyl fluorosulfate and phenyl triflate showed these groups to have similar coupling rates with an organotin reagent. Fluorosufate also has utility as an inexpensive triflate alternative (M. A. McGuire, E. Sorenson, F. W. Owings, T. M. Resnick, M. Fox, N. H. Baine, *J. Org. Chem.* 1994, 59, 6683-6686). Fluorosulfate prepared from the corresponding phenol and fluorosulfonic acid anhydride, the most common procedure at the time, engaged in efficient palladium catalyzed methoxycarbonylation on a 50-gallon scale.

Figure 14:
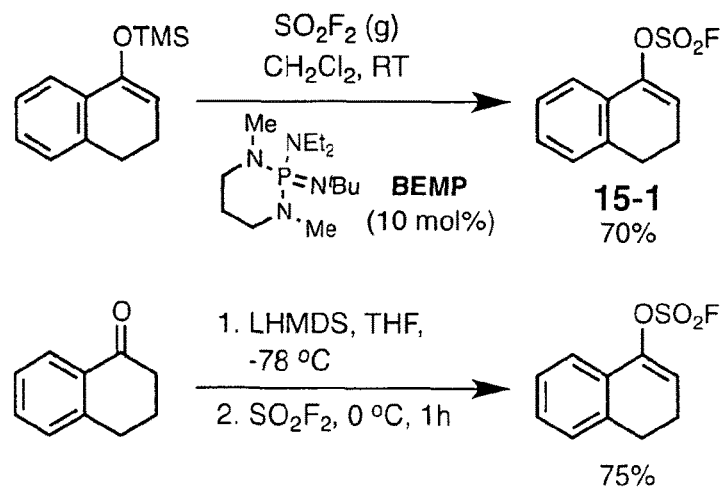
FIG. 14 illustrates preparations of enol fluorosulfates.

The replacement of triflate (OTf) with fluorosulfate ($OSO_2F$) was also shown to be practical for enol ethers. Thus, fluorosulfonyl enolates participate in Stille (G. P. Roth, C. Sapino, *Tetrahedron Lett.* 1991, 32, 4073-4076) and Suzuki cross-couplings (L. N. Pridgen, G. K. Huang, *Tetrahedron Lett.* 1998, 39, 8421-8424), and can also be used as precursors to allenes (J. Kant, J. A. Roth, C. E. Fuller, D. G. Walker, D. A. Benigni, V. Farina, *J. Org. Chem.* 1994, 59, 4956-4966) and alkynes (M. Y. Lebedev, E. S. Balenkova, Zh. *Org. Khim.* 1988, 24, 1156-1161). We have found $SO_2F_2$ to be an effective reagent for the synthesis of fluorosulfonyl enol ethers from the related lithium enolate or silyl ether (FIG. 14).

Figure 15:
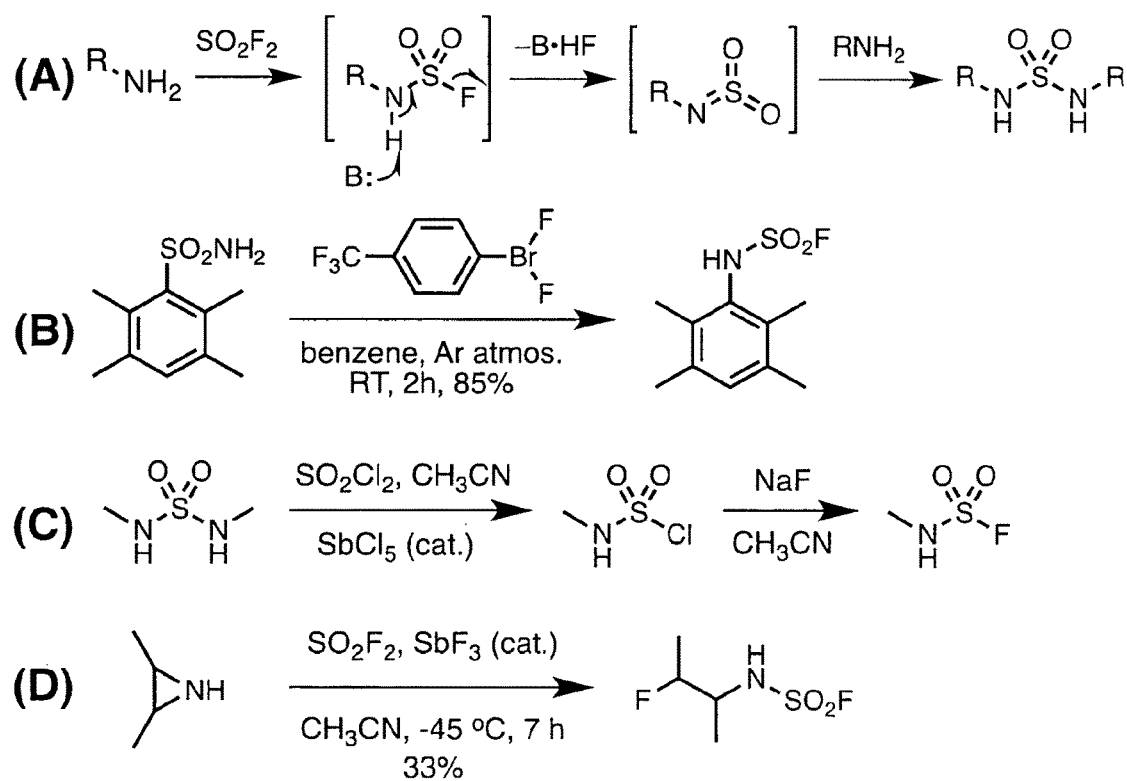
FIG. 15 illustrates, in Panels B-D, preparations of N-monosubstituted sulfamoyl fluorides; Panel A provides a comparison with the direct reaction of primary amines with $SO_2F_2$, which does not result in N-monosubstituted sulfamoyl fluoride formation.

Primary amines are rapidly fluorosulfonylated by $SO_2F_2$ gas, but the resulting adducts undergo facile elimination to azasulfene intermediates by virtue of the acidic nature of the N-sulfamoyl proton. Capture by amine provides symmetrically substituted sulfamides (FIG. 15, Panel A). A few reports are available on the synthesis of monosubstituted sulfamoyl fluorides by other means. These include Hofmann rearrangement of aryl sulfonamides (FIG. 15, Panel B), halide exchange of parent alkyl sulfamoyl chlorides (FIG. 15, Panel C), and ring opening of an aziridine under fluorinating conditions (FIG. 15, Panel D). All of these processes were performed under acidic or neutral conditions to avoid the aforementioned elimination of HF from the products.

Figure 16:
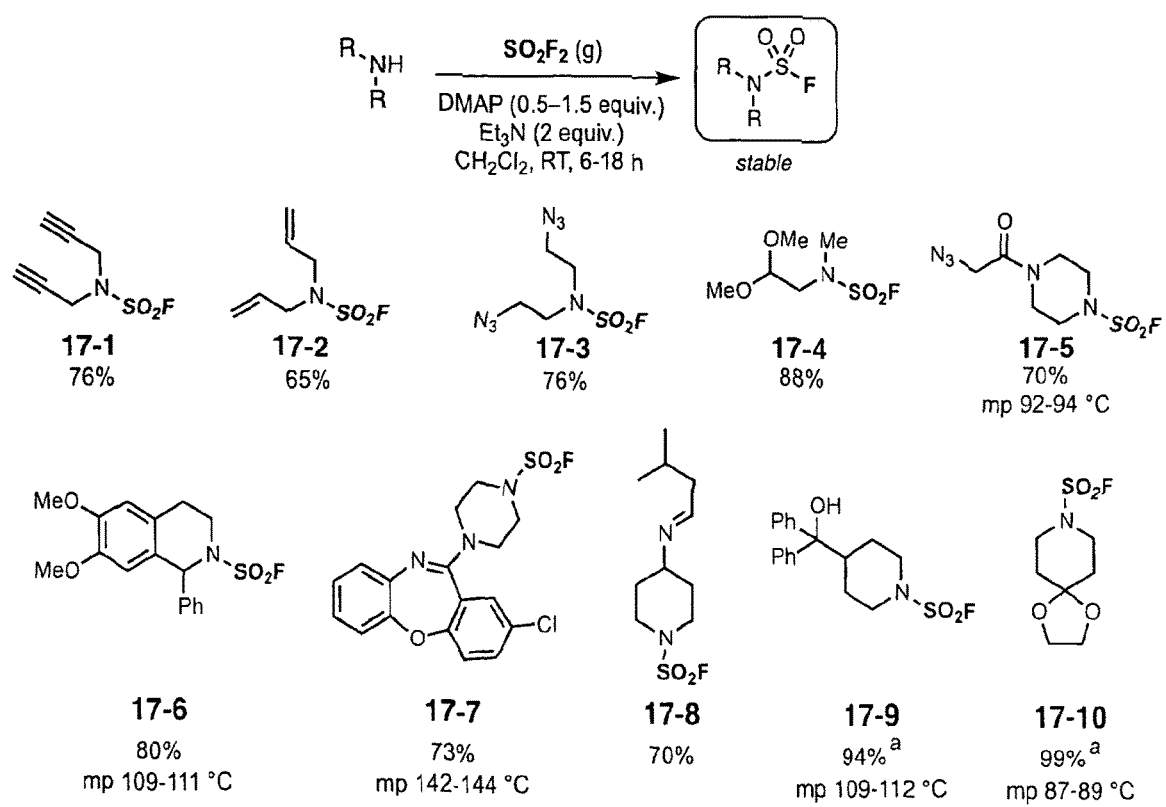
FIG. 16 illustrates formation of N-disubstituted sulfamoyl fluorides, with selected examples. Yields are of analytically pure material isolated after extraction. (a) DMAP (30 mol %), MgO (5 equiv.), 4/1 $CH_2Cl_2$/$H_2O$, RT, 18 hours.

In contrast, secondary amines react smoothly with $SO_2F_2$ to give N-disubstituted sulfamoyl fluorides as remarkably stable compounds, dramatically more robust than analogous chlorides (FIG. 16). Typically, an activating agent such as DMAP or DABCO is required, ranging from 0.5 equiv. for cyclic amines (exothermic reaction) to a full equivalent for acyclic amines. A variety of solvents can be used, with $CH_2Cl_2$ or THF providing the best reaction rates, and the reaction setup is identical to that described above for the synthesis of fluorosulfates (FIG. 11). The resulting sulfamoyl fluorides are purified by a simple acidic wash. Poor nucleophiles such as disubstituted anilines do not participate in the reaction with $SO_2F_2$ under these conditions within a reasonable period of time.

Figure 17:
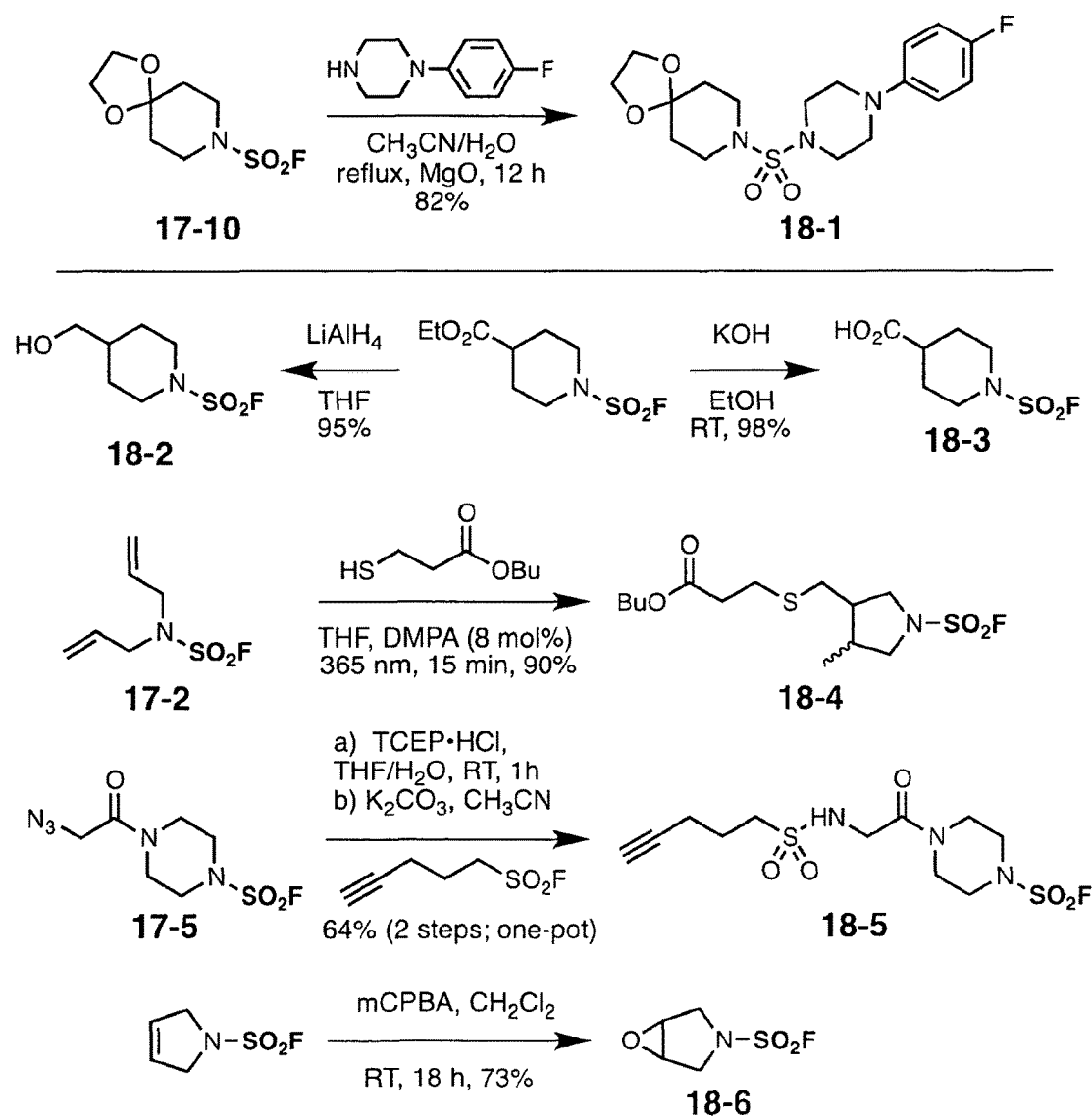
FIG. 17 provides (Top) example of sulfamoyl fluoride substitution by secondary amine; (Bottom) examples of transformations performed in the presence of the sulfamoyl fluoride moiety.
Figure 18:
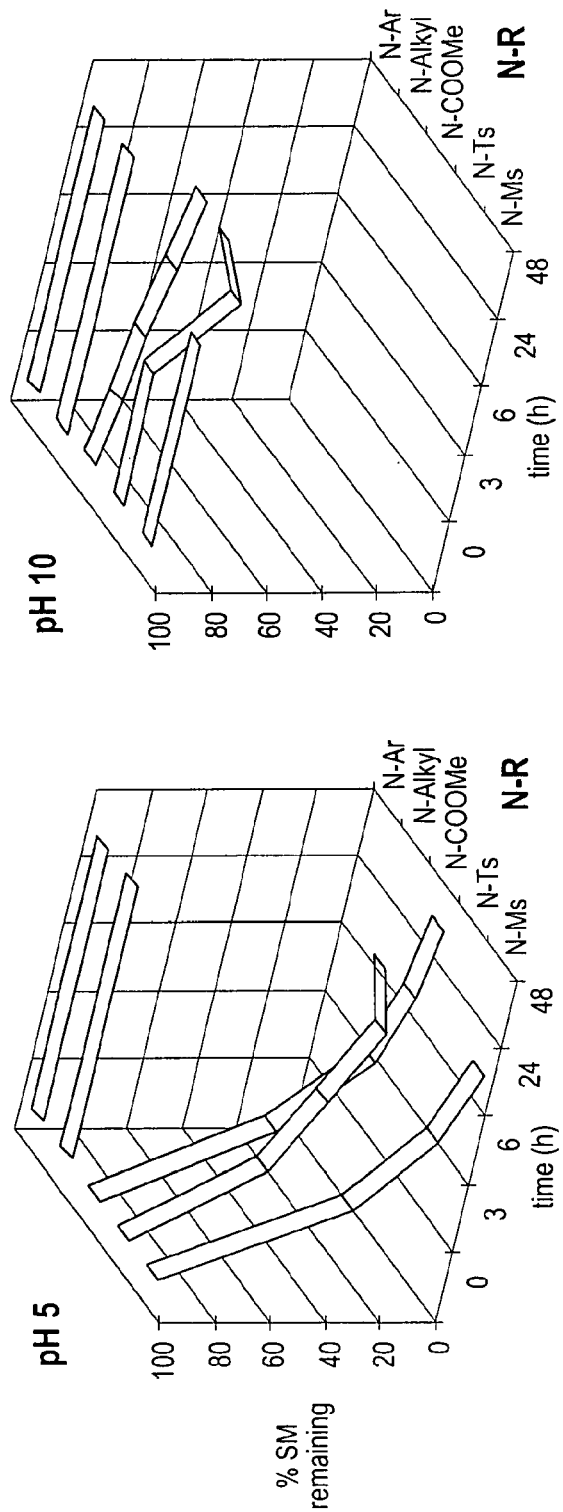
FIG. 18 graphically illustrates loss of sulfonimidoyl fluorides as a function of pH and nitrogen substituent.

We have found N-disubstituted sulfamoyl fluorides to be stable toward hydrolysis under basic conditions at room temperature for more than a week. Nucleophilic displacement of fluoride in this system requires heating and some assistance for the departure of fluoride by a hydrogen-bonding solvent, such as water (FIG. 17, top). The reaction is likely to have both $S_N1$ and $S_N2$ character, depending on the nature of the substituents and nucleophile. Furthermore, this type of sulfamoyl fluoride is remarkably inert toward a wide range of nucleophiles at room temperature in organic solvents, including amines, phosphines, thiols, organolithium and Grignard reagents, hydride, phenoxide, and hydroxide. FIG. 17 shows results from evaluations of the compatibility of the $R_2NSO_2F$ group with a variety of useful synthetic transformations, including those involving strong nucleophiles, reducing agents, oxidants, radicals, and strong acids and bases.

Three key features characterize the SuFEx reactions described herein. First, the $SO_2$—bond is unusually strong, so that undesired substitution (such as hydrolysis) is minimized. This allows precise modifications of complex targets such as biopolymers. Second, the fluoride radical is inaccessibly energetic, and so radical pathways that complicate the chemistry of other sulfonyl halides do not exist for sulfonyl fluorides. Third, two partners offer versatile ways to make and activate $SO_2$—F bonds. The proton forms unusually strong hydrogen bonds to fluoride. Even weakly acidic solvents, additives, and especially interfaces can thereby assist the heterolytic cleavage of the $SO_2$—F bond. Furthermore, the bifluoride ion ($HF_2^-$) is an excellent source of moderately nucleophilic fluoride for substitution reactions. Under non-protic conditions, silicon is useful, as Si and F form the strongest single bond in nature, allowing for the rapid formation of $SO_2$—O bonds from very stable silyl ether precursors.

These factors allow for robust methods for the synthesis of carbon-, oxygen-, and nitrogen-substituted sulfonyl fluorides (sulfonyl fluorides, fluorosulfates, and sulfamoyl fluorides), spanning a wide range of stabilities and allowing them to be used in a predictable and powerful manner in a variety of settings. For synthetic chemists, the fluorosulfate group can function as an inexpensive triflate alternative. With regard to medicinal chemistry, fluorosulfate and sulfamoyl fluoride groups are useful pharmacophores, and controllable covalent modifiers of biomolecules. In all applications, simple, inexpensive, and easily scalable preparative methods are strongly enabling; we hope that those shown here using sulfuryl fluoride gas will spur the development of fluorosulfuryl building blocks for many useful purposes. The capacity to ignore the irrelevant and respond forcefully to the desired target or condition makes $SO_2F$ groups particularly useful to probe complex molecular landscapes such as protein surfaces, or make small-molecule connections with absolute reliability.

Hydrolysis and Conversion of $ArOSO_2F$ groups to ArOH or $ArO$—$SO_3^-$ Groups.

In addition to providing biologically active compounds, the $ArOSO_2F$ group also can be utilized as a simple and selective protecting group for any ArOH and $ArOSO_3^-$ groups or a convenient means for preparing $ArOSO_3^-$ salts. For example, $ArOSO_2F$ compounds can be selectively reductively hydrolyzed with aqueous sulfite to afford the corresponding ArOH compounds in very high yield. This facile hydrolysis can be achieved by simply stirring the $ArOSO_2F$ compound with an aqueous sulfite salt such as potassium sulfite, sodium sulfite, and the like (e.g., about 20 mM to about 2 M sulfite in water). Alternatively, the $ArOSO_2F$ compounds can be hydrolyzed to $ArOSO_3^-$ salts by reaction with anhydrous ammonia in methanol in the presence of a carbonate salt such as potassium carbonate or cesium carbonate (e.g., about 2 molar equivalents of potassium or cesium carbonate). The reaction to form $ArOSO_3^-$ is rapid and clean, unlike most syntheses of such compounds. For example, the 4-fluorosulfonyloxyphenylacetamide was readily converted to 4-hydroxyphenylacetamide and to phenylacetamide-4-sulfate in essentially quantitative yields by these procedures.

The following non-limiting examples are provided to further illustrate various features and aspects of the compositions and methods described herein.

EXAMPLE 1

EX. 1(A)

Abbreviations

BEMP=2-tert-butylimino-2-diethylamino-1,3-dimethylperhydro-1,3,2-diazaphosphorine, DBN=1,5-diazabicyclo[4.3.0]non-5-ene, DBU=1,8-diazabicyclo[5.4.0]undec-7-ene, LHMDS=lithium bis(trimethylsilyl)amide, TCEP=tris(2-carboxyethyl)phosphine hydrochloride, TMS=trimethylsilyl, TBS=tert-butyldimethylsilyl

EX. 1(B)

General Methods $^1$H and $^{13}$C NMR spectra were recorded on Bruker DRX-500, Bruker DRX-600, Bruker AMX-400 instruments and the chemical shifts (δ) are expressed in parts per million relative to residual $CHCl_3$, acetone, acetonitrile or DMSO as internal standards. Proton magnetic resonance ($^1$H NMR) spectra were recorded at 600, 500, or 400 MHz. Carbon magnetic resonance ($^{13}$C NMR) spectra were recorded at 150, 125, or 101 MHz. Fluorine magnetic resonance ($^{19}$F NMR) spectra were recorded at 376 MHz. NMR acquisitions were performed at 295 K unless otherwise noted. Abbreviations are: s, singlet; d, doublet; t, triplet; q, quartet, p, pentet; br s, broad singlet. Infrared spectra were recorded as pure undiluted samples using a THERMONICOLET AVATAR 370 Fourier transform infrared spectrometer with a SMART MIRACLE HATR attachment. Melting points (mp) were determined using a THOMAS-HOOVER melting point apparatus and are uncorrected. GC-MS data were recorded on an AGILENT 7890A GC system with an AGILENT 5975C Inert MSD system operating in the electron impact (EI+) mode [Method: $T_0$=50° C., t=2.25 min; $T_1$=300° C., ramp=60° C./min, then $T_1$=300° C., t=4 min]. HPLC was performed on an AGILENT 1100 LC/MSD with an Agilent 1100 SL mass spectrometer (electrospray ionization, ES) eluting with 0.1% trifluoroacetic acid in $H_2O$ and 0.05% trifluoroacetic acid in $CH_3CN$. High resolution mass spectrometry was performed on an Agilent ES-TOF instru-

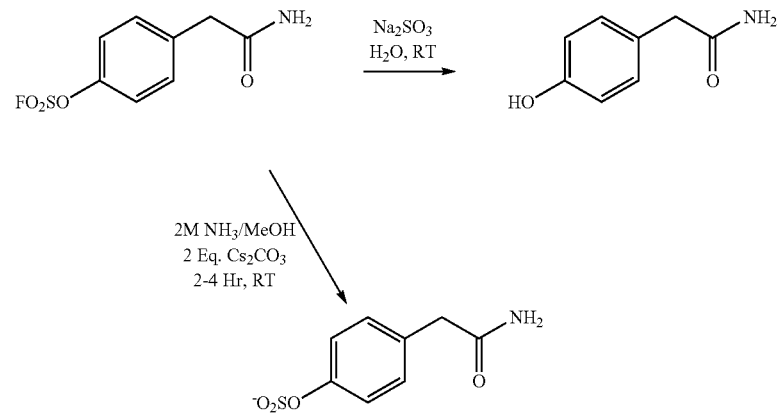

EX. 1(C)

Reactions Illustrating the Properties of Sulfonyl Fluorides vs. Other Sulfonyl Halides

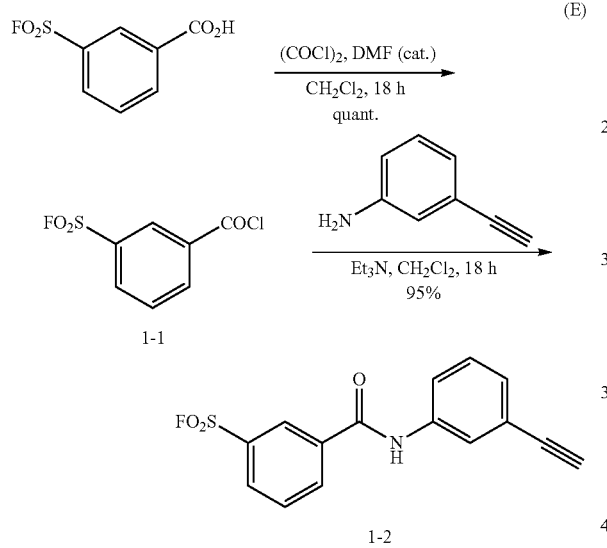

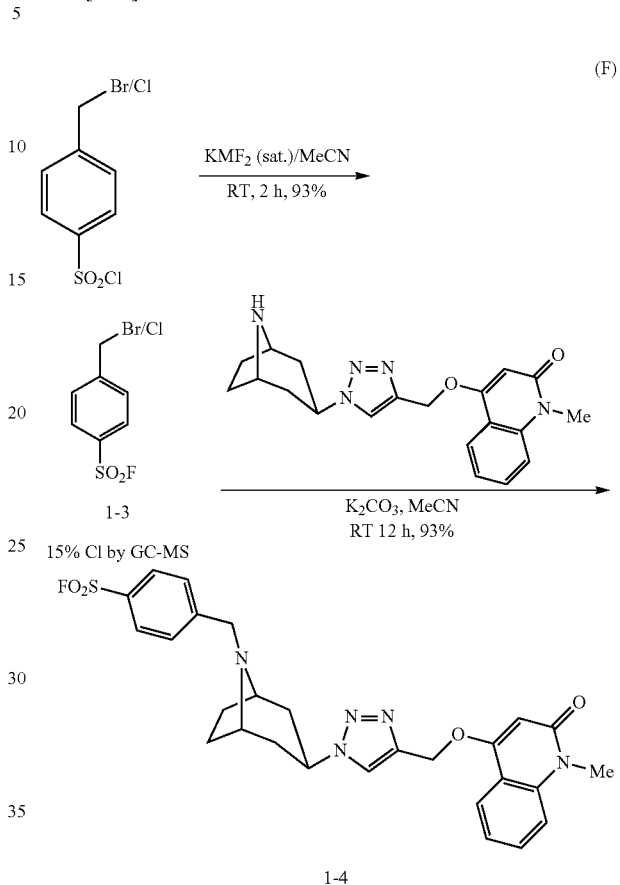

3-(Fluorosulfonyl)benzoyl chloride (1-1). 3-(Fluorosulfonyl)benzoic acid (2.1 g; 10 mmol) was dissolved in CH$_2$Cl$_2$ (20 mL) at room temperature and oxalyl chloride (40 mL of 1M solution in CH$_2$Cl$_2$, 2 equiv) was added at 0° C., followed by slow addition of DMF (0.2 mL). The reaction was stirred at room temperature for 6-8 hours. After that time, solvent and volatiles were removed by rotary evaporation to give 3-(fluorosulfonyl)benzoyl chloride as a yellow oil, which was used directly in the next step.

3-((3-Ethynylphenyl)carbamoyl)benzene-1-sulfonyl fluoride (1-2). After cooling to 0° C. on an ice bath, a solution of compound 1-1 in CH$_2$Cl$_2$ (20 mL) was treated with 3-ethynylaniline (1.2 g, 10 mmol) in CH$_2$Cl$_2$ (20 mL), followed by slow addition of Et$_3$N (1.5 mL, 11 mmol, 1.1 equiv). The reaction mixture was stirred at room temperature overnight, monitored by TLC. After that time, the reaction was washed twice with 1N HCl, extracted with CH$_2$Cl$_2$ (100 mL×2). The combined organic layers were dried over Na$_2$SO$_4$ and concentrated. The crude product was purified by column chromatography (3:1 hexane:EtOAc, R$_f$ 0.35) to give the desired product as a white solid in 95% yield (2.85 g for 2 steps). mp 155-157° C. $^1$H NMR (400 MHz, CDCl$_3$) δ 8.60 (s, 1H), 8.40 (d, J=8.0 Hz, 1H), 8.24 (d, J=8.0 Hz, 1H), 7.88-7.84 (m, 2H), 7.70 (m, 1H), 7.33 (t, J=8.0 Hz, 1H), 7.26-7.23 (m, 1H), 3.50 (s, 1H); $^{13}$C NMR (101 MHz, CDCl$_3$) δ 165.8, 139.7, 138.0, 136.0, 134.7 (d, J=25 Hz), 132.2, 131.6, 130.0, 129.3, 128.7, 125.3, 124.3, 122.5, 84.0, 78.9; $^{19}$F NMR (376 MHz, CDCl$_3$) δ +64.7; ESI-MS (m/z): 304 [MH]$^-$.

4-(Bromomethyl)benzene-1-sulfonyl fluoride (1-3) was obtained in 93% yield as a white solid (0.9 g). GC-MS analysis revealed contamination of the titled compound with 15% of the chloro analogue (4-(chloromethyl)benzene-1-sulfonyl fluoride). This mixture was used in the next step without purification.

4-(((1R,3S,5S)-3-(4-(((1-Methyl-2-oxo-1,2-dihydroquinolin-4-yl)oxy)methyl)-1H-1,2,3-triazol-1-yl)-8-azabicyclo[3.2.1]octan-8-yl)methyl)benzene-1-sulfonyl fluoride (1-4)

Crude 4-(bromomethyl)benzene-1-sulfonyl fluoride (51 mg; 0.2 mmol) and the 3-triazolyl-8-azabicyclo[3.2.1]octane amine (see Grimster, N. P.; Stump, B.; Fotsing, J. R.; Weide, T.; Talley, T. T.; Yamauchi, J. G.; Nemecz, A.; Kim, C.; Ho, K.-Y.; Sharpless, K. B. *J Am Chem Soc* 2012, 134, 6732-6740.) (73 mg; 0.2 mmol) were mixed in CH$_3$CN (1 mL) at room temperature. Potassium carbonate (30 mg; 1.1 equiv) was added and the reaction mixture was stirred at room temperature overnight, monitored by LC-MS. After completion, the reaction mixture was concentrated by rotary evaporation and the residue purified by column chromatography (6/1 EtOAc/MeOH), giving the desired product as a yellow oil (99 mg, 93% yield). $^1$H NMR (400 MHz, CD$_3$OD) δ 8.28 (s, 1H), 7.97 (d, J=8.0 Hz, 2H), 7.82 (d, J=8.0 Hz, 1H), 7.77 (d, J=8.0 Hz, 2H), 7.56 (m, 1H), 7.39 (d, J=8.0 Hz, 1H), 7.16 (t, J=8.0 Hz, 1H), 6.14 (s, 1H), 5.27

(s, 2H), 4.95 (m, 1H), 4.90 (s, 1H), 3.81 (s, 2H), 3.38 (m, 2H), 2.34 (t, J=4.0 Hz, 2H), 2.22-2.19 (m, 2H), 2.08-2.01 (m, 2H), 1.97 (s, 1H), 1.84 (d, J=12.0 Hz, 2H); $^{13}$C NMR (101 MHz, CD$_3$OD) δ 165.4, 163.2, 150.0, 143.0, 140.6, 132.8, 132.5 (d, J=25 Hz), 131.1, 129.5, 124.5, 124.2, 123.3, 117.3, 115.7, 97.6, 63.1, 60.4, 56.1, 54.9, 38.7, 29.7, 27.2; $^{19}$F NMR (376 MHz, CD$_3$OD) δ +64.6; ESI-MS (m/z): 538 [MH]$^+$.

EX. 1(D)

Demonstration of Hydrolytic Stability of Sulfonimidoyl Fluorides

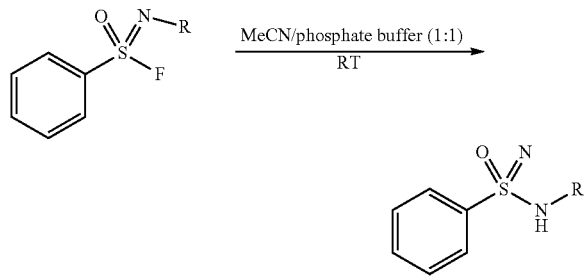

Figure 19:
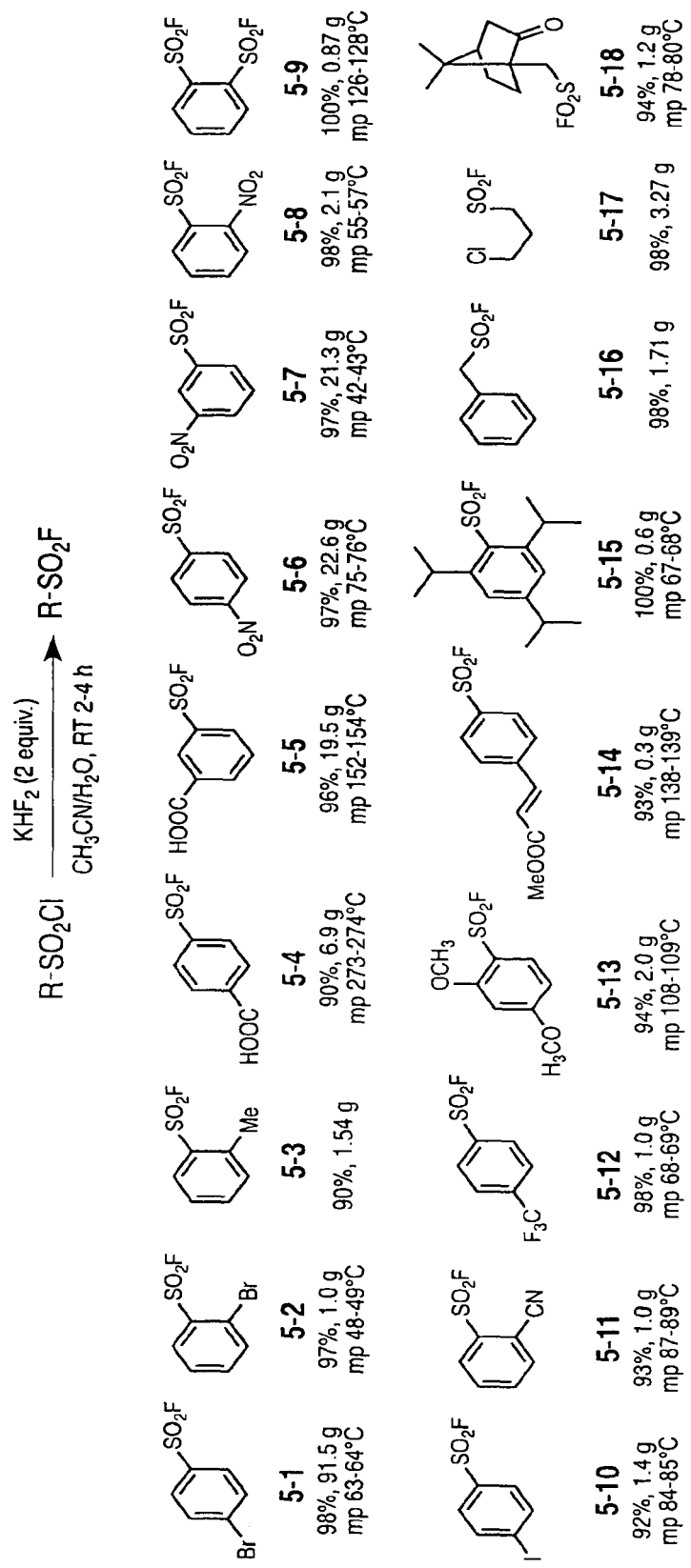
FIG. 19 provides examples of sulfonyl fluorides made from the corresponding chlorides using potassium bifluoride.

Sulfonimidoyl fluoride (1 mmol) was dissolved in acetonitrile (0.1 M), diluted with equal amount of buffer to initiate the hydrolysis process, and stirred at room temperature for several hours. Aliquots were taken at time periods and the composition of the mixture analyzed by mass spectrometry. FIG. 19 shows the loss of starting fluoride as a function of time.

Ex. 1(E)

Sulfonyl Fluorides Made with Potassium Bifluoride (see FIG. 19)

Representative procedure for the synthesis of sulfonyl fluorides using saturated aqueous KHF$_2$ and CH$_3$CN. 4-Bromobenzene-1-sulfonyl fluoride (5-1).

KHF$_2$ (71 g; 2.3 equiv) was dissolved in H$_2$O (200 mL) to make a saturated solution (endothermic reaction), which was treated with a solution of 4-bromobenzene-1-sulfonyl chloride (100 g, 1 equiv) in acetonitrile (400 mL). The reaction mixture was stirred at room temperature for 3 h, monitored by GC-MS. After that time, the reaction mixture was transferred to a separatory funnel and the organic layer was collected. The aqueous phase was extracted with EtOAc (300 mL), and the combined organic extracts were washed with 10% aqueous NaCl (2×), saturated sodium chloride (1x), dried over sodium sulfate, and concentrated by rotary evaporation to give the desired product as a white solid (91.5 g, 98% yield). mp 63-64° C. $^1$H NMR: (400 MHz, CDCl$_3$) δ 7.88 (dd, J=9.2 Hz, 2 Hz, 2H), 7.78 (dd, J=9.2 Hz, 2 Hz, 2H); $^{13}$C NMR: (101 MHz, CDCl$_3$) δ 133.1, 131.9 (d, J=25.5 Hz), 131.3, 129.8; $^{19}$F NMR (376 MHz, CDCl$_3$) δ +65.9; GC-MS: 4.68 min; EI (m/z): 240/238 [M]$^+$.

None of the sulfonyl fluoride compounds prepared by this procedure required extra purification.

2-Bromobenzene-1-sulfonyl fluoride (5-2): light yellow crystals (1.1 g, 97% yield). mp 48-49° C. $^1$H NMR (400 MHz, CDCl$_3$) δ 8.12 (dd, J=7.2 Hz, 2.4 Hz, 1H), 7.84 (dd, J=7.2 Hz, 1.6 Hz, 1H), 7.56 (m, 2H); $^{13}$C NMR (101 MHz, CDCl$_3$) δ 136.1, 135.9, 133.8 (d, J=23.9 Hz), 132.0, 127.9, 121.0; $^{19}$F NMR (376 MHz, CDCl$_3$) δ +57.4; GC-MS (t$_R$): 34.8 min; EI-MS (m/z): 240/238 [M]$^+$.

2-Methylbenzene-1-sulfonyl fluoride (5-3): colorless oil (1.54 g, 90% yield). $^1$H NMR (400 MHz, CDCl$_3$) δ 8.01 (d, J=8 Hz, 1H), 7.64-7.60(m, 1H), 7.43-7.38 (m, 2H), 2.68 (s, 3H); $^{13}$C NMR (101 MHz, CDCl$_3$) δ 139.0, 135.4, 132.9, 132.3 (d, J=22.2 Hz), 130.0, 126.7, 20.2; $^{19}$F NMR (376 MHz, CDCl$_3$) δ +59.8; GC-MS (t$_R$): 4.1 min; EI-MS (m/z): 174 [M]$^+$.

4-(Fluorosulfonyl)benzoic acid (5-4): white solid (6.9 g, 90% yield) prepared by the above procedure using THF instead of acetonitrile. mp 273-274° C. $^1$H NMR (400 MHz, CD$_3$OD-d$_4$) δ 8.21-8.18 (m, 2H), 8.07-8.03 (m, 2H); $^{13}$C NMR (101 MHz, CD$_3$OD-d$_4$) δ 167.3, 138.9, 137.6 (d, J=25.3 Hz), 132.0, 129.7; $^{19}$F NMR (376 MHz, CD$_3$OD-d$_4$) δ +64.2; EI-MS (m/z): 205 [M]$^+$.

3-(Fluorosulfonyl)benzoic acid (5-5): white solid (19.5 g, 96% yield) prepared by the above procedure using THF instead of acetonitrile. mp 152-154° C. $^1$H NMR (400 MHz, CD$_3$OD-d$_4$) δ 8.45 (s, 1H), 8.33 (d, J=8 Hz, 1H), 8.12 (d, J=8 Hz, 1H), 7.71 (t, J=8 Hz, 1H); $^{13}$C NMR (101 MHz, CD$_3$OD-d$_4$) δ 166.9, 137.7, 134.7 (d, J=25.3 Hz), 134.2, 133.2, 131.7, 130.3; $^{19}$F NMR (376 MHz, CD$_3$OD-d$_4$) δ +64.5; EI-MS (m/z): 205 [M]$^+$.

4-Nitrobenzene-1-sulfonyl fluoride (5-6): white solid (22.6 g, 97% yield). mp 75-76° C. $^1$H NMR (400 MHz, CDCl$_3$) δ 8.49 (d, J=8 Hz, 2H), 8.25 (d, J=8 Hz, 2H); $^{13}$C NMR (101 MHz, CDCl$_3$) δ 151.9, 138.4 (d, J=27.3 Hz), 130.1, 125.0; $^{19}$F NMR (376 MHz, CDCl$_3$) δ +66.0; GC-MS (t$_R$): 4.9 min; EI-MS (m/z): 205 [M]$^+$.

3-Nitrobenzene-1-sulfonyl fluoride (5-7): white solid (22.3 g, 97% yield). mp 42-43° C. $^1$H NMR (400 MHz, CDCl$_3$) δ 8.86 (t, J=2.4 Hz, 1H), 8.64 (d, J=8 Hz, 1H), 8.35 (d, J=8 Hz, 1H), 7.93 (t, J=8 Hz, 1H); $^{13}$C NMR (101 MHz, CDCl$_3$) δ 148.4, 134.9 (d, J=28.3 Hz), 133.8, 131.4, 130.0, 123.9; $^{19}$F NMR (376 MHz, CDCl$_3$) δ +65.9; GC-MS (t$_R$): 4.85 min; EI-MS (m/z): 205 [M]$^+$.

2-Nitrobenzene-1-sulfonyl fluoride (5-8): yellow solid (2.1 g, 98% yield). mp 55-57° C. $^1$H NMR (400 MHz, CDCl$_3$) δ 8.23 (dd, J=8 Hz, 1.6 Hz, 1H), 8.04 (d, J=8 Hz, 1H), 7.97 (dt, J=8 Hz,1.6 Hz,1H), 7.88 (m,1H); $^{13}$C NMR (101 MHz, CDCl$_3$) δ 136.7, 133.4, 131.7, 126.8 (d, J=28.6 Hz), 125.8; $^{19}$F NMR (376 MHz, CDCl$_3$,) δ +64.5; GC-MS (t$_R$): 5.2 min; EI-MS (m/z): 205 [M]$^+$.

Benzene-1,2-disulfonyl difluoride (5-9): white solid (0.87 g, 100% yield). mp 126-128° C. $^1$H NMR (400 MHz, CDCl$_3$) δ 8.44 (dd, J=5.6 Hz, 3.2 Hz, 2H), 8.07 (dd, J=6 Hz, 3.2 Hz, 2H); $^{13}$C NMR (101 MHz, CDCl$_3$) δ 136.1, 133.5, 132.2 (d, J=28.7 Hz); $^{19}$F NMR (376 MHz, CDCl$_3$) δ +65.3; GC-MS (t$_R$): 5.15 min; ELMS (m/z): 242 [M]$^+$.

4-Iodobenzene-1-sulfonyl fluoride (5-10): white solid (1.4 g, 92% yield). mp 84-85° C. $^1$H NMR (400 MHz, CDCl$_3$) δ 8.02 (d, J=8.8 Hz, 2H), 7.71 (d, J=8.8 Hz, 2H), 7.84 (d, J=8.8 Hz, 2H); $^{13}$C NMR (101 MHz, CDCl$_3$) δ 139.03, 132.5 (d, J=25.5 Hz), 129.4, 104; $^{19}$F NMR (376 MHz, CDCl$_3$) δ +65.6; GC-MS (t$_R$): 5.0 min; ELMS (m/z): 286 [M]$^+$.

2-Cyanobenzene-1-sulfonyl fluoride (5-11): white solid (0.97 g, 97% yield). mp 87-89° C. $^1$H NMR (400 MHz, CDCl$_3$) δ 8.23-8.21 (m, 1H), 8.03-8.01 (m, 1H), 7.98-7.92 (m, 2H); $^{13}$C NMR (101 MHz, CDCl$_3$) δ 135.8,135.7, 134.7(d, J=26.5 Hz), 133.6, 130.8, 114.1, 111.5; $^{19}$F NMR (376 MHz, CDCl$_3$) δ +64.0; GC-MS (t$_R$): 5.0 min; ELMS (m/z): 185 [M]$^+$.

4-(Trifluoromethyl)benzene-1-sulfonyl fluoride (5-12): white crystalline solid (1.0 g, 98% yield). mp 68-69° C. $^1$H NMR (400 MHz, CDCl$_3$) δ 8.17 (d, J=8.4 Hz, 2H), 7.92 (d, J=8.4 Hz, 2H); $^{13}$C NMR (101 MHz, CDCl$_3$) δ 137.0 (q, J=33.5 Hz), 136.4 (d, J=26.7 Hz), 129.1, 126.9 (q, J=3.7 Hz), 122.7(q, J=271.7 Hz); $^{19}$F NMR (376 MHz, CDCl$_3$) δ +65.4, −64.0; GC-MS (t$_R$): 3.7 min; ELMS (m/z): 228 [M]$^+$.

2,4-Dimethoxybenzene-1-sulfonyl fluoride (5-13): white solid (2 g, 94% yield). mp 108-109° C. $^1$H NMR (400 MHz, CDCl$_3$) δ 7.41 (d, J=3.2 Hz, 1H), 7.24 (dd, J=9.2 Hz, 3.2 Hz, 1H), 7.04 (d, J=9.2 Hz,1H), 3.95 (s, 3H), 3.81 (s, 3H); $^{13}$C NMR (101 MHz, CDCl$_3$) δ 152.9,152.2, 123.6, 121.3(d, J=23.3 Hz), 114.9, 114.3, 56.9, 56.1; $^{19}$F NMR (376 MHz, CDCl$_3$) δ +58.6; GC-MS (t$_R$): 6.0 min; EI-MS (m/z): 236 [M]$^+$.

(E)-Methyl 3-(4-(fluorosulfonyl)phenyl)acrylate (5-14): white solid (0.3 g, 93% yield). mp 138-139° C. $^1$H NMR (400 MHz, CDCl$_3$) δ 8.01 (d, J=8.4 Hz, 2H), 7.74 (d, J=8.4 Hz,2H), 7.69(d, J=16 Hz, 1H), 6.58 (d, J=16 Hz, 1H), 3.83(s, 3H); $^{13}$C NMR (101 MHz, CDCl$_3$) δ 166.2, 141.6, 141.4, 133.6 (d, J=25.1 Hz), 129.0, 128.7, 122.8, 52.8; $^{19}$F NMR (376 MHz, CDCl$_3$) δ +65.6; GC-MS (t$_R$): 5.9 min; ELMS (m/z): 244 [M]$^+$.

2,4,6-Triisopropylbenzene-1-sulfonyl fluoride (5-15): white solid (0.6 g, 100% yield). mp 67-68° C. $^1$H NMR (400 MHz, CDCl$_3$) δ 7.25 (s, 2H), 3.96 (dq, J=6.8 Hz, 2.4 Hz, 2H), 2.95 (q, J=6.8 Hz, 1H), 1.30 (d, J=6.8 Hz, 12H), 1.27 (d, J=6.8 Hz, 6H); $^{13}$C NMR (101 MHz, CDCl$_3$) δ 155.3, 150.7, 128.0 (d, J=18.4 Hz), 124.0, 34.4, 30.1, 24.5, 23.4; $^{19}$F NMR (376 MHz, CDCl$_3$) δ +72.2; GC-MS (t$_R$): 5.7 min; ELMS (m/z): 286 [M]$^+$.

Phenylmethanesulfonyl fluoride (PMSF) (5-16): white solid (1.7 g, 98% yield). mp 93-94° C. $^1$H NMR (400 MHz, CDCl$_3$) δ 7.46-7.44 (m, 5H), 4.59 (d, J=4 Hz, 2H); $^{13}$C NMR (101 MHz, CDCl$_3$) δ 130.8, 130.0, 129.4, 125.6, 56.9 (d, J=17.2 Hz); $^{19}$F NMR (376 MHz, CDCl$_3$) δ +50.5; GC-MS (t$_R$): 4.5 min; EI-MS (m/z): 174 [M]$^+$.

3-Chloropropane-1-sulfonyl fluoride (5-17): light yellow oil (3.27 g, 98% yield) prepared by the above procedure but omitting acetonitrile (the reaction was performed in suspension on water). $^1$H NMR (400 MHz, CDCl$_3$) δ 3.70 (t, J=6.4 Hz, 2H), 3.58 (dt, J=4.8 Hz, 7.6 Hz, 2H), 2.40 (m,2H); $^{13}$C NMR (101 MHz, CDCl$_3$) δ 48.0 (d, J=17.7 Hz), 41.6, 26.4; $^{19}$F NMR (376 MHz, CDCl$_3$) δ +53.9; GC-MS (t$_R$): 3.7 min; EI-MS (m/z): 160 [M]$^+$.

((1R,4R)-7,7-Dimethyl-2-oxobicyclo[2.2.1]heptan-1-yl) methanesulfonyl fluoride (5-18): colorless crystals (1.2 g, 94% yield). mp 78-80° C. $^1$H NMR (400 MHz, CDCl$_3$) δ 3.82 (dd, J=15.2 Hz, 2.8 Hz, 1H), 3.29 (dd, J=15.2 Hz, 2.8 Hz, 1H), 2.45-2.29 (m, 2H), 2.16 (t, J=4.4 Hz, 1H), 2.07(m, 1H), 1.98 (d, J=18.8 Hz, 1H), 1.73(m, 1H), 1.48(m, 1H),1.11 (s, 3H), 0.90 (s, 3H); $^{13}$C NMR (101 MHz, CDCl$_3$) δ 213.0, 57.7, 48.3, 48.1 (d, J=19.4 Hz), 42.8, 42.2, 26.7, 25.1, 19.5; $^{19}$F NMR (376 MHz, CDCl$_3$) δ +63.7; GC-MS (t$_R$): 5.34 min; EI-MS (m/z): 234 [M]$^+$.

EX. 1(F)

Sulfonyl Fluorides made from Sulfonic Acids

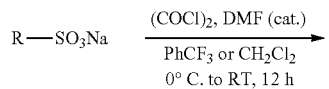

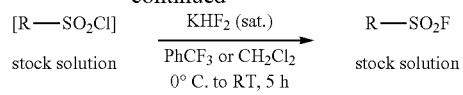

Representative procedure for the synthesis of 3-azidopropane-1-sulfonyl fluoride (6-1). Sodium 3-azidopropane-1-sulfonate was obtained as a white solid (16.25 g, 87% yield) according to the procedure in Kong, X., et al. US 2008/0146642 A1.

Sodium 3-azidopropane-1-sulfonate (9.35 g, 50 mmol) was suspended in trifluoromethylbenzene (20 mL, 2.5M). Oxalyl chloride (4.3 mL; 50 mmol) was added to the reaction mixture at 0° C., followed by 5 drops of DMF. The resulting white suspension was stirred at room temperature under a dry atmosphere (nitrogen or a drying tube packed with desiccant). The reaction mixture was then added to a cold saturated aqueous solution of KHF$_2$ (approx. 4.5 M, 2.5 equiv) in a plastic bottle and the biphasic suspension was stirred at room temperature. GC-MS analysis after five hours showed full conversion, and the mixture was filtered into a reparatory funnel using extra organic solvent to wash the solid material. The organic phase was separated, washed with brine, and dried over anhydrous sodium sulfate. The separated aqueous phase was back-extracted with trifluoromethylbenzene, and the organic phase was dried and combined with the primary organic solution. Since 3-azidopropane-1-sulfonyl fluoride is a volatile compound, the solution was stored and used as a stock solution. The concentration of sulfonyl fluoride was established as 16 wt-% by quantitative $^1$H NMR against the solvent, consistent with a quantitative yield. The analogous procedure was performed using 0.5M CH$_2$Cl$_2$ in MeCN as the solvent, a 1M concentration of 3-azidopropane-1-sulfonate (25 mmol scale), and 1.5 equiv. of oxalyl chloride gave the sulfonyl fluoride 6-1 in 87% yield (23 wt-% stock solution) measured by $^1$H NMR integration. $^1$H NMR (400 MHz, CDCl$_3$) δ 3.54 (t, J=6.3 Hz, 2H), 3.51-3.45 (m, 2H), 2.19 (dq, J=8.8, 6.4 Hz, 2H); $^{13}$C NMR (101 MHz, CDCl$_3$) δ 48.9, 48.1 (d, J=17.6 Hz), 23.5; $^{19}$F NMR (376 MHz, CDCl$_3$) δ 53.7; R$_f$ (9:1 hexane:EtOAc): 0.22; GC (t$_R$): 3.8 min; EI-MS (m/z): 139 [M−28]$^+$.

3-Azidobutane-1-sulfonyl fluoride (6-2). Sodium 3-azidobutane-1-sulfonate was obtained as a white solid (21.6 g, 90% yield) according to the procedure in Kong, X., et al. US 2008/0146642 A1. Here, the above method in trifluoromethylbenzene gave a 74% yield of 6-2, whereas the reaction in 0.5M CH$_2$Cl$_2$ in MeCN provided the desired product in 92% yield (30 wt-% stock solution). $^1$H NMR (400 MHz, CDCl$_3$) δ 3.45-3.40 (m, 2H), 3.38 (t, J=6.3 Hz, 2H), 2.17-2.04 (m, 2H), 1.84-1.72 (m, 2H); $^{13}$C NMR (101 MHz, CDCl$_3$) δ 50.5, 50.3 (d, J=17.1 Hz), 27.1, 21.1; $^{19}$F NMR (376 MHz, CDCl$_3$) δ 53.2; R$_f$(9:1 hexane:EtOAc): 0.28; GC (t$_R$): 5.0 min; EI-MS (m/z): 153 [M−28]$^+$.

Pent-4-yne-1-sulfonyl fluoride (6-3). Pent-4-yne-1-chloride (0.2 mol) and Na$_2$SO$_3$ (0.2 mol) were heated in water (200 mL) at 95° C. for 16 h. The solution was concentrated and dried under vacuum to provide a mixture of sodium pent-4-yne-1-sulfonate and NaCl. This material was used in the above procedure without further purification. The reaction in trifluoromethylbenzene (25 mmol scale) gave a 50% yield (three steps from pent-4-yne-1-chloride) of the sulfonyl chloride (as a 5.3 wt-% stock solution), whereas the reaction in 0.5M CH$_2$Cl$_2$ in MeCN provided the desired product, 6-3, in 60% yield (three steps, 27 wt-% solution). $^1$H NMR (400 MHz, CDCl$_3$) δ 3.63-3.56 (m, 2H), 2.48 (td, J=6.7, 2.6 Hz, 2H), 2.28-2.17 (m, 3H); $^{13}$C NMR (101 MHz, CDCl$_3$) δ 80.8, 70.8, 49.5 (d, J=17.6 Hz), 22.6, 16.8; $^{19}$F NMR (376 MHz, CDCl$_3$) δ 53.4; R$_f$ (9:1 hexane:EtOAc): 0.30.

4-(3-Bromopropyl)benzene-1-sulfonyl fluoride (6-4). A solution of 3-bromopropyl)benzene (1.1 g) in CHCl$_3$ (10 mL) was cooled to 0° C. on an ice bath and was treated with chlorosulfuric acid (2.2 mL, 6 equiv) slowly by syringe with continued cooling. After 30 min, the ice bath was removed and the reaction mixture was stirred at room temperature overnight. The mixture was poured into an ice-water mixture (100 g) and the crude sulfonyl chloride was extracted with EtOAc (2×30 mL). The combined organic extracts were washed with brine and concentrated. The resulting crude sulfonyl chloride was dissolved in acetonitrile (10 mL) and treated with saturated aqueous KHF$_2$ (5 mL). The reaction mixture was stirred at room temperature overnight, monitoring by GC-MS. Upon completion, the sulfonyl fluoride was extracted with EtOAc (3×20 mL), and the combined organic phases were dried over anhydrous Na$_2$SO$_4$ and concentrated to give 6-4 as a yellow oil (1.4 g, 90% yield for two steps). $^1$H NMR (400 MHz, CDCl$_3$) δ 7.92 (d, J=8.0 Hz, 2H), 7.47 (d, J=8.0 Hz, 2H), 3.39 (t, J=8.0 Hz, 2H), 2.92 (t, J=8.0 Hz, 2H), 2.20 (m, 2H); $^{13}$C NMR (101 MHz, CDCl$_3$) δ 149.7, 130.8 (d, J=25 Hz), 129.9, 128.7, 34.0, 33.4, 32.4; $^{19}$F NMR (376 MHz, CD$_3$OD) δ +65.8; GC-MS (t$_R$): 5.8 min; EI.MS (m/z): 280 [M]$^+$.

4-Hydroxybenzene-1-sulfonyl fluoride (6-5). A 50 mL round-bottom flask was charged with 4-hydroxybenzenesulfonate (2.56 g). Thionyl chloride (10 mL) was added and the mixture was heated to reflux under a nitrogen atmosphere for 6 hours. The bulk of the excess thionyl chloride was removed by distillation, and the last traces were removed by addition of toluene (10 mL) and rotary evaporation. The resulting crude sulfonyl chloride (a yellow oil) was dissolved in CH$_3$CN (20 mL) and treated with saturated aqueous KHF$_2$ (5 mL). The reaction mixture was stirred at room temperature overnight and monitored by GC-MS. Upon completion, the sulfonyl fluoride was extracted with EtOAc (3×20 mL), dried over anhydrous Na$_2$SO$_4$, and concentrated. The desired product was obtained as colorless crystals (1.84 g, 80% yield for two steps). $^1$H NMR (400 MHz, CDCl$_3$) δ 7.86 (d, J=12.0 Hz, 2H), 7.04 (m, 2H); $^{13}$C NMR (101 MHz, CDCl$_3$) δ 162.7, 131.2, 123.2 (d, J=23 Hz), 116.7; $^{19}$F NMR (376 MHz, CDCl$_3$) δ +66.8; ESI-MS (m/z): 177 [MH]$^+$.

EX. 1(G)

Sulfonimidoyl Fluorides Prepared from Corresponding Chlorides

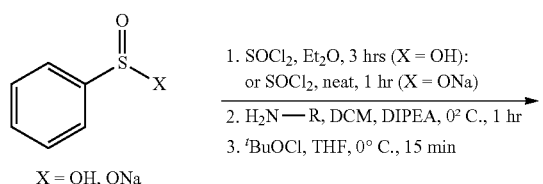

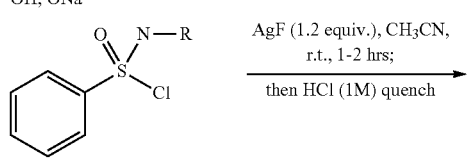

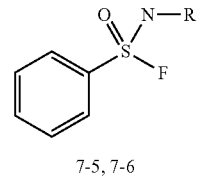

7-5, 7-6

General procedure: The starting sulfonimidoyl chloride was dissolved in acetonitrile (0.33 M) and an equal volume of saturated aqueous KHF$_2$ was added with stirring. The reaction mixture was stirred at room temperature for several hours. Upon completion (monitored by LC-MS or GC), the acetonitrile layer was separated, dried over Na$_2$SO$_4$ and concentrated. In cases in which crude sulfonimidoyl chlorides were used, pure samples of the product fluoride were obtained by column chromatography.

N-(Methylsulfonyl)benzenesulfonimidoyl fluoride (7-1) was isolated as a white solid in 95% yield (0.9 g). mp 77-78° C.; $^1$H NMR (500 MHz, CD$_3$CN) δ 8.15 (d, J=8.0 Hz, 2H), 7.93 (t, J=7.5 Hz, 1H), 7.76 (t, J=8.0 Hz, 2H), 3.28 (s, 3H); $^{13}$C NMR (126 MHz, CD$_3$CN) δ 137.9, 133.4 (d, J=19.9 Hz), 131.3, 128.9, 45.0; $^{19}$F NMR (376 MHz, CDCl$_3$) δ 71.9; R$_f$ (7:3 hexane:EtOAc): 0.31; ESI-MS (m/z): 238 [MH]$^+$.

N-Tosylbenzenesulfonimidoyl fluoride (7-2). Starting from the crude sulfonimidoyl chloride, the crude fluoride product was purified by short column chromatography (9:1 hexane:EtOAc to 1/1) to give a white solid (3.8 g, 71% yield). mp 60-61° C.; $^1$H NMR (400 MHz, CDCl$_3$) δ 8.04 (d, J=8.5 Hz, 2H), 7.94 (d, J=8.2 Hz, 2H), 7.79 (t, J=7.5 Hz, 1H), 7.62 (t, J=7.9 Hz, 2H), 7.33 (d, J=8.0 Hz, 2H), 2.43 (s, 3H); $^{13}$C NMR (1 MHz, CDCl$_3$) δ 144.5, 139.0, 136.3, 133.3 (d, J=20.2 Hz), 129.9, 129.8, 128.2, 127.2, 21.8; $^{19}$F NMR (376 MHz, CDCl$_3$) δ 73.5; R$_f$ (6:4 hexane:EtOAc): 0.46; ESI-MS (m/z): 294 [MH]$^+$.

N-((3-Azidopropyl)sulfonyl)benzenesulfonimidoyl fluoride (7-3). Starting from the crude sulfonimidoyl chloride, the crude fluoride product was purified by short column chromatography (1:1 CH$_2$Cl$_2$:hexane) to give a colorless oil (1.32 g, 79% yield). $^1$H NMR (500 MHz, CD$_3$CN) δ 8.13 (d, J=6.9 Hz, 2H), 7.96-7.88 (m, 1H), 7.78-7.70 (m, 2H), 3.53-3.46 (m, 2H), 3.46-3.39 (m, 2H), 2.17-2.07 (m, 2H); $^{13}$C NMR (126 MHz, CD$_3$CN) δ 137.9, 133.3 (d, J=19.6 Hz), 131.2, 128.9, 54.4, 50.0, 24.3; $^{19}$F NMR (376 MHz, CDCl$_3$) δ 72.9; R$_f$ (6:4 hexane:EtOAc): 0.49; ESI-MS (m/z): 329 [MNa]$^+$.

N-Methylcarbonatebenzenesulfonimidoyl fluoride (7-4). The product was isolated as yellow oil in 82% yield (0.9 g). $^1$H NMR (400 MHz, CDCl$_3$) δ 8.09-8.05 (m, 2H), 7.78-7.72 (m, 1H), 7.63-7.57 (m, 2H), 3.78 (s, 3H); $^{13}$C NMR (101 MHz, CDCl$_3$) δ 154.3, 135.8, 133.3 (d, J=20.6 Hz), 129.7, 128.1, 54.2; $^{19}$F NMR (376 MHz, CDCl$_3$) δ 68.5; R$_f$ (8:2 hexane:EtOAc): 0.40; ESI-MS (m/z): 218 [MH]$^+$.

General procedure. Sulfonimidoyl fluorides with alkyl or aryl substituents on nitrogen were prepared according to the sequence previously described by Kowalczyk, R.; Edmunds, A. J. F.; Hall, R. G.; Bolm, C. Org. Lett. 2011, 13, 768-771. The starting sulfonimidoyl or sulfamoyl chlorides were dissolved in acetonitrile (0.1 M) and treated with AgF (1.2-1.5 equiv) in a foil-wrapped flask for 1 hour. Upon completion, the reaction was quenched with 1M HCl (0.2 M) and stirred at room temperature for 30-60 min, then filtered through CELITE, washed with CH$_2$Cl$_2$, concentrated, and purified by short silica gel column chromatography.

N-(3-Ethynylphenyl)benzenesulfonimidoyl fluoride (7-5) was isolated as a brown oil (0.5 g, 80% yield). $^1$H NMR (600 MHz, CD$_3$CN) δ 8.22-8.19 (m, 2H), 7.85 (t, J=7.5 Hz, 1H), 7.72 (t, J=7.9 Hz, 2H), 7.38-7.34 (m, 2H), 7.31-7.30 (m, 1H), 7.30-7.28 (m, 1H), 3.43 (s, 1H); $^{13}$C NMR (151 MHz, CD$_3$CN) δ 140.6 (d, J=5.4 Hz), 136.4, 136.3, 135.6 (d, J=24.8 Hz), 130.8, 129.0, 128.6, 127.9 (d, J=5.0 Hz), 125.5 (d, J=4.6 Hz), 124.1, 83.5, 79.4; $^{19}$F NMR (376 MHz, CD$_3$CN) δ 80.3; R$_f$ (6:4 hexane:EtOAc): 0.47; ESI-MS (m/z): 260 [MH]$^+$.

N-(1-Ethynylcyclohexyl)-4-nitrobenzene-1-sulfonimidoyl fluoride (7-6). The starting sulfonimidoyl chloride was prepared starting from the sulfenyl amide, followed by oxidation with mCPBA. Using the above general procedure, 7-6 was isolated as a yellow oil 1.0 g, 81% yield). $^1$H NMR (400 MHz, CDCl$_3$) δ 8.37 (d, J=8.8 Hz, 2H), 8.23 (d, J=8.8 Hz, 2H), 2.55 (s, 1H), 2.15-2.04 (m, 2H), 1.92-1.83 (m, 2H), 1.72-1.61 (m, 4H), 1.59-1.50 (m, 1H), 1.37-1.26 (m, 1H); $^{13}$C NMR (101 MHz, CDCl$_3$) δ 150.8, 142.5 (d, J=30.2 Hz), 142.4, 129.1, 124.3, 86.1 (d, J=5.8 Hz), 72.3, 56.4 (d, J=3.2 Hz), 41.0 (d, J=2.2 Hz), 40.8 (d, J=4.0 Hz), 25.1, 22.9 (d, J=3.8 Hz); $^{19}$F NMR (376 MHz, CDCl$_3$) δ 90.5; R$_f$ (7:3 hexane:EtOAc): 0.68; ESI-MS (m/z): 311 [MH]$^+$.

EX. 1(H)

Preparation of 2-chloroethanesulfonyl fluoride and ESF (adapted from Hyatt et al. JOC, 1979, 44, 3847-3858).

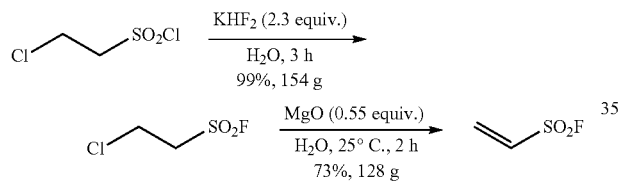

All manipulations with 2-chloroethane-1-sulfonyl chloride, 2-chloroethane-1-sulfonyl fluoride, and ESF must be performed in a well-ventilated fume hood. As powerful alkylating agents, care must be taken to avoid inhalation or skin contact.

2-Chloroethanesulfonyl fluoride. A 1 L round-bottom flask was charged with a magnetic stirring bar, KHF$_2$ (187 g, 2.4 mol) and water (0.5 L). The reaction mixture was stirred at room temperature for 20 min until complete dissolution of KHF$_2$ was achieved (this is an endothermic process, reaching an internal temperature of 5° C.). 2-Chloroethane-1-sulfonyl chloride (180.7 g, 1.05 mol) was poured into the cold saturated potassium bifluoride solution, and the reaction mixture was vigorously stirred at room temperature for 3 hours. The reaction was monitored by GC-MS (using a low injection and column temperature) or by NMR. Upon completion, the organic layer of the neat sulfonyl fluoride was separated and washed with brine, giving approximately 150 g of 2-chloroethane-1-sulfonyl fluoride as a light yellow oil. The rest of the product was extracted from the aqueous KHF$_2$ layer with CH$_2$Cl$_2$ (100 mL). This organic extract was washed with brine, concentrated, and combined with the first batch of product. $^1$H NMR (400 MHz, CDCl$_3$) δ 3.94-3.90 (m, 2H), 3.83-3.78 (m, 2H); $^{13}$C NMR (101 MHz, CDCl$_3$) δ 52.5 (d, J=7.2 Hz), 35.0; $^{19}$F NMR (376 MHz, CDCl$_3$) δ +57.2; GC-MS (t$_R$): 2.3 min; ELMS (m/z): 146 [M]$^+$.

The recovered bifluoride solution (now containing a mixture of KH$_2$F$_3$ and KCl) was recharged by adding 1 equiv KF solution. The above reaction was repeated using this solution at 0.5 mol scale, providing 2-chloroethanesulfonyl fluoride in 100% yield. Two more re-charge/reaction cycles at the same scale each gave 98% yields.

Ethenesulfonyl fluoride (ESF). A 1 L 2-necked round-bottom flask equipped with stirring bar and internal thermometer was placed in an ice-water bath. The reaction flask was charged with ice-cold water (0.4 L) and 2-chloroethane-1-sulfonyl fluoride (232.5 g; 1.59 mol; 1 equiv). MgO (35.3 g; 0.875 mol; 0.55 equiv) was added portion-wise to the vigorously stirred reaction mixture, keeping the reaction temperature below 35° C., with optimal temperature being about 25° C. (Higher temperatures result in decreased yields, lower reaction temperatures slow down the reaction too much). After final portion of MgO was added, the reaction mixture was stirred for an additional 2-3 hours. Upon completion (monitored by GC, NMR), the bottom layer of neat ESF was removed in a separatory funnel. The product was dried by stirring with MgSO$_4$ for 20 min and filtered giving 125.7 g of neat ESF (72% yield), which was stored in a plastic bottle. The rest of the product (about 2.3 g) was extracted from the aqueous layer with dichloromethane (150 mL) and dried over MgSO$_4$. The resulting solution can be either used as a stock solution, or can be concentrated under low-pressure vacuum to give neat ESF.

EX. 1(I)

ESF Decorations of Nitrogen, Oxygen, and Carbon Nucleophiles

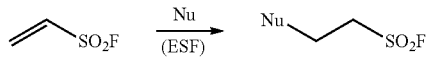

Section A: (S)-1-(2-(Fluorosulfonyl)ethyl)pyrrolidine-2-carboxylic acid (10-1). Proline (5 g; 43 mmol) was suspended in 95:5 EtOH:H$_2$O (100 mL) and treated with ESF (4 mL, 44 mmol). The reaction mixture was stirred at room temperature for several hours. Upon completion, the yellow solution was concentrated and dried under vacuum to give the product as white solid (9.45 g, 97% yield). $^1$H NMR (600 MHz, DMSO-d$_6$) δ 4.18-4.03 (m, $_2$H), 3.35-3.28 (m, 1H), 3.25 (dt, J=13.6, 7.0 Hz, 1H), 3.04-2.94 (m, 2H), 2.55-2.51 (m, 1H), 2.07-1.97 (m, 1H), 1.87-1.79 (m, 1H), 1.77-1.67 (m, 2H); $^{13}$C NMR (151 MHz, CDCl$_3$) δ 174.4, 64.2, 51.9, 48.9 (d, J=11.5 Hz), 28.7, 23.0; $^{19}$F NMR (376 MHz, CDCl$_3$) δ +57.6; ESI-MS (m/z): 226 [MH]$^+$.

(7R)-7-((R)-2-(Bis(2-(fluorosulfonyl)ethyl)ammonio)-2-(4-hydroxyphenyl)acetamido)-3-methyl-8-oxo-5-thia-1-azabicyclo[4.2.0]oct-2-ene-2-carboxylate (10-2). Cefadroxil (363 mg; 1 mmol) was suspended in absolute EtOH (2 mL) and treated with ESF (0.2 mL; 2.2 mmol). The reaction mixture was stirred at 50° C. overnight. The resulting yellow solution was concentrated by rotary evaporation and the residue purified by column chromatography (90:10:3 to 90:10:6 EtOAc:EtOH:H$_2$O) to give the desired product as a white solid (0.5 g, 86% yield). mp 225-230° C. (dec.); $^1$H NMR (400 MHz, DMSO-d$_6$) δ 9.56 (bs, 1H), 9.00 (d, J=8 Hz, 1H), 7.13 (d, J=8 Hz, 2H), 6.70 (d, J=8 Hz, 2H), 5.59 (t, J=8 Hz, 1H), 5.00 (d, J=4 Hz, 1H), 4.70 (s, 1H), 4.13-4.06 (m, 2H), 3.90-3.82 (m, 2H), 3.46 (d, J=16 Hz, 1H), 3.23-3.18 (m, 3H), 3.06-2.99 (m, 2H), 1.94 (s, 3H); $^{13}$C NMR (101 MHz, DMSO-d$_6$) δ 172.0, 163.7, 157.7, 130.3, 126.5, 115.6, 66.5, 58.8, 57.4, 49.3 (d, J=10 Hz), 45.1, 29.3, 19.8; $^{19}$F NMR (376 MHz, DMSO-$d_6$) δ +57.9; $R_f$ (EtOAc/EtOH/H$_2$O—90/10/6): 0.41; ESI-MS (m/z): 606 [MNa]$^+$.

Section B: General procedure for the reaction of primary and secondary amines with ESF (adapted from Krutak, J. J.; Burpitt, R. D.; Moore, W. H.; Hyatt, J. A. *J. Org. Chem.* 1979, 44, 3847-3858). The starting amine (1 equiv) was dissolved in organic solvent (usually CH$_2$Cl$_2$ or THF, 0.1-0.5 M in substrate) and treated with ESF (1-2.5 equiv). The reaction mixture was stirred at room temperature for several minutes to several hours, monitoring conversion by LC-MS. Upon completion, the solvent and excess of ESF were removed by rotary evaporation and dried under vacuum, usually providing clean product. When purification by column chromatography is mentioned, it was done to remove trace impurities.

2,2'-((2-(1H-Indol-3-yl)ethyl)azanediyl)diethanesulfonyl fluoride (10-3). Reaction in CH$_2$Cl$_2$; the product was further purified by flash column chromatography (9:1 to 6:4 hexane:EtOAc) to obtain 11-3 as a yellow oil (1.9 g, 100% yield). $^1$H NMR (400 MHz, CDCl$_3$) δ 8.04 (s, 1H), 7.57 (d, J=7.8 Hz, 1H), 7.37 (d, J=7.9 Hz, 1H), 7.23 (t, J=7.5 Hz, 1H), 7.16 (t, J=7.4 Hz, 1H), 7.01 (br s, 1H), 3.48-3.39 (m, 4H), 3.15-3.05 (m, 4H), 2.96-2.89 (m, 2H), 2.89-2.80 (m, 2H); $^{13}$C NMR (101 MHz, CDCl$_3$) δ 136.3, 127.1, 122.3, 122.2, 122.1, 119.6, 118.5, 113.0, 111.5, 54.2, 49.4 (d, J=13.2 Hz), 47.9, 23.3; $^{19}$F NMR (376 MHz, CDCl$_3$) δ +57.9; $R_f$ (7:3 hexane:EtOAc): 0.27; ESI-MS (m/z): 381 [MH]$^+$.

2,2'-((Furan-2-ylmethyl)azanediyl)diethanesulfonyl fluoride (10-4). Reaction in CH$_2$Cl$_2$ (0.33 M) in the presence of 2 equiv ESF. The crude product was purified by column chromatography (95:5 to 7:3 hexane:EtOAc) to give 11-4 as a yellow oil (1.6 g, 99% yield). $^1$H NMR (400 MHz, CDCl$_3$) δ 7.41 (dd, J=1.9, 0.8 Hz, 1H), 6.37 (dd, J=3.2, 1.9 Hz, 1H), 6.28 (dd, J=3.2, 0.7 Hz, 1H), 3.81 (s, 2H), 3.53 (td, J=6.9, 3.6 Hz, 4H), 3.16 (td, J=7.0, 1.2 Hz, 4H); $^{13}$C NMR (101 MHz, CDCl$_3$) δ 149.9, 143.1, 110.7, 110.1, 49.6, 49.4 (d, J=11.1 Hz), 47.9; $^{19}$F NMR (376 MHz, CDCl$_3$) δ +57.9; $R_f$ (7:3 hexane:EtOAc): 0.47; ESI-MS (m/z): 340 [MNa]$^+$.

2-((4-(2-Oxopiperidin-1-yl)phenyl)amino)ethanesulfonyl fluoride (10-5). Reaction in DMF (0.38 g substrate, 2 mmol) and ESF (0.2 mL, 1.1 equiv). The reaction mixture was stirred at 50° C. overnight, monitored by LC-MS. After that time, reaction mixture was concentrated by rotary evaporation and the crude product was purified by column chromatography to give a beige solid (570 mg, 95% yield). mp 188-189° C. $R_f$(EtOAc): 0.2. $^1$H NMR (400 MHz, DMSO-$d_6$) δ 7.08 (d, J=8 Hz, 2H), 6.61 (d, J=8 Hz, 2H), 5.96 (t, J=8 Hz, 1H), 4.07 (dd, J=12, 4 Hz, 2H), 3.59 (dd, J=12, 4 Hz, 2H), 3.47 (t, J=4 Hz, 2H), 2.31 (t, J=4 Hz, 2H), 1.80 (m, 4H); $^{13}$C NMR (101 MHz, DMSO-$d_6$) δ 168.6, 145.5, 133.3 127.1, 112.1, 51.3, 49.7 (d, J=10 Hz), 37.6, 32.5, 23.1, 21.0; $^{19}$F NMR (376 MHz, DMSO-$d_6$) δ +58.4; ESI-MS (m/z): 301 [MH]$^+$.

2-(1-((1S,2S)-2-Hydroxycyclohexyl)-2-(4-methylbenzoyl)-hydrazinyl)ethanesulfonyl fluoride (10-6). Reaction in THF with substrate (0.5 g, 2 mmol) and ESF (0.2 mL, 1.1 equiv), giving a white crystalline solid (mp 174-176° C.) in quantitative yield (0.712 g). $^1$H NMR (400 MHz, CDCl$_3$) δ 7.67 (d, J=8.2 Hz, 2H), 7.27 (d, J=8.0 Hz, 3H), 7.18 (s, 1H), 3.81-3.71 (m, 1H), 3.65-3.57 (m, 1H), 3.57-3.50 (m, 2H), 3.26 (ddd, J=11.0, 9.4, 4.6 Hz, 1H), 2.66 (ddd, J=11.4, 9.3, 3.6 Hz, 1H), 2.42 (s, 3H), 2.10-2.02 (m, 1H), 1.91 (d, J=10.2 Hz, 1H), 1.84-1.77 (m, 1H), 1.77-1.68 (m, 1H), 1.40-1.13 (m, 4H); $^{13}$C NMR (101 MHz, CDCl$_3$) δ 168.4, 143.5, 129.7, 129.1, 127.3, 72.0, 70.4, 49.9 (d, J=15.3 Hz), 49.8, 33.0, 25.0, 24.2, 24.1, 21.7; $^{19}$F NMR (376 MHz, CDCl$_3$) δ +56.8; ESI-MS (m/z): 359 [MH]$^+$.

4-(3-Carboxy-1-cyclopropyl-6-fluoro-4-oxo-1,4-dihydroquinolin-7-yl)-1-(2-(fluorosulfonyl)ethyl)piperazin-1-ium chloride (10-7). A suspension of the starting material (HCl salt) in DMF (0.5 M in substrate) was treated with 4 equiv ESF and the reaction mixture was stirred at 50° C. overnight. The product was collected as a white precipitate by filtration, washed with hexanes, and dried (4.2 g, 88% yield). $^1$H NMR (400 MHz, TFA-$d_1$) δ 9.35 (s, 1H), 8.28 (d, J=12 Hz, 1H), 8.00 (d, J=4 Hz, 1H), 4.34-4.29 (m, 4H), 4.14-4.11 (m, 3H), 4.04 (t, J=8 Hz, 2H), 3.91 (t, J=12 Hz, 2H), 3.69 (t, J=12 Hz, 2H), 1.69(d, J=8 Hz, 2H), 1.44 (d, J=4 Hz, 2H); $^{13}$C NMR (151 MHz, DMSO-$d_6$ with Py-$d_5$) δ 176.5, 166.1, 153.1 (d, J=250.0 Hz), 147.8, 145.0 (d, J=10.1 Hz), 139.0, 118.8 (d, J=7.8 Hz), 111.0 (d, J=22.7 Hz), 106.9, 106.3 (d, J=3.2 Hz), 51.7, 50.9, 49.2 (d, J=4.6 Hz), 48.1 (d, J=11.5 Hz), 35.7, 7.5; $^{19}$F NMR (376 MHz, DMSO-$d_6$ with Py-$d_5$) δ +59.3, −121.4; ESI-MS (m/z): 442 [MH]$^+$.

2-(4-(2-chlorodibenzo[b,f][1,4]oxazepin-11-yl)piperazin-1-yl)ethanesulfonyl fluoride (10-8). Reaction in CH$_2$Cl$_2$ with the starting amine (314 mg, 1 mmol) and ESF (0.1 mL, 1.1 equiv), giving the desired product as a white solid (420 mg, quant. yield). mp 158-159° C. $^1$H NMR (400 MHz, Acetone-$d_6$) δ 7.57 (dd, J=8, 4 Hz, 1H), 7.46 (d, J=4 Hz, 1H), 7.37 (d, J=8 Hz, 1H), 7.17-7.15 (m, 1H), 7.12-7.07 (m, 2H), 7.03-6.98 (m, 1H), 4.03 (m, 2H), 3.57 (m, 4H), 3.07 (m, 2H), 2.79 (m, 4H); $^{13}$C NMR (101 MHz, CDCl$_3$) δ 159.3, 158.7, 151.9, 139.8, 134.4, 132.8, 130.3, 129.0, 127.1, 125.9, 124.9, 124.8, 122.8, 120.2, 52.4, 51.2, 48.7 (d, J=15 Hz), 47.2; $^{19}$F NMR (376 MHz, CDCl$_3$) δ +57.5; ESI-MS (m/z): 424 [MH]$^+$ .

2-(2-Methyl-4-nitro-1H-imidazol-1-yl)ethanesulfonyl fluoride (10-9). Reaction in THF with starting imidazole (38 mg, 0.3 mmol) and ESF (0.03 mL; 1.1 equiv), giving a white crystalline solid. Further purification was performed by flash column chromatography to provide the desired product (65 mg, 91% yield). mp 164-165° C. $R_f$(EtOAc): 0.60; $^1$H NMR (400 MHz, Acetone-$d_6$) δ 8.23 (s, 1H), 4.81 (t, J=8 Hz, 2H), 4.53 (q, J=8 Hz, 2H), 2.50 (s, 3H); $^{13}$C NMR (101 MHz, acetone-$d_6$) δ 206.3, 146.3, 121.7, 50.6 (d, J=16.2 Hz), 41.7, 12.9; $^{19}$F NMR (376 MHz, Acetone-$d_6$) δ +56.8; ESI-MS (m/z): 238 [MH]$^+$.

Section C: General procedure for the reaction of ESF with sulfonamides and alcohols. The starting material (1 equiv) and triphenylphosphine (0.1 equiv) were dissolved in CH$_2$Cl$_2$ (0.33 M in substrate) and treated with ESF (1-2.5 equiv). The reaction mixture was stirred at room temperature overnight, monitoring conversion by LC-MS, GC-MS, or TLC as appropriate. Upon completion, CH$_2$Cl$_2$ and excess of ESF were removed by rotary evaporation and the crude product was purified by chromatography on a short silica gel column.

2-(4-Methyl-N-(prop-2-yn-1-yl)phenylsulfonamido)ethanesulfonyl fluoride (10-10) was obtained as a white solid (251 mg, 78% yield). $R_f$ (5:1 hexane:EtOAc): 0.25; mp 125-126° C.; $^1$H NMR (400 MHz, CDCl$_3$) δ 7.74 (d, J=8.3 Hz, 2H), 7.35 (d, J=8.5 Hz, 2H), 4.15 (d, J=2.5 Hz, 2H), 3.87-3.80 (m, 2H), 3.71-3.65 (m, 2H), 2.45 (s, 3H), 2.19 (t, J=2.5 Hz, 1H); $^{13}$C NMR (101 MHz, CDCl$_3$) δ 144.8, 134.5, 130.1, 127.9, 76.2, 75.0, 50.4 (d, J=16.0 Hz), 41.9, 38.8, 21.8; $^{19}$F NMR (376 MHz, CDCl$_3$) δ 55.9; ESI-MS (m/z): 320 [MH]$^+$.

2,2'-(((4-(3-Phenyl-5-(trifluoromethyl)-1H-pyrazol-1-yl)phenyl)sulfonyl)azanediyl)-diethanesulfonyl fluoride (10-11) was obtained as a white solid (175 mg, 60% yield). $R_f$ (5:1 hexane:EtOAc): 0.21; mp 135-137° C.; $^1$H NMR (400 MHz, CDCl$_3$) δ 7.84 (d, J=8.6 Hz, 2H), 7.58 (d, J=8.6 Hz, 2H), 7.47-7.43 (m, 1H), 7.43-7.39 (m, 1H), 7.28-7.23 (m, 3H), 6.80 (s, 1H), 3.86-3.80 (m, 4H), 3.71-3.66 (m, 4H); $^{13}$C NMR (101 MHz, CDCl$_3$) δ 145.4, 144.8 (d, J=38.3 Hz), 143.9, 135.7, 130.0, 129.4, 129.0, 128.8, 128.6, 117.4 (d, J=336.3 Hz), 107.2, 50.7, 50.6 (d, J=16.1 Hz), 45.6; $^{19}$F NMR (376 MHz, CDCl$_3$) δ +59.4, −62.8; ESI-MS (m/z): 588 [MH]$^+$.

2-(Prop-2-yn-1-yloxy)ethanesulfonyl fluoride (10-12) was isolated as a colorless oil (2 g, 60% yield). Since the product is quite volatile, evaporative removal of EtOAc was done gently, leaving a small amount of the solvent in the sample. R$_f$ (7:3 hexane:EtOAc): 0.43. $^1$H NMR (400 MHz, CDCl$_3$) δ 4.20 (d, J=4 Hz, 2H), 4.00 (dt, J=4, 8 Hz, 2H), 3.66 (m, 2H), 2.51 (t, J=4 Hz, 1H); $^{13}$C NMR (101 MHz, CDCl$_3$) δ 78.3, 75.9, 62.5, 58.6, 51.0 (d, J=17.2 Hz); $^{19}$F NMR (376 MHz, CDCl$_3$) δ +58.5. ELMS (m/z): 166 [M]$^+$.

Section D: 2,2'-((3-Ethynylphenyl)azanediyl)diethanesulfonyl fluoride (10-13). (adapted from Hyatt et al. *J. Org. Chem.*, 1979, 44, 3847-3858) ESF (1.8 mL, 20 mmol) was added to aniline (1.17 g, 10 mmol) in glacial acetic acid (3 mL) and the reaction mixture was stirred at 50° C. for 24 h. Upon completion, the crude product was isolated by filtration, washed with hexanes, and recrystallized from CCl$_4$—CH$_2$Cl$_2$. The desired product was obtained as light brown crystals (2.94 g, 87% yield). mp 98-100° C. $^1$H NMR (400 MHz, CDCl$_3$) δ 7.31 (t, J=8.0 Hz, 1H), 7.10-7.06 (m, 1H), 6.85-6.82 (m, 1H), 6.78-6.73 (m, 1H), 4.01 (t, J=6.4 Hz, 4H), 3.67-3.59 (m, 4H), 3.10 (s, 1H); $^{13}$C NMR (101 MHz, CDCl$_3$) δ 144.0, 130.5, 124.3, 124.2, 117.6, 115.0, 83.3, 78.0, 48.3 (d, J=14.4 Hz), 46.8; $^{19}$F NMR (376 MHz, CDCl$_3$) δ +57.2; ESI-MS (m/z): 338 [MH]$^+$.

Section E: 2-(Naphthalen-2-yloxy)ethanesulfonyl fluoride (10-14). 2-Naphthol (0.29 g; 2 mmol) dissolved in THF (2 mL) was treated with ESF (0.2 mL, 1.1 mmol), followed by addition of tetrabutylammonium fluoride (0.2 mL of 1M solution in THF, 10 mol %). The reaction mixture was stirred at room temperature for 48 h. After removal of solvent by rotary evaporation, the crude product was purified by column chromatography (95:5 hexane:EtOAc) to give the product as a white solid (0.42 g, 81% yield). mp 70-72° C. $^1$H NMR (400 MHz, CDCl$_3$) δ 7.82-7.74 (m, 3H), 7.50 (t, J=8 Hz, 1H), 7.41 (t, J=8 Hz, 1H) 7.19-7.13 (m, 2H), 4.54 (m, 2H); $^{13}$C NMR (101 MHz, CDCl$_3$) δ 155.3 134.2, 130.0, 129.6, 127.8, 126.9, 126.8, 124.4, 118.5, 107.3, 61.0, 50.6 (d, J=17.1 Hz); $^{19}$F NMR (376 MHz, CDCl$_3$) δ +59.1; GC-MS (t$_R$): 6.56 min; ELMS (m/z): 254 [M]$^+$.

Section F: General procedure for the reaction of ESF with 1,3-dicarbonyl compounds. The starting compound (1 equiv) and quinine (0.1 equiv) were dissolved in CH$_2$Cl$_2$ (0.33M in substrate) and treated with ESF (1.1 equiv). The reaction mixture was stirred at room temperature for several hours, monitoring conversion by LC-MS, GC-MS, or TLC, as appropriate. Upon completion, CH$_2$Cl$_2$ and excess of ESF were removed by rotary evaporation and the crude product was purified by short column chromatography (9:1 to 6:4 hexane:EtOAc).

2-(1-Acetyl-2-oxocyclopentyl)ethanesulfonyl fluoride (10-15) was obtained as a white solid (2.23 g, 95% yield). mp 76-78° C. $^1$H NMR (400 MHz, CDCl$_3$) δ 3.47-3.31 (m, 4H), 2.60-2.47 (m, 1H), 2.43 (br s, 2H), 2.34-2.24 (m, 2H), 2.15 (s, 3H), 2.07-1.96 (m, 4H), 1.81 (dt, J=12.6, 6.5 Hz, 1H); $^{13}$C NMR (101 MHz, CDCl$_3$) δ 215.3, 203.5, 65.7, 46.7 (d, J=18.2 Hz), 38.4, 32.6, 26.9, 26.5, 19.7; $^{19}$F NMR (376 MHz, CDCl$_3$) δ +51.8; R$_f$ (7:3 hexane:EtOAc): 0.29; ELMS (m/z): 194 [M-COMe]$^+$, 236 [M]$^+$.

Ethyl 1-(2-(fluorosulfonyl)ethyl)-2-oxocyclopentane-carboxylate (10-16) was obtained as a white solid (2.4 g, 88% yield). mp 36-38.5° C. $^1$H NMR (400 MHz, CDCl$_3$) δ 4.17 (qq, J=7.2, 3.6 Hz, 2H), 3.87-3.73 (m, 1H), 3.57-3.43 (m, 1H), 2.56-2.42 (m, 2H), 2.41-2.27 (m, 1H), 2.30-2.17 (m, 2H), 2.15-2.03 (m, 1H), 2.03-1.86 (m, 2H), 1.23 (t, J=7.1 Hz, 3H); $^{13}$C NMR (101 MHz, CDCl$_3$) δ 213.9, 170.6, 62.2, 57.5, 46.9 (d, J=17.6 Hz), 38.0, 34.9, 27.3, 19.7, 14.1; $^{19}$F NMR (376 MHz, CDC$_3$) δ +51.4; R$_f$ (7:3 hexane:EtOAc): 0.50; ELMS (m/z): 266 [M]$^+$.

3-Cyano-4-oxo-4-(piperidin-1-yl)butane-1-sulfonyl fluoride (10-17) was obtained as thick yellow oil (2.0 g, 76% yield). $^1$H NMR (400 MHz, CDCl$_3$) δ 3.96 (t, J=8 Hz, 1H), 3.81-3.68 (m, 2H), 3.65-3.51 (m, 2H), 3.49-3.39 (m, 2H), 2.60 (m, 2H), 1.80-1.58 (m, 6H); $^{13}$C NMR (101 MHz, CDCl$_3$) δ 160.5, 115.8, 47.8 (d, J=18.1 Hz), 47.1, 44.0, 31.8, 25.7, 25.2, 23.9, 23.4; $^{19}$F NMR (376 MHz, CDCl$_3$) δ +53.7; R$_f$ (7:3 hexane:EtOAc): 0.29; EI-MS (m/z): 262 [M]$^+$.

EX. 1(J)

Aryl Fluorosulfates Prepared by a Convenient Procedure with Gaseous SO$_2$F$_2$

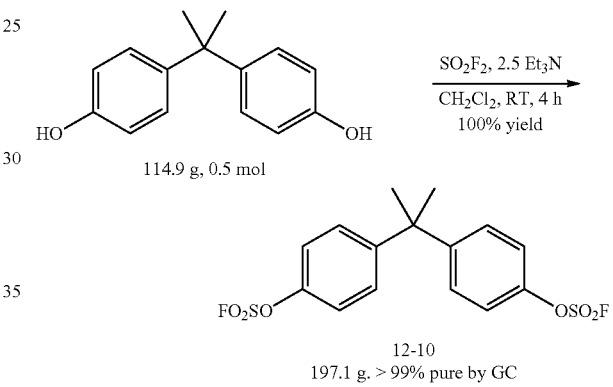

114.9 g, 0.5 mol

SO$_2$F$_2$, 2.5 Et$_3$N
―――――――→
CH$_2$Cl$_2$, RT, 4 h
100% yield 12-10
197.1 g, >99% pure by GC Section A. Representative procedure using triethylamine as base: propane-2,2-diylbis(4,1-phenylene) difluorosulfonate (12-10). A 2-liter single-neck round-bottom flask was charged with bisphenol-A (114.9 g, 0.5 mol), CH$_2$CL$_2$ (1 L) and Et$_3$N (174 mL, 1.25 mol, 2.5 equiv). The mixture was stirred at room temperature for 10 min. The reaction flask was then sealed with a septum, the atmosphere above the solution was removed with gentle vacuum, and SO$_2$F$_2$ gas (sulfuryl fluoride, VIKANE) was introduced by needle from a balloon filled with the gas. For large scale reactions such as this, depletion of the sulfuryl fluoride from the balloon was easily observed, and more reagent was introduced with a fresh balloon when required. For small scale reactions, SO$_2$F$_2$ was used in excess. These reactions can be easily followed by TLC.

The reaction mixture was vigorously stirred at room temperature for 2-4 hours, monitoring by GC-MS and TLC. After completion, the solvent was removed by rotary evaporation, the residue was dissolved in EtOAc (1 L), and the solution was washed with 1N HCl (2×500 mL) and brine (2×500 mL). The organic phase was dried over anhydrous Na$_2$SO$_4$ and concentrated. The resulting solid was dried under high vacuum at 60° C. overnight to give the desired compound as a white crystalline solid in quantitative yield (197.1 g, 100% yield). mp 48-49° C. $^1$H NMR (400 MHz, CDCl$_3$) δ 7.34-7.32 (m, 2H), 7.28-7.26 (m, 2H), 1.72 (s, 3H); $^{13}$C NMR (101 MHz, CDCl$_3$) δ 150.4, 148.2, 128.7, 120.5, 42.9, 28.4, 30.7; $^{19}$F NMR (376 MHz, CDCl$_3$) δ +37.0; GC-MS (t$_R$): 7.2 min; ELMS (m/z): 392 [M]$^+$.

Phenyl fluorosulfonate (12-1) was isolated as a colorless oil in 94% yield (1.65 g). $^1$H NMR (400 MHz, CDCl$_3$) δ 7.51-7.47(m, 2H), 7.43-7.41 (m, 1H), 7.36-7.34(2H); $^{13}$C NMR (101 MHz, CDCl$_3$) δ 150.1, 130.4, 128.6, 120.8; $^{19}$F NMR (376 MHz, CDCl$_3$) δ +37.0; GC-MS (t$_R$): 3.85 min; EI-MS (m/z): 176 [M]$^+$.

3-Acetamidophenyl fluorosulfonate (12-2) was isolated as a light brown solid (mp 113-114° C.) in 99% yield (2.3 g). $^1$H NMR (400 MHz, CDCl3) δ 8.45 (bs, 1H), 7.80 (s, 1H), 7.44-7.41 (m,1H), 7.38-7.34 (m, 1H), 7.06-7.04 (m, 1H), 2.19 (s, 3H); $^{13}$C NMR (101 MHz, CDCl3) δ 169.4, 150.1, 139.9, 130.4, 119.5, 116.1, 112.5, 24.3; $^{19}$F NMR (376 MHz, CDCl3) δ +37.4; GC-MS (t$_R$): 6.0 min; EI-MS (m/z): 233 [M]$^+$.

(1,1'-Biphenyl)-4-yl fluorosulfonate (12-3) was isolated as a white solid (mp 89-90° C.) in 99% yield (5.0 g). $^1$H NMR: (400 MHz, CDCl$_3$) δ 7.70-7.66 (m, 2H), 7.60-7.57 (m, 2H), 7.52-7.47 (m,2H), 7.45-7.41 (m, 3H); $^{13}$C NMR: (101 MHz, CDCl$_3$) δ 149.4, 141.9, 139.2, 129.0, 128.1, 127.2, 121.1; $^{19}$F NMR (376 MHz, CDCl$_3$) δ +37.1; GC-MS (t$_R$): 5.9 min; ELMS (m/z): 252 [M]$^+$.

4-Nitrophenyl fluorosulfonate (12-4) was isolated as yellow oil in 95% yield (4.2 g). $^1$H NMR (400 MHz, CDCl$_3$) δ 8.37 (dd, J=7.2 Hz, 2.4 Hz, 2H), 7.55 (m, 2H); $^{13}$C NMR (101 MHz, CDCl$_3$) δ 153.3, 147.3, 126.1, 122.1; $^{19}$F NMR (376 MHz, CDCl$_3$) δ +38.9; GC-MS (t$_R$): 4.9 min; ELMS (m/z): 221 [M]$^+$.

4-Aminophenyl fluorosulfonate (12-5) was isolated as brown solid (mp 41-42° C.) in 91% yield (8.0 g) according to the general procedure F17 using 3 equiv of Et$_3$N. $^1$HNMR (400 MHz, CDCl$_3$) δ 7.08 (d, J=8.5 Hz, 1H), 6.65 (d, J=8.7 Hz, 1H), 3.87 (br s, 1H); $^{13}$C NMR (101 MHz, CDCl$_3$) δ 146.9, 142.1, 121.8, 115.6, 115.5; $^{19}$F NMR (376 MHz, CDCl$_3$) δ +35.5; GC-MS (t$_R$): 5.0 min; EI-MS (m/z): 191 [M]$^+$.

2-Isopropyl-5-methylphenyl fluorosulfonate (12-6) was isolated as a colorless oil in 99% yield (2.4 g). $^1$H NMR (400 MHz, CDCl$_3$) δ 7.29 (d, J=8 Hz, 1H), 7.18 (d, J=8 Hz, 1H), 7.13 (s,1H), 3.28 (q, J=2.8 Hz, 1H), 2.37 (s, 3H), 1.27 (d, J=2.4 Hz, 3H), 1.25 (d, J=2.4 Hz, 3H); $^{13}$C NMR (101 MHz, CDCl$_3$) δ 147.8, 137.8, 137.4, 129.6, 127.6, 120.9, 26.7, 23.1, 20.8; $^{19}$F NMR (376 MHz, CDCl$_3$) δ +38.9; GC-MS (t$_R$): 4.6 min; EI-MS (m/z): 232 [M]$^+$.

3-Methoxyphenyl fluorosulfonate (12-7) was isolated as a colorless oil in 91% yield (0.4 g). $^1$H NMR (400 MHz, CDCl$_3$) δ 7.36 (m, 1H), 6.96-6.92 (m, 2H), 6.86 (m,1H), 3.83 (s, 3H); $^{13}$C NMR (101 MHz, CDCl$_3$) δ 161.0, 150.8, 130.8, 114.5, 112.7, 107.0, 55.8; $^{19}$F NMR (376 MHz, CDCl$_3$) δ +37.2; GC-MS (t$_R$): 4.5 min; EI-MS (m/z): 206 [M]$^+$.

Naphthalen-2-yl fluorosulfonate (12-8) was isolated as an off-white solid (mp 34-35° C.) in 98% yield (22.13 g). $^1$H NMR (400 MHz, CDCl$_3$) δ 7.95 (d, J=9.1 Hz, 1H), 7.93-7.87 (m, 2H), 7.82 (d, J=2.6 Hz, 1H), 7.64-7.54 (m, 2H), 7.44 (ddd, J=9.0, 2.5, 0.9 Hz, 1H); $^{13}$C NMR (101 MHz, CDCl$_3$) δ 147.7, 133.5, 132.6, 131.0, 128.2, 128.1, 127.8, 127.5, 119.1, 119.0; $^{19}$F NMR (376 MHz, CDCl$_3$) δ 37.2; GC (t$_R$): 5.4 min; ELMS (m/z): 226 [M]$^+$.

1,4-Phenylene difluorosulfonate (12-9) was isolated as a light brown solid (mp 92-93° C.) in 92% yield (5.1 g). $^1$H NMR (400 MHz, CDCl$_3$) δ 7.21 (s, 4H); $^{13}$C NMR (101 MHz, CDCl$_3$) δ 142.6, 125.3, 111.7; $^{19}$F NMR (376 MHz, CDCl$_3$) δ +40.6; GC-MS (t$_R$): 4.7 min; EI-MS (m/z): 274 [M]$^+$.

(E)-Hex-3-ene-3,4-diylbis(4,1-phenylene)difluorosulfonate (12-11) was isolated as a white solid (mp 122-123° C.) in 95% yield (0.8 g). $^1$H NMR (400 MHz, CDCl$_3$) δ 7.38-7.36 (m, 2H), 7.33-7.30 (m, 2H), 2.12 (q, J=7.6 Hz, 2H), 0.78 (t, J=7.6 Hz, 3H); $^{13}$C NMR (101 MHz, CDCl$_3$) δ 148.7, 142.6, 138.7, 130.5, 120.6, 28.4, 13.1; $^{19}$F NMR (376 MHz, CDCl$_3$) δ +37.0; GC-MS (t$_R$): 7.5 min; ELMS (m/z): 432 [M]$^+$.

(E)-2-((2-Fluorosulfoxybenzylidene)amino)benzene fluorosulfate (12-12) was isolated as a grey solid (mp 78-79° C.) in 95% yield (1.8 g). $^1$H NMR (400 MHz, CDCl$_3$) δ 8.79 (s, 1H), 8.39 (dd, J=8.0, 2.0 Hz, 1H), 7.66-7.62 (m, 1H), 7.57-7.53 (m, 1H), 7.49-7.37 (m, 2H), 7.35-7.26 (m, 1H), 7.25 (dd, J=8.0, 2 Hz, 1H); $^{13}$C NMR (100 MHz, CDCl$_3$) δ 155.3, 149.8, 143.6, 143.4, 133.7, 129.7, 129.6, 129.2, 127.9, 122.1, 121.5, 120.2; $^{19}$F NMR (375 MHz, CDCl$_3$) δ 40.0, 38.4; GC-MS (t$_R$): 6.9 min; EI-MS (m/z): 377 [M]$^+$.

(3-Oxo-1,3-dihydroisobenzofuran-1,1-diyl)bis(4,1-phenylene)difluorosulfonate (12-13) was isolated as a white solid (mp 89-91° C.) in 94% yield (11.3 g). $^1$H NMR: (400 MHz, CDCl$_3$) δ 7.98 (d, J=8.0 Hz, 1H), 7.79 (m, 1H), 7.66-7.63 (m, 1H), 7.59 (d, J=7.6 Hz, 1H), 7.49-7.45 (m, 4H), 7.36-7.33 (m, 4H); $^{13}$C NMR (101 MHz, CDCl$_3$) δ 168.5, 150.2, 149.9, 140.9, 134.8, 130.2, 129.2, 126.6, 125.2, 123.8, 121.3, 89.5; $^{19}$F NMR (376 MHz, CDCl$_3$) δ +37.7; GC-MS (t$_R$): 9.9 min; ELMS (m/z): 482 [M]$^+$.

Ethane-1,1,1-triyltris(benzene-4,1-diyl)trifluorosulfonate (12-14) was isolated as a white solid (mp 94-95° C.) in quantitative yield (5.6 g). $^1$H NMR (400 MHz, CDCl$_3$) δ 7.33-7.30 (m, 6H), 7.21-7.18 (m, 6H), 2.23 (s,3H); $^{13}$C NMR (101 MHz, CDCl$_3$) δ 148.6, 148.0, 130.4, 120.8, 52.0, 30.8; $^{19}$F NMR: (376 MHz, CDCl$_3$) δ +37.4; GC-MS (t$_R$): 9.3 min; EI-MS (m/z): 454 [M-OSO2F]$^+$.

(8R,9S,13S,14S,17R)-17-Ethynyl-17-hydroxy-13-methyl-7,8,9,11,12,13,14,15,16,17-decahydro-6H-cyclopenta[a]phenanthren-3-yl fluorosulfonate (12-15) was isolated as a thick colorless gel in 96% yield (0.8 g). $^1$H NMR (400 MHz, CDCl$_3$) δ 7.36 (d, J=8.4 Hz, 1H), 7.09 (dd, J=8.8 Hz, 2.4 Hz 1H), 7.03 (d, J=2.0 Hz, 1H), 2.90-2.87 (m, 2H), 2.62 (s,1H), 2.38-2.25 (m, 3H), 2.17 (s, 1H), 2.05 (m, 1H), 1.94-1.90 (m, 2H), 1.81-1.68 (m, 3H), 1.53-1.36 (m, 4H), 0.89 (s, 3H); $^{13}$C NMR (101 MHz, CDCl$_3$) δ 147.9, 140.9, 139.5, 127.2, 120.5, 117.5, 87.3, 79.6, 74.1, 49.3, 46.9, 43.6, 38.8, 38.6, 32.5, 29.4, 26.6, 26.1, 22.7, 12.5; $^{19}$F NMR (376 MHz, CDCl$_3$) δ +36.8; GC-MS (t$_R$): 8.5 min; EI-MS (m/z): 378 [M]$^+$.

3-(Diphenylphosphoryl)phenyl fluorosulfonate (12-16) was isolated as a thick yellow oil in 97% yield (3.7 g). $^1$H NMR (400 MHz, CDCl$_3$) δ 7.72-7.65 (m, 2H), 7.65-7.57 (m, 8H), 7.57-7.51 (m, 5H), 7.51-7.48 (m, 1H), 7.48-7.41 (m, 8H); $^{13}$C NMR (101 MHz, CDCl$_3$) δ 145.0, 149.8, 136.9, 135.9, 132.6, 132.60, 132.2, 132.1, 132.0, 131.9, 131.5, 131.0, 130.9, 130.5, 128.9, 128.8, 124.5 (d, J=5.3 Hz), 124.4 (d, J=3.2 Hz); $^{19}$F NMR (376 MHz, CDCl$_3$) δ 38.0; R$_f$ (EtOAc): 0.6; ESI-MS (m/z): 377 [MH]$^+$.

5-Chloroquinolin-8-yl fluorosulfonate (12-17) was isolated as a pale yellow solid (mp 105-107° C.) in 99% yield (6.5 g) following general procedure F17 with 2 equivalents of DIPEA. $^1$H NMR (400 MHz, CDCl$_3$) δ 9.09 (dd, J=4.1, 1.6 Hz, 1H), 8.60 (dd, J=8.6, 1.6 Hz, 1H), 7.72-7.61 (m, 3H); $^{13}$C NMR (101 MHz, CDCl$_3$) δ 152.4, 144.8, 141.0, 133.4, 132.1, 127.9, 125.9, 123.6, 121.4; $^{19}$F NMR (376 MHz, CDCl$_3$) δ 40.5; R$_f$ (7:3 hexane:EtOAc): 0.67; GC (t$_R$): 5.98 min; EI-MS (m/z): 261 [M]$^+$.

2-Oxo-2H-chromen-7-yl fluorosulfonate (12-18) was isolated as an off-white solid (mp 121-124° C.) in 98% yield (11.9 g). $^1$H NMR (400 MHz, CDCl$_3$) δ 7.73 (dd, J=9.7, 0.6

Hz, 1H), 7.62 (d, J=8.6 Hz, 1H), 7.35 (d, J=2.3 Hz, 1H), 7.29 (ddd, J=8.5, 2.4, 0.9 Hz, 1H), 6.50 (d, J=9.7 Hz, 1H); $^{13}$C NMR (101 MHz, CDCl$_3$) δ 159.3, 154.8, 151.3, 142.2, 129.8, 119.1, 118.1, 117.3, 110.4; $^{19}$F NMR (376 MHz, CDCl$_3$) δ 38.8; GC (t$_R$): 5.94 min; EI-MS (m/z): 244 [M]$^+$.

4-(2-Amino-2-oxoethyl)phenyl fluorosulfonate (12-19) was isolated as a white solid (mp 109-110° C.) in 96% yield (11.22 g). $^1$H NMR (400 MHz, CDCl$_3$) δ 7.38 (d, J=8.6 Hz, 2H), 7.31 (d, J=8.4 Hz, 2H), 6.18 (br s, 1H), 5.70 (br s, 1H), 3.58 (s, 2H); $^{13}$C NMR (101 MHz, CDCl$_3$) δ 172.9, 149.3, 135.7, 131.5, 121.4, 42.2; $^{19}$F NMR (376 MHz, CDCl$_3$) δ 37.2; ESI-MS (m/z): 234 [MH]$^+$.

2-(2H-Benzo[d][1,2,3]triazol-2-yl)-4-methylphenyl fluorosulfonate (12-20) was isolated as a thick colorless oil (solidifies upon standing) was isolated in 98% yield (4.54 g) following the general procedure using 4 equivalents of triethylamine. Further purification was performed by silica gel column chromatography (5-20% EtOAc in hexane). mp 63-64° C. $^1$H NMR (400 MHz, CDCl$_3$) δ 8.04 (d, J=2.1 Hz, 1H), 7.98-7.92 (m, 2H), 7.50-7.42 (m, 3H), 7.35 (dd, J=8.5, 2.2 Hz, 1H), 2.49 (s, 3H); $^{13}$C NMR (101 MHz, CDCl$_3$) δ 145.3, 140.4, 139.6, 132.5, 131.2, 127.9, 127.0, 123.0, 118.7, 21.1; $^{19}$F NMR (376 MHz, CDCl$_3$) δ 42.4; R$_f$ (9:1 hexane:EtOAc): 0.44; ESI-MS (m/z): 308 [MH]$^+$.

Benzo[d][1,3]dioxol-5-yl fluorosulfonate (12-21) was isolated as a colorless oil in 88% yield (9.68 g). $^1$H NMR (400 MHz, CDCl$_3$) δ 6.83-6.80 (m, 3H), 6.05 (s, 2H); $^{13}$C NMR (101 MHz, CDCl$_3$) δ 148.7, 147.8, 144.2, 114.2, 108.4, 103.1, 102.7; $^{19}$F NMR (376 MHz, CDCl$_3$) δ δ 36.1; R$_f$ (9:1 hexane:EtOAc): 0.54; GC (t$_R$): 4.82 min; EI-MS (m/z): 220 [M]$^+$.

6-Methylpyridin-3-yl fluorosulfonate (12-22) was isolated as colorless needles in 78% yield (2.97 g). Crude product was purified by extraction with EtOAc (50 mL×2); wash with NaHCO$_3$ (35 mL), brine (10 mL), followed by filtration through short column (SiO2; 30% EtOAc in hexane). mp 33-34.5° C.; $^1$H NMR (400 MHz, CDCl$_3$) δ 8.52 (d, J=2.9 Hz, 1H), 7.57 (dd, J=8.6, 2.6 Hz, 2H), 7.27 (d, J=8.6 Hz, 1H), 2.60 (s, 3H); $^{13}$C NMR (101 MHz, CDCl$_3$) δ 159.5, 145.4, 141.8, 128.8, 124.5, 24.1; $^{19}$F NMR (376 MHz, CDCl$_3$) δ 37.4; R$_f$(7:3 hexane:EtOAc): 0.46; ESI-MS (m/z): 192 [MH]$^+$.

5-Formyl-2-methoxyphenyl fluorosulfonate (12-23) was isolated as yellow oil in 98% yield (4.25 g). Crude product was purified by flash column chromatography (SiO2; 30% EtOAc in hexane). $^1$H NMR (400 MHz, CDCl$_3$) δ 9.84 (s, 1H), 7.87 (dd, J=8.5, 2.0 Hz, 1H), 7.81 (dd, J=2.0, 1.2 Hz, 1H), 7.18 (d, J=8.5 Hz, 1H), 3.98 (s, 3H); $^{13}$C NMR (101 MHz, CDCl$_3$) δ 189.1, 156.0, 139.2, 132.4, 129.9, 122.7, 113.4, 56.7; $^{19}$F NMR (376 MHz, CDCl$_3$) δ 40.1; R$_f$ (7:3 hexane:EtOAc): 0.41; GC (t$_R$): 5.4 min; ELMS (m/z): 234 [M]$^+$.

4-Formyl-2-methoxyphenyl fluorosulfonate (12-24) was isolated as yellow solid (mp 45-49° C.) in 97% yield (45.37 g). $^1$H NMR (400 MHz, CDCl$_3$) δ 9.94 (s, 1H), 7.70-7.34 (m, 3H), 3.96 (s, 3H); $^{13}$C NMR (101 MHz, CDCl$_3$) δ 190.4, 152.0, 142.7, 137.1, 123.9, 123.2, 112.2, 56.5; $^{19}$F NMR (376 MHz, CDCl$_3$) δ 40.4; R$_f$(9:1 hexane:EtOAc): 0.36; GC (t$_R$): 5.2 min; EI-MS (m/z): 234 [M]$^+$.

4-Allyl-2-methoxyphenyl fluorosulfonate (12-25) was isolated as a colorless oil in 97% yield (119.56 g). Crude product was purified by filtration through a short pad of silica (10% EtOAc in hexane) to remove brown impurities. $^1$H NMR (400 MHz, CDCl$_3$) δ 7.23 (dd, J=8.3, 1.3 Hz, 1H), 6.90 (d, J=2.0 Hz, 1H), 6.83 (ddt, J=8.3, 2.0, 0.6 Hz, 1H), 6.02-5.91 (m, 1H), 5.16 (td, J=1.5, 0.9 Hz, 1H), 5.15-5.11 (m, 1H), 3.90 (s, 3H), 3.43-3.40 (m, 2H); $^{13}$C NMR (101 MHz, CDCl$_3$) δ 151.0, 142.4, 137.4, 136.3, 122.1, 120.9, 116.9, 113.7, 56.1, 40.1; $^{19}$F NMR (376 MHz, CDCl$_3$) δ 38.9; R$_f$ (9:1 hexane:EtOAc): 0.64; GC (t$_R$): 5.3 min; EI-MS (m/z): 246 [M]$^+$.

Mesityl fluorosulfonate (12-26) was prepared using 4 equiv triethylamine, followed by short filtration through a plug of silica gel to give the desired product in 85% yield (0.68 g) as a colorless liquid. $^1$H NMR (400 MHz, CDCl$_3$) δ 6.97-6.94 (m, 2H), 2.39-2.36 (m, 6H), 2.32 (s, 3H); $^{13}$C NMR (101 MHz, CDCl$_3$) δ 146.9, 138.2, 130.5, 129.2, 20.7, 16.5; $^{19}$F NMR (376 MHz, CDCl$_3$) δ 42.4; R$_f$(95:5 hexane:EtOAc): 0.72; GC (t$_R$): 4.6 min; EI-MS (m/z): 218 [M]$^+$.

Catechol cyclic sulfate (12-27) was obtained as a colorless crystalline solid (1.6 g, 92% yield). mp 33-35.5° C. $^1$H NMR (400 MHz, CDCl$_3$) δ 7.23-7.18 (m, 4H); $^{13}$C NMR (101 MHz, CDCl$_3$) δ 142.6, 125.3, 111.7; GC-MS (t$_R$): 4.4 min; ELMS (m/z): 172 [M]$^+$.

7,7,7',7'-Tetramethyl-6,6',7,7'-tetrahydro-5,5'-spirobi[indeno[5,6-d][1,3,2]dioxathiold 2,2,2',2'-tetraoxide (12-28). The above procedure was employed with 6 equiv Et$_3$N in CH$_2$Cl$_2$ solvent (0.25 M in substrate). The crude product was suspended in a small amount of hexane (dissolving a brown impurity) and 12-28 was isolated by filtration as a white crystalline solid (15.27 g). A second batch of the product was obtained after concentration of the mother liquor (3.18 g), giving a total of (18.55 g, 80% yield). mp 223-225° C. R$_f$ (9:1 hexane:EtOAc) 0.54. $^1$H NMR (400 MHz, CDCl$_3$) δ 7.02 (s, 2H), 6.62 (s, 2H), 2.32 (dd, J=90.4, 13.3 Hz, 4H), 1.41 (s, 6H), 1.35 (s, 6H); $^{13}$C NMR (101 MHz, CDCl$_3$) δ 149.45, 146.07, 142.40, 142.14, 107.79, 106.06, 58.81, 58.31, 44.24, 31.70, 30.20.

3-(o-Tolyl)naphtho[2,3-e][1,2,3]oxathiazin-4(3H)-one 2,2-dioxide (12-29). The above procedure was employed with 3.5 equiv Et$_3$N. The crude product was suspended in a small amount of CH$_2$Cl$_2$ and filtered. The pure product was collected as a white powder and dried (2.81 g, 78% yield). mp 203-204° C. $^1$H NMR (400 MHz, CDCl$_3$) δ 8.81 (s, 1H), 8.08-8.05 (m, 1H), 7.96-7.93 (m, 1H), 7.81 (s, 1H), 7.74 (ddd, J=8.3, 6.9, 1.3 Hz, 1H), 7.64 (ddd, J=8.2, 6.9, 1.2 Hz, 1H), 7.48-7.34 (m, 4H), 2.36 (s, 3H); $^{13}$C NMR (101 MHz, CDCl$_3$) δ 160.4, 145.9, 138.5, 136.7, 133.8, 131.9, 131.1, 131.0, 130.9, 130.7, 130.0, 129.8, 127.9, 127.7, 127.6, 116.1, 116.0, 18.1; ELMS (m/z): 339 [M]$^+$.

II. Representative procedure for biphasic reaction conditions. 3,5-Bis(fluorosulfonate)benzoic acid (12-30). 3,5-Dihydroxybenzoic acid (0.77 g, 5 mmol) was dissolved in a 3:2 CH$_2$Cl$_2$:water mixture (0.5 M). Diisopropylethylamine (4.5 mL, 25 mmol) was added, the reaction flask was sealed with a septum, air was evacuated, and a balloon filled with SO$_2$F$_2$ gas was introduced. The reaction mixture was vigorously stirred under SO$_2$F$_2$ atmosphere at room temperature overnight. Upon completion, the volatiles were removed by rotary evaporation, and the residue was acidified and extracted with CH$_2$Cl$_2$. The desired product was obtained as a white solid (1.45 g, 91% yield). mp 127-128° C. $^1$H NMR (400 MHz, CDCl$_3$) δ 10.8 (br s, 1H), 8.19 (d, J=2.3 Hz, 2H), 7.68 (t, J=2.3 Hz, 1H); $^{13}$C NMR (101 MHz, CDCl$_3$) δ 168.1, 150.1, 133.8, 123.3, 120.3; $^{19}$F NMR (376 MHz, CDCl$_3$) δ +39.1; ESI-MS (m/z): 317 [M]$^-$.

(4R,4aS,7aR,12bS)-3-(Cyclopropylmethyl)-4a-hydroxy-7-oxo-2,3,4,4a,5,6,7,7a-octahydro-1H-4,12-methanobenzofuro[3,2-e]isoquinolin-9-yl fluorosulfate (12-31). The above procedure was performed starting with Naltrexone-HCl salt dihydrate (50 mg, 0.12 mmol) and 3 equiv Et$_3$N in 1:1 CH$_2$Cl$_2$:water (0.1 M). After workup (sat. NaHCO$_3$) and purification by column chromatography (95:5 CH$_2$Cl$_2$:MeOH, R$_f$ 0.47), the desired product was obtained as a white solid (42 mg, 82% yield). mp 135-138° C. $^1$H NMR (600 MHz, CDCl$_3$) δ 7.06 (d, J=8.4 Hz, 1H), 6.75 (d, J=8.4 Hz, 1H), 4.80 (s, 1H), 3.23 (d, J=5.8 Hz, 1H), 3.11 (d, J=19.0 Hz, 1H), 3.04 (td, J=14.5, 5.0 Hz, 1H), 2.73 (dd, J=12.3, 4.8 Hz, 2H), 2.63 (dd, J=18.9, 5.9 Hz, 1H), 2.46 (td, J=12.7, 5.3 Hz, 1H), 2.41 (dd, J=6.5, 1.8 Hz, 2H), 2.33 (dt, J=14.5, 3.2 Hz, 1H), 2.08 (td, J=12.3, 3.8 Hz, 1H), 1.92 (ddd, J=13.3, 5.0, 2.8 Hz, 1H), 1.57 (ddd, J=26.4, 13.3, 3.5 Hz, 2H), 0.86 (p, J=5.7 Hz, 1H), 0.60-0.53 (m, 2H), 0.15 (q, J=4.8 Hz, 2H); $^{13}$C NMR (151 MHz, CDCl$_3$) δ 206.7, 147.6, 133.9, 131.9, 131.5, 122.6, 120.2, 91.7, 69.9, 61.7, 59.2, 51.1, 43.3, 36.1, 31.4, 30.8, 23.2, 9.4, 4.1, 3.9; $^{19}$F NMR (376 MHz, CDCl$_3$) δ 38.3; ESI-MS (m/z): 424 [MH]$^+$.

(S)-2-Azido-3-(4-((fluorosulfonyl)oxy)phenyl)propanoic acid (12-32). The above procedure was performed starting with the dicyclohexyl amine salt of (S)-2-azido-3-(4-((fluorosulfonyl)oxy)phenyl)propanoic acid and 2 equiv Et$_3$N. The product was obtained as a yellow oil (0.65 g, 89% yield). $^1$H NMR (400 MHz, CDCl$_3$) δ 8.02 (bs, 1H), 7.38 (m, 2H), 7.31 (m, 2H), 4.20 (q, J=4.4 Hz, 1H), 3.23 (dd, J=14.4 Hz, 3.2 Hz, 1H), 3.05 (dd, J=14.4 Hz, 8.8 Hz, 1H); $^{13}$C NMR (101 MHz, CDCl$_3$) δ 174.4, 149.2, 136.7, 131.3, 121.1, 62.6, 36.5; $^{19}$F NMR (376MHz, CDCl$_3$) δ +37.2; ESI-MS (m/z): 262 [(M−N$_2$)H]$^+$, 312[(M+Na)]$^+$.

(E)-2-((4-((Fluorosulfonyl)oxy)phenyl)diazenyl)benzoic acid (12-33). The above procedure was performed with 2 equiv Et$_3$N. The crude product was purified by quick filtration through silica gel, washing away impurities with 50% EtOAc in hexanes and eluting the product with 70% EtOAc in hexanes. R$_f$(1:1 hexane:EtOAc) 0.19. The desired product was obtained as an orange solid in (7.16 g, 88% yield). mp 101-102° C. $^1$H NMR (400 MHz, CDCl$_3$) δ 8.46-8.36 (m, 1H), 8.04-7.92 (m, 3H), 7.76-7.68 (m, 2H), 7.58 (d, J=8.5 Hz, 2H); $^{13}$C NMR (101 MHz, CDCl$_3$) δ 166.5, 152.4, 151.0, 149.7, 134.0, 133.4, 133.2, 127.7, 125.5, 122.6, 116.3; $^{19}$F NMR (376 MHz, CDCl$_3$) δ 38.5; ESI-MS (m/z): 262 [M−H].

4-(5-Thioxo-4,5-dihydro-1H-tetrazol-1-yl)phenyl fluorosulfate (12-34). The above procedure was performed with 1.2 equiv Et$_3$N. The product was obtained as a pink solid (6.29 g, 98% yield). mp 130-131° C. (dec.). $^1$H NMR (400 MHz, DMSO-d$_6$) δ 8.18-8.12 (m, 2H), 7.92-7.86 (m, 2H); $^{13}$C NMR (101 MHz, CDCl$_3$) δ 49.3, 134.2, 126.9, 126.5, 122.4; $^{19}$F NMR (376 MHz, CDCl$_3$) δ 39.8; ESI-MS (m/z): 277 [MH]$^+$.

2-Oxo-7-(((2S,3R,4S,5S,6R)-3,4,5-trihydroxy-6-(hydroxymethyl)tetrahydro-2H-pyran-2-yl)oxy)-2H-chromen-6-yl fluorosulfate (12-35). The above procedure was performed starting with esculin hydrate (540 mg, 1.5 mmol) and approximately 10.6 equiv Et$_3$N (added in 2 portions) in CH$_2$Cl$_2$:water (9 mL:6 mL, overall 0.1 M in substrate). The crude product was purified by column chromatography on silica gel [99:1-97:3 CH$_3$CN:water, R$_f$(95:5 CH$_3$CN:water) 0.49]. After evaporation from acetonitrile solution, the desired product was obtained as a white solid (469 mg, 74% yield). mp 145-147° C. $^{19}$F NMR indicated the presence of a mixture of two conformational isomers in a 9:1 ratio. $^{19}$F NMR (376 MHz, DMSO-d$_6$) δ 41.4 (major), 38.5(minor); $^1$H NMR (major isomer) (500 MHz, DMSO-d$_6$) δ 7.55 (d, J=9.7 Hz, 1H), 7.45 (s, 1H), 7.30 (s, 1H), 6.16 (d, J=9.7 Hz, 1H), 4.91 (d, J=5.0 Hz, 1H), 4.67 (d, J=4.5 Hz, 1H), 4.63 (d, J=5.4 Hz, 1H), 4.61 (d, J=7.3 Hz, 1H), 4.12 (t, J=5.8 Hz, 1H), 3.27 (ddd, J=7.5, 5.5, 2.1 Hz, 1H), 3.05 (dt, J=11.6, 5.8 Hz, 1H), 2.99-2.94 (m, 1H), 2.86-2.82 (m, 2H), 2.79-2.73 (m, 1H); $^{13}$C NMR (major isomer) (126 MHz, DMSO-d$_6$) δ 159.3, 147.7, 144.9, 143.2, 139.8, 119.6, 117.9, 115.8, 111.6, 100.9, 77.3, 76.8, 73.1, 69.5, 60.5; ESI-MS (m/z): 423 [MH]$^+$.

III. Representative Procedure using NaH as Base. Mesityl fluorosulfonate (12-26):

The starting mesityl phenol (2.89 g, 21 mmol) was dissolved in dry THF and NaH (1.26 g of 60% suspension in mineral oil, 31.5 mmol, 1.5 equiv) was added under inert atmosphere at 0° C. The reaction mixture was warmed to room temperature and stirred for 15-30 min. After evolution of H$_2$ ceased, the mixture was cooled to 0° C., the inert gas inlet was removed, a low vacuum was created, and SO$_2$F$_2$ gas was introduced from a balloon with vigorous stirring. After 15 min at 0° C., the reaction mixture was warmed to room temperature. After 1 hour, GC-MS showed 97% conversion to the fluorosulfate, a residual amount of starting phenol, and a small amount of disulfate (less than 1%). The reaction mixture was opened to air, quenched with 1N HCl (about 35 mL) until a pH of 3-4 was established, extracted with EtOAc (2×50 mL), washed with brine, dried over MgSO$_4$ and concentrated. The crude product was further purified by short column chromatography to give a colorless oil (4.37 g, 94% yield). R$_f$(95:5 hexane:EtOAc) 0.72.

Fluorosulfate of (+)-α-tocopherol (12-36). (+)-α-Tocopherol was extracted from a commercially available mixture of (+)-α-tocopherol and vegetable oil according to the literature procedure of Isso, B.; Ryan, D. *Eur. J. Lipid Sci. Technol.* 2012, 114, 927-932. The vitamin E/oil mixture (20 g, approximately 60% vitamin E) was dissolved in hexane (40 mL). A mixture of 20 mL acetonitrile and 20 mL methanol was added and the resulting mixture was vortexed for 1 min, then allowed to stand for 5 min to separate. The top acetonitrile-methanol layer was isolated, washed with hexanes, and concentrated, providing 13.4 g of (+)-α-tocopherol (77% recovery). R$_f$(95:5 hexane:EtOAc) 0.56.

After subjection to the above SO$_2$F$_2$ reaction procedure, the crude fluorosulfate of (+)-α-tocopherol was purified by column chromatography (100:0 to 95:5 hexane:Et$_2$O). R$_f$ (95:5 hexane:EtOAc) 0.90. The product was obtained as a thick colourless oil (9.82 g, 82% yield). $^1$H NMR (400 MHz, CDCl$_3$) δ 2.62 (t, J=6.8 Hz, 2H), 2.25 (s, 3H), 2.22 (s, 3H), 2.13 (s, 3H), 1.83 (ddt, J=35.5, 13.2, 6.8 Hz, 2H), 1.66-1.50 (m, 3H), 1.51-1.36 (m, 4H), 1.36-1.22 (m, 8H), 1.27 (s, 3H), 1.20-1.05 (m, 6H), 0.93-0.85 (m, 12H); $^{13}$C NMR (101 MHz, CDCl$_3$) δ 151.1, 142.0, 127.6, 126.2, 124.5, 118.5, 75.9, 40.1, 39.5, 37.6, 37.5, 37.4, 33.0, 32.8, 31.0, 28.1, 25.0, 24.6, 24.0, 22.9, 22.8, 21.1, 20.8, 19.9, 19.8, 13.7, 12.9, 12.1; $^{19}$F NMR (376 MHz, CDCl$_3$) δ 40.8; Anal. Calcd. for C$_{29}$H$_{49}$FO$_4$S: C, 67.93; H, 9.63; F, 3.71. Found: C, 67.73; H, 9.56; F, 3.72.

2,5-Dimethyl-4-(morpholinomethyl)phenyl fluorosulfate (12-37). In the above procedure, 3 equiv NaH was used with 2,5-dimethyl-4-(morpholinomethyl)phenol-HCl hydrate as the starting material. Column chromatography (9:1 to 7:3 hexane:EtOAc) gave the desired product as a white solid (2.4 g, 54% yield). mp 93.5-95.5° C. $^1$H NMR (400 MHz, CDCl$_3$) δ 7.20 (s, 1H), 7.08 (s, 1H), 3.69 (br s, 4H), 3.41 (s, 2H), 2.43 (br s, 4H), 2.35 (s, 3H), 2.32 (s, 3H); $^{13}$C NMR (101 MHz, CDCl$_3$) δ 147.9, 137.7, 136.8, 133.4, 127.1, 122.4, 67.2, 60.6, 53.8, 19.0, 15.7; $^{19}$F NMR (376 MHz, CDCl$_3$) δ 38.4; ESI-MS (m/z): 304 [MH]$^+$.

IV. Representative procedure using DBU as base. Dinaphtho[2,1-d:1',2'-f][1,3,2]dioxathiepine 4,4-dioxide (12-38). Binaphthol (1.0 g, 3.5 mmol) was dissolved in acetonitrile (35 mL, 0.1 M in substrate). The reaction flask was sealed with a septum, air was evacuated, and a balloon filled with SO$_2$F$_2$ gas was introduced, followed by addition of DBU by syringe (1.1 mL, 7.2 mmol, 2.05 equiv). The reaction mixture was vigorously stirred under $SO_2F_2$ atmosphere at room temperature for several hours, monitoring by GC-MS and TLC. Upon completion, the reaction was diluted with EtOAc (50 mL), washed with 1N HCl (2×25 mL), brine 10 mL), dried over $MgSO_4$, and concentrated. The desired product was obtained as a white solid (1.21 g, quant.). mp 198-199° C. $R_f$ (7:3 hexane:EtOAc) 0.33. GC-MS ($t_R$): 9.6 min; ELMS (m/z): 348 [M]$^+$. NMR spectra matched the data reported previously by Koy, C.; Michalik, M.; Oehme, G.; Alm, J.; Kempe, R. *Sulfur Letters*, 1998, 21(2), 75-88.

EX. 1(K)

Fluorosulfates and Sulfates via Silyl-Fluoride Metathesis

Section A. Representative procedure for the synthesis of fluorosulfates from silylated phenols and sulfuryl fluoride gas in the presence of DBU. 4-(methylamino)phenyl fluorosulfonate (13A-1). TBS protected phenol (2.4 g, 10.15 mmol) was dissolved in dry acetonitrile (20 mL, 0.5 M in substrate). The reaction flask was sealed with septa, air was evacuated, a balloon filled with $SO_2F_2$ gas was introduced, and DBU was injected by syringe (145 µL, 1 mmol). The reaction mixture was vigorously stirred at room temperature for several hours, monitoring by GC-MS or LC-MS. Upon completion, the reaction was quenched with 1N HCl (50 mL) and extracted with EtOAc (2×100 mL). The organic extracts were washed with brine (35 mL), dried over $MgSO_4$, and concentrated. The product was obtained as a brown oil, which solidified upon standing (2.05 g, 99% yield). mp 37-40° C. $R_f$ (7:3 hexane:EtOAc): 0.55. $^1$H NMR (400 MHz, $CDCl_3$) δ 7.15-7.12 (m, 2H), 6.59 (m, 2H), 4.12 (bs, 1H), 2.83 (s, 3H); $^{13}$C NMR (101 MHz, $CDCl_3$) δ 148.9, 141.4, 121.6, 112.8, 30.7; $^{19}$F NMR (376 MHz, $CDCl_3$) δ +35.3; GC ($t_R$): 5.2 min; EI-MS (m/z): 205 [M]$^+$.

Polar aprotic solvents (acetonitrile, NMP and DMF) facilitate the transformation. Aprotic solvents ($CH_2Cl_2$, chloroform, trifluorotoluene, THF) can be used as well, at the cost of longer reaction times. The choice of the phenolic silyl ether group also has a pronounced effect on reaction rate. Reactions involving TMS-protected phenols usually require 1-4 h to reach completion, whereas reactions with the bulkier TBS group require 6-8 h. The DBU catalyst can be replaced with DBN or BEMP.

Benzene-1,3,5-triyl trifluorosulfonate (13A-2). The use of 1,3,5-tris((tert-butyldimethylsilyl)oxy)benzene (1.0 g, 2.1 mmol) in $CH_3CN$:THF (10 mL+10 mL) and 30 mol % of DBU gave a white solid. Additional purification was performed by column chromatography (9:1 hexane:EtOAc) to give the desired compound as a white solid (0.69 g, 86% yield). mp 96-98° C. $R_f$ (9:1 hexane:EtOAc) 0.62. $^1$H NMR (400 MHz, $CDCl_3$) δ 7.53 (s, 3H); $^{13}$C NMR (101 MHz, $CDCl_3$) δ 150.3, 115.7; $^{19}$F NMR (376 MHz, $CDCl_3$) δ 39.5; GC-MS ($t_R$): 4.9 min; EI-MS (m/z): 372 [M]$^+$.

2,2-Dioxidobenzo[d][1,3,2]dioxathiol-4-yl fluorosulfonate (13A-3). 1,2,3-Tris((trimethylsilyl)oxy)benzene (3.42 g, 10 mmol) in $CH_3CN$ (100 mL) was treated with DBU (30 mol %, 450 µL) and $SO_2F_2$ gas was introduced to the solution cooled to 0° C. in an ice bath. The reaction mixture was vigorously stirred for 4-5 hours, after which EtOAc was used instead of ether for the reaction workup. The crude product was purified by column chromatography (95:5 to 7:3 hexane:EtOAc) to give the desired compound as a colorless oil (1.9 g, 70% yield). $R_f$ (7:3 hexane:EtOAc) 0.66. $^1$H NMR (400 MHz, $CDCl_3$) δ 7.39-7.29 (m, 1H); $^{13}$C NMR (101 MHz, $CDCl_3$) δ 143.72, 134.49, 132.87, 125.81, 119.03, 112.24; $^{19}$F NMR (376 MHz, $CDCl_3$) δ 40.2; GC-MS ($t_R$): 5 min; EI-MS (m/z): 270 [M]$^+$.

(S)-tent-Butyl (3-(2,2-dioxidobenzo[d][1,3,2]dioxathiol-5-yl)-1-(methoxy(methyl)amino)-1-oxopropan-2-yl)carbamate (13A-4). The bis-TBS protected phenol (1.62 g, 2.85 mmol) was taken up in $CH_3CN$ (20 mL). DBU (20 mol %; 85 µL) and $SO_2F_2$ gas were introduced at room temperature as described above, and the reaction mixture was vigorously stirred for 18 h. The crude material was passed through a short plug of silica gel, eluting with hexane:EtOAc (3:1 to 1:1) to give the desired product as a pure colorless oil that solidified on standing (1.1 g, 96% yield). mp 108-111° C. $R_f$ (3:2 hexane:EtOAc) 0.41. $^1$H NMR (500 MHz, $CDCl_3$) δ 7.04 (d, J=8.4 Hz, 1H), 7.02 (s, 1H), 6.96 (d, J=8.5 Hz, 1H), 5.49 (d, J=8.4 Hz, 1H), 4.88-4.80 (m, 1H), 3.68 (s, 3H), 3.12 (s, 3H), 3.01 (dd, J=13.7, 5.4 Hz, 1H), 2.80 (dd, J=13.8, 7.8 Hz, 1H), 1.30 (s, 9H); $^{13}$C NMR (126 MHz, $CDCl_3$) δ 171.4, 155.1, 142.3, 141.3, 135.1, 126.2, 112.7, 111.3, 79.7, 61.6, 51.4, 38.4, 32.0, 28.1; ELMS (m/z): 425 [M+Na]$^+$.

Section B. Representative procedure for the synthesis of sulfates from silylated phenols and fluorosulfates in the presence of DBU. Silylated ether (1 equiv) was dissolved in acetonitrile (0.1-0.5 M in substrate), fluorosulfate (1 equiv) was added, and the reaction mixture was stirred for several minutes to obtain a homogeneous solution. DBU (10-30 mol %) was then added and the reaction mixture was stirred at room temperature (unless noted otherwise) for several hours, monitoring reaction progress by LC-MS or TLC. Note that the reaction vessel must be vented to allow for escape of the volatile silyl fluoride byproduct. Upon completion, the reaction was quenched with 1N HCl (unless amine functionality was present in the substrate), extracted with EtOAc, washed with brine, dried over $MgSO_4$, and concentrated. Crude products were purified by column chromatography when necessary.

Polar aprotic solvent (acetonitrile, NMP, DMF) facilitate the transformation. When the silyl ether has poor solubility in acetonitrile, THF can be used as a co-solvent. The choice of the silyl group on the phenol component should be adjusted depending on the steric properties of the fluorosulfate component. Since sterically hindered fluorosulfates require prolonged reaction time and elevated temperatures, the use of more stable TBS-protected phenols as coupling partners in this case generally provide cleaner transformations. More reactive fluorosulfates give cleaner transformations with more reactive TMS-protected phenols. In cases when reactive fluorosulfates are coupled with slow TBS protected phenols, the symmetric product of homocoupling of fluorosulfates can be observed in various amounts. DBU catalyst can be replaced with DBN or BEMP.

(8R,9S,13S,14S,17R)-17-Ethynyl-17-hydroxy-13-methyl-7,8,9,11,12,13,14,15,16,17-decahydro-6H-cyclopenta[a]phenanthren-3-yl ((R)-2,5,7,8-tetramethyl-2-((4R, 8R)-4,8,12-trimethyltridecyl)chroman-6-yl) sulfate (13B-1). Prepared from fluorosulfate (493 mg, 0.96 mmol), acetonitrile (4 mL), the TBS-protected steroid (381 µL, 0.96 mmol), and DBU (30 µL, 0.19 mmol), with stirring at 80° C. overnight. Column chromatography (9:1 to 7:3 hexane: EtOAc) provided the desired product as a white foam (0.73 g, 98% yield). $R_f$ (7:3 hexane:EtOAc) 0.47. $^1$H NMR (600 MHz, $CDCl_3$) δ 7.33 (d, J=8.1 Hz, 1H), 7.11 (d, J=7.3 Hz, 1H), 7.05 (s, 1H), 2.88 (br s, 1H), 2.62 (br s, 2H), 2.43-2.32 (m, 2H), 2.27 (s, 3H), 2.23 (s, 3H), 2.12 (s, 3H), 2.10-2.00 (m, 2H), 2.00-1.88 (m, 2H), 1.88-1.68 (m, 4H), 1.66-1.28 (m, 20 H), 1.27 (s, 6H), 1.20-1.03 (m, 6H), 0.95-0.81 (m, 12H).

2,5-Dimethyl-4-(morpholinomethyl)phenyl phenyl sulfate (13B-2). Prepared from fluorosulfate (883 mg, 2.91 mmol), acetonitrile (6 mL, 0.5 M in substrate), trimethyl (phenoxy)silane (527 µL, 2.91 mmol), and DBU (44 µL; 0.28 mmol), with stirring at room temperature for 5 h and quenching of the reaction with sat. NaHCO$_3$ (5 mL). Column chromatography (9:1 to 7:3 hexane:EtOAc) gave the desired product as a colorless oil (0.95 g, 86% yield). R$_f$(7:3 hexane:EtOAc) 0.42. $^1$H NMR (400 MHz, CDCl$_3$) δ 7.40-7.25 (m, 5H), 7.12 (s, 1H), 7.06 (s, 1H), 3.63 (t, J=4.6 Hz, 4H), 3.35 (s, 2H), 2.37 (t, J=4.5 Hz, 4H), 2.28 (s, 3H), 2.20 (s, 3H); $^{13}$C NMR (101 MHz, CDCl$_3$) δ 150.3, 147.8, 137.0, 135.5, 133.0, 129.9, 127.5, 127.2, 122.3, 121.2, 66.9, 60.4, 53.5, 18.8, 15.6; ESI-MS (m/z): 378 [MH]$^+$.

Bis(2-oxo-2H-chromen-7-yl) (propane-2,2-diylbis(4,1-phenylene)) bis(sulfate) (15B-3). Prepared from fluorosulfate (513 mg, 2.1 mmol), acetonitrile (5 mL), TMS-protected bisphenol A (373 mg, 1 mmol), and DBU (30 µL; 0.2 mmol), with stirring at room temperature for 4 h. The product was isolated directly as a precipitated white solid (filtered and washed with acetonitrile, 0.5 g, 75% yield). mp 169-174° C. $^1$H NMR (500 MHz, CDCl$_3$) δ 7.67 (d, J=9.6 Hz, 2H), 7.51 (d, J=8.4 Hz, 2H), 7.26-7.20 (m, 12H), 6.41 (d, J=9.6 Hz, 6H); $^{13}$C NMR (126 MHz, CDCl$_3$) δ 159.7, 154.8, 152.2, 145.0, 148.5, 142.5, 129.4, 128.7, 120.8, 118.2, 117.6, 117.4, 110.1, 43.0, 30.9; ESI-MS (m/z): 677 [MH]$^+$.

(S)-Benzyl 2-amino-3-(4-((((6-methylpyridin-3-yl)oxy)sulfonyl)oxy)phenyl)propanoate (13B-4). Prepared from fluorosulfate (478 mg, 2.5 mmol), acetonitrile (10 mL), TBS-protected tyrosine derivative (964 mg, 2.5 mmol), and DBU (75 µL, 0.5 mmol), with stirring at room temperature for 4 h. Column chromatography (9:1 CH$_2$Cl$_2$/MeOH) gave the desired compound as a yellow oil (0.9 g, 83% yield). R$_f$ (9:1 CH$_2$Cl$_2$:MeOH) 0.44. $^1$H NMR (600 MHz, CDCl$_3$) δ 8.43 (d, J=2.9 Hz, 1H), 7.52 (dd, J=8.5, 3.0 Hz, 1H), 7.36-7.27 (m, 6H), 7.20 (d, J=8.3 Hz, 1H), 7.18 (m, 3H), 5.12 (q, J=12.2 Hz, 2H), 3.74 (t, J=6.5 Hz, 1H), 3.05 (dd, J=13.6, 5.7 Hz, 1H), 2.90 (dd, J=13.6, 7.3 Hz, 1H), 2.57 (s, 3H), 1.66 (br s, 2H); $^{13}$C NMR (101 MHz, CDCl$_3$) δ 174.6, 158.1, 149.1, 145.5, 142.0, 137.2, 135.4, 131.1, 129.0, 128.7, 128.6, 128.6, 124.1, 120.9, 66.9, 55.6, 40.2, 24.0; ELMS (m/z): 443 [MH]$^+$.

4-(2-Amino-2-oxoethyl)phenyl (4-(1-((tert-butyldimethylsilyl)oxy)-2-(methylamino)ethyl)-phenyl) sulfate (13B-5). Prepared from fluorosulfate (483 mg, 2.07 mmol), acetonitrile (10 mL), TBS-protected phenol (818 mg, 2.07 mmol), and DBU (75 µL, 0.5 mmol), with stirring at room temperature overnight. Column chromatography (reversed-phase, 0-60% gradient of acetonitrile in water) gave the desired product as a white solid (0.8 g, 75% yield). mp 108-110° C. $^1$H NMR (600 MHz, CDCl$_3$) δ 7.39 (d, J=8.6 Hz, 2H), 7.34 (d, J=8.6 Hz, 2H), 7.29 (d, J=8.8 Hz, 2H), 7.28 (d, J=8.7 Hz, 2H), 5.56 (d, J=122.4 Hz, 2H), 4.85 (dd, J=8.3, 4.0 Hz, 1H), 3.59 (s, 2H), 2.75 (dd, J=12.1, 8.2 Hz, 1H), 2.64 (dd, J=12.1, 3.9 Hz, 1H), 2.45 (s, 3H), 0.89 (s, 9H), 0.05 (s, 3H), -0.14 (s, 3H); $^{13}$C NMR (151 MHz, CDCl$_3$) δ 172.5, 149.7, 149.5, 143.4, 134.5, 131.2, 127.8, 121.7, 120.9, 73.4, 60.7, 42.5, 36.4, 25.9, -4.4, -4.8; ESI-MS (m/z): 495 [MH]$^-$.

1,4-Phenylene bis(4-allyl-2-methoxyphenyl)bis(sulfate) (13-B6). Prepared from fluorosulfate (1.23 g, 5 mmol), acetonitrile (5 mL), 1,4-bis((trimethylsilyl)oxy)benzene (636 mg, 2.5 mmol), and DBU (75 µL, 0.5 mmol), with stirring at 50° C. for 5 h. The crude product was purified on a short column chromatography (9:1 to 8:2 hexane:EtOAc) to give a white solid (1.3 g, 92% yield). mp 62-65° C. R$_f$(9:1 hexane:EtOAc) 0.22. $^1$H NMR (400 MHz, CDCl$_3$) δ 7.48 (s, 4H), 7.20 (d, J=8.2 Hz, 2H), 6.81 (s, 2H), 6.78 (d, J=8.3 Hz, 2H), 5.93 (ddt, J=18.1, 9.5, 6.7 Hz, 2H), 5.13 (s, 2H), 5.09 (d, J=4.3 Hz, 2H), 3.78 (s, 6H), 3.38 (d, J=6.7 Hz, 4H). $^{13}$C NMR (101 MHz, CDCl$_3$) δ 151.2, 149.1, 141.4, 137.7, 136.6, 122.9, 122.5, 120.9, 116.8, 113.5, 56.0, 40.1; EI-MS (m/z): 563 [MH]$^+$.

5-Chloroquinolin-8-yl (4-(methylamino)phenyl)sulfate (13-B7). Prepared from fluorosulfate (786 mg, 3 mmol), acetonitrile (12 mL), TBS-protected phenol (711 mg, 3 mmol), and DBU (90 µL, 0.6 mmol), with stirring at room temperature overnight. Column chromatography (9:1 to 6:4 hexane:EtOAc) gave the product as a yellow solid (0.7 g, 61% yield). mp 99-100.5° C. R$_f$ (1:1 hexane:EtOAc) 0.62. $^1$H NMR (400 MHz, CDCl$_3$) δ 9.08 (dd, J=4.3, 1.7 Hz, 1H), 8.58 (dd, J=8.6, 1.7 Hz, 1H), 7.64-7.53 (m, 3H), 7.31 (d, J=8.9 Hz, 2H), 6.58 (d, J=8.9 Hz, 2H), 2.83 (s, 3H); $^{13}$C NMR (151 MHz, CDCl$_3$) δ 151.9, 148.7, 145.6, 141.7, 141.5, 133.1, 130.4, 127.6, 125.9, 123.1, 122.4, 121.1, 112.5, 30.8; ESI-MS (m/z): 365 [MH]$^+$.

EX. 1(L)

Synthesis of Enol Fluorosulfates 3,4-Dihydronaphthalen-1-yl sulfonate from silylated enol ether (15-1). A round-bottom flask was charged with ((3,4-dihydronaphthalen-1-yl)oxy)trimethylsilane (436 mg, 2 mmol) and dry CH$_2$Cl$_2$ (5 mL), then sealed with septa. Air was evacuated and SO$_2$F$_2$ gas was introduced in a balloon, followed by addition of 1M solution of BEMP in hexane by syringe (200 µL, 0.2 mmol, 10 mol %). The reaction mixture was stirred at room temperature overnight, monitoring by TLC. Upon completion, the solvent was removed by rotary evaporation and the crude product was purified by column chromatography (10:1 hexane:EtOAc) to give a colorless oil (350 mg, 77% yield). R$_f$(8:2 hexane:EtOAc) 0.67. $^1$H NMR (400 MHz, CDCl$_3$) δ 7.40-7.37 (m, 1H), 7.31-7.26 (m, 2H), 7.22-7.19 (m, 1H), 6.11 (dt, J=8 Hz, 4 Hz, 1H), 2.90 (t, J=8 Hz, 2H), 2.57-2.51 (m, 2H); $^{13}$C NMR (101 MHz, CDCl$_3$) δ 147.2, 136.4, 129.4, 128.0, 127.0, 121.2, 117.6, 26.9, 22.2; $^{19}$F NMR (376 MHz, CDCl$_3$) δ +39.1; GC-MS (t$_R$): 5.2 min; ELMS (m/z): 228 [M]$^+$.

Note: The analogous reaction in acetonitrile was complete within several minutes.

3,4-Dihydronaphthalen-1-yl sulfonate from lithium enolate generated in situ (15-1). A Schlenk flask was charged with a-tetralone (333 µL, 2.5 mmol) in dry THF (5 mL) and cooled to -78° C. under dry atmosphere. LHMDS (3.75 mL of 1M in THF, 3.75 mmol) was added by syringe and the reaction mixture was stirred at -78° C. for an additional 30 min. Low vacuum was then applied, SO$_2$F$_2$ was introduced from a balloon, the reaction was allowed to warm to 0° C., and stirring continued for 1 hour at that temperature. The reaction was monitored by TLC and GC-MS. Upon completion, the reaction was quenched with water (5 mL), extracted with EtOAc (2×10 mL), washed with brine, and concentrated. Purification by chromatography on a short silica column (10:1 hexane:EtOAc) gave the desired compound as a colorless oil (400 mg, 75% yield).

EX. 1(M)

Synthesis of Sulfamoyl Fluorides

General Procedure. Secondary amine (1 equiv), DMAP (0.5-1 equiv) and triethylamine (2 equiv) were mixed in CH$_2$CL$_2$ (0.33 M) in a round-bottom flask filled to one-third capacity. The flask was sealed with septa, air was evacuated, and SO$_2$F$_2$ gas was introduced from a balloon. The reaction mixture was stirred vigorously at room temperature for 3-18 h, and reaction progress was monitored by GC or LC-MS. Upon completion, the mixture was concentrated, dissolved in EtOAc, washed with 1N HCl and brine, dried over MgSO$_4$, and concentrated to give the desired compound, usually in quite pure form. In some cases, additional purification was performed by passage through a short silica gel column.

Activated cyclic amines react rapidly with SO$_2$F$_2$; in some cases, cooling of the reaction mixture with a water bath is required. Acyclic amines require 1-1.5 equiv DMAP. When 1.5 equiv of DMAP are used, the addition of triethylamine or other extra base is not required. Activated amines can even react in buffer at pH 8 (phosphate, borate, or HEPES buffers).

Di(prop-2-yn-1-yl)sulfamoyl fluoride (17-1) was prepared with 1 equiv DMAP and 2 equiv Et$_3$N. Brown impurities in the product were removed by passing the material through a short plug of silica gel (9:1 hexane:EtOAc). The product was obtained as a pink oil (3.3 g, 76% yield, accounting for CH$_2$CL$_2$ impurity by $^1$H NMR). $^1$H NMR (400 MHz, CDCL$_3$) δ 4.28 (t, J=2.2 Hz, 4H), 2.47 (t, J=2.4 Hz, 2H); $^{13}$C NMR (101 MHz, CDCl$_3$) δ 75.7, 74.8 (d, J=1.6 Hz), 37.9 (d, J=1.3 Hz); $^{19}$F NMR (376 MHz, CDCl$_3$) δ 46.4; R$_f$(9:1 hexane:EtOAc) 0.29; ELMS (m/z): 174 [M]$^+$.

Diallylsulfamoyl fluoride (17-2) was prepared with 1 equiv DMAP and 2 equiv Et$_3$N, obtained as a yellow oil (2.9 g, 65% yield). $^1$H NMR (400 MHz, CDCl$_3$) δ 5.81 (ddtd, J=16.8, 10.2, 6.5, 1.1 Hz, 2H), 5.36-5.28 (m, 4H), 3.94 (d, J=6.3 Hz, 4H); $^{13}$C NMR (101 MHz, CDCl$_3$) δ 130.7 (d, J=1.6 Hz), 120.9, 50.8 (d, J=2.0 Hz); $^{19}$F NMR (376 MHz, CDCl$_3$) δ 50.00; R$_f$(7:3 hexane:EtOAc): 0.72; GC-MS (t$_R$): 3.7 min; EI-MS (m/z): 178 [M]$^+$.

Bis(2-azidoethyl)sulfamoyl fluoride (17-3) was prepared from the bis(2-azidoethyl)amine mesylate salt, 1 equiv DMAP, and 3 equiv Et$_3$N, isolated as a yellow oil (4.49 g, 76% yield). $^1$H NMR (400 MHz, CDCl$_3$) δ 3.64-3.59 (m, 4H), 3.59-3.54 (m, 4H); $^{13}$C NMR (101 MHz, CDCl$_3$) δ 50.2 (d, J=1.9 Hz), 49.7 (d, J=1.6 Hz); $^{19}$F NMR (376 MHz, CDCl$_3$) δ 50.0; R$_f$(9:1 hexane:EtOAc): 0.52; HRMS (ESI-TOF) (m/z): [M+H]$^+$ calcd for C$_4$H$_8$FN$_7$O$_2$S, 238.0517; found 238.0524.

(2,2-Dimethoxyethyl)(methyl)sulfamoylfluoride (17-4) was prepared with 1 equiv DMAP and 2 equiv Et$_3$N, obtained as a colorless oil (3.4 g, 88% yield). $^1$H NMR (400 MHz, CDCl$_3$) δ 4.50 (t, J=5.4 Hz, 1H), 3.41 (s, 6H), 3.35 (dd, J=5.4, 2.0 Hz, 2H), 3.08 (d, J=2.3 Hz, 3H); $^{13}$C NMR (101 MHz, CDCl$_3$) δ 103.0 (d, J=2.4 Hz), 55.0, 52.8 (d, J=2.1 Hz), 37.9 (d, J=1.5 Hz); $^{19}$F NMR (376 MHz, CDCl$_3$) δ 50.0; R$_f$ (7:3 hexane:EtOAc): 0.44; ELMS (m/z): 201 [M]$^+$.

4-(2-Azidoacetyl)piperazine-1-sulfamoylfluoride (17-5) was prepared from 2-azido-1-(piperazin-1-yl)ethanone-TFA salt, 0.5 equiv DMAP, and 5 equiv Et$_3$N. The product was obtained as a pink solid (4.4 g, 70% yield). mp 92-94° C. $^1$H NMR (400 MHz, CDCl$_3$) δ 3.93 (br s, 2H), 3.72 (br s, 2H), 3.55-3.30 (m, 6H); $^{13}$C NMR (101 MHz, CDCl$_3$) δ 165.9, 50.7, 46.7, 44.0, 40.8; $^{19}$F NMR (376 MHz, CDCl$_3$) δ 40.1; R$_f$(1:1 hexane:EtOAc): 0.44; GC-MS (t$_R$): 6.3 min; EI-MS (m/z): 251 [M]$^+$.

6,7-Dimethoxy-1-phenyl-3,4-dihydroisoquinoline-2(1H)-sulfamoylfluoride (17-6) was prepared with 1 equiv DMAP and 2 equiv Et$_3$N, obtained as a white solid (0.6 g, 80% yield). mp 109-111° C. $^1$H NMR (400 MHz, CDCl$_3$) δ 7.35-7.32 (m, 3H), 7.26-7.19 (m, 2H), 6.70 (s, 1H), 6.44 (s, 1H), 6.11 (s, 1H), 3.98-3.89 (m, 1H), 3.91 (s, 3H), 3.75 (s, 3H), 3.43-3.29 (m, 1H), 3.21-3.12 (m, 1H), 2.75 (ddd, J=16.6, 4.4, 1.6 Hz, 1H); $^{13}$C NMR (101 MHz, CDCl$_3$) δ 148.8, 148.0, 139.8 (d, J=2.3 Hz), 129.1, 128.7, 128.7, 125.4, 124.1, 111.4, 110.7, 60.5 (d, J=1.4 Hz), 56.1 (d, J=5.5 Hz), 40.6 (d, J=2.7 Hz), 26.8; $^{19}$F NMR (376 MHz, CDCl$_3$) δ 50.0; R$_f$(7:3 hexane:EtOAc): 0.56; GC-MS (t$_R$): 8.3 min; EI-MS (m/z): 351 [M]$^+$.

4-(Dibenzo[b,f][1,4]oxazepin-11-yl)piperazine-1-sulfamoyl fluoride (17-7) was prepared with 0.5 equiv DMAP and 2 equiv Et$_3$N, obtained as a white solid (0.5 g, 73% yield). mp 142-144° C. $^1$H NMR (400 MHz, CDCl$_3$) δ 7.44 (d, J=6.2 Hz, 1H), 7.31 (s, 1H), 7.25-7.00 (m, 5H), 3.66 (s, 4H), 3.58 (s, 4H); $^{13}$C NMR (101 MHz, CDCl$_3$) δ 159.6, 158.4, 151.8, 139.5, 133.3, 130.8, 128.7, 127.3, 126.1, 125.6, 124.6, 123.1, 120.4, 46.6, 46.65 (m); $^{19}$F NMR (376 MHz, CDCl$_3$) δ 38.6; R$_f$(9:1 hexane:EtOAc): 0.48; ELMS (m/z): 396 [MH]$^+$.

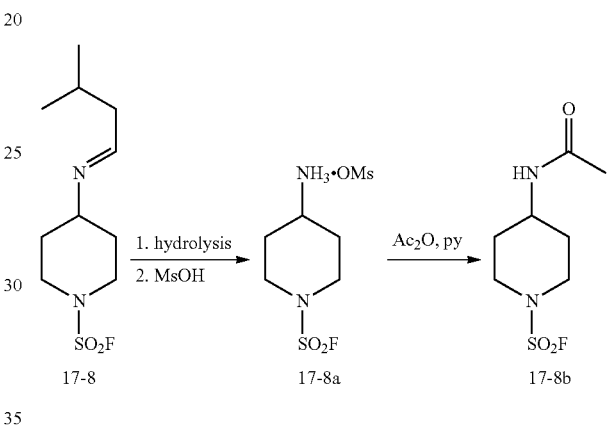

4-((3-Methylbutylidene)amino)piperidine-1-sulfamoyl fluoride (17-8) was prepared with 0.5 equiv DMAP and 2 equiv Et$_3$N. Upon completion, the reaction mixture was washed with water, dried, and concentrated. The product was obtained as a yellow oil yield (1.8 g, 70% yield, accounting for DMAP contamination in $^1$H NMR). For characterization, the imine group was hydrolyzed (treatment with $^1$PrOH/water mixture at 50° C. for 1.5 hours) followed by treatment with MsOH to make the shelf stable salt (17-8a). EI-MS (m/z): 183 [MH]$^+$.

The amine was then converted to the corresponding acetamide (17-8b) (treatment with Ac$_2$O/Py in CH$_2$Cl$_2$ at room temperature for 18 h, followed by acidification (1M HCl) and extraction with CH$_2$Cl$_2$). The amide was obtained as a beige solid in 48% yield (3 steps from crude 4-((3-methylbutylidene)amino)piperidine-1-sulfonyl fluoride, 160 mg). $^1$H NMR (400 MHz, CDCl$_3$) δ 5.71 (s, 1H), 4.02-3.82 (m, 2H), 3.13 (t, J=12.6 Hz, 2H), 2.04 (d, J=12.2 Hz, 2H), 1.97 (s, 3H), 1.63-1.46 (m, 2H); $^{13}$C NMR (101 MHz, CDCl$_3$) δ 169.8, 46.5, 45.6, 30.9, 23.5; $^{19}$F NMR (376 MHz, CDCl$_3$) δ (pm): 41.4; R$_f$(CH$_2$Cl$_2$/MeOH—9/1): 0.54; EI-MS (m/z): 225 [MH]$^-$.

4-(Hydroxydiphenylmethyl)piperidine-1-sulfamoyl fluoride (17-9). The amine precursor (6.68 g, 25 mmol), DMAP (1.5 g, 12.5 mmol), and MgO (2.5 g, 62.5 mmol) were mixed in a 4:1 CH$_2$Cl$_2$:water mixture (0.5 M in substrate) in a 500 mL round-bottom flask. The flask was sealed with septa, air was evacuated, and a SO$_2$F$_2$-filled balloon was introduced. The reaction was vigorously stirred at room temperature for 6-18 h. Upon completion, the mixture was filtered through a short plug of CELITE®, and washed with water (50 mL) and then CH$_2$Cl$_2$ (200 mL). The organic layer was washed with 1N HCl (50 mL), brine (50 mL), dried over MgSO$_4$, and concentrated. The product was obtained as a white solid (8.2 g, 94% yield). mp 109-112° C. $^1$H NMR (400 MHz, CDCl$_3$) δ 7.61-7.42 (m, 4H), 7.42-7.29 (m, 4H), 7.29-7.18 (m, 2H), 3.94 (d, J=9.4 Hz, 2H), 3.02 (br s, 2H), 2.58 (br s, 1H), 2.33 (s, 1H), 1.74-1.51 (m, 4H); $^{13}$C NMR (101 MHz, CDCl$_3$) δ 145.0, 128.5, 127.1, 125.7, 79.4, 47.7, 43.3, 25.6; $^{19}$F NMR (376 MHz, CDCl$_3$) δ (pm): 39.2; R$_f$ (7:3 hexane:EtOAc): 0.56; ELMS (m/z): 332 [(M−H$_2$O)H]$^+$.

1,4-Dioxa-8-azaspiro[4.5]decane-8-sulfamoyl fluoride (17-10) was obtained as a yellow solid (5.6 g, 99% yield) using the same general procedure as described above for the synthesis of 17-9, but with 1,4-dioxa-8-azaspiro[4.5]decane as the amine precursor. mp 87-89° C. $^1$H NMR (400 MHz, CDCl$_3$) δ 3.97 (s, 2H), 3.62-3.53 (m, 2H), 1.81 (t, J=5.9 Hz, 2H); $^{13}$C NMR (101 MHz, CDCl$_3$) δ 105.5, 64.7, 45.8 (d, J=1.3 Hz), 34.1 (d, J=1.2 Hz); $^{19}$F NMR (376 MHz, CDCl$_3$) δ 41.7; R$_f$ (7:3 hexane:EtOAc): 0.41; GC-MS (t$_R$): 5.35 min; EI-MS (m/z): 225 [M]$^+$.

EXAMPLE 2

Modified Antibiotics

ArOSO$_2$F is a non-polar functional group on an aromatic ring. It is an electrophile that can coexist with nucleophiles and withstand biological systems. ArOSO$_2$F is very stable and can selectively react with different protein targets. Its non-polar functionality means introduction of the functional group on the parent minimally impacts, if at all, the affinity for the parent molecule.

Any known small molecule drugs which have one or more aromatic substitution can be readily converted to ArOSO$_2$F. Many antibiotics include functional groups such as aryl-OH, amino groups, and the like, which can be derivatized to introduce an SO$_2$F group (e.g., OSO$_2$F, NCH$_2$CH$_2$SO$_2$F, or NSO$_2$F) into the antibiotic structure. In this study, five fluorosulfonyl antibiotic derivatives (cephalosporin derivative 10-2, ciprofloxacin derivative 10-7, and three vancomycin derivatives—vancomycin-SF, vancomycin-SF-1 and vancomycin-SF-2, the latter two of which include N-propargyl groups as potential reactants in copper-catalyzed azide/alkyne click coupling reactions) were evaluated for antimicrobial activity against E. coli and/or B. subtilis in comparison to the non-modified versions of the antibiotics. See FIG. 20 for the structures of the antibiotic compounds.

The antibiotic compounds were serially diluted in LB medium (10 g/L tryptone, 5 g/L yeast extract, 10 g/L NaCl in deionized water) on a 96-well culture plate from DMSO stock solution. Bacteria were inoculated into the wells and allowed to grow overnight at 37° C., 300 rpm. Overnight growth was assessed by measuring the turbidity of the media by absorbance at 605 nm in a plate reader. The results for Bacillus subtilis are shown in Table 2, and the results for E. coli are shown in Table 3. Low turbidity (low optical density at 605 nm, OD$_{605}$) relative to medium or vehicle alone indicates antibacterial activity.

TABLE 2

Bacillus subtilis (Gram positive) results.

Figure 20:
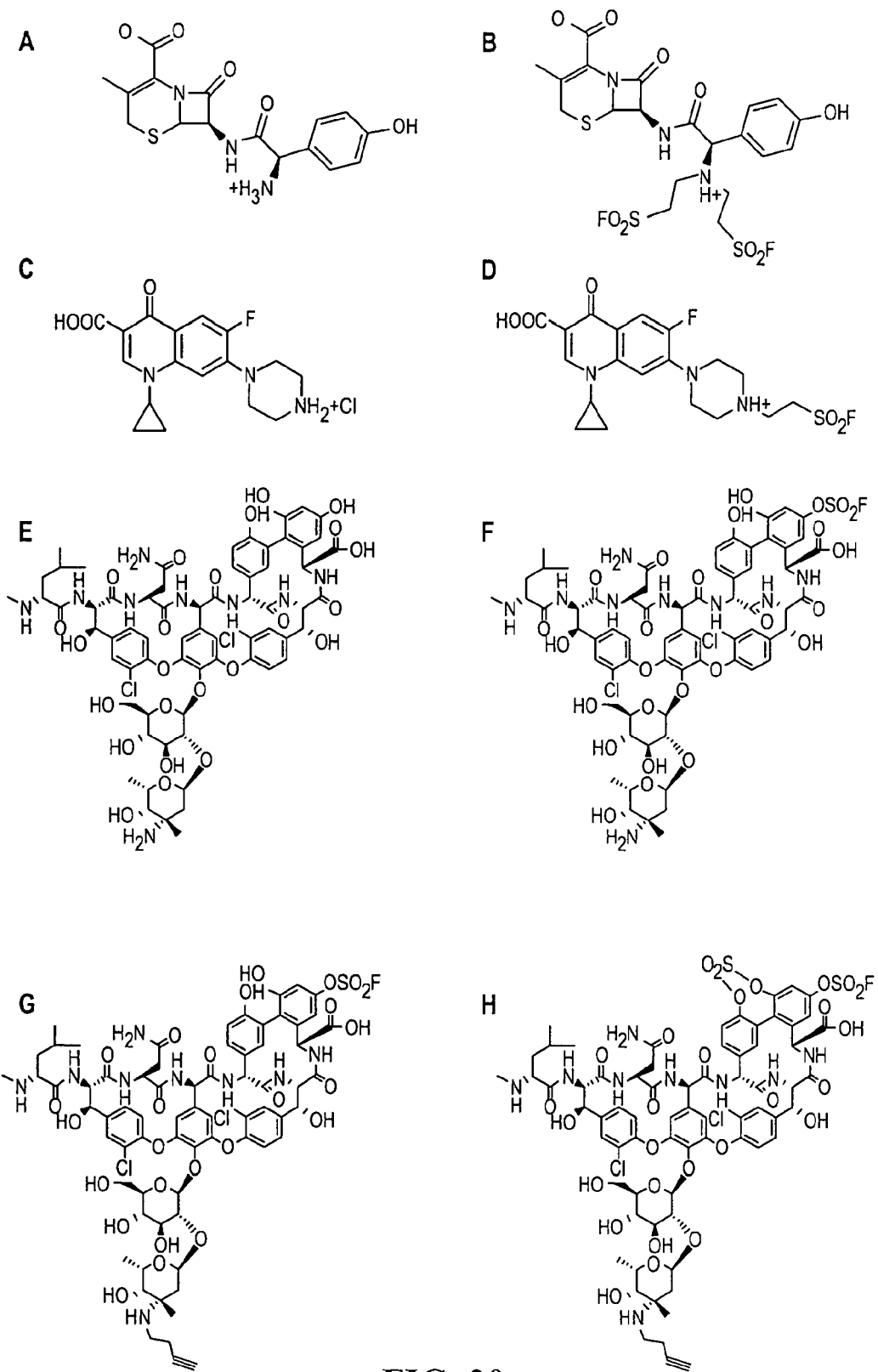
FIG. 20 illustrates structures of antibiotic compounds and fluorosulfonated derivatives thereof which were evaluated for activity against E. coli and B. subtilis.

| Antibiotic 50 μM | Structure in FIG. 20 | OD$_{605}$ after overnight growth |
|---|---|---|
| LB medium only | N/A | 0.425 |
| Vehicle (DMSO) | N/A | 0.422 |

TABLE 2-continued

Bacillus subtilis (Gram positive) results.

| Antibiotic 50 μM | Structure in FIG. 20 | OD$_{605}$ after overnight growth |
|---|---|---|
| Cephalosporin | A | 0.527 |
| Cephalosporin-SF | B | 0.16 |
| Ciprofloxacin | C | 0.036 |
| Ciprofloxacin-SF | D | 0.036 |
| Vancomycin | E | 0.036 |
| Vancomycin-FS | F | 0.037 |
| Vancomycin-FS-1 | G | 0.037 |
| Vancomycin-FS-2 | H | 0.049 |

TABLE 3

Escherichia coli (Gram negative) results.

| Antibiotic 20 μM | Structure in FIG. 20 | OD$_{605}$ after overnight growth |
|---|---|---|
| Vehicle (DMSO) | — | 0.325 |
| Cephalosporin | A | 0.253 |
| Cephalosporin-SF | B | 0.339 |
| Ciprofloxacin | C | 0.036 |
| Ciprofloxacin-SF | D | 0.037 |

The results in Tables 2 and 3 clearly indicate that the fluorosulfonylated antibiotics exhibit similar activity to the non-derivatized antibiotics, although the cephalosporin derivative appears to have improved activity against B. subtilis relative to cephalosporin itself in these tests.

EXAMPLE 3

Modified Tyrosine and Peptides Prepared Therewith

Fluorosulfate-Fmoc tyrosine is a useful building block for peptide synthesis.

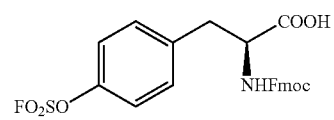

Using fluorosulfate-Fmoc tyrosine, several analogues of market peptide drugs were synthesized with tyrosine-OSO$_2$F instead of tyrosine in sequence by standard solid phase peptide synthesis methods that are well known in the art, demonstrating the utility of this functional group in peptide chemistry.

Tyrosine O-sulfation is a common enzymatic post-translational modification that occurs while the secreted and transmembrane proteome traffics through the Golgi compartment of the cell. While it is clear that phosphorylation and sulfation of tyrosine (Tyr) similarly modulate protein-protein interactions and affect conformational changes within a protein, much less is known about sulfation partly because sulfotyrosine (sY) peptides cannot be easily made by laboratories without substantial chemistry expertise.

Currently, several approaches are used for the solid-phase peptide synthesis (SPPS) of sY-containing peptides, all of which have drawbacks. In one embodiment, the present invention provided an efficient approach to make sY-containing peptides wherein Fmoc-protected fluorosulfated Tyrosine (Y(OSO$_2$F)) is incorporated into the peptide-ofinterest using a near-standard Fmoc solid phase synthesis strategy either manually or by using a peptide synthesizer. Like other sulfur(VI) fluorides, aromatic fluorosulfates are hydrolytically stable, redox-resistant, and they do not serve as halogenation agents. They are very stable toward hydrolysis under neutral or acidic conditions and are stable for up to two weeks in phosphate buffer at pH 10. However, they can become reactive in the presence of an appropriate nucleophile under conditions that stabilize the departure of the fluoride leaving group.

The ease of obtaining Fmoc protected Y(OSO2F) building block and the high stability of aromatic fluorosulfates enables the efficient synthesis of peptides containing the Ar—O—$SO_2$F substructure using an Fmoc chemistry strategy. The Fmoc-Y($OSO_2$F)—OH (Fmoc-Y-SF, 1) used in SPPS is prepared in one step in high yield from the reaction of commercially available Fmoc-protected Tyr with sulforyl fluoride (gas) as described elsewhere herein (Scheme 1). Conveniently, 2-methyl-piperidine (2-MP) was used to remove the Fmoc primary amine protecting group during each SPPS coupling cycle (Scheme 2) instead of piperidine, as piperidine inefficiently reacts with the fluorosulfate functionality lowering the yield and purity of the desired Y($OSO_2$F)-containing peptides. The fluorosulfate functional group is stable under the standard Rink amide resin-peptide cleavage (95:2.5:2.5=TFA:TIPS:$H_2$O) conditions used to liberate the side chain deprotected peptide from the resin. Y($OSO_2$F) residue(s) in the peptide-of-interest were then converted into the sY functionality by hydrolysis with a base ($Cs_2CO_3$, or 1,8-diazabicyclo[5.4.0]undec-7-ene(DBU)) dissolved in ethylene glycol at 25° C. for 60-120 min with stirring (Scheme 3).

Five sY peptides 2-6 were prepared by an optimized protocol of Y($OSO_2$F)-containing peptide synthesis and arylfluorosulfate hydrolysis employing $Cs_2CO_3$/ethylene glycol(Table 4). The sequence of first peptide DADEsYL-$NH_2$ (P2; SEQ ID NO: 1) corresponds to a sequence in the epidermal growth factor receptor (EGFR) and P2 is expected to be a good inhibitor of protein tyrosine phosphatase 1B. The sequence of a monosulfated peptide sYEsYLDsYDF-$NH_2$ (P3; SEQ ID NO: 2) and a trisulfated peptide sYEsYLDsYDF-$NH_2$ (P4; SEQ ID NO: 3) corresponds to residue 5-12 of mature P-selectin glycoprotein ligand 1 (PGSL-1) that binds to P-selectin and plays important role in the rolling adhesion of leukocytes on vascular endothelium. Disulfated peptide TTPDsYGHsYDDKDTLDLNTPVDK-$NH_2$ (P5; SEQ ID NO: 4) is from C5aR, a classical G-protein coupled receptor that is implicated in many inflammatory diseases. The sequence of tetrasulfated peptide DADSENSSFsYsYsYDsYLDEVAF-$NH_2$ (P6; SEQ ID NO: 5) corresponds to residue 14-33 of chemokine receptor D6, which scavenges extracellular pro-inflammatory CC chemokines and suppresses inflammation and tumergenesis. Peptides P4-P6contain multiple sY residues and their synthesis poses significant challenge to the coupling efficiency, stability and efficiency of hydrolysis for Y($OSO_2$F) in different sequence environments.

For all couplings in SPPS, including the coupling of amino acid 1, we used 5 equiv. of the appropriate side chain protected amino acid preactivated with HCTU/HOBt/DIPEA for 30min)(refs). The activated amino acid was added to the resin-bound primary amine with shaking for a coupling period of 30-60 min to generate a new amide bond. Every Fmoc protecting group was removed employing 3 applications of 20% 2-MP in dimethylformamide or N-methyl-2-pyrrolidone for 10 min. We used and prefer a 95:2.5:2.5=TFA:TIPS:$H_2$O deprotection solution (25 ° C., 180 min) to cleave the peptide-of-interest off the Rink resin and to liberate the side chain protecting groups, however the other cleavage/deprotection cocktail mentioned above performs similarly. The crude yield of Y($OSO_2$F) peptides carried out on a 200 μmol scale ranged from 77-89%. The Y($OSO_2$F)-containing peptides can be easily purified by reverse phase-high performance liquid chromatography (RP-HPLC), exemplified by DADEY($OSO_2$F)L-$NH_2$ (P7; SEQ ID NO: 6) in a 64% yield. Fluorosulfate hydrolysis in peptide 7 was accomplished in ethylene glycol utilizing $Cs_2CO_3$ as a base (10 equiv) and was followed by semi-preparative RP-HPLC using a C18 column and an 20 mM ammonium acetate/$CH_3$CN mobile phase gradient, revealing near-quantitative conversion (FIG. 1A, S1 and S2).

In the optimization of the hydrolysis of Y($OSO_2$F)-containing peptide 7 to sY-containing peptide 2, we observed significant desulfation of sY in the presence of base in aqueous solutions. Upon treating peptide 7 with $Cs_2CO_3$ dissolved in methanol, we observed the apparent methylation of carboxylate side chains, presumably owing to the formation of a Tyr-O—$SO_2$—$OCH_3$ intermediate. Although no consensus sequence is reached for tyrosine sulfation, acidic residues preponderate the known sites of tyrosine sulfation and such side reaction is likely to happen to other sulfated tyrosine sequences. (Lin 1992, Kehoe 2000, Seibert 2007, Teramoto 2013) While utilization of methanol/$NH_3$ (2M)/$Cs_2CO_3$ attenuated methylation, it was still observed. Utilizing $Cs_2CO_3$ dissolved in ethanol resulted in peptide ethylation, consistent with formation of Tyr-O—$SO_2$—$OCH_2CH_3$ intermediate. With $Cs_2CO_3$ dissolved in isopropanol or tertiary butyl alcohol, no reaction occurred. Notably, while $Cs_2CO_3$/ethylene glycol and $Cs_2CO_3$/1,4 butanediol afforded quantitative hydrolysis with no side reactions, $Cs_2CO_3$/1,3 propanediol afforded <50% yield of sY peptide 2 and numerous side products.

Outside of hydrolysis methodology development explored in the preceding paragraph, there is no need to purify the crude Y($OSO_2$F) peptides resulting from 95:2.5:2.5=TFA:TIPS:$H_2$O treatment. Thus, the crude Y($OSO_2$F)-containing peptides were directly subjected to arylfluorosulfate hydrolysis using ethylene glycol/$Cs_2CO_3$ method. Using this approach sY peptides P2-P6 were obtained in 36-67% yield (Table 4) after RP-HPLC purification using the column and conditions mentioned above.

The synthesis of GDsYDSMKEPCFR-$NH_2$ (P8; SEQ ID NO. 7), a sY peptide containing Cys residue, is achieved by a different protocol employing DBU as the base in ethylene glycol. The sequence of 8 corresponds to residue 19-30 of CXCR4, which is crucial for embryonic development and have been implicated in cancer metastasis and HIV infection. sY has been reported to make the largest contribution to CXCR4-CXCL12 binding. Using the optimized SPPS strategy and side chain deprotection/resin cleavage strategy outlined above, the crude peptide GDY($OSO_2$F)DSMKEP-CFR-$NH_2$ (P9; SEQ ID NO 8) (Table 4) was successfully synthesized. Peptide 9 was HPLC purified in an isolated yield of 30% in order to optimize the hydrolysis strategy for producing Cys-containing sY peptides. The standard ethylene glycol/$Cs_2CO_3$ method didn't perform well because it appeared that we generated a Cys-S—COOH containing peptide. hydrolysis of peptide P9 employing 5% DBU in ethylene glycol containing 0.5% dithiothreitol (DTT) was effective, however. This approach afforded sY peptide P8 in 25% isolated yield (Table 4). Adding DTT was the key to minimize the formation of byproducts.

The Fmoc synthesis of Y($OSO_2$F) containing peptides described herein is both practical and efficient. Standard side chain deprotection and resin cleavage solutions perform well. Two different fluorosulfate hydrolysis protocols are introduced for the efficient production of sY peptides. The method used depends on whether the peptide lacks or contains a Cys residue. The facile synthesis described herein takes advantage of the unique reactivity of sulfur(VI) fluorides. This approach can easily be implemented by commercial and academic peptide synthesis facilities.

Scheme 1. Synthesis of protected amino acid 1

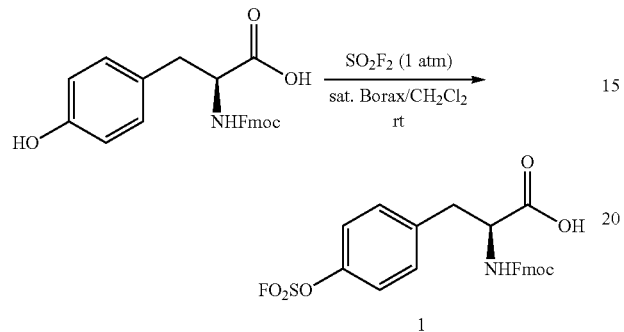

Scheme 2. Overview of Y(OSO₂F)-containing peptide synthesis

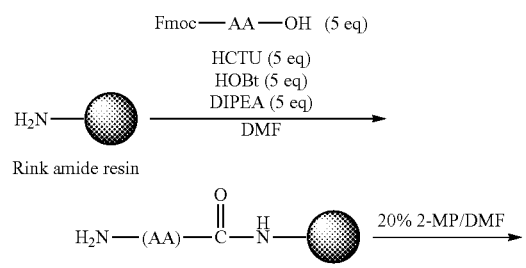

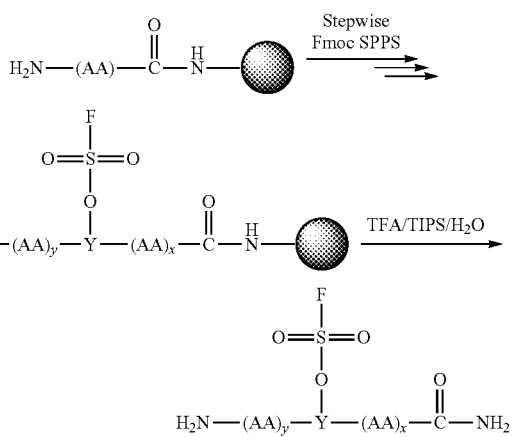

Scheme 3. Overview of arylfluorosulfate hydrolysis to afford sY peptides

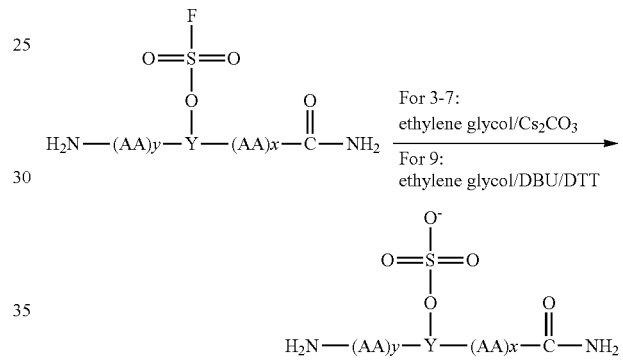

TABLE 4

| Peptide | Protein | Sequence | Isolated Yield | SEQ ID NO: |
|---|---|---|---|---|
| P2 | EGFR (988-993) | DADEsYL-NH2 | 67% | SEQ ID NO: 1 |
| P3 | PGSL-1 (5-12) | YEsYLDYDF-NH2 | 54% | SEQ ID NO: 2 |
| P4 | PGSL-1 (5-12) | sYEsYLDsYDF-NH2 | 58% | SEQ ID NO: 3 |
| P4 | C5aR (7-28) | TTPDsYGHsYDDKDTLDLNTPVDK-NH2 | 54% | SEQ ID NO: 4 |
| P6 | D6 (14-33) | DADSENSSFsYsYsYDsYLDEVAF-NH2 | 36% | SEQ ID NO: 5 |
| P7 | EGFR (988-993) | DADEY(OSO2F)L-NH2 | 64% | SEQ ID NO: 6 |
| P8 | CXCR (19-30) | GDsYDSMKEPCFR-NH2 | 25% | SEQ ID NO: 7 |
| P9 | CXCR (19-30) | GDY(OSO2F)DSMKEPCFR-NH2 | 30% | SEQ ID NO: 8 |

Four other commercial peptide drug derivatives were synthesized using the fluorosulfate-Fmoc tyrosine: Thymopentin LY001:RKDVYG*GG(SEQ ID NO: 9); Oxytocin LY002:cYIQNCPLG*GG(SEQ ID NO: 10); Arginine vasopressin (2 modified forms) LY003:CYFQNCPRG*GG(SEQ ID NO: 11); and Indolicidin LY005: I*GPWKWPYWPWRR-NH$_2$ (SEQ ID NO: 12) where Y is modified tyrosine (fluorosulfonated) and *G is propargylglycine.

Modified Oxytocin (SEQ ID NO: 10); Modified Indolicidin (SEQ ID NO: 12):

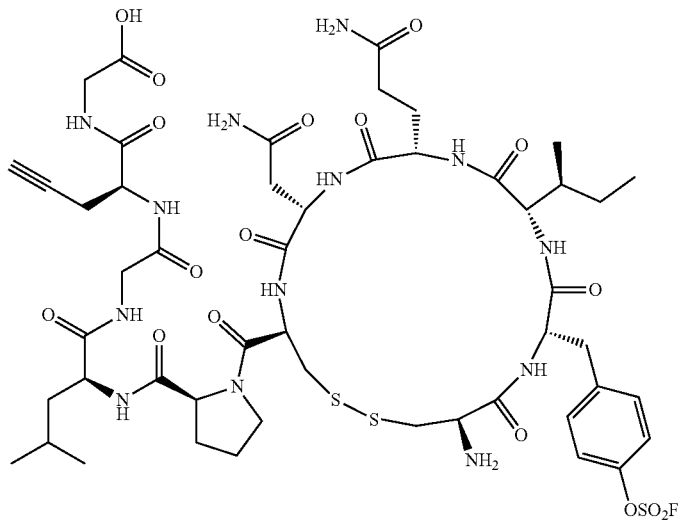

Modified Oxytocin

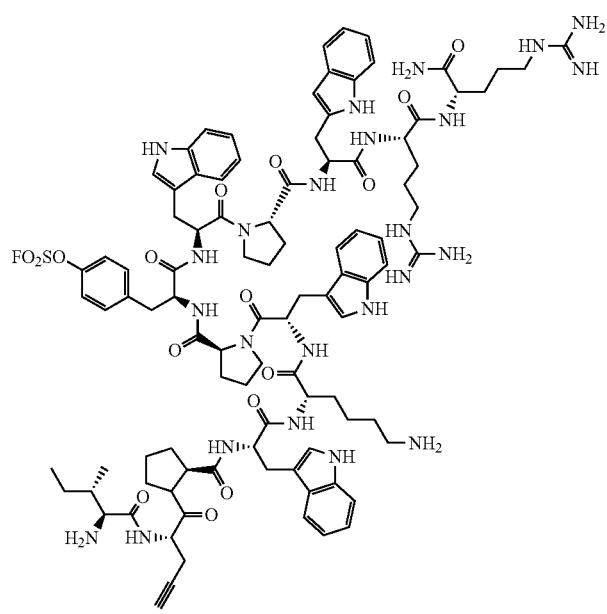

Modified Indolicidin

-continued

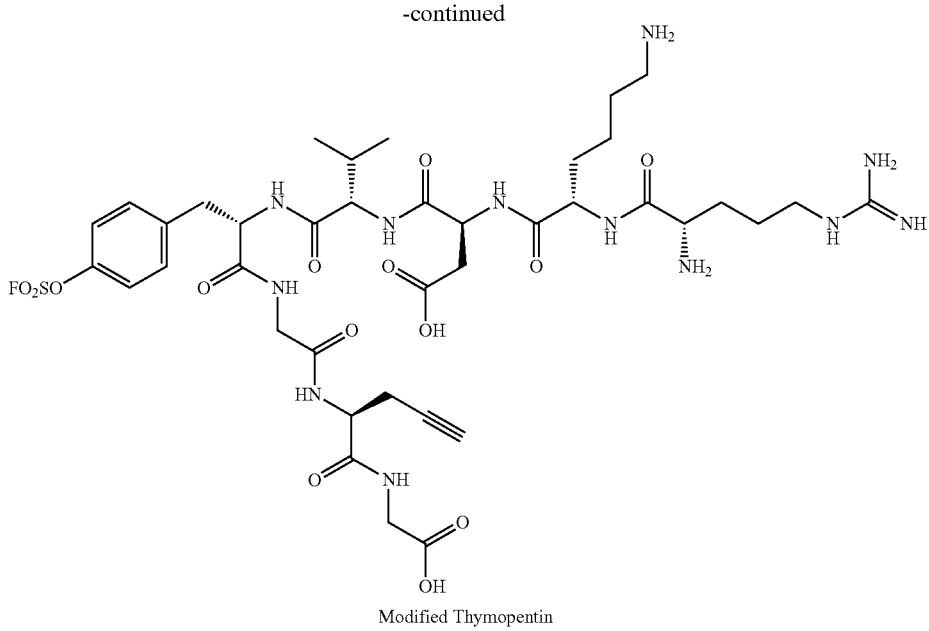
Modified Thymopentin

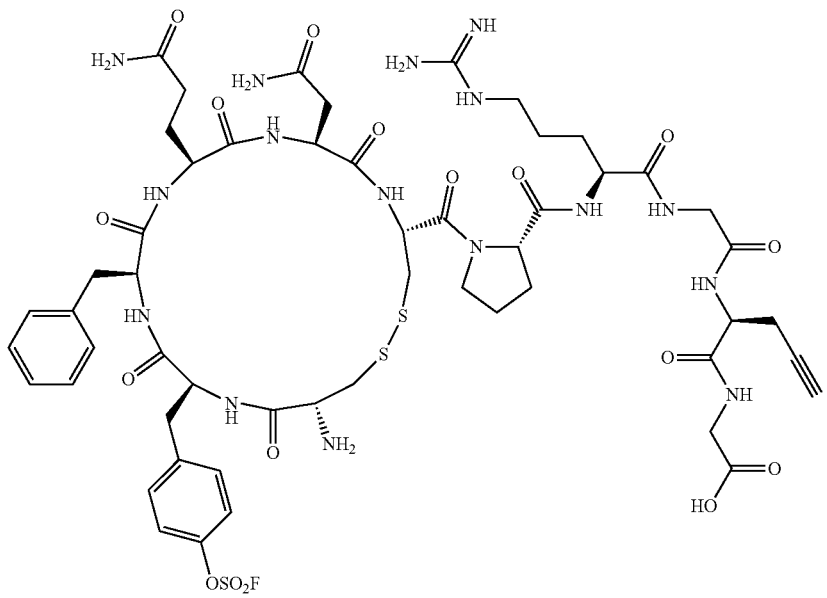
Modified Arginine Vasopressin

Modified Thymopentin (SEQ ID NO: 9); Modified Arginine Vasopressin (SEQ ID NO: 11):

The fluorosulfate ester groups of such peptides also can be converted to sulfate esters by selective hydrolysis with cesium carbonate and ammonia in methanol. For example, the modified indolicin was hydrolyzed to the corresponding sulfate ester as verified by LCMS after direct transfer to PBS buffer.

EXAMPLE 4

Fluorosulfate TTR Substrates

An $ArOSO_2F$ functional group can serve as a covalent modifier in drug design. Almost 30% of the marketed drugs whose molecular targets are enzymes act by irreversible inhibition. J. Singh, R. C. Petter, T. A. Baille, A. Whitty, Nat. Rev. Drug Discov. 2011, 10, 307-317. By installing an $ArOSO_2F$ functional group on azo analogs of tafamidis, a reversible stabilizer substrate of transthyretin (TTR), the analogs can be transformed into an irreversible stabilizer. Small molecule analogues of tafamidis react with TTR protein in PBS buffer (half-life is about 80 min). As shown, below, installation of an-$OSO_2F$ group via the general procedure for reactions of phenolic compounds with gaseous $SO_2F_2$ (Ex. 1(J)), above, changes the reversible parent inhibitor to irreversible versions (i.e. azo compounds 4, 5, 6, and 7) which had half-lives ranging from about 80 min to well over 6 hours after reaction with TTR.

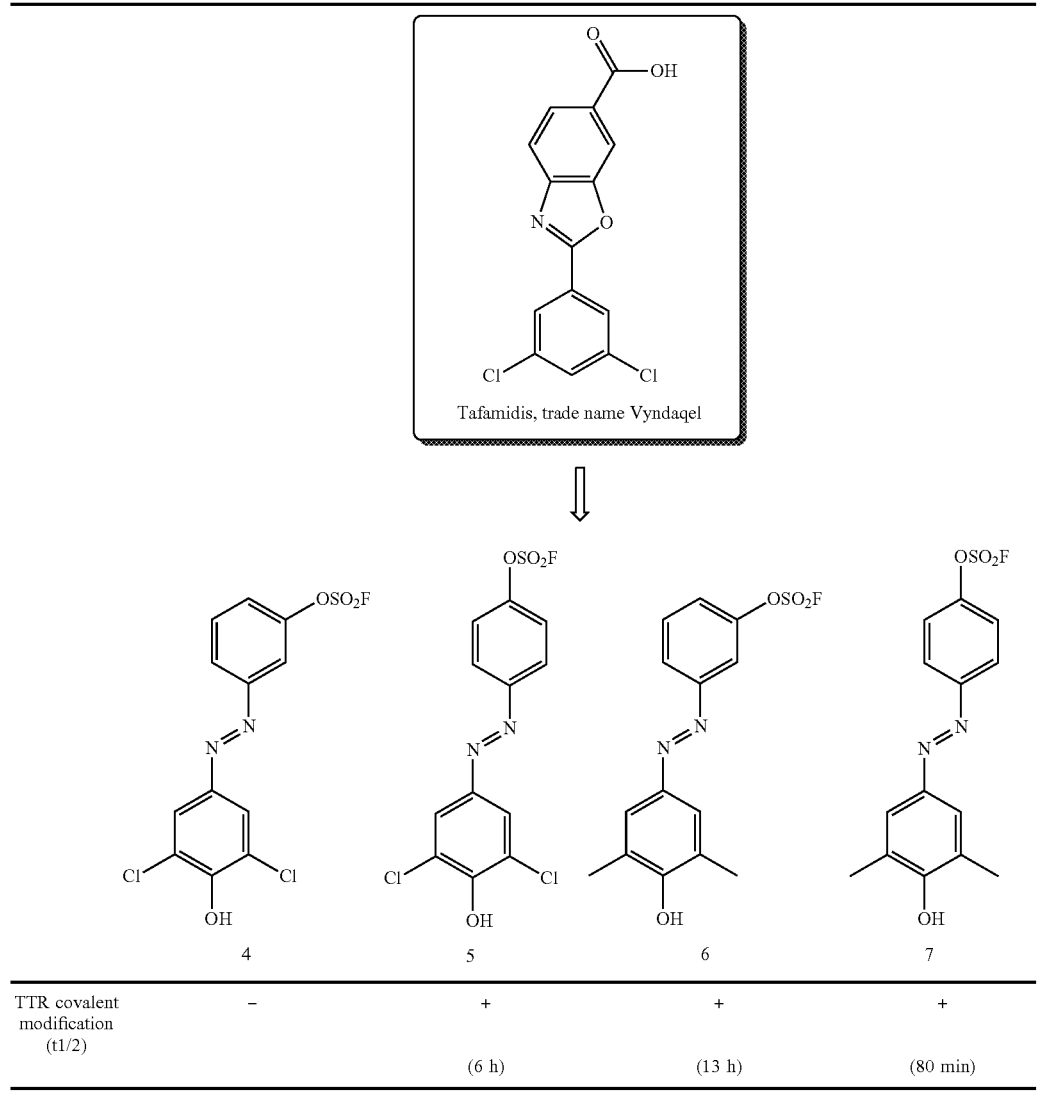

Additionally, compounds in which the diazo group has been replaced by an oxadiazole have been prepared, as well. These compounds also exhibited TTR binding activity with covalent binding to the active site, albeit with subsequent hydrolysis by a lysine residue to form a sulfated lysine in the active site.

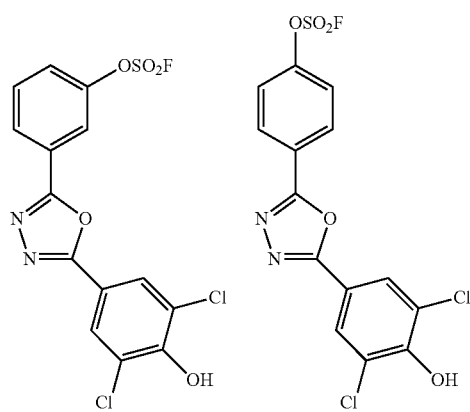

EXAMPLE 5

Fluorosulfate Compounds for $^{18}$F PET Scan Applications

Due to its stability and ability to maintain affinity of the parent molecule, ArOSO$_2$F is a useful compound for performing $^{18}$F PET scans for small molecules, peptides, and proteins. If a covalent reaction occurs, fast releasing fluoride ion will be readily confirmed by the enrichment of $^{18}$F ion in bones, which would then be detectable by PET scan techniques. The reaction conditions are simple, fast, and provide for direct loading of $^{18}$F on the target molecule. For example, a compound with a phenol group can be reacted with sulfuryl fluoride gas for about 1-2 hours in buffer under mild condition to afford an Ar—OSO$_2$F compound. The very high conversion rate allows for simply removing the buffer without purification. Subsequent exchange of $^{19}$F by $^{18}$F can be readily accomplished by, e.g., exposure to Ag$^{18}$F, or preferably $^{18}$F bifluoride. Proteins are an attractive target for this application as there is currently no known simple chemical way to install a small enough piece containing a stable F molecule onto proteins. This process is similar to known bioconjugation; however, this generally requires multiple steps and larger molecules. For example, derivatization of dapagliflozin by replacing the OEt group with an OSO$_2$F group provides a means of accessing an $^{18}$F version of dapagliflozin by $^{18}$F/$^{19}$F exchange.

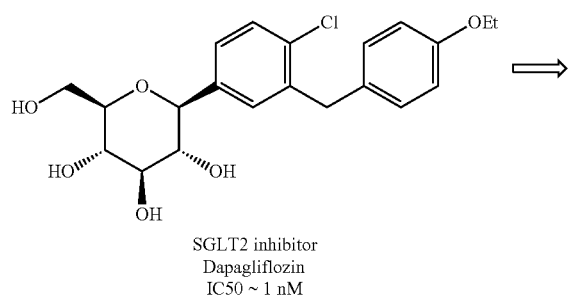

SGLT2 inhibitor
Dapagliflozin
IC50 ~ 1 nM

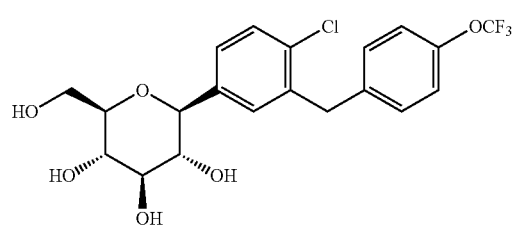

~1 nM in SGLT2 assays

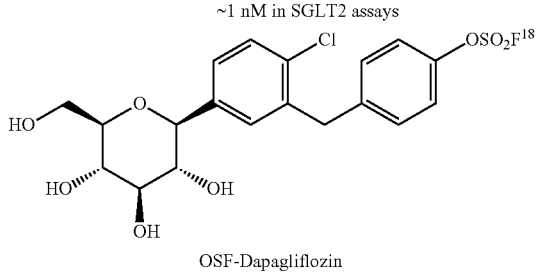

OSF-Dapagliflozin

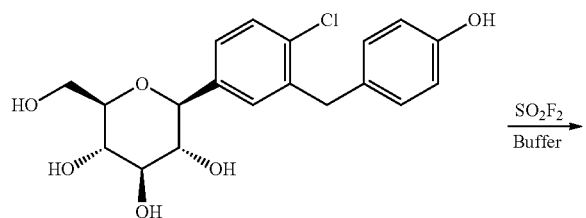

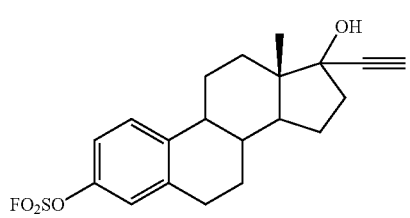

Molecular Weight: 378.46

OSF-Dapagliflozin

O-(2-[$^{18}$F]fluoroethyl)-L-tyrosine has been used as a PET reagent in a clinical study. O-fluorosulfonyl-L-tyrosine is a fluorosulfonyl ester analog of O-(2-fluoroethyl)-L-tyrosine, and is stable in HEK cell lysates for at least 3 hours, which is a sufficient biostability for PET applications. The $^{18}$F version of O-fluorosulfonyl-L-tyrosine can be used for PET imaging, and can be prepared rapidly and efficiently by exchange of $^{19}$F by $^{18}$F by contacting the of non-radiolabeled O-fluorosulfonyl-L-tyrosine with $^{18}$F-enriched potassium bifluoride and a potassium complexing agent in a solvent such as acetonitrile.

EXAMPLE 6

Fluorosulfate Compounds as "Click-Tag" Reagents and Probes for Drug Discovery

Including an SO$_2$F group on a biologically active molecule can also provide an opportunity to probe the active site of receptor molecules (e.g., by covalent reaction of the fluorosulfonyl moiety with an amino acid side chain of a receptor when the fluorosulfonylated molecule is docked in the active site). In this regard, the SO$_2$F group also can be conveniently combined with other functional probe/linking groups, for participation in additional coupling reactions with other useful materials, such as dyes or other markers. For example, a molecule with both an SO$_2$F group and an alkynyl group can be utilized as a coupling partner in an azide/alkyne "click" coupling reaction. This process affords a convenient and selective means of designing new fluorosulfonyl-based probes that include markers or other useful groups attached to the biologically active drug structure.

In one example, ethynylestradiol fluorosulfate was readily reacted with an azo-substituted fluorescein derivative via a copper catalysed azide/alkyne complexing reaction ("click reaction") to tether the estradiol derivative to fluorescein without affecting the OSO$_2$F group.

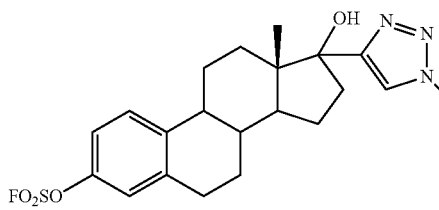 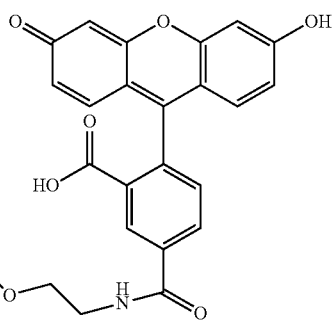

Probe-ethinylestradiol-OSO2F
Molecular Weight: 955.01

In the case of ethynylestradiol, the alkyne moiety already is part of the normal drug structure. Alternatively, an alkyne can be separately introduced onto the drug structure in addition to the fluorosulfonyl group, such as in the fluorosulfonylated propargyl vancomycin compounds, vancomycin-FS-1 and vancomycin-FS-2, from Example 2. Such probes can selectively pull down substrates for the biologically active portion of the probe from cell lysates and other complex mixtures of proteins and other biomolecules.

Ethynylestradiol fluorosulfate probes effectively capture tryptophanase from E coli lysates. The affinity of the ethynylestradiol fluorosulfate probe described above for tryptophanase was as verified with recombinant tryptophanase, which was tagged with the probe with greater than 90% modification (50 micromolar tryptophanase, 500 micromolar probe, in TBS pH 8 buffer for 16 hours at 37° C.). Tryptophanase has been implicated in biofilm formation, thus, the ethynylestradiol fluorosulfate materials provides a means for inhibiting biofilm formation.

EXAMPLE 7

Covalent Attachment of SO$_2$F Compounds to Receptor Sites

Figure 21:
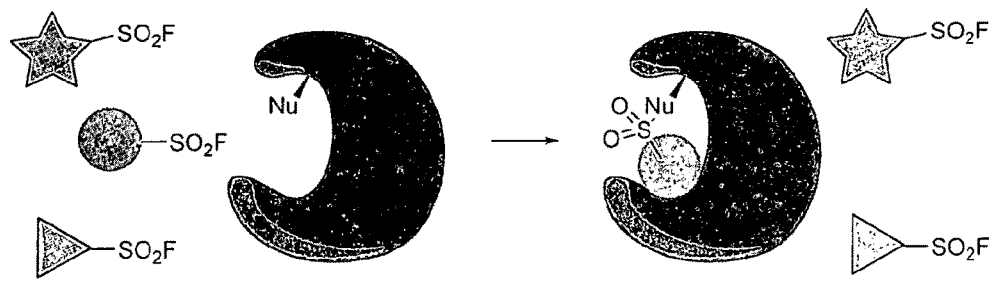
FIG. 21 graphically illustrates reactions of fluorosulfates and sulfonyl fluorides with nucleophilic amino acid side chains in receptor active sites.
Figure 21:
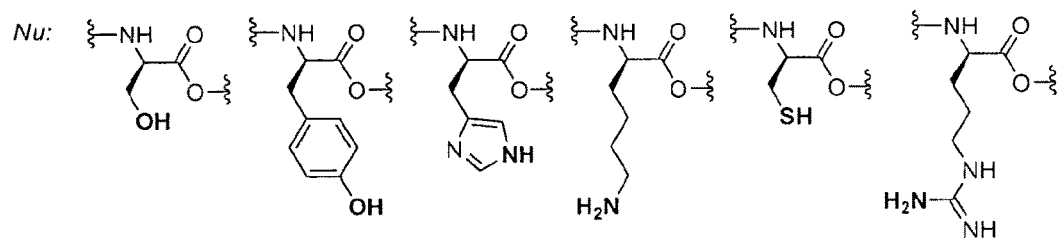
Figure 21:
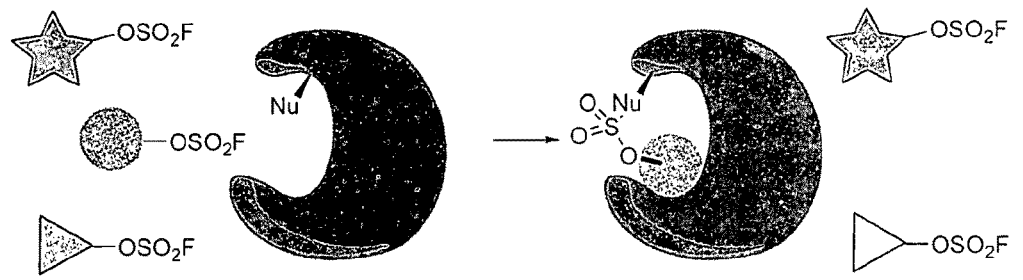
Figure 21:
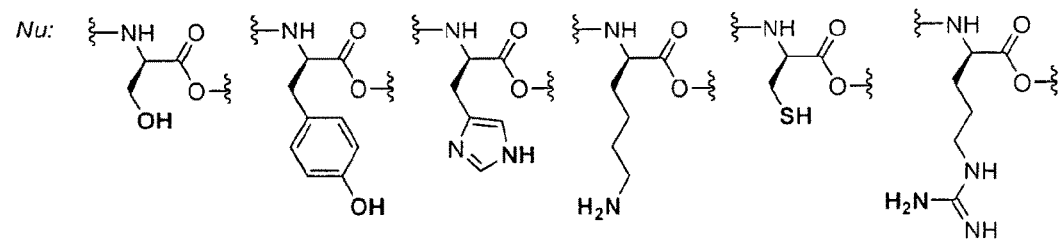
Figure 22:
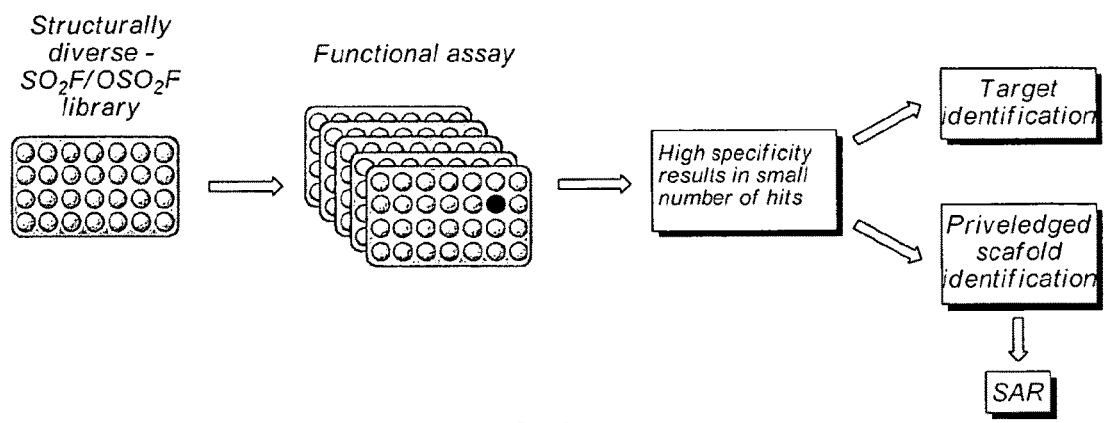
FIG. 22 schematically illustrates an screening assay embodiment.

The SO$_2$F moiety, in the various forms described herein also, in some cases, can provide a handle for covalent attachment of organic compounds to receptor sites that include a nucleophilic amino acid side chain, such as a phenolic OH group, an amino group, a thiol, and the like, in the reactive site in an orientation that can react to displace fluoride from sulfur. This concept is summarized in FIG. 21, which graphically illustrates docking of fluorosulfate and fluorosulfonyl-substituted substrate molecules in a receptor site, and subsequent reaction to displace fluoride and covalently bind the substrate molecule in the active site. When several fluorosulfates or sulfonyl fluorides are present for potential reaction with the receptor, only molecules that have an appropriate molecular configuration will interact/dock with the active site of the receptor bind to the receptor site. Thus, this process can be utilized as a screening assay, where a series of SO$_2$F substituted candidate molecules (i.e., a library) are screened in a functional assay for binding to a target receptor protein (see FIG. 22).

EXAMPLE 8

Figure 23:
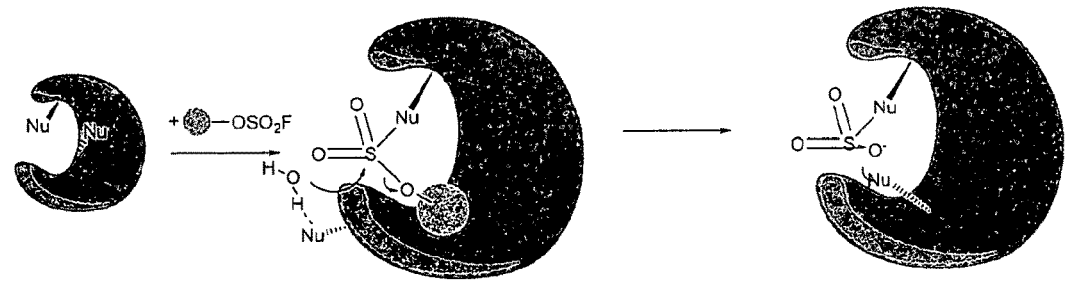
FIG. 23 schematically illustrates reactions of fluorosulfates with multiple nucleophilic amino acid side chains in a receptor active site.
Figure 24:
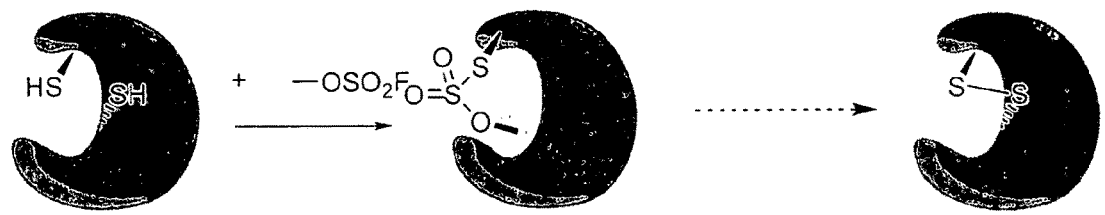
FIG. 24 schematically illustrates reactions of fluorosulfates with multiple thiol amino acid side chains in a receptor active site.

Selective Sulfonation of Nucleophilic Amino Acid Side Chains in Receptor Active Sites In addition, the biologically active —OSO$_2$F compounds described herein can be utilized in some instances to sulfonate a nucleophilic amino acid side chain in the active site of a receptor protein, e.g., by initial reaction of a receptor-docked fluorosulfate to displace fluoride, and subsequent reaction with another nucleophilic side chain (Nu) to displace the substrate molecule and form a Nu-SO$_3$— group, as illustrated in FIG. 23. In some cases, if the nucleophilic side chains both comprise thiols, an additional elimination step can occur to form a disulfide bond in the active site, as illustrated in FIG. 24.

EXAMPLE 9

Sulfur(VI) Fluoride-Based Functional Groups on Probes that Selectively and Covalently Modify Enzymes and Non-Enzymes in Living Cells The binding-induced activation of sulfur (VI) fluoride functional groups also can be used in modifying proteins in biological systems. Aryl-SO$_2$F and aryl-OSO$_2$F probes were studied in live HeLa cells using gel-based assays and SILAC-based mass spectrometry approaches. Selective labeling of proteins by both aryl-SO$_2$F and aryl-OSO$_2$F probes were observed and the protein targets were identified.

Figure 25:
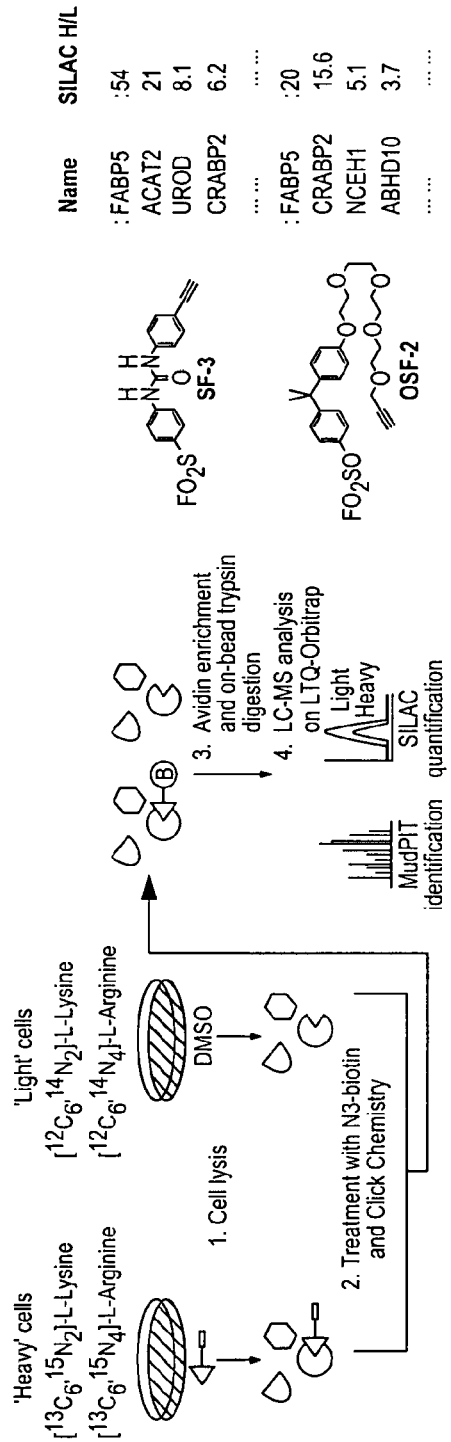
FIG. 25 illustrates work flow of SILAC identification of labeled protein targets using aryl-SF and aryl-OSF probes. High heavy/light ratio for FABPS and CRABP2 indicates that they are covalently labeled by SF and OSF probes.
Figure 26:
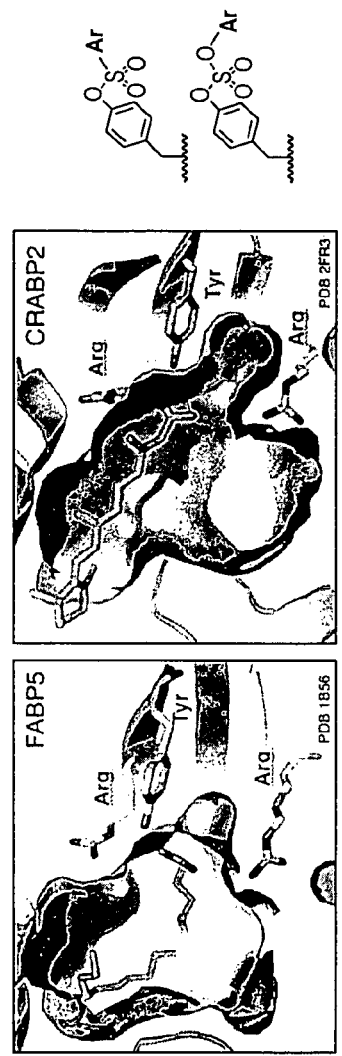
FIG. 26 shows recombinant FABPS and CRABP2 were incubated with SF-3 and OSF-4 and the site of modification was identified by tandem mass spectrometry. The tyrosine residues in the Arg-Tyr-Arg modules are modified. Mutations of the tyrosine and arginine residues prevent or significantly impair the modification event.

We examined the reactivity and selectivity of covalent labeling by aryl-SO$_2$F and aryl-OSO$_2$F probes and select probes SF-3 and OSF-2 for target identification via the SILAC technique (FIG. 25). Target proteins for both probes were found to befunctional unrelated enzymes or non-enzymes. Surprisingly, two non-enzymes, FABP5 and CRABP2, were labeled in both cases. Using recombinant FABP5 and CRABP2 the labeling event was confirmed and the site of labeling was identified as a functionally important tyrosine in an Arg-Tyr-Arg cluster that could bind the carboxyl group in fatty acids (FIG. 26). Since the expressions of these intracellular lipid-binding proteins (iLBPs) are quite tissue specific it was hypothesized that other iLBPs with this structural feature could be labeled by SF-3 and OSF-2. Such labeling was confirmed using recombinant FABP3 and FABP4.

Figure 27:
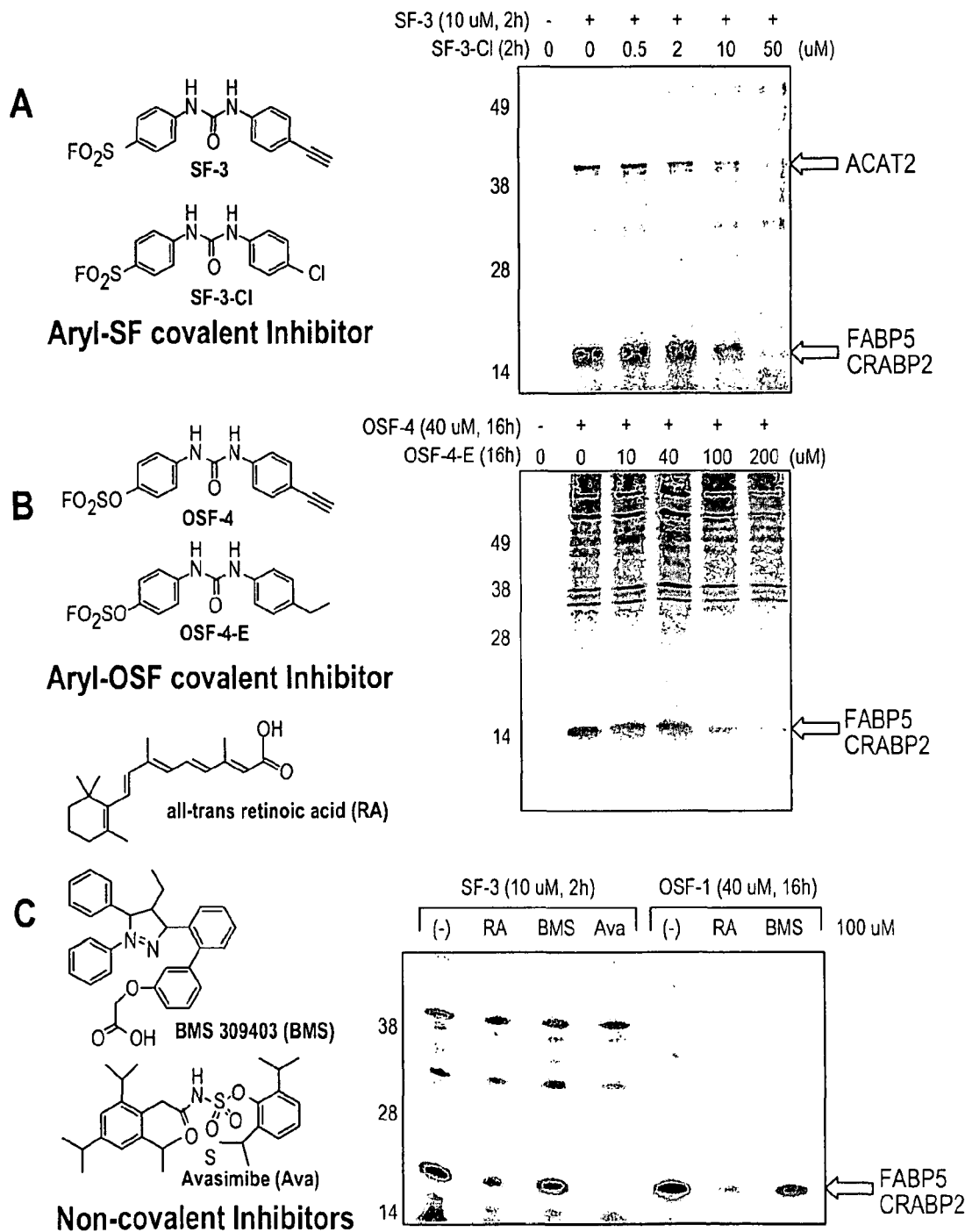
FIG. 27 illustrates competition experiments using SF and OSF probes suggest chemoselective labeling. Covalent inhibitor SF-3-Cl (A) and OSF-4-E (B) could out-compete the labeling of FABPS/CRABP2 in live HeLa cells by SF-3 probe (A) or OSF-4 (B), respectively. Non-covalent inhibitors all-trans retinoic acid (RA), aP2 inhibitor BMS 309403 (BMS) or SOAT2 inhibitor Avamisibe could out compete the selective labeling of FABPS/CRABP2 in live HeLa cells by aryl-SF and aryl-OSF probes (C).
Figure 28:
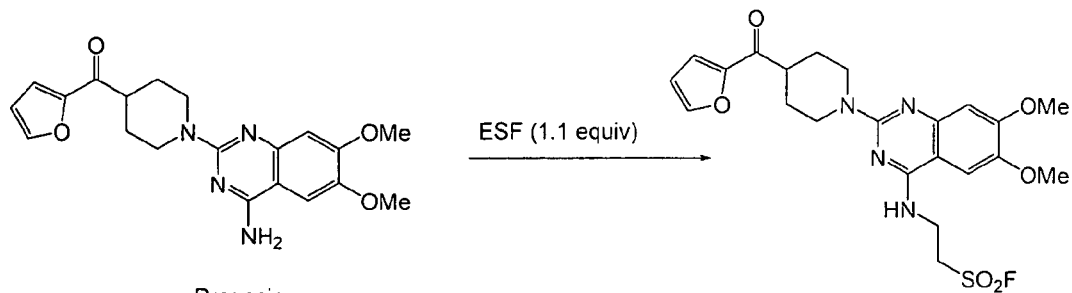
FIG. 28 illustrates additional examples of biologically active molecules that can be reacted with ESF.
Figure 28:
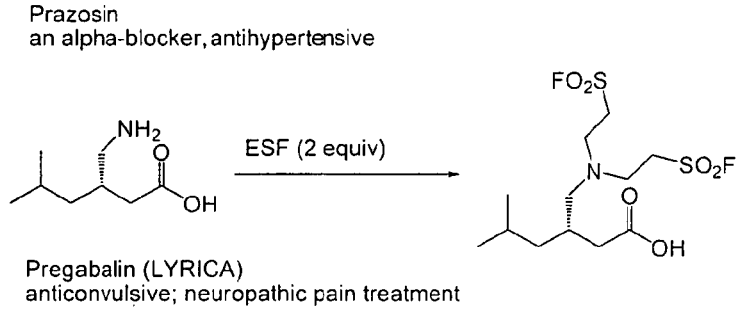
Figure 28:
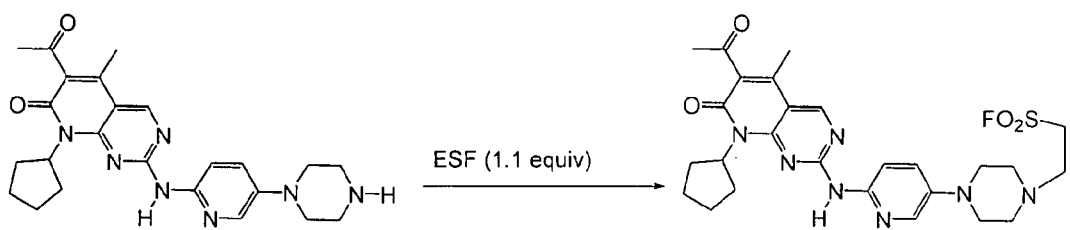
Figure 28:
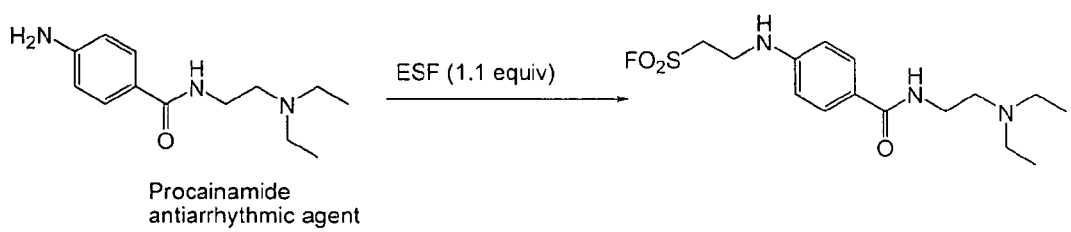
Figure 28:
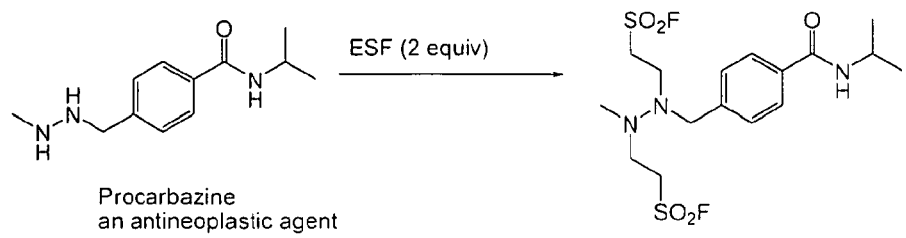
Figure 29:
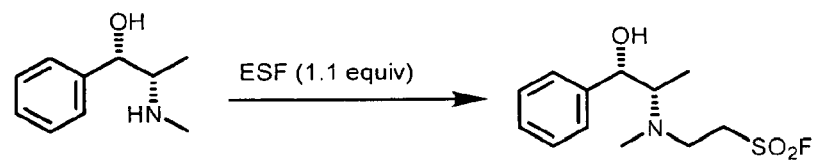
FIG. 29 illustrates additional examples of biologically active molecules that can be reacted with ESF.
Figure 29:
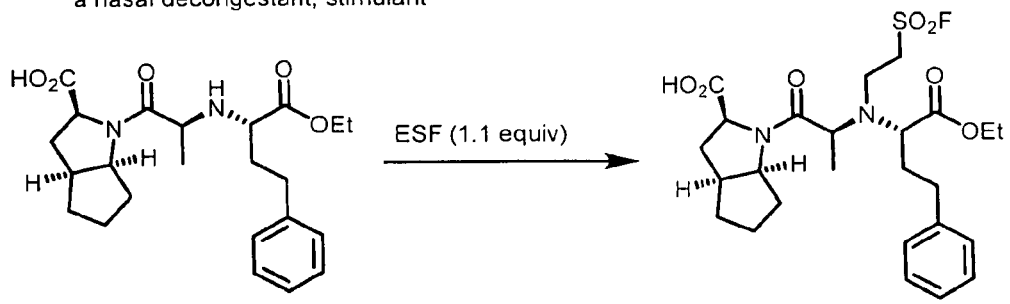
Figure 29:
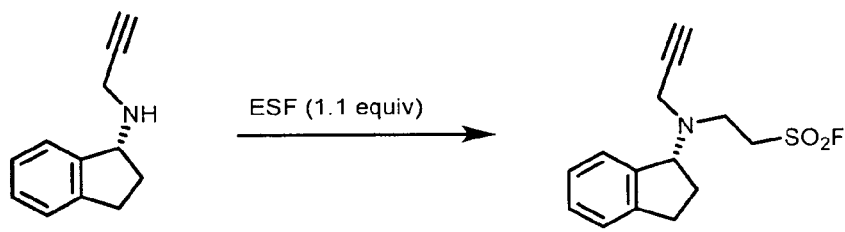
Figure 29:
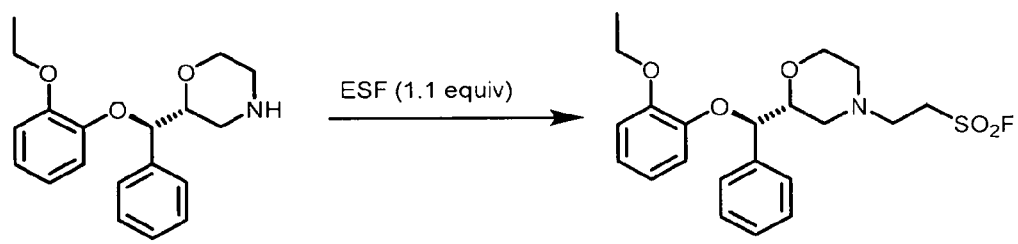
Figure 29:
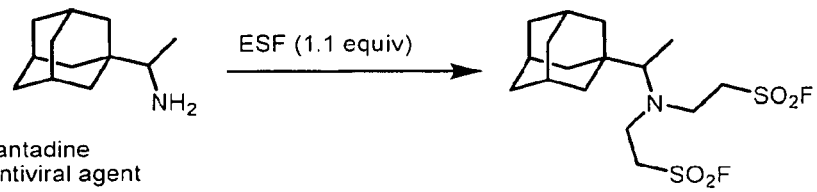
Figure 30:
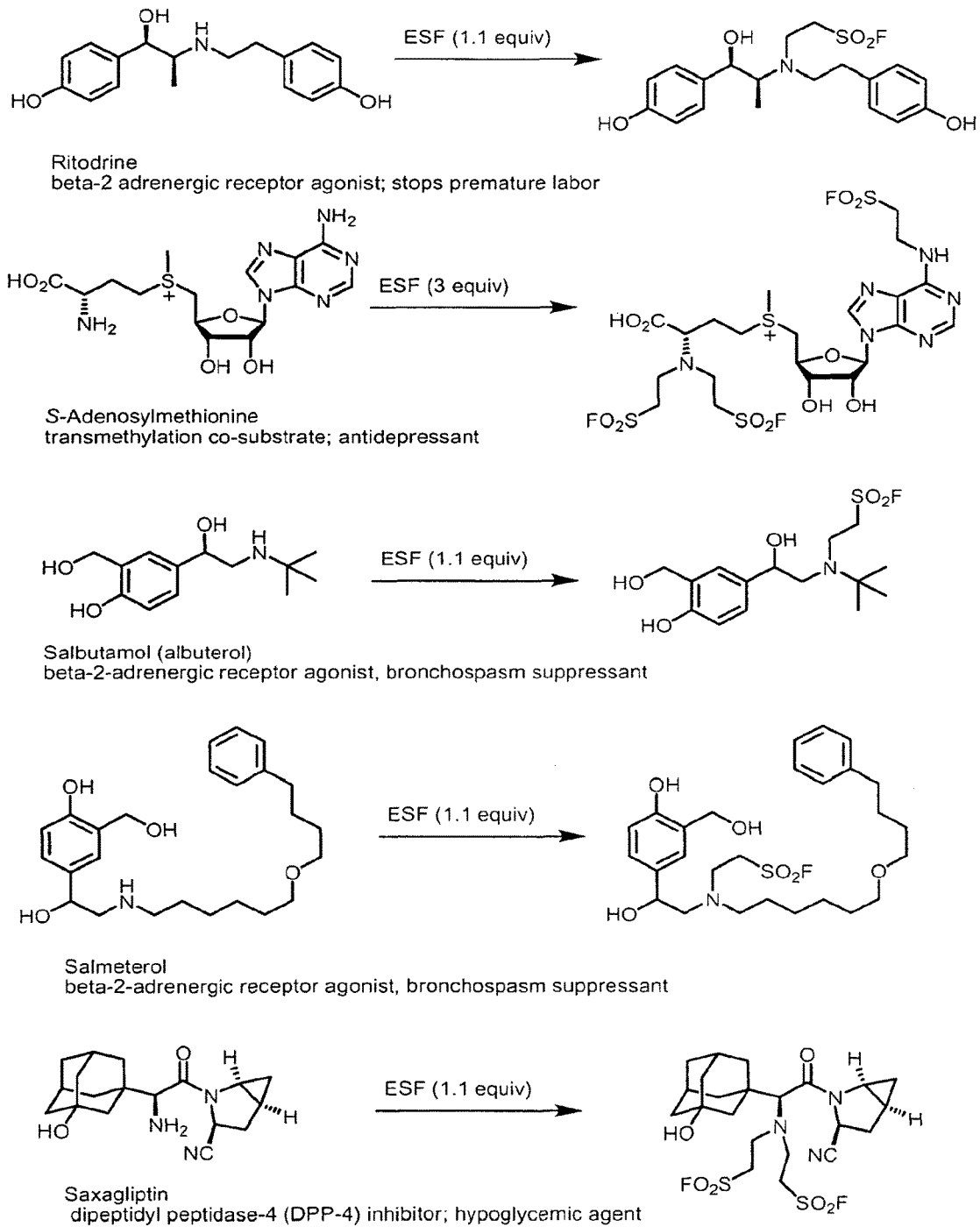
FIG. 30 illustrates additional examples of biologically active molecules that can be reacted with ESF.
Figure 31:
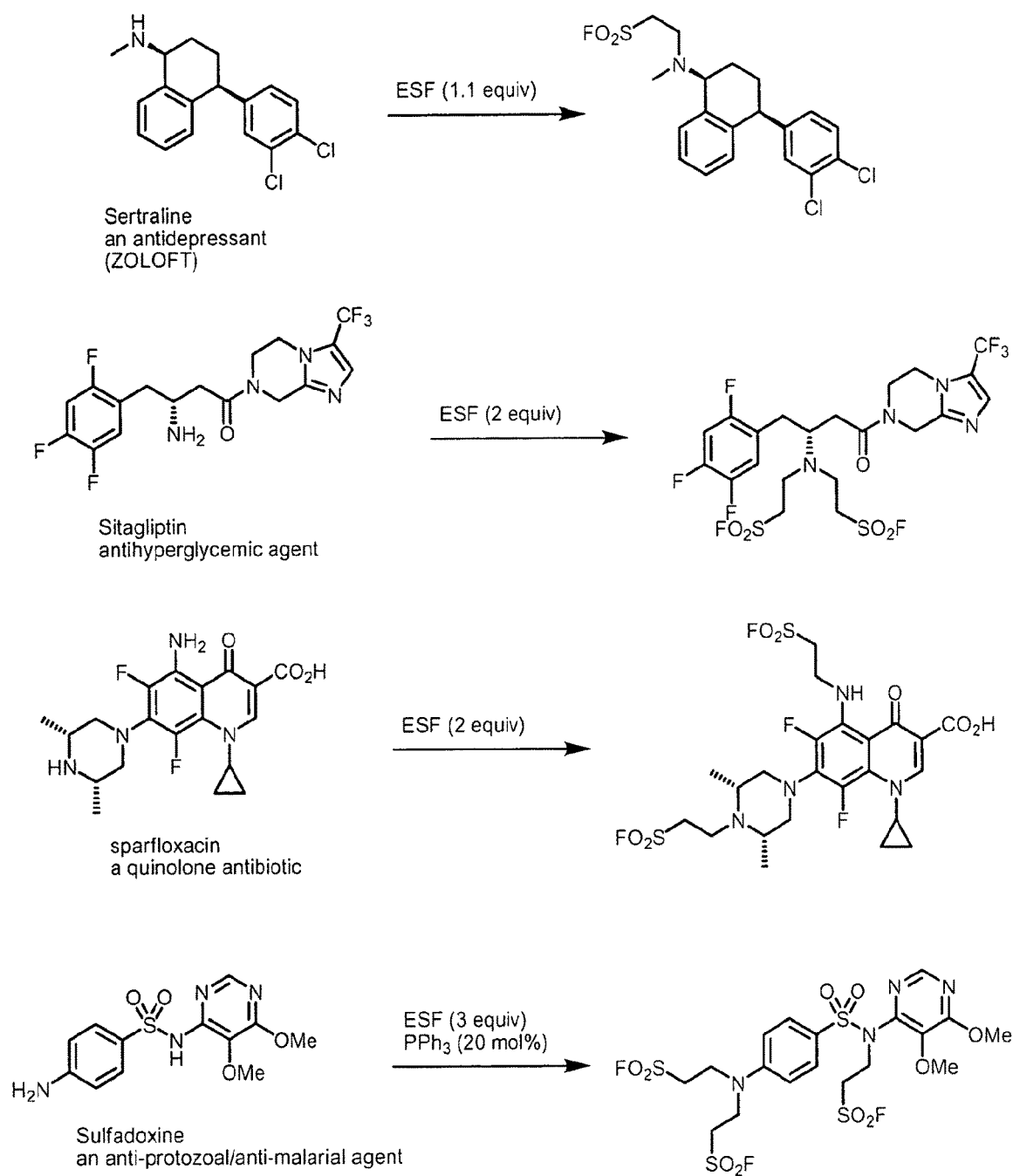
FIG. 31 illustrates additional examples of biologically active molecules that can be reacted with ESF.
Figure 32:
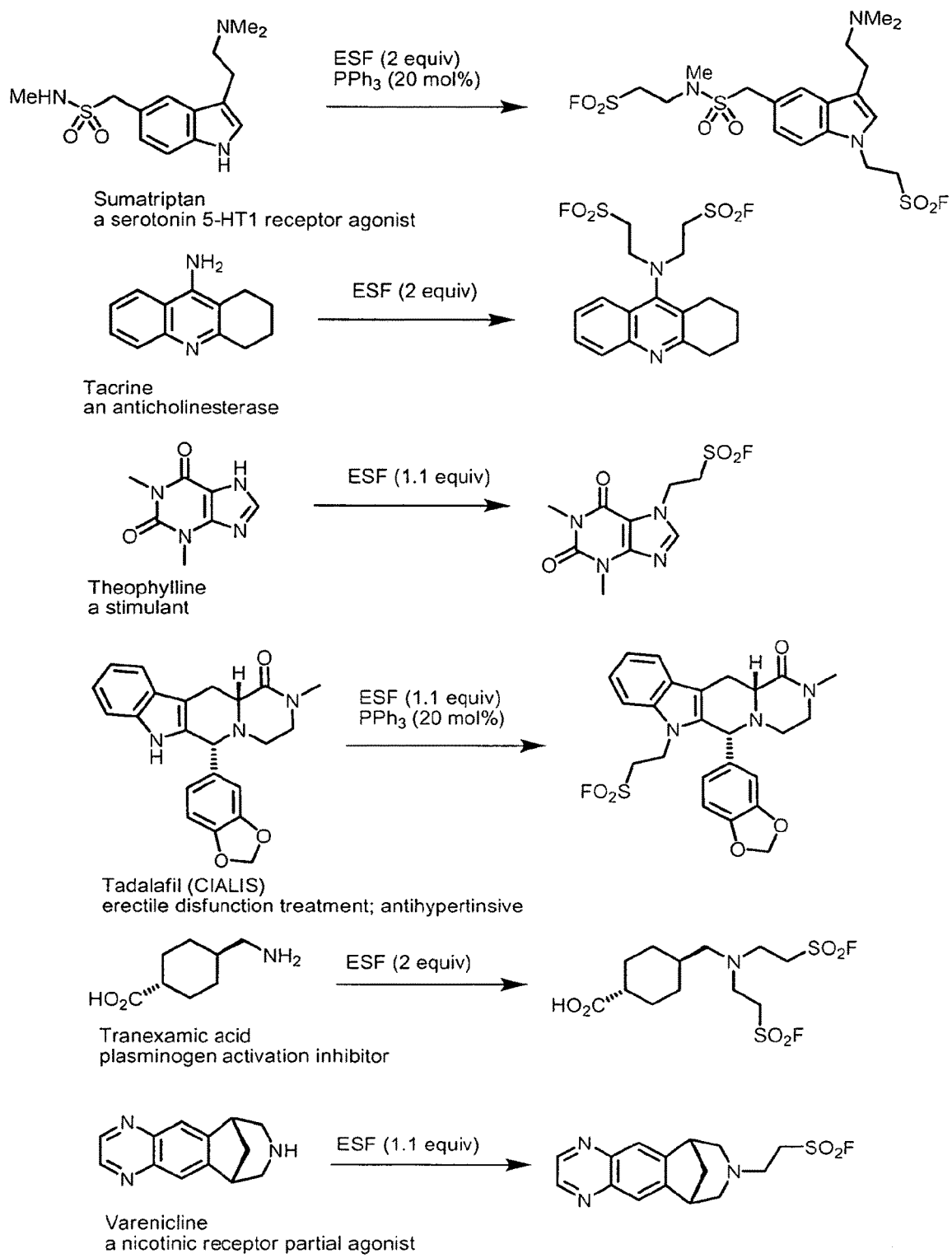
FIG. 32 illustrates additional examples of biologically active molecules that can be reacted with ESF.
Figure 33:
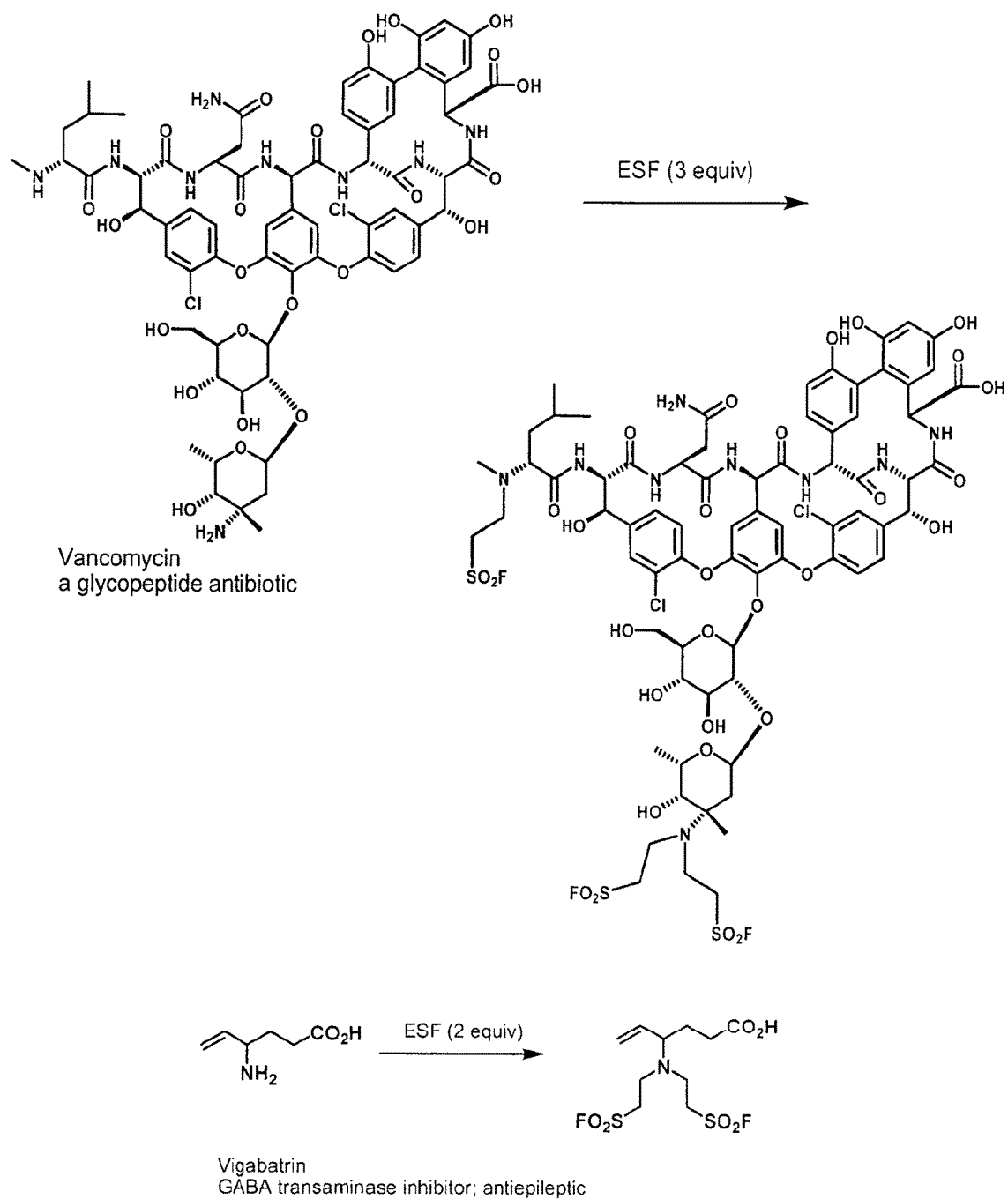
FIG. 33 illustrates additional examples of biologically active molecules that can be reacted with ESF.
Figure 34:
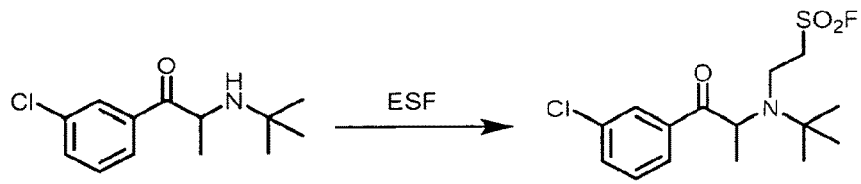
FIG. 34 illustrates additional examples of biologically active molecules that can be reacted with ESF.
Figure 34:
Figure 34:
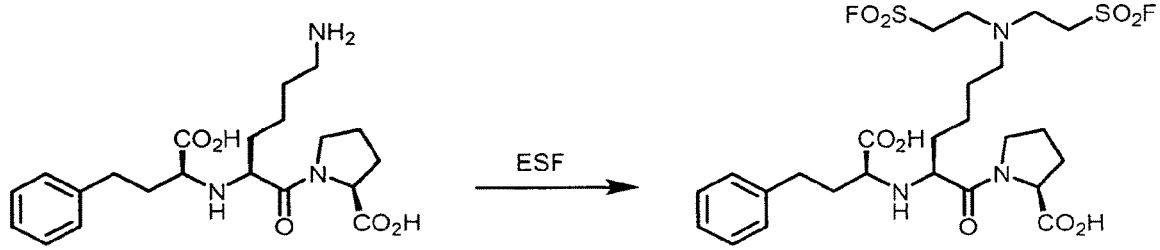
Figure 34:
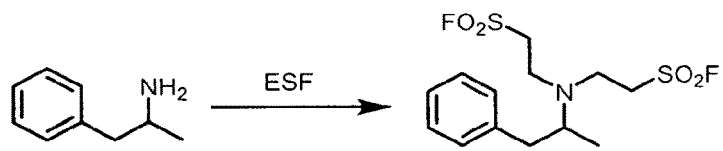
Figure 34:
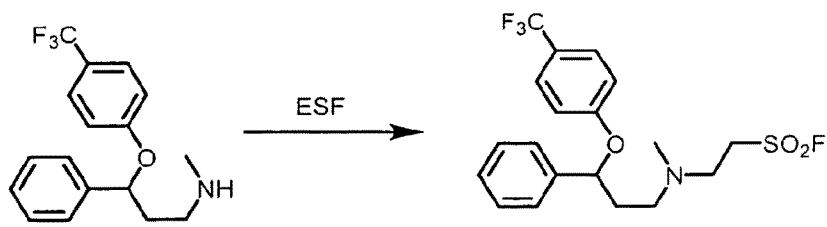
Figure 35:
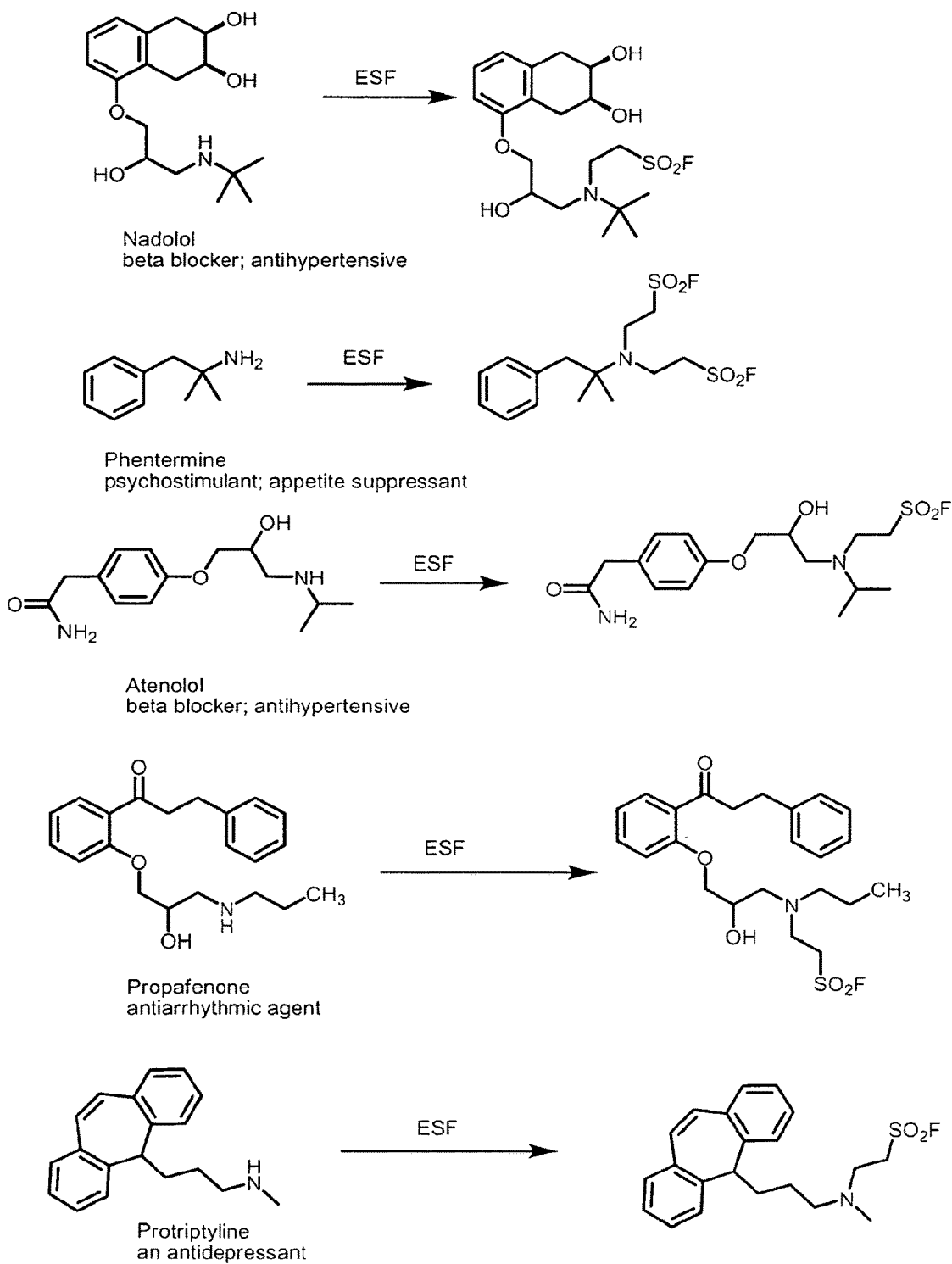
FIG. 35 illustrates additional examples of biologically active molecules that can be reacted with ESF.

Covalent inhibitors based on SF-3 and OSF-2 (similar molecules without an alkyne handle) were synthesized and used to compete with the probes (FIGS. 27(A and B)). With increasing concentrations of covalent inhibitors a decreasing labeling event toward FABP5/CRABP2 was observed, suggesting the labeling is chemoselective and could be completed at certain concentration. These SO$_2$F and OSO$_2$F probes also were used to examine known and previously unknown non-covalent inhibitors of iLBPs in live HeLa cells (FIG. 27(C)). Surprisingly, an SOAT inhibitor (Avasimibe Pfizer, phase III) could compete out the labeling on FABP5 and CRABP2 in live HeLa cells suggesting strong binding in the substrate binding pockets. These studies provide a new way to covalently target iLBPs and suggest that the promiscuous reactivity of sulfur (VI) fluoride functional groups can be tuned and utilized for selective protein modification.

EXAMPLE 10

Additional Examples of ESF and $SO_2F_2$ Modified Drugs and Other Biologically Active Compounds Biologically active compounds, such as drugs, enzyme inhibitors, other therapeutic agents, agrochemicals (e.g., herbicides, fungicides, and pesticides), and the like, which have a pendant primary or secondary amino nitrogen group are readily reactive toward ethylenesulfonyl fluoride (ESF), as described in detail herein, to form an ESF derivative via Michael addition of the amino group to the ESF double bond. In the case of primary amino compounds, one or two ESF groups can be added, by controlling the stoichiometry (one equivalent of ESF will replace one hydrogen of a primary amine with an fluorosulfonylethyl group; if two equivalents of ESF are used, both hydrogens of the amino group will be replaced by fluorosulfonylethyl groups). The reaction with ESF can be carried out in the presence of hydroxyl groups, includeing phenolic hydroxyl groups, without any substantial interference. FIGS. 28 to 35 provide examples of biologically active compounds that can be reacted with ESF to form ESF adducts according to the methods described herein.

Figure 36:
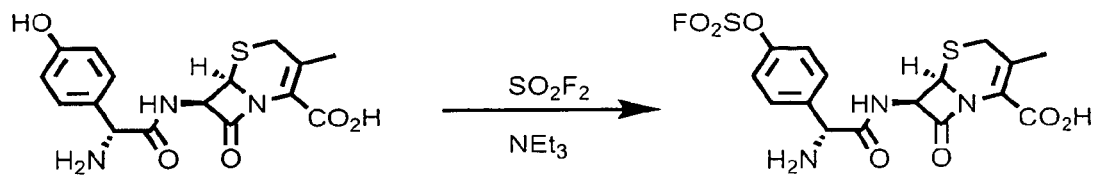
FIG. 36 illustrates additional examples of biologically active molecules that can be reacted with $SO_2F_2$.
Figure 36:
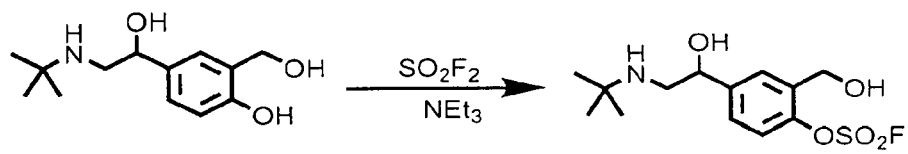
Figure 36:
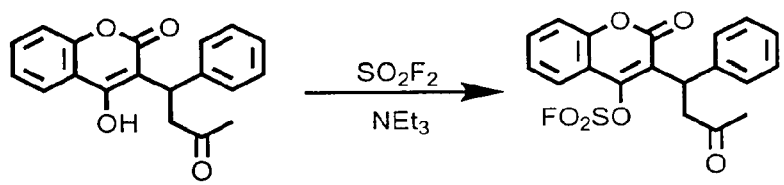
Figure 36:
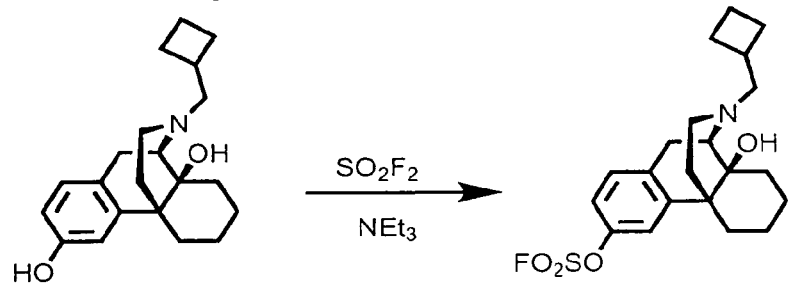
Figure 36:
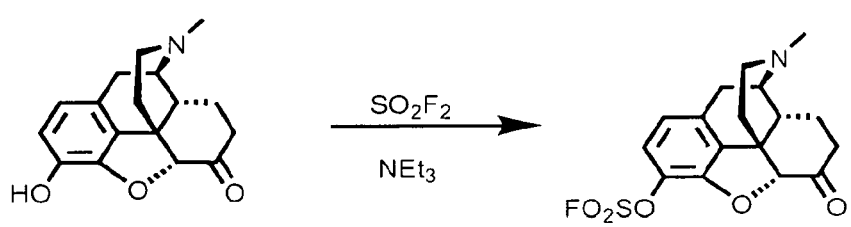
Figure 37:
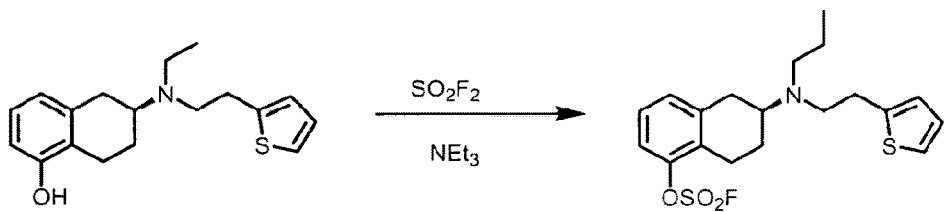
FIG. 37 illustrates additional examples of biologically active molecules that can be reacted with $SO_2F_2$.
Figure 37:
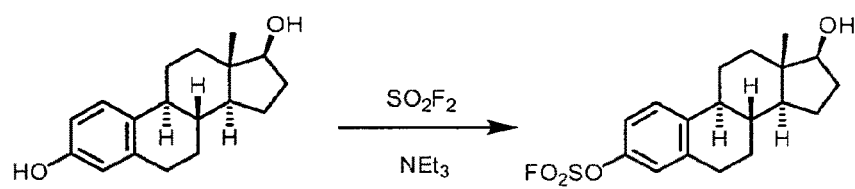
Figure 37:
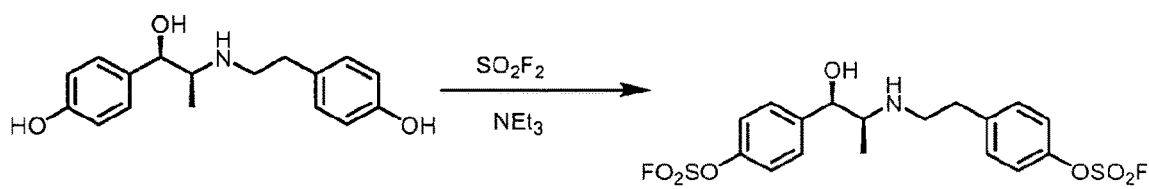
Figure 37:
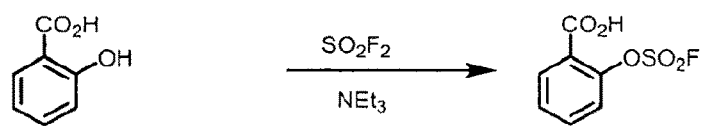
Figure 37:
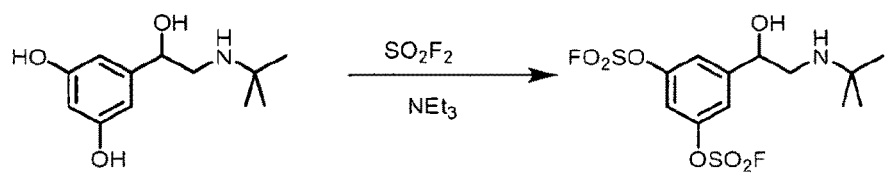

Biologically active compounds that have one or more pendant aromatic or heteroaromatic hydroxyl group or a pendant secondary amino group are readily reactive toward $SO_2F_2$ in the presence of a base (e.g., a teriary amine) to form fluorosulfate esters with the hydroxyl group, or a fluorosulfamate with the amino group, as described in detail herein. FIGS. 36 and 37 provide examples of biologically active compounds that can be reacted with $SO_2F_2$ in the presence of a base to form fluorosulfates and fluorosulfamides, according to the methods described herein.

Methods for evaluating the activity of the various modified biologically active compounds described herein are well known in the art, as most of the biologically active core compounds from which the fluorosulfonyl-containing derivatives (e.g., fluorosulfates, fluorosufamates, and ESF adducts, collectively referred to as SF-modified compounds) are prepared have been extensively studied in the literature and many are or have been commercial drugs or products. Non-limiting examples of methods for evaluating the activity of some of the SF-modified compounds described herein are based on methods for assaying the activity of the parent compounds, as described in the paragraphs below.

Mephentermine is obtained from Cerilliant (Saint Louis, Mo.). The SF-modified Mephentermine is evaluated for activity in assay as described by G. Fawaz and J. Simaan, "The Tachyphylaxis caused by mephentermine and tyramine," British Journal of Pharmacology, Vol 24 (1965) pp. 526-531.

Mecamylamine hydrochloride is obtained from Sigma-Aldrich® (Milwaukee, Wis.). The SF-modified mecamylamine is evaluated for activity in assay as described by N. Gentile, et al., "Sexually diergic hypothalamic-pituitary-adrenal (HPA) responses to single-dose nicotine, continuous nicotine infusion, and nicotine withdrawal by mecamylamine in rats," Brain Research Bulletin, Vol 85 (2011) pp. 145-152.

Levallorphan tartrate salt is obtained from Sigma-Aldrich® (Milwaukee, Wis.). The SF-modified levallorphan compound is evaluated for activity in assay as described by B. Brdar and P. Fromageot, "Inhibition of viral RNA synthesis by levallorphan," FEBS Letters, Vol. 6, No. 3 (1970) pp. 190-192.

Naltrexone Hydrochloride is obtained from Sigma-Aldrich® (Milwaukee, Wis.). The SF-modified naltrexone compound is evaluated for activity in assay as described by C. Moore, "The efficacy of a low dose combination of topiramate and naltrexone on ethanol reinforcement and consumption in rat models," Pharmacology, Biochemistry and Behavior, Vol. 116 (2014) pp. 107-115.

Levothyroxine is obtained from Sigma-Aldrich® (Saint Louis, Mo.). The SF-modified compound is evaluated for activity in assay as described by D. Pabla, et al., "Intestinal permeability enhancement of levothyroxine sodium by straight chain fatty acids studied in MDCK epithelial cell line," Eurpoean Journal of Pharmacetical Sciences, Vol. 40 (2010) pp. 466-472.

Liothyronine is obtained from Sigma-Aldrich® (Milwaukee, Wis.). The SF-modified liothyronine compound is evaluated for activity in assay as described by S. Wu, et al., "Tissue responses to thyroid hormone in a kindred with resistance to thyroid hormone harboring a commonly occurring mutation in the thyroid hormone receptor β gene (P453T)," Journal of Laboratory and Clinical Medicine, Vol. 146, Issue 2 (2005) pp. 85-94.

Metaraminol is obtained from Sigma-Aldrich® (Milwaukee, Wis.). The SF-modified metaraminol compound is evaluated for activity in assay as described by A. Sagie, et al., "Effect of metaraminol during acute inferior wall myocardial infarction accompanied by hypotension: preliminary study," Journal of the American College of Cardiology, Vol. 10, Issue 5 (1987) pp. 1139-1144.

Nabilone is obtained from Sigma-Aldrich® (Saint Louis, Mo.). The SF-modified nabilone compound is evaluated for activity in assay as described by J. Lile, et al., "Separate and combine effects of the cannabinoid agaonists nabilone and Δ9-THC in humans discriminating Δ9-THC," Drug and Alcohol Dependence, Vol. 116, Issues 1-3 (2011) pp. 86-92.

Sulfadoxine is obtained from Sigma-Aldrich® (Milwaukee, Wis.). The The SF-modified compound is evaluated for activity in assay as described by C. Happi, et al., "Polymorphisms in *Plasmodium falciparum* dhfr and dhps genes and age related in vivo sulfadoxine-pyrimethamine resistance in malaria-infected patients from Nigeria" Acta Tropica, Vol. 95 (2005) pp. 183-193.

Sumatriptan is obtained from Sigma-Aldrich® (St. Louis, Mo.). The SF-modified sumatriptan compound is evaluated for activity in assay as described by Y. Watanabe, et al., "Monitoring cortical hemodynamic changes after sumatriptan injection during migraine attack by near-infrared spectroscopy," Neuroscience Research, Vol. 69 (2011) pp. 60-66.

Tacrine is obtained from Sigma-Aldrich® (St. Louis, Mo.). The SF-modified tacrine compound is evaluated for activity in assay as described by C. Gao, et al., "Tacrine induces apoptosis through lysosome- and mitochondria-dependent pathway in HepG2 cells," Toxicology In Vitro, Vol. 28, Issue 4 (2004) pp. 667-674.

Theophyline is obtained from Sigma-Aldrich® (St. Louis, Mo.). The SF-modified theophyline compound is evaluated for activity in assay as described by E. Hashimoto, et al., "Adenosine as an endogenous mediator of hypoxia for induction of vascular endothelial growth factor mRNA in U-937 cells," Biochemical and Biophysical Research Communications, Vol. 204, No. 1 (1994) pp. 318-324.

Tadalafil is obtained from Sigma-Aldrich® (St. Louis, Mo.). The SF-modified tadalafil compound is evaluated for activity in assay as described by C. Zhu, et al., "Preventive effect of phosphodiesterase 5 inhibitor Tadalafil on experimental post-pyelonephritic renal injury in rats," Journal of Surgical Research, Vol. 186 92014) pp. 253-261.

Tranexamic is obtained from Sigma-Aldrich® (St. Louis, Mo.). The SF-modified tranexamic compound is evaluated for activity in assay as described by H. Kakiuchi, et al., "Tranexamic acid induces kaolin intake stimulating a pathway involving tachykinin neurokinin 1 receptors in rats," European Journal of Pharmacology, Vol. 723 (2014) pp. 1-6.

Varenicline is obtained from Sigma-Aldrich® (St. Louis, Mo.). SF-Modified varenicline compound is evaluated for activity in assay as described by C. Cunningham and L. McMahon, "The effects of nicotine, varenicline, and cystine on schedule-controlled responding in mice: Differences in α4β2 nicotinic receptor activation," European Journal of Pharmacology, Vol. 654 (2011) pp. 47-52.

Vancomycin is obtained from Sigma-Aldrich® (St. Louis, Mo.). The SF-modified compound is evaluated for activity in assay as described by T. Dilworth, et al., "Vancomycin and piperacillin-tazobactam against methicillin-resistant staphylococcus aureus and vancomycin-intermediate staphylococcus aureus in an in vitro pharmacokinetic/pharmacodynamic model," Clinical Therapeutics, Vol. 36 (2014) pp. 1335-1344.

Vigabatrin is obtained from Sigma-Aldrich® (St. Louis, Mo.). The SF-modified compound is evaluated for activity in assay as described by J. Plum, et al., "The anti-epileptic drug substance vigabatrin inhibits taurine transport in intestinal and renal cell culture models," International Journal of Pharmaceutics, Vol. 473 (2014) pp. 395-397.

Salicyclic Acid is obtained from Sigma-Aldrich® (St. Louis, Mo.). The SF-modified compound is evaluated for activity in assay as described by H. Chen, et al., "Salicylic acid mediates alternative signal transduction pathways for pathogenesis-related acidic β-1,3-glucanase (protein N) induction in tobacco cell suspension culture," Journal of Plant Physiology, Vol. 159 (2002) pp. 331-337.

Terbutaline is obtained from Sigma-Aldrich® (St. Louis, Mo.). The SF-modified compound is evaluated for activity in assay as described by A. Hodi, et al., "Tocopherol inhibits the relaxing effect of terbutaline in the respiratory and reproductive tracts of the rat: The role of the oxidative stress index," Life Sciences, Vol 105 (2014) pp. 48-55.

Rotigotine is obtained from Sigma-Aldrich® (St. Louis, Mo.). The SF-modified compound is evaluated for activity in assay as described by S. Oster, et al., "Rotigotine protects against glutamate toxicity in primary dopaminergic cell culture," European Journal of Pharmacology, Vol. 724 (2014) pp. 31-42.

Prazosin hydrochloride is obtained from Alfa Aesar® (Ward Hill, Mass.). The SF-modified Prazosin compound is evaluated for activity in assay as described by A. Antonello, et al., "Design, synthesis, and biological evaluation of prazosin-related derivatives as multipotent compounds," Journal of Medicinal Chemistry, Vol. 48, No. 1 (2005), pp. 28-31.

Pregabalin is obtained from Sigma-Aldrich® (St. Louis, Mo.). The SF-modified Pregabalin compound is evaluated for activity in assay as described by K. Fink, et al., "Inhibition of neuronal Ca2+ influx by gabapentin and pregabalin in the human neocortex," Neuropharmacology, Vol. 42 (2002) pp. 229-236.

Procainamide is obtained from Alfa Aesar® (Ward Hill, Mass.). The SF-modified procainamide compound is evaluated for activity in assay as described by B. Lee, et al., "Procainamide is a specific inhibitor of DNA methyltransferase 1," The Journal of Biological Chemistry, Vol. 280, No. 49 (2005) pp. 40749-40756.

Procarbazine is obtained from Sigma-Aldrich® (St. Louis, Mo.). The SF-modified procarbazine compound is evaluated for activity in assay as described by D. Clive, et al., "Procarbazine is a potent mutagen at the heterozygous thymidine kinase (tk+/−) locus of mouse lymphoma assay," Mutagenesis, Vol. 3, No. 2 (1988) pp. 83-87.

Propafenone is obtained from Alfa Aesar® (Ward Hill, Mass.). The SF-modified propafenone compound is evaluated for activity in assay as described by H. Komura and M. Iwaki, "Nonlinear pharmacokinetics of propafenone in rats and humans: application of a substrate depetion assay using hepatocytes for assessment of nonlinearity," Drug Metabolism and disposition, Vol. 33 (2005), pp. 726-732.

Protriptyline is obtained from Sigma-Aldrich® (St. Louis, Mo.). The SF-modified protriptyline compound is evaluated for activity in assay as described by S. Bansode, et al., "Molecular investigations of protriptyline as a multi-target directed ligand in alzheimer's disease," PLoS ONE, Vol. 9, Issue. 8 (2014) e105196. doi:10.1371/journal.pone.0105196.

Pseudoephedrine is obtained from Sigma-Aldrich® (St. Louis, Mo.). The SF-modified pseudoephedrine compound is evaluated for activity in assay as described by Z. Wu, et al., "Pseudoephedrine/ephedrine shows potent anti-inflammatory activity against TNF-α-mediated acute liver failure induced by lipopolysaccharide/D-galactosamine," European Journal of Pharmacology, Vol. 724 (2014), pp. 112-121.

Ramipril is obtained from Sigma-Aldrich® (St. Louis, Mo.). The SF-modified ramipril compound is evaluated for activity in assay as described by X. Ji, et al., "Comparison of cardioprotective effects using ramipril and DanShen for the treatment of acute myocardial infarction in rats," Life Sciences, Vol. 72 (2003) pp. 1413-1426.

Rasagiline is obtained from Sigma-Aldrich® (St. Louis, Mo.). The SF-modified rasagiline compound is evaluated for activity in assay as described by Y. Aluf, et al., "Selective inhibition of monoamine oxidase A or B reduces striatal oxidative stress in rats with partial depletion of the nigrostriatal dopaminergic pathway," Neropharmacology, Vol. 65 (2013) pp. 48-57.

Reboxetine is obtained from Sigma-Aldrich® (St. Louis, Mo.). The SF-modified reboxetine compound is evaluated for activity in assay as described by B. Benedetto, et al., "N-desalkylquetiapine activates ERK1/2 to induce GDNF release in C6 glioma cells: A putative cellular mechanism for quetiapine as antidepressant," Neuropharmacology, Vol. 62 (2012) pp. 209-216.

Rimantadine is obtained from Sigma-Aldrich® (St. Louis, Mo.). The SF-modified rimantadine compound is evaluated for activity in assay as described by G. Stamatiou, et al., "Heterocyclic rimantadine analogues with antiviral activity," Bioorganic & Medicinal Chemistry, Vol. 11 (2003) pp. 5485-5492.

Ritodrine is obtained from Sigma-Aldrich® (St. Louis, Mo.). The SF-modified ritodrine compound is evaluated for activity in assay as described by F. Plenge-Tellechea, et al., "Ritodrine inhibition of the plasma membrane Ca2+-ATPase from human erythrocyte," Archives of Biochemistry and Biophysics, September 15, Vol. 357, No. 2 (1998) pp. 179-184.

S-adenosylmethionine is obtained from Sigma-Aldrich® (St. Louis, Mo.). The SF-modified s-adenosylmethionine compound is evaluated for activity in assay as described by F. Zhang, et al., "S-adenosylmethionine inhibits the activated phenotype of human hepatic stellate cells via Racl and Matrix metalloproteinases," International Immunopharmacology, Vol. 19 (2014) pp. 193-200.

Salmeterol is obtained from Sigma-Aldrich® (St. Louis, Mo.). The SF-modified salmeterol compound is evaluated for activity in assay as described by Andrea Teschemacher and Horst Lemoine, "Kinetic analysis of drug-receptor interactions of long-acting β2 sympathomimetics in isolated receptor membranes: evidence against prolonged effects of salmeteroland formoterol on receptor-coupled adenylyl cyclase," The Journal of Pharmocology and Experimental Therapeutics, Vol. 288, No. 3 (1999) pp. 1084-1092.

Saxagliptin is obtained from Astatech Inc. (Bristol, Pa.). The SF-modified saxagliptin compound is evaluated for activity in assay as described by J. Kosaraju, et al., "Saxagliptin: a dipeptidyl peptidase-4 inhibitor ameliorates streptozotocin induced Alzheimer's disease," Neuropharmacology, Vol 72 (2013) pp. 291-300.

Sitagliptin is obtained from Astatech Inc. (Bristol, Pa.). The SF-modified sitagliptin compound is evaluated for activity in assay as described by Tremblay, A., "Effects of sitagliptin therapy on markers of low-grade inflammation and cell adhesion molecules in patients with type 2 diabetes," Metabolism Clinical and Experimental, Vol 63 (2014) pp. 1131-1148.

Sparfloxacin is obtained from Sigma-Aldrich® (Milwaukee, Wis.). The SF-modified sparfloxacin compound is evaluated for activity in assay as described by E. Efthimiadou, et al., "Mononuclear dioxomolybdenum (VI) complexes with the quinolones enrofloxacin and sparfloxacin: Synthesis, structure, antibacterial activity and interaction with DNA," Polyhedron, Vol. 27 (2008) pp. 349-356.

Gabapentin is obtained from Sigma-Aldrich® (Milwaukee, Wis.). The SF-modified gabapentin compound is evaluated for activity in assay as described by F. Kilic, et. al., "Antinociceptive effects of gabapentin & its mechanism of action in experimental animal studies," Indian J. Med. Res., May; 135(5) (2012) pp. 630-635.

Sertraline hydrochloride is obtained from Sigma-Aldrich® (Milwaukee, Wis.). The SF-modified sertraline compound is evaluated for activity in assay as described by R. Vij aya and K. Ruckmani, "In vitro and In vivo characterization of the transdermal delivery of sertraline hydrochloride Films," Journal of Pharmaceutical Sciences, Vol. 19, No. 6 (2011) pp. 424-432.

Lisinopril is obtained from Sigma-Aldrich® (Milwaukee, Wis.). The SF-modified lisinopril compound is evaluated for activity in assay as described by C. Constantinescu, et. al., "Catopril and lisinopril suppress production of interleukin-12 by human peripheral blood mononuclear cells," Immunology Letters, 62 (1998) pp. 25-31.

Amphetamine is obtained from Sigma-Aldrich® (Milwaukee, Wis.). The SF-modified amphetamine compound is evaluated for activity in assay as described by T. Kanbayashi, et. al., "Implication of dopaminergic mechanisms in the wake-promoting effects of amphetamine: A study of D- and L-derivatives in canine narcolepsy," Neuroscience, Vol. 99, No. 4 (2000) pp. 651-659.

Fluoxetine is obtained from Sigma-Aldrich® (Milwaukee, Wis.). The SF-modified fluoxetine compound is evaluated for activity in assay as described by M. Bianchi, et. al., "Effects of chlomipramine and fluoxetine on subcutaneous carrageenin-induced inflammation in the rat," Inflammation Research, Vol. 44 (1995), pp. 466-469.

Bupropion is obtained from Sigma-Aldrich® (Milwaukee, Wis.). The SF-modified bupropion compound is evaluated for activity in assay as described by S. Learned-Coughlin, "In vivo activity of bupropion at the human dopamine transporter as measured by positron emission tomography," Biological Psychiatry, Vol. 54 (2003), pp. 800-805.

Nadolol is obtained from Sigma-Aldrich® (Milwaukee, Wis.). The SF-modified nadolol compound is evaluated for activity in assay as described by W. Wu and S. Pruett, "Suppression of splenic natural killer cell activity in a mouse model for binge drinking, II. Role of the neuroendocrine system," The Journal of Pharmacology and Experimental Therapeutics, 278 (1996) pp. 1331-1339.

Albuterol sulfate is obtained from Sigma-Aldrich® (Milwaukee, Wis.). The SF-modified albuterol compound is evaluated for activity in assay as described by J. Cancado, et. al., "Effect of airway acidosis and alkalosis on airway vascular smooth muscle responsiveness to albuterol," BMC Pharmacology and Toxicology, (2015) 16:9.

Phentermine is obtained from Sigma-Aldrich® (Round Rock, Tex.). The SF-modified phentermine compound is evaluated for activity in assay as described by J. Kang, et. al., "Randomized controlled trial to investigate the effects of a newly developed formulation of phentermine diffuse-controlled release for obesity," Diabetes, Obesity and Metababolism, Vol. 12 (2010) pp. 876-882.

Atenolol is obtained from Sigma-Aldrich® (Milwaukee, Wis.). The SF-modified atenolol compound is evaluated for activity in assay as described by S. Dey, et. al., "Formulation and evaluation of fixed-dose combination of bilayer gastroretentive matrix table containing atorvastatin as fast-release and atenolol as sustained-release," Biomed Research International, Volume 2014, Article ID 396106, 12 pages.

Cefadroxil is obtained from Sigma-Aldrich® (Milwaukee, Wis.). The SF-modified cefadroxil compound is evaluated for activity in assay as described by X. Chen, et. al., "Effect of transporter inhibition on the distribution of cefadroxil in rat brain," Fluid Barriers of the CNS, (2014) 11:25.

Warfarin is obtained from Sigma-Aldrich® (Milwaukee, Wis.). The SF-modified warfarin compound is evaluated for activity in assay as described by T. Li, et. al., "Identification of the gene for vitamin K epoxide reductase," Nature, Vol. 427 (2004) p. 541-543.

Butorphanol is obtained from Sigma-Aldrich® (St. Louis, Mo.). The SF-modified hydromorphone compound is evaluated for activity in assay as described by S. Walsh, et. al., "Enadoline, a selective kappa opioid agaonist: comparison with butorphanol and hydromorphone in humans," Psychopharmacology, Vol. 157 (2001) pp. 151-162.

Hydromorphone hydrochloride is obtained from Sigma-Aldrich® (Milwaukee, Wis.). The SF-modified hydromorphone compound is evaluated for activity in assay as described by S. Walsh, et. al., "Enadoline, a selective kappa opioid agaonist: comparison with butorphanol and hydromorphone in humans," Psychopharmacology, Vol. 157 (2001) pp. 151-162.

Estradiol is obtained from Sigma-Aldrich® (Milwaukee, Wisconsin). The SF-modified estradiol compound is evaluated for activity in assay as described by V. Pentikainen, et. al., "Estradiol acts as a germ cell survival factor in the human testis in vitro," The Journal of Clinical Endocrinology & Metabolism, Vol. 85, Vol. 5 (2000) pp. 2057-2067.

Indolicidin is obtained from AnaSpec, Inc. (Fremont, Calif.). The SF-modified indolicidin compound is evaluated for activity in assay as described by Selsted, et. al., "Indolicidin, a Novel Bactericidal Tridecapeptide Amide from Neutrophils," The Journal of Biological Chemistry, Vol. 267, No. 7, Issue of March 5 (1992) pp. 4292-4295.

Thymopentin is obtained from Sigma-Aldrich® (Milwaukee, Wis.). The SF-modified thymopentin compound is evaluated for activity in assay as described by Fan, et. al., "Thymopentin (TP5), an immunomodulatory peptide, suppresses proliferation and induces differentiation in HL-60 cells," Biochimica et Biophysica Acta, Vol. 1763 (2006) pp. 1059-1066.

Oxytocin is obtained from Sigma-Aldrich® (Milwaukee, Wis.). The SF-modified oxytocin compound is evaluated for activity in assay as described by U.S. Pharmacopeia Pharmacopeial Forum: Volume No. 29(6) p. 1946.

Arginine Vasopressin is obtained from Sigma-Aldrich® (Milwaukee, Wis.). The SF-modified arginine vassopressin compound is evaluated for activity in assay as described by U.S. Pharmacopeia Pharmacopeial Forum: Volume No. 29(6)31(4) p. 1127.

Tetrahydrocannabinol is obtained from Sigma-Aldrich® (Saint Louis, Mo.). The SF-modified tetrahydrocannabinol compound is evaluated for activity in assay as described by M. Parolini and A. Binelli, "Oxidative and genetic responses induced by Δ9-Tetrahydrocannabinol (Δ-9-THC) to Dreissena polymorpha," Science of the Total Environment, Vol. 468-469 (2014) pp. 68-76.tette Methylphenidate is obtained from Sigma-Aldrich® (Saint Louis, Mo.). The SF-modified methylphenidate compound is evaluated for activity in assay as described by A. Issy and E. Del Bel, "7-Nitroinadazole blocks the prepulse inhibition disruption and c-Fos increase induced by methylphenidate," Behavioural Brain Research, Vol. 262 (2014) pp. 74-83.

Desloratadine is obtained from Sigma-Aldrich® (Milwaukee, Wis.). The SF-modified desloratadine compound is evaluated for activity in assay as described by Y. Lin, et al., "Design, synthesis and biological activity evaluation of desloratadine analogues as H1 receptor antagonists," Bioorganic 7 Medicinal Chemistry, Vol. 21 (2013) pp. 4178-4185.

Anisomycin is obtained from Sigma-Aldrich® (Milwaukee, Wis.). The SF-modified anisomycin compound is evaluated for activity in assay as described by X. Guo, et al., "Epigenetic mechanisms of amyloid-β production in anisomycin-treated SH-SYSY cells," Neuroscience, Vol. 194 (2011) pp. 272-281.

Strobilurin F is isolated as described by A. Fredenhagen, et al., "Strobilurins F, G and H, three new antifungal metabolites from Bolineau Lutea I. fermentation, isolation and biological activity," The Journal of Antibiotics, Vol. XLIII, No. 6 (1990) pp. 655-660. The SF-modified strobilurin compound is evaluated for activity in assay as described by J. Sudisha, et al., "Comparative efficacy of strobilurin fungicides against downy mildew disease of pearl millet," pesticide biochemistry and Physiology, Vol. 81 (2005) pp. 188-197).

Cyclopamine is obtained from Sigma-Aldrich® (Milwaukee, Wis.). The SF-modified cyclopamine compound is evaluated for activity in assay as described by T. Takahasi, et al., "cyclopamine induces eosinophilic differentiation and upregulates CD44 expression in myeloid leukemia cells," Leukemia Research, Vol. 35 (2011) pp. 638-645.

Capsaicin is obtained from Sigma-Aldrich® (Milwaukee, Wis.). The SF-modified capsaicin compound is evaluated for activity in assay as described by R. Terayama, et al., "Assessment of intraoral mucosal pain induced by the application of capsaicin," Oral Biology, Vol. 59 (2014) pp. 1334-1341.

Trifloxystrobin is obtained from Sigma-Aldrich® (Milwaukee, Wis.). The SF-modified trifloxystrobin compound is evaluated for activity in assay as described by B. Zhu, et al., "Assessment of trifloxystrobin uptake kinetics, developmental toxicity and mRNA espression in rare minnow embryos," Chemosphere, Vol. 120 (2015) pp. 447-455.

Impidacloprid is obtained from Sigma-Aldrich® (Milwaukee, Wis.). The SF-modified impidacloprid compound is evaluated for activity in assay as described by X. Yang, et al., "Two cytochrome P450 genes are involved in imidacloprid resistance in field populations of the whitefly, Bemisia tabaci, in China," Pesticide Biochemistry and Physiology, Vol. 107, Issue 3 (2013) pp. 343-350.

Acetamiprid is obtained from Sigma-Aldrich® (Milwaukee, Wisconsin). The SF-modified acetamiprid compound is evaluated for activity in assay as described by T. Cavas, et al., "In vitro genotoxicity evaluation of acetamiprid in CaCo-2 cells using the micronucleus, comet and yH2AX foci assays," Pesticide Biochemistry and Physiology, Vol. 104 (2012) pp. 212-217.

Nitenpyram is obtained from Sigma-Aldrich® (Milwaukee, Wis.). The SF-modified nitenpyram compound is evaluated for activity in assay as described by T. Perry, et al., "Effects of mutations in Drosophila nicotinic acetylcholine receptor subunits on sensitivity to insecticides targeting nicotinic acetylcholine receptors," Pesticide Biochemistry and Physiology, Vol. 102 (2012) pp. 56-60.

Fipronil is obtained from Sigma-Aldrich® (Milwaukee, Wis.). The SF-modified fipronil compound is evaluated for activity in assay as described by C. Baker, et al., "Efficacy of a novel topical combination of fipronil, (S)-methoprene, eprinomectin and praziquantel against adult and immature stages of the cat flea (Ctenocephalides felis) on cats," Veterinary Parasitology, Vol. 202 (2014) p. 54-58.

Lufenuron is obtained from Sigma-Aldrich® (Milwaukee, Wis.). The SF-modified lufenuron compound is evaluated for activity in assay as described by M. Breijo, et al., "An insect growth inhibitor—lufenuron—enhances albendazole activity against hydatid cyst," Veterinary Parasitology, Vol. 181 (2011) pp. 341-344.

Fluconazole is obtained from Sigma-Aldrich® (Milwaukee, Wis.). The SF-modified fluconazole compound is evaluated for activity in assay as described by Q. Yu, et al., "In vitro activity of verapamil alone and in combination with fluconazole or tunicamycin against Candida albicans biofilms," International Journal of Antimicrobial Agents, Vol. 41 (2013) 179-182.

Nitroxoline (8-hyroxy-5-nitroquinoline) is obtained from Sigma-Aldrich® (Milwaukee, Wis.). The SF-modified nitroxoline compound is evaluated for activity in assay as described by by G. Murugasu-Oei and T. Dick, "In vitro activity of the chelating agents nitroxoline and oxine against mycobacterium bovis BCG," International Journal of Antimicrobial Agents, Vol. 18 (2001) pp. 579-582.

Pentazocine is obtained from Sigma-Aldrich® (Saint Louis, Mo.). The SF-modified pentazocine compound is evaluated for activity in assay as described by P. Martin, et al., "The signma receptor ligand (+)-pentazocine prevents apoptotic retinal ganglion cell death induced in vitro by homocysteine and glutamate," Molecular Brain Research, Vol. 123, Issues 1-2 (2004) pp. 66-75.

Isocarboxazid is obtained from Sigma-Aldrich® (Milwaukee, Wis.). The SF-modified isocarboxazid compound is evaluated for activity in assay as described by A. Klegeris and P. McGeer, "R-(–)-Deprenyl inhibits monocytic THP-1 cell neurotoxicity independently of monoamine oxidase inhibition," Experimental Neurology, Vol. 166 (2000) pp. 458-464.

Indapamide is obtained from Sigma-Aldrich® (Milwaukee, Wis.). The SF-modified indapamide compound is evaluated for activity in assay as described by C. Ren, et al., "Design and in vivo evaluation of an indapamide transdermal patch," International Journal of Pharmaceutics, Vol. 370 (2009) pp. 129-135.

Ketamine is obtained from Sigma-Aldrich® (Round Rock, Tex.). The SF-modified ketamine compound is evaluated for activity in assay as described by G. Vasconcelos, et al., "Alpha-lipoic acid alone and combined with clozapine reverses schizophrenia-like symptoms induced by ketamine in mice: participation of antioxidant, nitrergic and neurotrophic mechanisms," Schizophrenia Research, Vol. 165 (2015) pp. 163-170.

Lomefloxacin is obtained from Sigma-Aldrich® (Milwaukee, Wis.). The SF-modified lomefloxacin compound is evaluated for activity in assay as described by Y. Zhou, et al., "Synthesis, cytotoxicity and topoisomerase II inhibitory activity of lomefloxacin derivatives," Bioorganic & Medicinal Chemistry Letters, Vol. 23 (2013) pp. 2974-2978.

Moxifloxacin is obtained from Sigma-Aldrich® (Milwaukee, Wis.). The SF-modified moxifloxacin compound is evaluated for activity in assay as described by F. Hurtado, et al., "Enhanced penetration of moxifloxacin into rat prostate tissue evidenced by microdialysis," International Journal of Antimicrobial Agents, Vol. 44, Issue 4 (2014) pp. 327-333.

Paroxetine is obtained from Sigma-Aldrich® (Milwaukee, Wis.). The SF-modified paroxetine compound is evaluated for activity in assay as described by Y. Sugimoto, et al., "Involvement of the sigmal receptor in the antidepressant-like effects of fluvoxamine in the forced swimming test in comparison with the effects elicited by paroxetine," European journal of Pharmacology, Vol. 696, Issues 1-3 (2012) pp. 96-100.

Methazolamide is obtained from Sigma-Aldrich® (Milwaukee, Wis.). The SF-modified methazolamide compound is evaluated for activity in assay as described by M. Corena, et al., "Degradation and effects of the potential mosquito larvicides methazolamide and acetazolamide in sheepshead minnow (*Cyprinodon variegates*)," Ecotoxicology and Environmental Safety, Vol. 64 (2006) pp. 369-376.

Methylphenidate is obtained from Sigma-Aldrich® (Saint Louis, Mo.). The SF-modified methylphenidate compound is evaluated for activity in assay as described by C. Wrenn, et al., "Effects of clonidine and methylphenidate on motor activity in Fmr1 knockout mice," Neuroscience Letters, Vol. 585 (2015) pp. 109-113.

Milnacipran is obtained from Sigma-Aldrich® (Round Rock, Tex.). The SF-modified milnacipran compound is evaluated for activity in assay as described by M. Yamauchi, et al., "A combination of mirtazapine and milnacipran augments the extracellular levels of monoamines in the rat brain," Neuropharmacology, Vol. 62 (2012) pp. 2278-2287.

Maprotiline is obtained from Sigma-Aldrich® (Milwaukee, Wis.). The SF-modified maprotiline compound is evaluated for activity in assay as described by C. Jan, et al., "Mechanism of maprotiline-induced apoptosis: Role of [Ca2+]I, ERK, JNK and caspase-3 signaling pathways," Toxicology, Vol. 304 (2013) 1-12.

Nortriptyline is obtained from Sigma-Aldrich® (Milwaukee, Wis.). The SF-modified nortriptyline compound is evaluated for activity in assay as described by C. Piubelli, et al., "Nortriptyline influences protein pathways involved in carbohydrate metabolism and actin-related processes in a rat gene-environment model of depression," Eurpoean Neuropsycholpharmacology, Vol. 21, Issue 7 (2011) pp. 545-562.

In addition, a fluorosulfate analog of the drug Riluzole, which is used to treat amyotrophic lateral sclerosis, can be prepared by reaction of commercially available 2-amino-6-hydroxy-benzothiazole with $SO_2F_2$ in the presence of a base (e.g., triethylamine), as shown below.

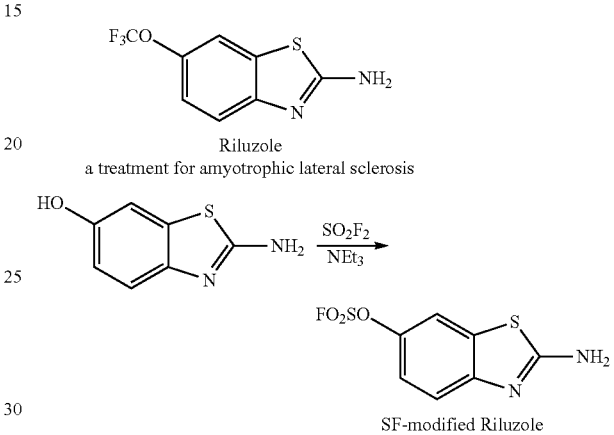

EXAMPLE 11

Inhibitors of Soluble Epoxidase Hydrolase (sEH)

Soluble epoxide hydrolase (sEH) is a bifunctional, homodimeric enzyme with hydrolase and phosphatase activity. sEH is highly expressed in the liver, but it is also expressed in tissues such as vascular endothelium, leukocytes, red blood cells, smooth muscle cells, adipocytes, as well as the kidney proximal tubule. sEH metabolizes cis-epoxyeicosatrienoic acids (EETs) as well as other lipid mediators, and as such sEH plays a role in several diseases including hypertension, cardiac hypertrophy, arteriosclerosis, brain and heart ischemia injury, cancer and pain. Fluorosulfonyl derivatives of soluble epoxide hydrolase (sEH) inhibitors are useful for treatment of sEH-mediated diseases or conditions.

A. Synthesis of (S)-4-(3-(1-(2-methylbutanoyl)piperidin-4-yl)ureido)phenyl sulfurofluoridate

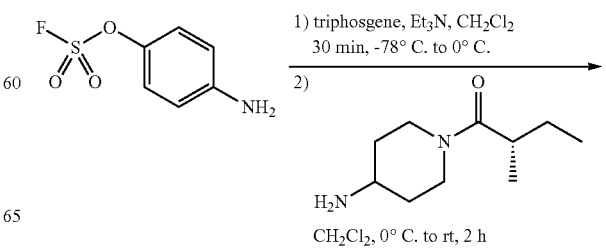

-continued

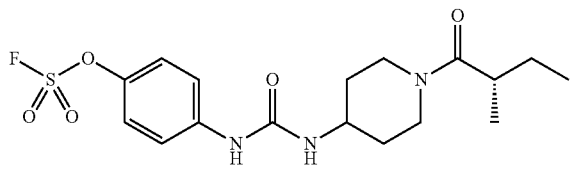

4-Aminophenyl sulfurofluoridate (also known as aniline-4-fluorosulfate; 80 mg, 419 μmol, 1.0 eq) and triethyl amine (Et$_3$N; 46.5 mg, 461 μmol, 1.1 eq) were dissolved in CH$_2$Cl$_2$ (5 mL) with stirring at −78° C. Triphosgene (46 mg, 155 μmol, 0.37 eq) dissolved in CH$_2$Cl$_2$ (5 mL) was added dropwise at −78° C. The reactants were then warmed to 0° C. and stirred for 30 min. Thereafter the reactants and reaction products were cooled to 0° C. (S)-1-(4-aminopiperidin-1-yl)-2-methylbutan-1-one (84 mg, 461 μmol, 1.2 eq) and Et$_3$N (46.5 mg, 461 μmol, 1.1 eq) dissolved in CH$_2$Cl$_2$ (DCM; 5 mL) were added slowly and the resulting reaction mixture was further stirred at room temperature for 12 h. The reaction was then quenched with the addition of HCl solution (1M, 15 mL). An organic layer was collected from the reaction mixture and the remaining aqueous layer was further extracted with EtOAc three times. The obtained organic layers were combined and washed with saturated NaCl solution. The washed organic layer was dried over anhydrous magnesium sulfate and was concentrated under vacuum. The obtained product (85 mg; 50.6%) was eluted by flash chromatography with (EtOAc:Hexane/7:3). The product was further purified by crystallization (MeOH with water). Yield 50.6%. $^1$H NMR (d$_6$-DMSO, 300 Mhz): ∂ 0.80-0.90 (m, 3H), 0.97 (t, J=5 Hz, 3H), 1.2-1.4 (m, 3H), 1.4-1.6 (m, 1H), 1.7-1.9 (m, 2H), 2.7-2.9 (m, 2H), 3.16 (t, J=12 Hz, 1H), 3.6-3.8 (m, 1H), 3.88 (d, J=12.6 Hz, 1H), 4.21 (br, 1H), 6.32 (t, J=7.5 Hz, 1H), 7.43 (d, J=9 Hz, 2H), 7.54 (d, J=9 Hz, 2H), 8.68 (d, J=8 Hz, 1H); Melting point (° C.): 186.5-188.0 (187.3).

B. Synthesis of 4-(3-(1-propionylpiperidin-4-yl)ureido)phenyl sulfurofluoridate

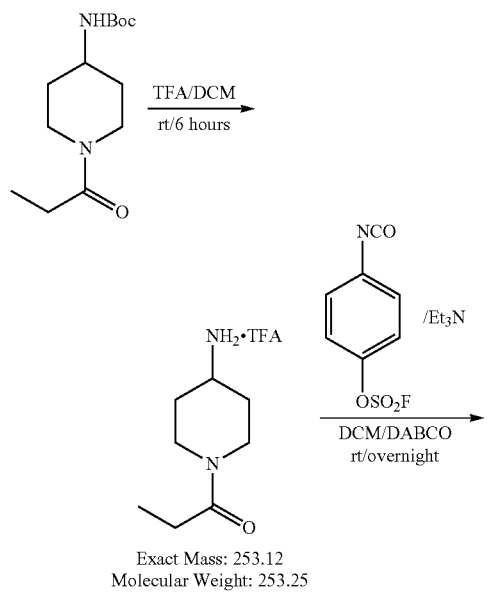

Exact Mass: 253.12
Molecular Weight: 253.25

-continued

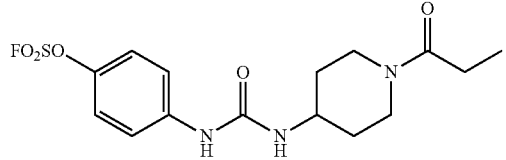

B (a). 26 mg (0.1 mmol scale) tert-butyl (1-propionylpiperidin-4-yl)carbamate dissolved in 0.5 mL DCM, 0.5 mL TFA added into the solution at room temperature. Reaction mixture was stirred at room temperature for 6 hours. The solvent and excess TFA was removed by rotary evaporation and dried under vacuum. The crude TFA salt was dissolved in DCM again and directly submitted for next step.

B (b). 1.1 eq Et$_3$N was added to free the TFA/amine salt using DCM as solvent. The crude product was purified by column chromatography (100% EtOAc, Rf: 0.14) to give the product as a white solid (0.1 mmol scale, 24 mg, 65% yield for two steps). $^1$H NMR (400 MHz, Methanol-d$_4$) δ 7.55-7.45 (m, 2H), 7.34-7.26 (m, 2H), 4.37 (dtd, J=13.6, 4.0, 1.8 Hz, 1H), 3.90 (dtd, J=14.1, 4.0, 1.8 Hz, 1H), 3.82 (tt, J=10.5, 4.1 Hz, 1H), 3.22 (ddd, J=14.2, 11.5, 2.9 Hz, 1H), 2.87 (ddd, J=14.0, 11.6, 3.1 Hz, 1H), 2.41 (q, J=7.5 Hz, 2H), 2.08-1.87 (m, 2H), 1.47-1.27 (m, 2H), 1.10 (t, J=7.5 Hz, 3H); $^{19}$F NMR (376 MHz, Methanol-d$_4$) δ 35.02; ESI-MS (m/z): 374 [MH].

C. Synthesis of 4-(((1s,4s)-4-(3-(4-((fluorosulfonyl)oxy)phenyl) ureido)cyclohexyl)oxy)benzoic acid

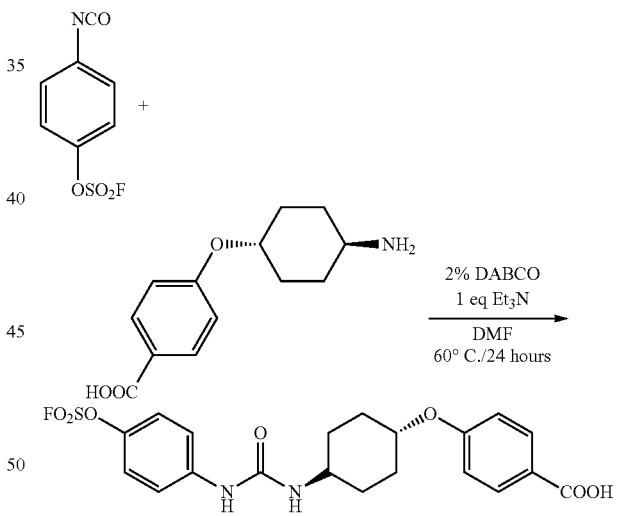

24 mg (0.1 mmol) 4-(((1r,4r)-4-aminocyclohexyl)oxy)benzoic acid was dissolved in 0.5 mL DMF, 15 μL Et$_3$N was added to the solution. Reaction mixture stirred at room temperature for 5 min. 0.1 mL 4-isocyanatophenyl sulfurofluoridate/DCM solution (0.1 mmol, 1 eq) was added by syringe, followed by 1 mg DABCO. Reaction was heated at 60° C. by an oil bath for 24 hours and was monitored by LCMS. Solvent was removed by rotary evaporation. Crude mixture was directly loaded to a column; purification by column chromatography (Rf=0.41, 100% EtOAc) to give the product as a white solid (0.1 mmol scale, 25 mg, 53% yield for two steps). $^1$H NMR (400 MHz, Methanol-d$_4$) δ 7.99-7.90 (m, 2H), 7.56-7.47 (m, 2H), 7.36-7.26 (m, 2H), 7.03-6.92 (m, 2H), 4.43 (ddd, J=10.0, 6.0, 4.0 Hz, 1H), 3.73-3.57 (m, 1H), 2.22-2.13 (m, 2H), 2.08 (dt, J=13.6, 3.8 Hz, 2H), 1.60 (tdd, J=12.8, 9.9, 3.2 Hz, 2H), 1.45 (tdd, J=13.0, 10.5, 3.2 Hz, 2H); $^{19}$F NMR (376 MHz, Methanol-$d_4$) δ 34.97; ESI-MS (m/z): 453 [MH]$^+$.

D. Synthesis of tert-butyl 4-(3-(4-((fluorosulfonyl)oxy)phenyl)ureido)piperidine-1-carboxylate

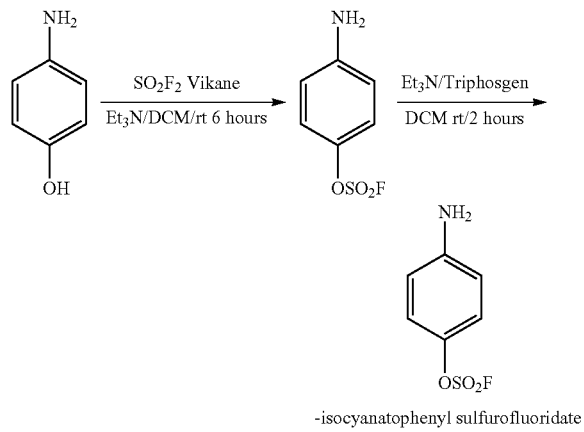

-isocyanatophenyl sulfurofluoridate

D (a). 4-Aminophenyl fluorosulfonate was readily prepared and isolated as a brown solid (mp 41-42° C.) in 91% yield (8.0 g) by reaction of 4-aminophenol with sulfuryl fluoride for 6 hours in DCM using 3 eq of Et$_3$N. $^1$HNMR (400 MHz, CDCl$_3$) δ 7.08 (d, J=8.5 Hz, 1H), 6.65 (d, J=8.7 Hz, 1H), 3.87 (br s, 1H); $^{13}$C NMR (101 MHz, CDCl$_3$) δ 146.9, 142.1, 121.8, 115.6, 115.5; $^{19}$F NMR (376 MHz, CDCl$_3$) δ +35.5; ELMS (m/z): 191 [M]$^+$.

D (b). 4-isocyanatophenyl sulfurofluoridate was prepared by reaction of 4-Aminophenyl fluorosulfonate with triphosgene and triethylamine n dichloromethane (DCM).

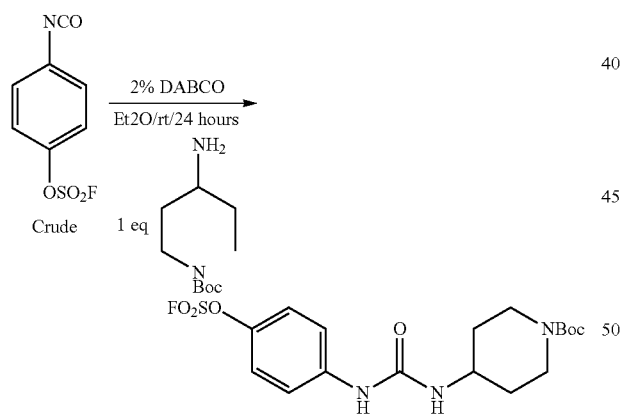

D (c). tert-butyl 4-(3-(4-((fluorosulfonyl)oxy)phenyl)ureido)piperidine-1-carboxylate was prepared from isocyanatophenyl sulfurofluoridate by reaction with the Boc-protected aminopiperadine as shown above and isolated as a white solid. The crude product was purified by column chromatography (50:50 hexane:EtOAc, Rf: 0.15) to give the product as a white solid (0.25 mmol scale, 93 mg, 88% yield for two steps); $^1$H NMR (400 MHz, Methanol-$d_4$) δ 7.57-7.47 (m, 2H), 7.39-7.23 (m, 2H), 3.99 (dt, J=14.1, 3.7 Hz, 2H), 3.75 (tt, J=10.5, 4.1 Hz, 1H), 2.96 (s, 2H), 2.01-1.78 (m, 2H), 1.46 (s, 9H), 1.44-1.27 (m, 2H); $^{19}$F NMR (376 MHz, Methanol-$d_4$) δ 35.02; ESI-MS (m/z): 318 [MH]$^+$-100.

E. Synthesis of 4-(3-(1-(methylsulfonyl)piperidin-4-yl)ureido)phenyl sulfurofluoridate

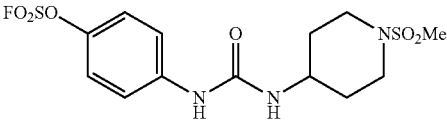

4-(3-(1-(methylsulfonyl)piperidin-4-yl)ureido)phenyl sulfurofluoridate was prepared by the same general process as in D(c) above by substituting the N-methylsulfonyl piperadine compound for the Boc-protected piperadine compound, as shown above; mp 227-229; $^1$H NMR (400 MHz, Methanol-$d_4$) δ 7.56-7.48 (m, 2H), 7.36-7.27 (m, 2H), 3.76-3.60 (m, 3H), 2.96-2.86 (m, 2H), 2.84 (s, 3H), 2.09-1.94 (m, 2H), 1.54 (dtd, J=12.8, 11.0, 4.1 Hz, 2H); $^{19}$F NMR (376 MHz, Methanol-$d_4$) δ 35.00; ESI-MS (m/z): 396 [MH]$^+$.

F. Synthesis of 4-(3-(1-(fluorosulfonyl)piperidin-4-yl)ureido)phenyl sulfurofluoridate

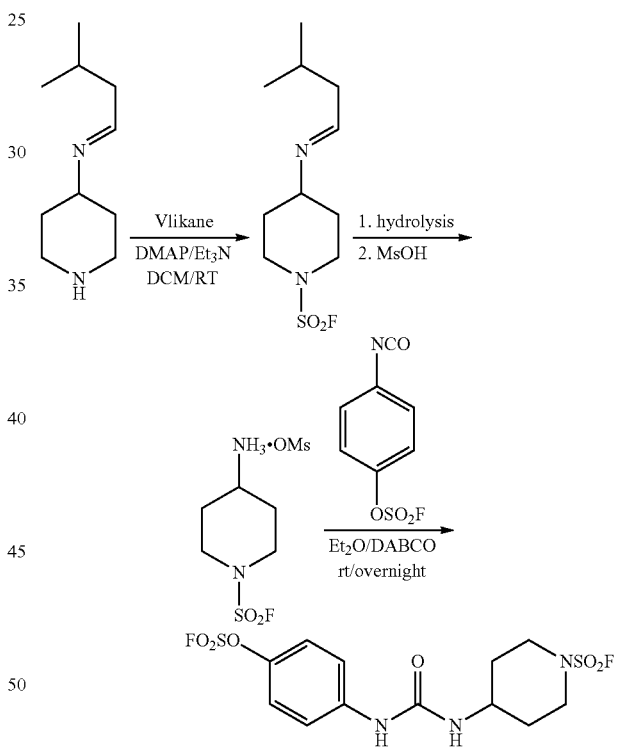

F(a). General Procedure for Synthesis of sulfamoyl fluorides. Secondary amine (1 eq), N,N-dimethylaminopyridine (DMAP; 0.5-1 eq) and triethylamine (2 eq) are mixed in CH$_2$Cl$_2$ (0.33 M) in a round-bottom flask filled to one-third capacity. The flask is sealed with septa and evacuated. SO$_2$F$_2$ gas is introduced from a balloon. The reaction mixture is stirred vigorously at room temperature for about 3 to 18 h, and reaction progress is monitored by GC or LC-MS. Upon completion, the mixture is concentrated, dissolved in EtOAc, washed with 1 N HCl and brine, dried over MgSO$_4$, and concentrated to provide the desired compound, usually in quite pure form. In some cases, additional purification is performed by passage through a short silica gel column.

F(b). 4-((3-Methylbutylidene)amino)piperidine-1-sulfamoyl fluoride was prepared according the general procedure F (a), above, with 0.5 eq DMAP and 2 eq Et$_3$N. Upon completion, the reaction mixture was washed with water, dried, and concentrated. The product was obtained as a yellow oil yield (1.8 g, 70% yield, accounting for DMAP contamination in $^1$H NMR). For characterization, the imine group was hydrolyzed (treatment with isopropanol/water mixture at 50° C. for 1.5 hours) followed by treatment with methanesulfonic acid (MsOH) to make the shelf stable salt. EI-MS (m/z): 183 [MH]$^+$.

F(c). 4-(3-(1-(fluorosulfonyl)piperidin-4-yl)ureido)phenyl sulfurofluoridate

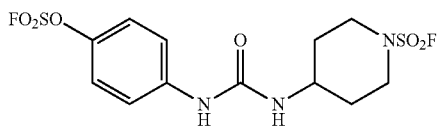

4-(3-(1-(fluorosulfonyl)piperidin-4-yl)ureido)phenyl sulfurofluoridate was prepared and isolated as a white solid. The crude product was purified by column chromatography (50:50 hexane:EtOAc, Rf: 0.57) to give the product as a white solid; mp 168-170° C.; 1H NMR (400 MHz, Methanol-d$_4$) δ 7.54-7.48 (m, 2H), 7.33-7.27 (m, 2H), 3.88-3.80 (m, 2H), 3.77 (td, J=6.4, 3.2 Hz, 1H), 3.24 (ddt, J=13.1, 11.5, 3.0 Hz, 2H), 2.11-1.98 (m, 2H), 1.59 (dtd, J=13.7, 11.0, 4.2 Hz, 2H); $^{19}$F NMR (376 MHz, Methanol-d$_4$) δ 35.06; ESI-MS (m/z): 400 [MH]$^+$.

G. Synthesis of 4-(3-(4-ethynylphenyOureido)piperidine-1-sulfonyl fluoride

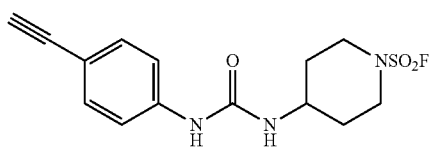

4-(3-(4-ethynylphenyl)ureido)piperidine-1-sulfonyl fluoride was prepared and isolated as a white solid according to the general procedure in F(a) above from 1-ethynyl-4-isocyanatobenzene. The crude product was purified by column chromatography (50:50 hexane:EtOAc, Rf: 0.70) to give the product as a white solid; mp 227-229° C.; $^1$H NMR (400 MHz, Methanol-d$_4$) δ 7.33 (s, 4H), 3.89-3.80 (m, 2H), 3.80-3.70 (m, 1H), 3.34 (s, 1H), 3.27-3.19 (m, 2H), 2.11-1.97 (m, 2H), 1.68-1.52 (m, 2H); $^{19}$F NMR (376 MHz, Methanol-d$_4$) δ 39.06; ESI-MS (m/z): 326 [MH]$^+$.

H. Synthesis of 4-(3-(4-(fluorosulfonyl)phenyl)ureido)piperidine-1-sulfonyl fluoride

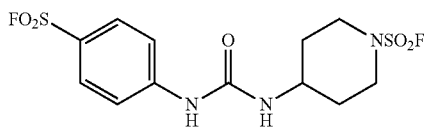

4-(3-(4-(fluorosulfonyl)phenyl)ureido)piperidine-1-sulfonyl fluoride was isolated as a white solid according to the general procedure in F(a) above from 4-isocyanatobenzenesulfonyl fluoride. The crude product was purified by column chromatography (50:50 hexane:EtOAc; Rf: 0.56) to give the product as a yellow gel; $^1$H NMR (400 MHz, Methanol-d$_4$) δ 7.93-7.86 (m, 2H), 7.72-7.65 (m, 2H), 3.92-3.73 (m, 3H), 3.29-3.21 (m, 2H), 2.06 (dt, J=13.2, 3.8 Hz, 2H), 1.71-1.52 (m, 2H); $^{19}$F NMR (376 MHz, Methanol-d$_4$) δ 65.58, 39.15; ESI-MS (m/z): 384 [MH]$^+$.

I. Synthesis of 2-(4-(3-(4-(trifluoromethoxy)phenyl)ureido)piperidin-1-yl)ethane-1-sulfonyl fluoride

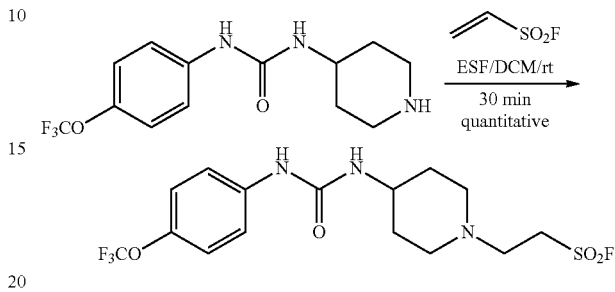

I(a). General procedure for the reaction of primary and secondary amines with ESF (adapted from Krutak, J. J.; Burpitt, R. D.; Moore, W. H.; Hyatt, J. A. J. Org. Chem. 1979, 44, 3847-3858). The starting amine (1 equiv) is dissolved in organic solvent (usually CH$_2$Cl$_2$ or THF, 0.1-0.5 M in substrate) and treated with ESF (1-2.5 equiv). The reaction mixture is stirred at room temperature for several minutes to several hours, monitoring conversion by LC-MS. Upon completion, the solvent and excess of ESF are removed by rotary evaporation and dried under vacuum, usually providing clean product. When purification by column chromatography is mentioned, it was done to remove trace impurities.

I (b). 2-(4-(3-(4-(trifluoromethoxy)phenyl)ureido)piperidin-1-yl)ethane-1-sulfonyl fluoride was prepared and isolated as a yellow solid (quantitative yield. 22 mg) according to the general ESF procedure I(a), above. The piperidine compound was mixed with 1.1 eq ESF (ethenesulfonyl fluoride) in DCM/CH$_3$CN at room temperature. Reaction finished in 10 minutes. mp 180-182° C.; $^1$H NMR (400 MHz, Methanol-d$_4$) δ 7.54-7.39 (m, 2H), 7.23-7.01 (m, 2H), 4.37 (d, J=13.1 Hz, 2H), 3.85 (s, 1H), 3.77-3.48 (m, 4H), 3.14 (s, 2H), 2.21-2.07 (m, 2H), 1.92 (d, J=12.8 Hz, 2H); $^{19}$F NMR (376 MHz, Methanol-d$_4$) δ 54.78, −59.37; ESI-MS (m/z): 414 [MH]$^+$.

The fluorosulfate, ESF, and fluorosulfamate derivatives described in this example were tested in an assay for sEH inhibition activity. The compounds exhibited IC$_{50}$ values against human sEH of less than 10 nM, with some having IC$_{50}$ values of less than 1 nM.

EXAMPLE 11

Naproxen-SF Derivative

Naproxen was extracted from commercially available caplet and was treated with 48% aqueous solution of hydrobromic acid under reflux condition to remove the methyl group from the methoxy substituent. After completion of the reaction and cooling the mixture to room temperature, the demethylated naproxen was obtained as yellow needle-like crystals. The crystals were suspended in a solvent comprising dichloromethane and water (3:2 v/v). Triethylamine (2 equiv) was added to the suspended crystals and the resulting mixture was stirred under a nitrogen atmosphere for about 10 minutes, followed by an atmosphere of sulfuryl fluoride (supplied by a balloon filled with sulfuryl fluoride sealed to the reaction vessel). After completion of the reaction of the sulfuryl fluoride with the demethylated hydroxyl group of the naproxen, volatiles were removed under reduced pressure. A solution of 1M hydrochloric acid was used to adjust the pH of aqueous phase to neutral or weak acidic, then the aqueous phase was extracted with ethyl acetate. The organic phase was then isolated, washed with brine, and dried over anhydrous sodium sulfate. After filtration and concentration, the naproxen-SF product was purified and isolated by flash column chromatography.

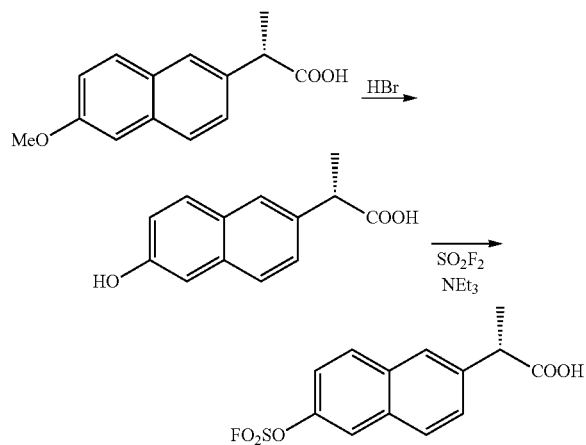

1H NMR (400 MHz, d6-DMSO) 12.45 (s, 1H), 8.20 (d, J=2.8 Hz, 1H), 8.15 (d, J=9.2 Hz, 1H), 8.04 (d, J=8.8 Hz, 1H), 7.96 (s, 1H), 7.69 (dd, J=9.2, and 2.8 Hz, 1H), 7.62 (dd, J=8.2, and 2.0 Hz, 1H), 3.91 (q, J=7.2, 1H), 1.47 (d, J=6.8, 3H); 13C NMR (101 MHz, d6-DMSO); 175.0, 147.1, 140.7, 132.3, 131.9, 130.9, 128.3, 128.0, 126.0, 119.4, 118.7, 44.7, 18.3; 19F NMR (376 MHz, d6-DMSO) 39.03; melting point: 146-147° C. (hexane/ethyl acetate).

EXAMPLE 12

Paracetamol-SF Derivative

Paracetamol was suspended in dichloromethane under a nitrogen nitrogen atmosphere and triethylamine (1.5 equiv) was added. The mixture was stirred for 10 minutes, and then a sulfuryl fluoride was introduced (via a balloon filled with sulfuryl fluoride) to form the paracetamol-SF analog. After completion of the reaction, the solvent was removed under reduced pressure, and the residue was dissolved in ethyl acetate. Filtration removed insoluble salts and the solution was concentrated in vacuo. The crude product was purified by flash column chromatography.

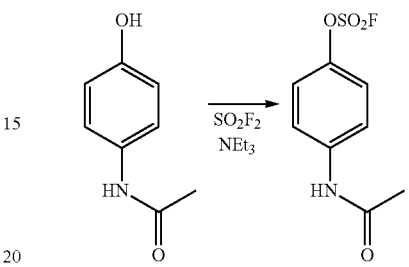

1H NMR (400 MHz, CDCl3) 7.63 (d, J=8.8 Hz, 2H), 7.30 (d, J=8.8 Hz, 2H), 2.20 (s, 3H); 13C NMR (101 MHz, CDCl3) 168.6, 145.9, 138.3, 121.7, 121.3, 24.7; 19F NMR (376 MHz, CDCl3) 36.91; melting point: 152-153° C.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

We claim:

1. An amino protected O-fluorosulfonyl-L-tyrosine of formula:

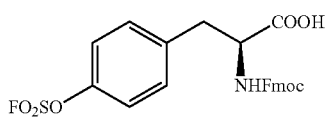

wherein "Fmoc" represents a 9-fluorenylmethyloxycarbonyl protecting group.

2. A polypeptide comprising an O-fluorosulfonyl-L-tyrosine residue.

3. The polypeptide of claim 2, wherein the polypeptide is selected from the group consisting of oxytocin, indolicin, thymopentin, and arginine vassopressin, in which the tyrosine residue thereof is replaced by an O-fluorosulfonyl-L-tyrosine residue.

4. A method of preparing a sulfated polypeptide comprising contacting the polypeptide of claim 2 with cesium carbonate and a solution of ammonia in methanol to selectively hydrolyze the fluoro group of the fluorosulfonyl-L-tyrosine residue and from a sulfated tyrosine residue therefrom.

* * * * *

UNITED STATES PATENT AND TRADEMARK OFFICE
CERTIFICATE OF CORRECTION

PATENT NO. : 10,117,840 B2
APPLICATION NO. : 15/316742
DATED : November 6, 2018
INVENTOR(S) : Jiajia Dong et al.

Page 1 of 3

It is certified that error appears in the above-identified patent and that said Letters Patent is hereby corrected as shown below:

In the Specification

Column 7,
Line 7, "CAPDXONE" should be -- CAPOXONE --.

Column 19,
Line 40, "[H$_2$F$_3$] ion" should be -- [H$_2$F$_3$]$^-$ ion --.

Column 20,
Lines 45, 47, 56, 60, "FABPS" should be -- FABP5 --.

Column 35,
Line 11, "(-hydrogens" should be -- α-hydrogens --.
Line 14, "(-position" should be -- α-position --.

Column 37,
Line 56, "( Cl., OH.)" should be -- (Cl•, OH•) --.

Column 45,
Lines 22-27, the chemical structure should be depicted as follows:
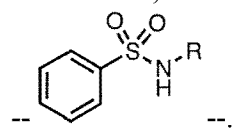
-- --.

Column 46,
Lines 51, 57, 64, "ELMS" should be -- EI-MS --.

Signed and Sealed this
Twenty-fifth Day of June, 2019

Andrei Iancu
*Director of the United States Patent and Trademark Office*

Column 47,
Lines 5, 21, 30, "ELMS" should be -- EI-MS --.

Column 49,
Line 27, "ELMS" should be -- EI-MS --.
Line 58, "0² C" should be -- 0 °C --.

Column 51,
Line 65, "ELMS" should be -- EI-MS --.

Column 55,
Lines 15, 45, 63, "ELMS" should be -- EI-MS --.

Column 56,
Line 7, "ELMS" should be -- EI-MS --.

Column 57,
Lines 2, 24, 29, 61, "ELMS" should be -- EI-MS --.

Column 58,
Lines 7, 26, "ELMS" should be -- EI-MS --.

Column 59,
Line 29, "δ δ 36.1" should be -- δ 36.1 --.
Line 51, "ELMS" should be -- EI-MS --.

Column 60,
Lines 17, 43, "ELMS" should be -- EI-MS --.

Column 63,
Line 9, "ELMS" should be -- EI-MS --.

Column 64,
Line 4, "(S)-tent-Butyl" should be -- (S)-tert-Butyl --.
Line 20, "ELMS" should be -- EI-MS --.

Column 65,
Line 43, "ELMS" should be -- EI-MS --.
Line 59, "495 [MH]" should be -- 495 [MH]$^+$ --.

Column 66,
Line 42, "ELMS" should be -- EI-MS --.
Line 47, "a-tetralone" should be -- α-tetralone --.

Column 67,
Lines 27, 52, "ELMS" should be -- EI-MS --.

Column 68,
Line 17, "ELMS" should be -- EI-MS --.
Line 57, "225 [MH]⁻" should be -- 225 [MH]⁺ --.

Column 69,
Line 9, "ELMS" should be -- EI-MS --.

Column 75,
Line 4, "LY002:cYIQNCPLG*GG" should be -- LY002:cCYIQNCPLG*GG --.

Column 84,
Lines 48, 50, "FABPS" should be -- FABP5 --.

Column 91,
Line 50, "SH-SYSY" should be -- SH-SY5Y --.

Column 97,
Lines 15-22, the chemical structure should be depicted as follows:

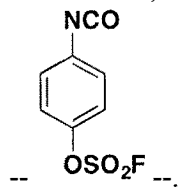

Line 33, "ELMS" should be -- EI-MS --.

Column 99,
Line 32, "4-(3-(4-ethynylphenyOureido)" should be -- 4-(3-(4-ethynylphenyl)ureido) --.

In the Claims

Column 108,
Line 62, "from" should be -- form --.